(12) United States Patent
Lu et al.

(10) Patent No.: US 10,260,055 B2
(45) Date of Patent: *Apr. 16, 2019

(54) DELIVERY OF CARGO PROTEINS VIA ARRDC1-MEDIATED MICROVESICLES (ARMMS)

(71) Applicants: President and Fellows of Harvard College, Cambridge, MA (US); The Board of Trustees of the Leland Stanford Junior University, Stanford, CA (US)

(72) Inventors: Quan Lu, Newton, MA (US); Qiyu Wang, Boston, MA (US); Stanley N. Cohen, Palo Alto, CA (US)

(73) Assignees: President and Fellows of Harvard College, Cambridge, MA (US); The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/809,470

(22) Filed: Nov. 10, 2017

(65) Prior Publication Data

US 2018/0119118 A1 May 3, 2018

Related U.S. Application Data

(62) Division of application No. 14/929,177, filed on Oct. 30, 2015, now Pat. No. 9,816,080.
(Continued)

(51) Int. Cl.
*A61K 9/127* (2006.01)
*C07K 7/06* (2006.01)
(Continued)

(52) U.S. Cl.
CPC ............ *C12N 9/16* (2013.01); *A61K 47/6455* (2017.08); *C07K 7/06* (2013.01); *C07K 14/4718* (2013.01);
(Continued)

(58) Field of Classification Search
CPC ...... A61K 47/62; A61K 47/64; A61K 47/645; A61K 47/6455; C07K 14/315; C07K 14/47

See application file for complete search history.

(56) References Cited

U.S. PATENT DOCUMENTS 4,235,871 A 11/1980 Papahadjopoulos et al.
4,501,728 A 2/1985 Geho et al.
(Continued)

FOREIGN PATENT DOCUMENTS

EP 2 604 255 A1 6/2013
JP 2011-523353 8/2011
(Continued)

OTHER PUBLICATIONS

U.S. Appl. No. 14/376,967, filed Aug. 6, 2014, Lu et al.
(Continued)

*Primary Examiner* — Jeffrey E. Russel
(74) *Attorney, Agent, or Firm* — Wolf, Greenfield & Sacks, P.C.

(57) ABSTRACT

Methods, systems, compositions and strategies for the delivery of WW domain-containing fusion proteins into cells in vivo, ex vivo, or in vitro via ARMMs are provided. Methods, systems, compositions and strategies for the delivery of cargo proteins, such as transcription factors, tumor suppressors, developmental regulators, growth factors, metastasis suppressors, pro-apoptotic proteins, nucleases, recombinases, and reprogramming factors into cells in vivo, ex vivo,
(Continued)

Interaction between the PPXY motif of ARRDC1 and the WW domain of the WW:Cas9 fusion protein or in vitro via fusion to ARMM associated proteins (e.g., ARRDC1 or TSG101) are also provided.

20 Claims, 9 Drawing Sheets

Specification includes a Sequence Listing.

Related U.S. Application Data

(60) Provisional application No. 62/073,241, filed on Oct. 31, 2014.

(51) Int. Cl.
    C07K 14/47 (2006.01)
    C07K 19/00 (2006.01)
    C12N 9/16 (2006.01)
    C12N 9/22 (2006.01)
    C12N 15/87 (2006.01)
    C12N 9/00 (2006.01)
    A61K 47/64 (2017.01)

(52) U.S. Cl.
    CPC ............... *C12N 9/22* (2013.01); *C12N 9/93* (2013.01); *A61K 9/1272* (2013.01); *C07K 2319/00* (2013.01); *C07K 2319/01* (2013.01); *C07K 2319/03* (2013.01); *C07K 2319/70* (2013.01); *C07K 2319/85* (2013.01); *C12N 2810/85* (2013.01)

(56) References Cited

U.S. PATENT DOCUMENTS

| | | | |
|---|---|---|---|
| 4,737,323 A | 4/1988 | Martin et al. |
| 4,837,028 A | 6/1989 | Allen |
| 5,767,099 A | 6/1998 | Harris et al. |
| 5,780,053 A | 7/1998 | Ashley et al. |
| 5,830,430 A | 11/1998 | Unger et al. |
| 5,851,548 A | 12/1998 | Dattagupta et al. |
| 5,855,910 A | 1/1999 | Ashley et al. |
| 7,479,573 B2 | 1/2009 | Chu et al. |
| 7,993,672 B2 | 8/2011 | Huang et al. |
| 8,569,256 B2 | 10/2013 | Heyes et al. |
| 8,680,069 B2 | 3/2014 | de Fougerolles et al. |
| 8,691,750 B2 | 4/2014 | Constien et al. |
| 8,709,466 B2 | 4/2014 | Coady et al. |
| 8,728,526 B2 | 5/2014 | Heller |
| 8,748,667 B2 | 6/2014 | Budzik et al. |
| 8,758,810 B2 | 6/2014 | Okada et al. |
| 8,759,103 B2 | 6/2014 | Kim et al. |
| 8,759,104 B2 | 6/2014 | Unciti-Broceta et al. |
| 8,795,965 B2 | 6/2014 | Zhang et al. |
| 8,771,728 B2 | 7/2014 | Huang et al. |
| 8,790,664 B2 | 7/2014 | Pitard et al. |
| 9,526,724 B2 | 12/2016 | Liu et al. |
| 9,737,480 B2 | 8/2017 | Lu et al. |
| 9,737,604 B2 | 8/2017 | Liu et al. |
| 9,816,080 B2 | 11/2017 | Lu et al. |
| 9,999,671 B2 | 6/2018 | Liu et al. |
| 2006/0188560 A1 | 8/2006 | Cheresh et al. |
| 2011/0053157 A1 | 3/2011 | Skog et al. |
| 2011/0151460 A1 | 6/2011 | Klass et al. |
| 2012/0129759 A1 | 5/2012 | Liu et al. |
| 2013/0344117 A1 | 12/2013 | Mirosevich et al. |
| 2014/0005269 A1 | 1/2014 | Ngwuluka et al. |
| 2014/0018404 A1 | 1/2014 | Chen et al. |
| 2014/0044793 A1 | 2/2014 | Goll et al. |
| 2014/0141094 A1 | 5/2014 | Smyth et al. |
| 2014/0141487 A1 | 5/2014 | Feldman et al. |
| 2014/0186958 A1 | 7/2014 | Zhang et al. |
| 2014/0273226 A1 | 9/2014 | Wu |
| 2014/0364588 A1 | 12/2014 | Haugwitz et al. |
| 2015/0037421 A1 | 2/2015 | Lu et al. |
| 2015/0050699 A1 | 2/2015 | Siksnys et al. |
| 2015/0071903 A1 | 3/2015 | Liu et al. |
| 2015/0071906 A1 | 3/2015 | Liu et al. |
| 2015/0118216 A1 | 4/2015 | Liu et al. |
| 2015/0315252 A1 | 11/2015 | Haugwitz et al. |
| 2016/0200779 A1 | 7/2016 | Liu et al. |
| 2016/0201089 A1 | 7/2016 | Gersbach et al. |
| 2016/0206566 A1 | 7/2016 | Lu et al. |
| 2018/0236081 A1 | 8/2018 | Liu et al. |

FOREIGN PATENT DOCUMENTS

| | | |
|---|---|---|
| JP | 2012-525146 | 10/2012 |
| WO | WO 2010/129023 A2 | 11/2010 |
| WO | WO 2011/127219 A1 | 10/2011 |
| WO | WO 2013/013105 A2 | 1/2013 |
| WO | WO 2013/119602 A1 | 8/2013 |
| WO | WO 2014/059255 A1 | 4/2014 |
| WO | WO 2014/093655 A2 | 6/2014 |
| WO | WO 2014/165825 A2 | 10/2014 |

OTHER PUBLICATIONS

U.S. Appl. No. 15/669,720, filed Aug. 4, 2017, Lu et al.
U.S. Appl. No. 14/929,177, filed Oct. 30, 2015, Lu et al.
PCT/US2013/024839, May 28, 2013, International Search Report and Written Opinion.
PCT/US2013/024839, Aug. 21, 2014, International Preliminary Report on Patentability.
PCT/US2014/054247, Mar. 27, 2015, International Search Report and Written Opinion.
PCT/US2014/054247, Mar. 17, 2016, International Preliminary Report on Patentability.
PCT/US2015/058479, Feb. 11, 2016, International Search Report and Written Opinion.
PCT/US2015/058479, May 11, 2017, International Preliminary Report on Patentability.
PCT/US2017/54912, Dec. 12, 2017, Invitation to Pay Additional Fees.
International Search Report and Written Opinion for PCT/US2013/024839, dated May 28, 2013.
International Preliminary Report on Patentability for PCT/US2013/024839, dated Aug. 21, 2014.
International Search Report and Written Opinion for PCT/US2014/054247, dated Mar. 27, 2015.
International Preliminary Report on Patentability for PCT/US2014/054247, dated Mar. 17, 2016.
International Search Report and Written Opinion for PCT/US2015/058479, dated Feb. 11, 2016.
International Preliminary Report on Patentability for PCT/US2015/058479, dated May 11, 2017.
Invitation to Pay Additional Fees for PCT/US/2017/54912, dated Dec. 12, 2017.
GenBank Submission; NIH/NCBI, Accession No. NC_015683. Trost et al., Jul. 6, 2013.
GenBank Submission; NIH/NCBI, Accession No. NC_016782. Trost et al., Jun. 11, 2013.
GenBank Submission; NIH/NCBI, Accession No. NC_016786. Trost et al., Aug. 28, 2013.
GenBank Submission; NIH/NCBI, Accession No. NC_017053. Fittipaldi et al., Jul. 6, 2013.
GenBank Submission; NIH/NCBI, Accession No. NC_017317. Trost et al., Jun. 11, 2013.
GenBank Submission; NIH/NCBI, Accession No. NC_017861. Heidelberg et al., Jun. 11, 2013.
GenBank Submission; NIH/NCBI, Accession No. NC_018010. Lucas et al., Jun. 11, 2013.
GenBank Submission; NIH/NCBI, Accession No. NC_018721. Feng et al., Jun. 11, 2013.
GenBank Submission; NIH/NCBI, Accession No. NC_021284. Ku et al., Jul. 12, 2013.
GenBank Submission; NIH/NCBI, Accession No. NC_021314. Zhang et al., Jul. 15, 2013.

(56) References Cited

OTHER PUBLICATIONS

GenBank Submission; NIH/NCBI, Accession No. NC_021846. Lo et al., Jul. 22, 2013.
GenBank Submission; NIH/NCBI, Accession No. NM_015277.5. Wilkars et al., Aug. 16, 2014. 9 pages.
GenBank Submission; NIH/NCBI, Accession No. NP_001155957. Skarnes et al., Feb. 26, 2014.
GenBank Submission; NIH/NCBI, Accession No. NP_006283. Rush et al., May 4, 2014.
GenBank Submission; NIH/NCBI, Accession No. NP_056092.2. Wilkars et al., Aug. 16, 2014. 3 pages.
GenBank Submission; NIH/NCBI, Accession No. NP_068684. Gunn et al., Feb. 26, 2014.
GenBank Submission; NIH/NCBI, Accession No. NP_472073. Glaser et al., Jun. 27, 2013.
GenBank Submission; NIH/NCBI, Accession No. NP_689498. Puca et al., Mar. 22, 2014.
GenBank Submission; NIH/NCBI, Accession No. NP_848495. Skarnes et al., Feb. 26, 2014.
GenBank Submission; NIH/NCBI, Accession No. NP_853659. Leithe et al., Aug. 10, 2014.
GenBank Submission; NIH/NCBI, Accession No. YP_002342100. Bernardini et al., Jun. 10, 2013.
GenBank Submission; NIH/NCBI, Accession No. YP_002344900. Gundogdu et al., Jul. 11, 2013.
GenBank Submission; NIH/NCBI, Accession No. YP_820832. Makarova et al., Aug. 27, 2013.
UniProt Submission; UniProt, Accession No. O00308. Last modified Oct. 29, 2014, version 141.
UniProt Submission; UniProt, Accession No. P46934. Last modified Oct. 29, 2014, version 152.
UniProt Submission; UniProt, Accession No. Q76N89. Last modified Oct. 29, 2014, version 95.
UniProt Submission; UniProt, Accession No. Q96J02. Last modified Oct. 29, 2014, version 129.
UniProt Submission; UniProt, Accession No. Q9H0M0. Last modified Oct. 29, 2014, version 136.
UniProt Submission; UniProt, Accession No. Q9HAU4. Last modified Oct. 29, 2014, version 143.
UniProt Submission; UniProt, Accession No. Q9HCE7.Last modified Oct. 29, 2014, version 136.
UniProt Submission; UniProt, Accession No. Q9P2P5. Last modified Oct. 29, 2014, version 105.
[No Author Listed], Invitrogen Lipofectamine™ 2000 product sheets, 2002. 2 pages.
[No Author Listed], Invitrogen Lipofectamine™ 2000 product sheets, 2005. 3 pages.
[No Author Listed], Invitrogen Lipofectamine™ LTX product sheets, 2011. 4 pages.
[No Author Listed], Thermo Fisher Scientific—How Cationic Lipid Mediated Transfection Works, retrieved from the internet Aug. 27, 2015. 2 pages.
Adrian et al., Targeted SAINT-O-Somes for improved intracellular delivery of siRNA and cytotoxic drugs into endothelial cells. J Control Release. Jun. 15, 2010;144(3):341-9. doi: 10.1016/j.jconrel. 2010.03.003. Epub Mar. 11, 2010.
Aguilera et al., Systemic in vivo distribution of activatable cell penetrating peptides is superior to that of cell penetrating peptides. Integr Biol (Camb). Jun. 2009;1(5-6):371-81. doi: 10.1039/b904878b. Epub May 11, 2009.
Allen et al., Liposomal drug delivery systems: from concept to clinical applications. Adv Drug Deliv Rev. Jan. 2013;65(1):36-48. doi: 10.1016/j.addr.2012.09.037. Epub Oct. 1, 2012.
Al-Taei et al., Intracellular traffic and fate of protein transduction domains HIV-1 TAT peptide and octaarginine. Implications for their utilization as drug delivery vectors. Bioconjug Chem. Jan.-Feb. 2006;17(1):90-100.
Altschul et al., Basic local alignment search tool. J Mol Biol. Oct. 5, 1990;215(3):403-10.

Alvarez, On the origins of arrestin and rhodopsin. BMC Evol Biol. Jul. 29, 2008;8:222. doi: 10.1186/1471-2148-8-222.
Andriole et al., Mortality results from a randomized prostate-cancer screening trial. N Engl J Med. Mar. 26, 2009;360(13):1310-9. doi: 10.1056/NEJMoa0810696. Epub Mar. 18, 2009. Erratum in: N Engl J Med. Apr. 23, 2009;360(17):1797.
Babst et al., Mammalian tumor susceptibility gene 101 (TSG101) and the yeast homologue, Vps23p, both function in late endosomal trafficking. Traffic. Mar. 2000;1(3):248-58.
Babst, A protein's final ESCRT. Traffic. Jan. 2005;6(1):2-9.
Bache et al., Hrs regulates multivesicular body formation via ESCRT recruitment to endosomes. J Cell Biol. Aug. 4, 2003;162(3):435-42.
Basha et al., Influence of cationic lipid composition on gene silencing properties of lipid nanoparticle formulations of siRNA in antigen-presenting cells. Mol Ther. Dec. 2011;19(12):2186-200. doi: 10.1038/mt.2011.190. Epub Oct. 4, 2011.
Bieniasz, The cell biology of HIV-1 virion genesis. Cell Host Microbe. Jun. 18, 2009;5(6):550-8. doi: 10.1016/j.chom.2009.05.015.
Boeckle et al., Melittin analogs with high lytic activity at endosomal pH enhance transfection with purified targeted PEI polyplexes. J Control Release. May 15, 2006;112(2):240-8. Epub Mar. 20, 2006.
Bork et al., The WW domain: a signaling site in dystrophin? Trends Biochem Sci. Dec. 1994;19(12):531-3.
Brown et al., Serine recombinases as tools for genome engineering. Methods. Apr. 2011;53(4):372-9. doi: 10.1016/j.ymeth.2010.12.031. Epub Dec. 30, 2010.
Carillo et al., The multiple sequence alignment problem in biology. SIAM J Appl Math. 1988;48:1073-1082.
Caron et al., Intracellular delivery of a Tat-eGFP fusion protein into muscle cells. Mol Ther. Mar. 2001;3(3):310-8.
Carroll, Progress and prospects: zinc-finger nucleases as gene therapy agents. Gene Ther. Nov. 2008;15(22):1463-8. doi: 10.1038/gt.2008.145. Epub Sep. 11, 2008.
Chantry, WWP2 ubiquitin ligase and its isoforms: new biological insight and promising disease targets. Cell Cycle. Aug. 1, 2011;10(15):2437-9. Epub Aug. 1, 2011.
Chavez et al., Therapeutic applications of the ΦC31 integrase system. Curr Gene Ther. Oct. 2011;11(5):375-81.
Chesnoy et al., Structure and function of lipid-DNA complexes for gene delivery. Annu Rev Biophys Biomol Struct. 2000;29:27-47.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Colletier et al., Protein encapsulation in liposomes: efficiency depends on interactions between protein and phospholipid bilayer. BMC Biotechnol. May 10, 2002;2:9.
Cong et al., Multiplex genome engineering using CRISPR/Cas systems. Science. Feb. 15, 2013;339(6121):819-23. doi: 10.1126/science.1231143. Epub Jan. 3, 2013.
Cramer et al., Ovarian cancer biomarker performance in prostate, lung, colorectal, and ovarian cancer screening trial specimens. Cancer Prev Res (Phila). Mar. 2011;4(3):365-74. doi: 10.1158/1940-6207.CAPR-10-0195.
Cronican et al., A class of human proteins that deliver functional proteins into mammalian cells in vitro and in vivo. Chem Biol. Jul. 29, 2011;18(7):833-8. doi: 10.1016/j.chembiol.2011.07.003.
Cronican et al., Potent delivery of functional proteins into mammalian cells in vitro and in vivo using a supercharged protein. ACS Chem Biol. Aug. 20, 2010;5(8):747-52. doi: 10.1021/cb1001153.
Deltcheva et al., CRISPR RNA maturation by trans-encoded small RNA and host factor RNase III. Nature. Mar. 31, 2011;471(7340):602-7. doi: 10.1038/nature09886.
Demirov et al., Overexpression of the N-terminal domain of TSG101 inhibits HIV-1 budding by blocking late domain function. Proc Natl Acad Sci U S A. Jan. 22, 2002;99(2):955-60.
Demirov et al., Retrovirus budding. Virus Res. Dec. 2004;106(2):87-102.
Denzer et al., Exosome: from internal vesicle of the multivesicular body to intercellular signaling device. J Cell Sci. Oct. 2000;113 Pt 19:3365-74.

(56) References Cited

OTHER PUBLICATIONS

Devereux et al., A comprehensive set of sequence analysis programs for the VAX. Nucleic Acids Res. Jan. 11, 1984;12(1):387-95.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Draheim et al., ARRDC3 suppresses breast cancer progression by negatively regulating integrin beta4. Oncogene. Sep. 9, 2010;29(36):5032-47. doi: 10.1038/onc.2010.250. Epub Jul. 5, 2010.
Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.
Esvelt et al., Genome-scale engineering for systems and synthetic biology. Mol Syst Biol. 2013;9:641. doi: 10.1038/msb.2012.66.
Ferretti et al., Complete genome sequence of an M1 strain of *Streptococcus pyogenes*. Proc Natl Acad Sci U S A Apr. 10, 2001;98(8):4658-63.
Freed et al., The cell biology of HIV-1 and other retroviruses. Retrovirology. Nov. 3, 2006;3:77.
Fuchs et al., Polyarginine as a multifunctional fusion tag. Protein Sci. Jun. 2005;14(6):1538-44.
Fujii et al., Beyond Tsg101: the role of Alix in 'ESCRTing' HIV-1. Nat Rev Microbiol. Dec. 2007;5(12):912-6.
Garrus et al., Tsg101 and the vacuolar protein sorting pathway are essential for HIV-1 budding. Cell. Oct. 5, 2001;107(1):55-65.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Gordley et al., Synthesis of programmable integrases. Proc Natl Acad Sci U S A. Mar. 31, 2009;106(13):5053-8. doi: 10.1073/pnas.0812502106. Epub Mar. 12, 2009.
Gottlinger et al., Effect of mutations affecting the p6 gag protein on human immunodeficiency virus particle release. Proc Natl Acad Sci U S A. Apr. 15, 1991;88(8):3195-9.
Groth et al., Phage integrases: biology and applications. J Mol Biol. Jan. 16, 2004;335(3):667-78.
Hammarstedt et al., Passive and active inclusion of host proteins in human immunodeficiency virus type 1 gag particles during budding at the plasma membrane. J Virol. Jun. 2004;78(11):5686-97.
Hartung et al., Correction of metabolic, craniofacial, and neurologic abnormalities in MPS I mice treated at birth with adeno-associated virus vector transducing the human alpha-L-iduronidase gene. Mol Ther. Jun. 2004;9(6):866-75.
Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.
Heitz et al., Twenty years of cell-penetrating peptides: from molecular mechanisms to therapeutics. Br J Pharmacol. May 2009;157(2):195-206. doi: 10.1111/j.1476-5381.2009.00057.x. Epub Mar. 20, 2009.
Henne et al., The ESCRT pathway. Dev Cell. Jul. 19, 2011;21(1):77-91. doi: 10.1016/j.devcel.2011.05.015.
Hirano et al., Site-specific recombinases as tools for heterologous gene integration. Appl Microbiol Biotechnol. Oct. 2011;92(2):227-39. doi: 10.1007/s00253-011-3519-5. Epub Aug. 7, 2011.
Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.
Hondares et al., Peroxisome Proliferator-activated Receptor α (PPARα) Induces PPARγ Coactivator 1α (PGC-1α) Gene Expression and Contributes to Thermogenic Activation of Brown Fat. J Biol. Chem Oct. 2011; 286(50):43112-22. doi: 10.1074/jbc.M111.252775.
Huang et al., p6Gag is required for particle production from full-length human immunodeficiency virus type 1 molecular clones expressing protease. J Virol. Nov. 1995;69(11):6810-8.
Hurley et al., Membrane budding. Cell. Dec. 10, 2010;143(6):875-87. doi: 10.1016/j.cell.2010.11.030.
Hurley et al., Molecular mechanisms of ubiquitin-dependent membrane traffic. Annu Rev Biophys. 2011;40:119-42. doi: 10.1146/annurev-biophys-042910-155404.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.
Karpenshif et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11, 2012.
Katzmann et al., Receptor downregulation and multivesicular-body sorting. Nat Rev Mol Cell Biol. Dec. 2002;3(12):893-905.
Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.
Kim et al., Targeted genome editing in human cells with zinc finger nucleases constructed via modular assembly. Genome Res. Jul. 2009;19(7):1279-88. doi: 10.1101/gr.089417.108. Epub May 21, 2009.
Komada et al., Hrs, a FYVE finger protein localized to early endosomes, is implicated in vesicular traffic and required for ventral folding morphogenesis. Genes Dev. Jun. 1, 1999;13(11):1475-85.
Kosaka et al., Secretory mechanisms and intercellular transfer of microRNAs in living cells. J Biol Chem. Jun. 4, 2010;285(23):17442-52.
Kuo et al., ARRDC1 as a mediator of microvesicle budding. PNAS. Mar. 2012;109(11):4025-4026.
Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.
Lawrence et al., Supercharging proteins can impart unusual resilience. J Am Chem Soc. Aug. 22, 2007;129(33):10110-2. Epub Aug. 1, 2007.
Lee et al., Recognition of liposomes by cells: in vitro binding and endocytosis mediated by specific lipid headgroups and surface charge density. Biochim Biophys Acta. Jan. 31, 1992;1103(2):185-97.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.
Lombardo et al., Gene editing in human stem cells using zinc finger nucleases and integrase-defective lentiviral vector delivery. Nat Biotechnol. Nov. 2007;25(11):1298-306. Epub Oct. 28, 2007.
Lu et al., TSG101 interaction with HRS mediates endosomal trafficking and receptor down-regulation. PNAS. Jun. 24, 2003;100(13):7626-31. Epub Jun. 11, 2003.
Lundberg et al., Delivery of short interfering RNA using endosomolytic cell-penetrating peptides. FASEB J. Sep. 2007;21(11):2664-71. Epub Apr. 26, 2007.
Maeder et al., Robust, synergistic regulation of human gene expression using TALE activators. Nat Methods. Mar. 2013;10(3):243-5. doi: 10.1038/nmeth.2366. Epub Feb. 10, 2013.
Maeder et al., Targeted DNA demethylation and activation of endogenous genes using programmable TALE-TET1 fusion proteins. Nat Biotechnol. Dec. 2013;31(12):1137-42. doi: 10.1038/nbt.2726. Epub Oct. 9, 2013.
Mak et al., The crystal structure of TAL effector PthXo1 bound to its DNA target. Science. Feb. 10, 2012;335(6069):716-9. doi: 10.1126/science.1216211. Epub Jan. 5, 2012.

(56) References Cited

OTHER PUBLICATIONS

Mali et al., RNA-guided human genome engineering via Cas9. Science. Feb. 15, 2013;339(6121):823-6. doi: 10.1126/science.1232033. Epub Jan. 3, 2013.

Mani et al., Design, engineering, and characterization of zinc finger nucleases. Biochem Biophys Res Commun. Sep. 23, 2005;335(2):447-57.

Martin-Serrano et al., HIV-1 and Ebola virus encode small peptide motifs that recruit Tsg101 to sites of particle assembly to facilitate egress. Nat Med. Dec. 2001;7(12):1313-9.

Martin-Serrano et al., Host factors involved in retroviral budding and release. Nat Rev Microbiol. Jun. 16, 2011;9(7):519-31. doi: 10.1038/nrmicro2596.

Martin-Serrano et al., Role of ESCRT-I in retroviral budding. J Virol. Apr. 2003;77(8):4794-804.

Mathivanan et al., Proteomics analysis of A33 immunoaffinity-purified exosomes released from the human colon tumor cell line LIM1215 reveals a tissue-specific protein signature. Mol Cell Proteomics. Feb. 2010;9(2):197-208. doi: 10.1074/mcp.M900152-MCP200. Epub Oct. 16, 2009.

McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.

Midoux et al., Chemical vectors for gene delivery: a current review on polymers, peptides and lipids containing histidine or imidazole as nucleic acids carriers. Br J Pharmacol. May 2009;157(2):166-78. doi: 10.1111/j.1476-5381.2009.00288.x.

Morita et al., Retrovirus budding. Annu Rev Cell Dev Biol. 2004;20:395-425.

Morris et al., A peptide carrier for the delivery of biologically active proteins into mammalian cells. Nat Biotechnol. Dec. 2001;19(12):1173-6.

Murphy, Phage recombinases and their applications. Adv Virus Res. 2012;83:367-414. doi: 10.1016/B978-0-12-394438-2.00008-6.

Myers et al., Optimal alignments in linear space. Comput Appl Biosci. 1988;4(1):11-17. doi: 10.1093/bioinformatics/4.1.11.

Nabhan et al., Arrestin domain-containing protein 3 recruits the NEDD4 E3 ligase to mediate ubiquitination of the beta2-adrenergic receptor. EMBO Rep. Aug. 2010;11(8):605-11. doi: 10.1038/embor.2010.80. Epub Jun. 18, 2010.

Nabhan et al., Formation and release of arrestin domain-containing protein 1-mediated microvesicles (ARMMs) at plasma membrane by recruitment of TSG101 protein. Proc Natl Acad Sci U S A. Mar. 13, 2012;109(11):4146-51. doi: 10.1073/pnas.1200448109. Epub Feb. 6, 2012.

Nichols et al., Formation of pluripotent stem cells in the mammalian embryo depends on the POU transcription factor Oct4. Cell. Oct. 30, 1998;95(3):379-91.

Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.

Ono et al., Cell-type-dependent targeting of human immunodeficiency virus type 1 assembly to the plasma membrane and the multivesicular body. J Virol. Feb. 2004;78(3):1552-63.

Ono et al., Relationship between human immunodeficiency virus type 1 Gag multimerization and membrane binding. J Virol. Jun. 2000;74(11):5142-50.

Pennisi, The CRISPR craze. Science. Aug. 23, 2013;341(6148):833-6. doi: 10.1126/science.341.6148.833.

Perez et al., Establishment of HIV-1 resistance in CD4+ T cells by genome editing using zinc-finger nucleases. Nat Biotechnol. Jul. 2008;26(7):808-16. doi: 10.1038/nbt1410. Epub Jun. 29, 2008.

Pisitkun et al., Identification and proteomic profiling of exosomes in human urine. Proc Natl Acad Sci U S A. Sep. 7, 2004;101(36):13368-73. Epub Aug. 23, 2004.

Pornillos et al., HIV Gag mimics the Tsg101-recruiting activity of the human Hrs protein. J Cell Biol. Aug. 4, 2003;162(3):425-34.

Pornillos et al., Structure and functional interactions of the Tsg101 UEV domain. EMBO J. May 15, 2002;21(10):2397-406.

Pornillos et al., Structure of the Tsg101 UEV domain in complex with the PTAP motif of the HIV-1 p6 protein. Nat Struct Biol. Nov. 2002;9(11):812-7.

Properzi et al., Exosomes: the future of biomarkers in medicine. Biomark Med. Oct. 2013;7(5):769-78.

Qi et al., Repurposing CRISPR as an RNA-guided platform for sequence-specific control of gene expression. Cell. Feb. 28, 2013;152(5):1173-83. doi: 10.1016/j.cell.2013.02.022.

Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.

Rauch et al., Multiple interactions between the ESCRT machinery and arrestin-related proteins: implications for PPXY-dependent budding. J Virol. Apr. 2011;85(7):3546-56. doi: 10.1128/JVI.02045-10. Epub Dec. 29, 2010.

Razi et al., Distinct roles for Tsg101 and Hrs in multivesicular body formation and inward vesiculation. Mol Biol Cell. Aug. 2006;17(8):3469-83. Epub May 17, 2006.

Rotin et al., Physiological functions of the HECT family of ubiquitin ligases. Nat Rev Mol Cell Biol. Jun. 2009;10(6):398-409. doi: 10.1038/nrm2690. Epub May 13, 2009.

Roy et al., Candidate prognostic markers in breast cancer: focus on extracellular proteases and their inhibitors. Breast Cancer (Dove Med Press). Jul. 3, 2014;6:81-91. doi: 10.2147/BCTT.S46020.

Samal et al., Cationic polymers and their therapeutic potential. Chem Soc Rev. Nov. 7, 2012;41(21):7147-94. doi: 10.1039/c2cs35094g. Epub Aug. 10, 2012.

Schorey et al., Exosome function: from tumor immunology to pathogen biology. Traffic. Jun. 2008;9(6):871-81. doi: 10.1111/j.1600-0854.2008.00734.x. Epub Mar. 6, 2008.

Schröder et al., Screening and prostate-cancer mortality in a randomized European study. N Engl J Med. Mar. 26, 2009;360(13):1320-8. doi: 10.1056/NEJMoa0810084. Epub Mar. 18, 2009.

Schwarze et al., In vivo protein transduction: delivery of a biologically active protein into the mouse. Science. Sep. 3, 1999;285(5433):1569-72.

Scott et al., Structural and mechanistic studies of VPS4 proteins. EMBO J. Oct. 19, 2005;24(20):3658-69. Epub Sep. 29, 2005.

Sells et al., Delivery of protein into cells using polycationic liposomes. Biotechniques. Jul. 1995;19(1):72-6, 78.

Sen et al., Cellular unfolded protein response against viruses used in gene therapy. Front Microbiol. May 26, 2014;5:250. doi: 10.3389/fmicb.2014.00250. eCollection 2014.

Skog et al., Glioblastoma microvesicles transport RNA and proteins that promote tumour growth and provide diagnostic biomarkers. Nat Cell Biol. Dec. 2008;10(12):1470-6. doi: 10.1038/ncb1800. Epub Nov. 16, 2008.

Sundquist et al., Ubiquitin recognition by the human TSG101 protein. Mol Cell. Mar. 26, 2004;13(6):783-9.

Thery et al., Exosomes: composition, biogenesis and function. Nat Rev Immunol. Aug. 2002;2(8):569-79.

Thery et al., Membrane vesicles as conveyors of immune responses. Nat Rev Immunol. Aug. 2009;9(8):581-93. doi: 10.1038/nri2567. Epub Jun. 5, 2009.

Turan et al., Site-specific recombinases: from tag-and-target- to tag-and-exchange-based genomic modifications. FASEB J. Dec. 2011;25(12):4088-107. doi: 10.1096/fj.11-186940. Epub Sep. 2, 2011.

Tykodi, PD-1 as an emerging therapeutic target in renal cell carcinoma: current evidence. Onco Targets Ther. Jul. 25, 2014;7:1349-59. doi: 10.2147/OTT.S48443.

Urnov et al., Highly efficient endogenous human gene correction using designed zinc-finger nucleases. Nature. Jun. 2, 2005;435(7042):646-51. Epub Apr. 3, 2005.

Valadi et al., Exosome-mediated transfer of mRNAs and microRNAs is a novel mechanism of genetic exchange between cells. Nat Cell Biol. Jun. 2007;9(6):654-9. Epub May 7, 2007.

Venken et al., Genome-wide manipulations of *Drosophila melanogaster* with transposons, Flp recombinase, and ΦC31 integrase. Methods Mol Biol. 2012;859:203-28. doi: 10.1007/978-1-61779-603-6_12.

(56) References Cited

OTHER PUBLICATIONS

Verplank et al., Tsg101, a homologue of ubiquitin-conjugating (E2) enzymes, binds the L domain in HIV type 1 Pr55(Gag). Proc Natl Acad Sci U S A. Jul. 3, 2001;98(14):7724-9. Epub Jun. 26, 2001.
Von Schwedler et al., The protein network of HIV budding. Cell. Sep. 19, 2003;114(6):701-13.
Wadia et al., Modulation of cellular function by TAT mediated transduction of full length proteins. Curr Protein Pept Sci. Apr. 2003;4(2):97-104.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Wang et al., Neutralizing antibodies to therapeutic enzymes: considerations for testing, prevention and treatment. Nat Biotechnol. Aug. 2008;26(8):901-8. doi: 10.1038/nbt.1484.
Wehman et al., The P4-ATPase TAT-5 inhibits the budding of extracellular vesicles in *C. elegans* embryos. Curr Biol. Dec. 6, 2011;21(23):1951-9. doi: 10.1016/j.cub.2011.10.040. Epub Nov. 17, 2011.
Welton et al., Proteomics analysis of bladder cancer exosomes. Mol Cell Proteomics. Jun. 2010;9(6):1324-38. doi: 10.1074/mcp.M000063-MCP201. Epub Mar. 11, 2010.
Zelphati et al., Intracellular delivery of proteins with a new lipid-mediated delivery system. J Biol Chem. Sep. 14, 2001;276(37):35103-10. Epub Jul. 10, 2001.
Zhang et al., Conditional gene manipulation: Cre-ating a new biological era. J Zhejiang Univ Sci B. Jul. 2012;13(7):511-24. doi: 10.1631/jzus.B1200042.
International Search Report and Written Opinion for PCT/US/2017/54912, dated Feb. 13, 2018.

A

B

DELIVERY OF CARGO PROTEINS VIA ARRDC1-MEDIATED MICROVESICLES (ARMMS)

RELATED APPLICATIONS

The present application is a divisional of and claims priority under 35 U.S.C. § 120 to U.S. patent application U.S. Ser. No. 14/929,177, filed Oct. 30, 2015, now U.S. Pat. No. 9,816,080, which claims priority under 35 U.S.C. § 119(e) to U.S. provisional patent application, U.S. Ser. No. 62/073,241, filed Oct. 31, 2014, each of which is incorporated herein by reference.

GOVERNMENT SUPPORT

This invention was made with government support under contract HDTRA1-06-C-0039 awarded by the Defense Threat Reduction Agency, and under contract HL114769 awarded by the National Institutes of Health. The government has certain rights in this invention.

BACKGROUND OF THE INVENTION

The delivery of proteins (e.g., therapeutic proteins) to cells is limited by a number of factors, including the poor permeability and target specificity. Protein transduction represents one emerging technology for delivering proteins into cells by exploiting the ability of certain proteins to penetrate the cell membrane. However, the majority of the proteins delivered by this method are usually trapped and subsequently degraded in the endosomes or lysosomes of the recipient cells. Another option relies on virus mediated gene delivery (gene therapy), which has been widely pursued as viruses have the unique ability to infect cells and deliver the contents in the cytoplasm efficiently. However viruses present a variety of potential problems to the patient relating to toxicity, immune and inflammatory responses, gene control and targeting tissues. In addition, the possibility of the virus becoming virulent in the patient is an added risk.

One particular agent that holds a great deal of promise as a protein-based therapeutic is the RNA-guided DNA nuclease Cas9 that can make edits (e.g., additions or deletions) to single base pairs and longer stretches of DNA (Pennisi, E. "The CRISPR Craze". Science, 2013; 341 (6148): 833-836.). Cas9 has additionally been modified to make programmable transcription factors that allow the targeted activation or silencing of specific genes (Larson, M. H et al., "CRISPR interference (CRISPRi) for sequence-specific control of gene expression". Nature Protocols, 2013; 8 (11): 2180-96). Accordingly, Cas9 has the potential to correct specific target genes for treating both recessive and dominant genetic diseases, offering significant advantages over traditional gene therapy approaches, which have only been useful for correcting some recessive genetic disorders. Therefore, it is of critical importance to develop methods and systems for effectively delivering protein therapeutics, such as Cas9, to their desired target cells in order to realize the full potential of protein based therapeutics.

SUMMARY OF THE INVENTION

Some aspects of this invention relate to the discovery that Cas9 proteins and their variants can be loaded in microvesicles, specifically ARRDC1-mediated microvesicles (ARMMs), for delivery to a target cell. The ARMM delivery system, described herein, addresses many limitations of current delivery systems that prevent the safe and efficient delivery of targeted protein therapeutics to cells. As ARMMS are derived from an endogenous budding pathway, they are unlikely to elicit a strong immune response, unlike viral delivery systems, which are known to trigger inflammatory responses (Sen D. et al., "Cellular unfolded protein response against viruses used in gene therapy.", Front Microbiology. 2014; 5:250, 1-16.). Additionally, ARMMs allow for the specific packaging of any cargo protein of interest (e.g., a Cas9 protein or Cas9 variant with a guide RNA (gRNA)). These cargo proteins can then be delivered by fusion or uptake by specific recipient cells/tissues by incorporating antibodies or other types of molecules in ARMMs that recognize tissue-specific markers. ARMMs are microvesicles that are distinct from exosomes and which, like budding viruses, are produced by direct plasma membrane budding (DPMB). DPMB is driven by a specific interaction of TSG101 with a tetrapeptide PSAP (SEQ ID NO: 74) motif of the arrestin-domain-containing protein ARRDC1 accessory protein, which is localized to the plasma membrane through its arrestin domain. ARMMS have been described in detail, for example, in PCT application number PCT/US2013/024839, filed on Feb. 6, 2013 (published as WO2013119602 A1) by Lu Q. et al., and entitled Arrdc1-mediated microvesicles (armors) and uses thereof the entire contents of which are incorporated herein by reference. The ARRDC1/TSG101 interaction results in relocation of TSG101 from endosomes to the plasma membrane and mediates the release of microvesicles that contain TSG101, ARRDC1, and other cellular components.

Non-naturally occurring cargo proteins including, for example, Cas9 and Cas9 variants can be modified to associate with TSG101 or ARRDC1, facilitating their incorporation in ARMMs, which in turn can be used to deliver the cargo proteins into target cells. As one example, a cargo protein can be fused to one or more WW domains, which associate with the PPXY (SEQ ID NO: 75) motif of ARRDC1. This association facilitates loading of the cargo protein into the ARRDC1-containing ARMM. Alternatively, the cargo protein, for example a Cas9 protein or Cas9 variant, can be fused to an ARMM protein (e.g., TSG101 or ARRDC1) to load the Cas9 protein or Cas9 variant in an ARMM. The cargo protein can be fused to the ARMM protein (e.g., TSG101 or ARRDC1) via a linker that may be cleaved upon delivery in a target cell.

In some aspects of this invention, ARMMs containing a cargo protein fused to at least one WW domain are provided. In other aspects, ARMMs containing a Cas9 protein or Cas9 variant fused to an ARRDC1 protein, or variant thereof, or a TSG101 protein, or variant thereof, are provided. Such ARMMs may be derived from a subject, a biological sample, or a cell culture, or ARMMs may be prepared synthetically. Methods for generating and/or isolating ARMMs, including ARMMs that include cargo proteins to be delivered to a target cell or target cell population, are also provided herein. Methods for the use of ARMMs to deliver a cargo protein, for example, a Cas9 protein or Cas9 variant fused to at least one WW domain, to a target cell in vitro, in vivo, and ex vivo are also provided.

Some aspects of this invention include arrestin domain-containing protein 1 (ARRDC1)-mediated microvesicles (ARMMs) that comprise a lipid bilayer, an ARRDC1 protein, or variant thereof, and a cargo protein, wherein the cargo protein is fused to at least one WW domain or variant thereof. The microvesicle's cargo protein may be fused to multiple WW domains, for example two, three, four or five WW domains. The WW domain may be derived from any WW domain known in the art. For example, the WW domain may be from the ubiquitin ligase WWP1, WWP2, Nedd4-1, Nedd4-2, Smurf1, Smurf2, ITCH, NEDL1 or NEDL2. In certain embodiments, the microvesicle's cargo protein is a Cas9 protein or a Cas9 variant. The Cas9 protein or Cas9 variant may have one or more nuclear localization sequences (NLSs) to facilitate translocation into the nucleus of a target cell. In other embodiments, the microvesicle further comprises a guide RNA (gRNA). The gRNA may be expressed in an ARMM producing cell and load in an ARMM by associating with an RNA-guided nuclease (e.g., Cas9) or a variant of an RNA-guided nuclease fused to one or more WW domains. The gRNA may also be loaded in an ARMM by associating with an RNA-guided nuclease (e.g., Cas9) or a variant of an RNA-guided nuclease that is fused to an ARMM protein (e.g., TSG101 or ARRDC1).

Another aspect of this invention includes arrestin domain-containing protein 1 (ARRDC1)-mediated microvesicles (ARMMs) that comprise a lipid bilayer and an ARRDC1 protein or variant thereof, a Cas9 cargo protein or Cas9 variant, and/or a TSG101 protein or variant thereof. In certain embodiments, the Cas9 cargo protein or variant is linked to the TSG101 protein or variant thereof that contains a UEV domain. In other embodiments, the Cas9 cargo protein or variant is linked to the ARRDC1 protein or variant thereof. The Cas9 protein, or variant thereof, may be linked to ARRDC1 or TSG101, or variants thereof, by a linker. The linker could be a covalent bond or another linker, such as a cleavable linker. As an example, the linker may be protein linker engineered to have a protease recognition site or a UV-cleavable moiety. The cleavable linker may be cleaved in a target cell to release the cargo protein into the cytoplasm of the target cell.

Some aspects of this invention provide fusion proteins that can be loaded in an ARMM. For example, the fusion protein may be a Cas9 protein or a Cas9 variant fused to an ARRDC1 protein, or variant thereof, or a TSG101 protein, or variant thereof. Alternatively, the fusion protein may be a cargo protein (e.g., a Cas9 protein or Cas9 variant) fused to one or more WW domains. In order to facilitate translocation into the nucleus, a Cas9 fusion protein may comprise a nuclear localization sequence (NLS). An additional aspect of the invention provides nucleic acid constructs encoding any of the fusion proteins, or any associated gRNAs, described herein.

Some aspects of this invention provide microvesicle-producing cells containing recombinant expression constructs that encode any of the cargo proteins, described herein. For example, the microvesicle-producing cells may contain an expression construct encoding an ARRDC1 protein, or a variant thereof, under the control of a heterologous promoter, and a recombinant expression construct encoding a cargo protein under the control of a heterologous promoter, where the cargo protein is fused to at least one WW domain or variant thereof. Other aspects of this invention include microvesicle-producing cells containing recombinant expression constructs encoding an ARRDC1 protein or a variant thereof fused to a Cas9 cargo protein or variant thereof. In certain embodiments, the microvesicle-producing cells contain a recombinant expression vector encoding a TSG101 protein or variant thereof fused to a cas9 cargo protein or variant thereof. The microvesicle-producing cells may also contain expression constructs that encode one or more gRNAs which can associate with any of the RNA-guided nucleases, described herein. The microvesicle-producing cells, described herein, may be capable of producing an ARMM.

Various other aspects of this invention provide methods of delivering a cargo protein to a target cell by contacting the target cell with a microvesicle (e.g., an ARMM), which may be done by contacting the target cell with an isolated ARMM or co-culturing the target cell with a cell that produces an ARMM. The target cell may be contacted with an ARMM in vitro, in vivo, or ex vivo. In some embodiments, the target cell is a cell in a subject and the method comprises administering the microvesicle or the microvesicle-producing cell to the subject. The microvesicle may be linked to a targeting moiety, such as a membrane-bound immunoglobulin, that selectively binds an antigen, for example, a surface antigen of the target cell.

Other aspects of this invention provide methods of gene editing and methods of altering expression of at least one gene, comprising contacting the target cell with any of the ARMMs, or an ARMM producing cells, described herein. As one example, a Cas9 cargo protein may be delivered to a target cell, via an ARMM, to correct a genetic mutation in that cell. As another example, a nuclease inactive Cas9 variant fused to a transcriptional activator (e.g., VP64) may be delivered to a target cell, via an ARMM, to increase the expression of a gene of interest.

Other advantages, features, and uses of the invention will be apparent from the detailed description of certain exemplary, non-limiting embodiments; the drawings; the non-limiting working examples; and the claims.

DEFINITIONS

Figure 1:
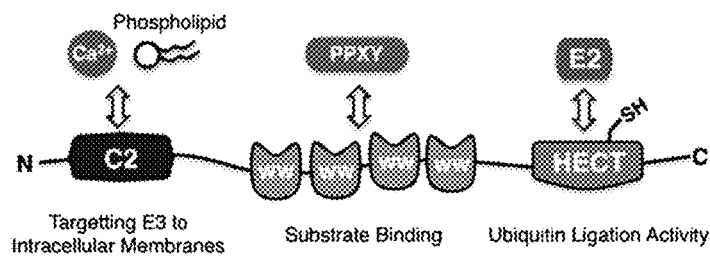
FIG. 1 is a schematic of a ubiquitin ligase protein (top) showing the conserved protein domains including the phospholipid binding C2 domain, four WW domains that bind PPXY (SEQ ID NO: 75) motifs, and the HECT ubiquitin ligase domain. Exemplary ubiquitin ligases (bottom) include Nedd4-1, Nedd4-2, WWP1, WWP2, Smurf1, Smurf2, ITCH, NEDL1, and NEDL2.
Figure 1:
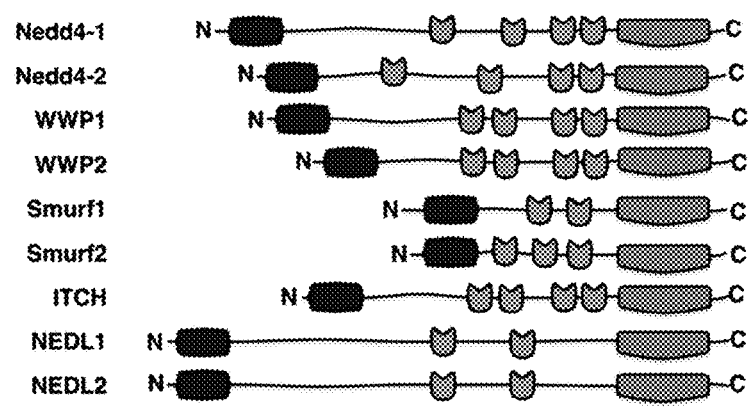

The term "ARMM," as used herein, refers to a microvesicle comprising an ARRDC1 protein or variant thereof, and/or TSG101 protein or variant thereof. In some embodiments, the ARMM is shed from a cell, and comprises a molecule, for example, a nucleic acid, protein, or small molecule, present in the cytoplasm or associated with the membrane of the cell. In some embodiments, the ARMM is shed from a transgenic cell comprising a recombinant expression construct that includes the transgene, and the ARMM comprises a gene product, for example, a transcript or a protein (e.g., a cargo protein) encoded by the expression construct. In some embodiments, the protein encoded by the expression construct is a Cas9 cargo protein fused to at least one WW domain, or variant thereof, which may associate with the ARRDC1 protein to facilitate loading of the Cas9 cargo protein into the ARMM. In some embodiments, the ARMM is produced synthetically, for example, by contacting a lipid bilayer within ARRDC1 protein, or variant thereof, in a cell-free system in the presence of TSG101, or a variant thereof. In other embodiments, the ARMM is synthetically produced by further contacting a lipid bilayer with HECT domain ligase, and VPS4a. In some embodiments, an ARMM lacks a late endosomal marker. Some ARMMs as provided herein do not include, or are negative for, one or more exosomal biomarker. Exosomal biomarkers are known to those of skill in the art and include, but are not limited to, CD63, Lamp-1, Lamp-2, CD9, HSPA8, GAPDH, CD81, SDCBP, PDCD6IP, ENO1, ANXA2, ACTB, YWHAZ, HSP90AA1, ANXA5, EEF1A1, YWHAE, PPIA, MSN, CFL1, ALDOA, PGK1, EEF2, ANXA1, PKM2, HLA-DRA, and YWHAB. For example, some ARMMs provided herein lack CD63, some ARMMs lack LAMP1, some ARMMs lack CD9, some ARMMs lack CD81, some ARMMs lack CD63 and Lamp-1, some ARMMs lack CD63, Lamp-1, and CD9, some ARMMs lack CD63, Lamp-1, CD81, and CD9, and so forth. Certain ARMMs provided herein may include an exosomal biomarker. Accordingly, some ARMMs may be negative for one or more exosomal biomarker, but positive for one or more different exosomal biomarker. For example, such an ARMM may be negative for CD63 and Lamp-1, but may include PGK1 or GAPDH; or may be negative for CD63, Lamp-1, CD9, and CD81, but may be positive for HLA-DRA. In some embodiments, ARMMs include an exosomal biomarker, but at a lower level than a level found in exosomes. For example, some ARMMs include one or more exosomal biomarkers at a level of less than about 1%, less than about 5%, less than about 10%, less than about 20%, less than about 30%, less than about 40%, or less than about 50% of the level of that biomarker found in exosomes. To give a non-limiting example, in some embodiments, an ARMM may be negative for CD63 and Lamp-1, include CD9 at a level of less than about 5% of the level of CD9 typically found in exosomes, and be positive for ACTB. Exosomal biomarkers in addition to those listed above are known to those of skill in the art, and the invention is not limited in this regard.

Cargo protein: The term "cargo protein", as used herein, refers to a protein that may be incorporated in an ARMM, for example, into the liquid phase of the ARMM or into the lipid bilayer of an ARMM. The term "cargo protein to be delivered" refers to any protein that can be delivered via its association with or inclusion in an ARMM to a subject, organ, tissue, or cell. In some embodiments, the cargo protein is to be delivered to a target cell in vitro, in vivo, or ex vivo. In some embodiments, the cargo protein to be delivered is a biologically active agent, i.e., it has activity in a cell, organ, tissue, and/or subject. For instance, a protein that, when administered to a subject, has a biological effect on that subject, is considered to be biologically active. In certain embodiments the cargo protein is a nuclease or variant thereof (e.g., a Cas9 protein or variant thereof). In certain embodiments, the nuclease may be a Cas9 nuclease, a TALE nuclease, a zinc finger nuclease, or any variant thereof. Nucleases, including Cas9 proteins and their variants, are described in more detail elsewhere herein. In some embodiments, the Cas9 protein or variant thereof is associated with a nucleic acid. For example, the cargo protein may be a Cas9 protein associated with a gRNA. In some embodiments, a cargo protein to be delivered is a therapeutic agent. As used herein, the term "therapeutic agent" refers to any agent that, when administered to a subject, has a beneficial effect. In some embodiments, the cargo protein to be delivered to a cell is a transcription factor, a tumor suppressor, a developmental regulator, a growth factor, a metastasis suppressor, a pro-apoptotic protein, a nuclease, or a recombinase. In some embodiments, the protein to be delivered is p53, Rb (retinoblastoma protein), BRCA1, BRCA2, PTEN, APC, CD95, ST7, ST14, a BCL-2 family protein, a caspase; BRMS1, CRSP3, DRG1, KAI1, KISS1, NM23, a TIMP-family protein, a BMP-family growth factor, EGF, EPO, FGF, G-CSF, GM-CSF, a GDF-family growth factor, HGF, HDGF, IGF, PDGF, TPO, TGF-α, TGF-β, VEGF; a zinc finger nuclease, Cre, Dre, or FLP recombinase. In some embodiments, the cargo protein is associated with a small molecule. In some embodiments, the cargo protein to be delivered is a diagnostic agent. In some embodiments, the cargo protein to be delivered is a prophylactic agent. In some embodiments, the cargo protein to be delivered is useful as an imaging agent. In some of these embodiments, the diagnostic or imaging agent is, and in others it is not, biologically active.

The term "linker," as used herein, refers to a chemical moiety linking two molecules or moieties, e.g., an ARRDC1 protein and a Cas9 nuclease. Typically, the linker is positioned between, or flanked by, two groups, molecules, or other moieties and connected to each one via a covalent bond, thus connecting the two. In some embodiments, the linker comprises an amino acid or a plurality of amino acids (e.g., a peptide or protein). In some embodiments, the linker is an organic molecule, group, polymer, or other chemical moiety. In some embodiments, the linker is a cleavable linker, e.g., the linker comprises a bond that can be cleaved upon exposure to, for example, UV light or a hydrolytic enzyme, such as a lysosomal protease. In some embodiments, the linker is any stretch of amino acids having at least 1, at least 2, at least 3, at least 4, at least 5, at least 6, at least 7, at least 8, at least 9, at least 10, at least 15, at least 20, at least 25, at least 30, at least 40, at least 50, or more amino acids. In other embodiments, the linker is a chemical bond (e.g., a covalent bond).

Animal: As used herein, the term "animal" refers to any member of the animal kingdom. In some embodiments, the term "animal" refers to a human of either sex at any stage of development. In some embodiments, the term "animal" refers to a non-human animal at any stage of development. In certain embodiments, the non-human animal is a mammal (e.g., a rodent, a mouse, a rat, a rabbit, a monkey, a dog, a cat, a sheep, cattle, a primate, or a pig). Animals include, but are not limited to, mammals, birds, reptiles, amphibians, fish, and worms. In some embodiments, the animal is a transgenic animal, genetically-engineered animal, or a clone. In some embodiments, the animal is a transgenic non-human animal, genetically-engineered non-human animal, or a non-human clone.

Approximately: As used herein, the term "approximately" or "about," as applied to one or more values of interest, refers to a value that is similar to a stated reference value. In certain embodiments, the term "approximately" or "about" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (for example, when such number would exceed 100% of a possible value).

Associated with: As used herein, the term "associated with," when used with respect to two or more entities, for example, with chemical moieties, molecules, and/or ARMMs, means that the entities are physically associated or connected with one another, either directly or via one or more additional moieties that serves as a linker, to form a structure that is sufficiently stable so that the entities remain physically associated under the conditions in which the structure is used, e.g., physiological conditions. An ARMM is typically associated with an agent, for example, a nucleic acid, protein, or small molecule, by a mechanism that involves a covalent or non-covalent association. In certain embodiments, the agent to be delivered is covalently bound to a molecule that is part of the ARMM, for example, an ARRCD1 protein or variant thereof, a TSG101 protein or variant thereof, or a lipid or protein that forms part of the lipid bilayer of the ARMM. In some embodiments, a peptide or protein is associated with an ARRCD1 protein or variant thereof, a TSG101 protein or variant thereof, or a lipid bilayer-associated protein by a covalent bond (e.g., an amide bond). In some embodiments, the association is via a linker, for example, a cleavable linker. In some embodiments, an entity is associated with an ARMM by inclusion in the ARMM, for example, by encapsulation of an entity (e.g., a protein) within the ARMM. For example, in some embodiments, an agent present in the cytoplasm of an ARMM-producing cell is associated with an ARMM by encapsulation of the cytoplasm with the agent in the ARMM upon ARMM budding. Similarly, a membrane protein or other molecule associated with the cell membrane of an ARMM producing cell may be associated with an ARMM produced by the cell by inclusion into the ARMM's membrane upon budding.

Biologically active: As used herein, the phrase "biologically active" refers to a characteristic of any substance that has activity in a cell, organ, tissue and/or subject. For instance, a substance that, when administered to an organism, has a biological effect on that organism, is considered to be biologically active. As one example, a nuclease cargo protein may be considered biologically active if it increases or decreases the expression of a gene product when administered to a subject.

Conserved: As used herein, the term "conserved" refers to nucleotides or amino acid residues of a polynucleotide sequence or amino acid sequence, respectively, that are those that occur unaltered in the same position of two or more related sequences being compared. Nucleotides or amino acids that are relatively conserved are those that are conserved amongst more related sequences than nucleotides or amino acids appearing elsewhere in the sequences. In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95% identical, about 98% identical, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another.

The term "engineered," as used herein refers to a protein, nucleic acid, complex, substance, or entity that has been designed, produced, prepared, synthesized, and/or manufactured by a human. Accordingly, an engineered product is a product that does not occur in nature. In some embodiments, an engineered protein or nucleic acid is a protein or nucleic acid that has been designed to meet particular requirements or to have particular design features. For example, a Cas9 cargo protein may be engineered to associate with the ARRDC1 by fusing one or more WW domains to the Cas9 protein to facilitate loading of the Cas9 cargo protein into an ARMM. As another example, a guide RNA (gRNA) may be engineered to target the delivery of a Cas9 cargo protein to a specific genomic sequence.

Expression: As used herein, "expression" of a nucleic acid sequence refers to one or more of the following events: (1) production of an RNA transcript from a DNA sequence (e.g., by transcription); (2) processing of an RNA transcript (e.g., by splicing, editing, 5'cap formation, and/or 3' end processing); (3) translation of an RNA transcript into a polypeptide or protein; and (4) post-translational modification of a polypeptide or protein.

Fusion protein: As used herein, a "fusion protein" includes a first protein moiety, e.g., an ARRCD1 protein or variant thereof, or a TSG101 protein or variant thereof, associated with a second protein moiety, for example, a cargo protein to be delivered to a target cell through a peptide linkage. In certain embodiments, the fusion protein is encoded by a single fusion gene.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as gRNAs, RNAi agents, ribozymes, tRNAs, etc. For the purpose of clarity it should be noted that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Green fluorescent protein: As used herein, the term "green fluorescent protein" (GFP) refers to a protein originally isolated from the jellyfish *Aequorea victoria* that fluoresces green when exposed to blue light or a derivative of such a protein (e.g., an enhanced or wavelength-shifted version of the protein). The amino acid sequence of wild type GFP is as follows:

```
                                           (SEQ ID NO: 35)
MSKGEELFTG VVPILVELDG DVNGHKFSVS GEGEGDATYG

KLTLKFICTT GKLPVPWPTL VTTFSYGVQC FSRYPDHMKQ

HDFFKSAMPE GYVQERTIFF KDDGNYKTRA EVKFEGDTLV

NRIELKGIDF KEDGNILGHK LEYNYNSHNV YIMADKQKNG

IKVNFKIRHN IEDGSVQLAD HYQQNTPIGD GPVLLPDNHY

LSTQSALSKD PNEKRDHMVL LEFVTAAGIT HGMDELYK
```

Proteins that are at least 70%, at least 75%, at least 80%, at least 85%, at least 90%, at least 95%, at least 98%, or at least 99% homologous are also considered to be green fluorescent proteins.

Homology: As used herein, the term "homology" refers to the overall relatedness between nucleic acids (e.g. DNA molecules and/or RNA molecules) or polypeptides. In some embodiments, nucleic acids or proteins are considered to be "homologous" to one another if their sequences are at least 50%, at least 55%, at least 60%, at least 65%, at least 70%, at least 75%, at least 80%, at least 85%, at least 90%, at least 95%, or at least 99% identical. In some embodiments, nucleic acids or proteins are considered to be "homologous" to one another if their sequences are at least 50%, at least 55%, at least 60%, at least 65%, at least 70%, at least 75%, at least 80%, at least 85%, at least 90%, at least 95%, or at least 99% similar. The term "homologous" necessarily refers to a comparison between at least two sequences (nucleotide sequences or amino acid sequences). In accordance with the invention, two nucleotide sequences are considered to be homologous if the polypeptides they encode are at least about 50% identical, at least about 60% identical, at least about 70% identical, at least about 80% identical, or at least about 90% identical for at least one stretch of at least about 20 amino acids. In some embodiments, homologous nucleotide sequences are characterized by the ability to encode a stretch of at least 4-5 uniquely specified amino acids. Both the identity and the approximate spacing of these amino acids relative to one another must be considered for sequences to be considered homologous. For nucleotide sequences less than 60 nucleotides in length, homology is determined by the ability to encode a stretch of at least 4-5 uniquely specified amino acids. In accordance with the invention, two protein sequences are considered to be homologous if the proteins are at least about 50% identical, at least about 60% identical, at least about 70% identical, at least about 80% identical, or at least about 90% identical for at least one stretch of at least about 20 amino acids.

Identity: As used herein, the term "identity" refers to the overall relatedness between nucleic acids or proteins (e.g. DNA molecules, RNA molecules, and/or polypeptides). Calculation of the percent identity of two nucleic acid sequences, for example, can be performed by aligning the two sequences for optimal comparison purposes (e.g., gaps can be introduced in one or both of a first and second nucleic acid sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Sequence Analysis in Molecular Biology*, von Heinje, G., Academic Press, 1987; *Computer Analysis of Sequence Data, Part I*, Griffin, A. M., and Griffin, H. G., eds., Humana Press, New Jersey, 1994; and *Sequence Analysis Primer*, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., *SIAM J Applied Math.*, 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research*, 12(1), 387 (1984)), BLASTP, BLASTN, and FASTA Atschul, S. F. et al., *J. Molec. Biol.*, 215, 403 (1990)).

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe).

Isolated: As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Nucleic acid: As used herein, the term "nucleic acid," in its broadest sense, refers to a compound and/or substance that is or can be incorporated into an oligonucleotide chain via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably to refer to a polymer of nucleotides (e.g., a string of at least two nucleotides). In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, at least 4, at least 5, at least 6, at least 7, at least 8, at least 9, at least 10, or more residues. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g. polynucleotides and residues, including nucleotides and/or nucleosides) that have not been chemically modified in order to facilitate or achieve delivery.

Protein: As used herein, the term "protein," refers to a string of at least two amino acids linked to one another by one or more peptide bonds. Proteins may include moieties other than amino acids (e.g., may be glycoproteins) and/or may be otherwise processed or modified. Those of ordinary skill in the art will appreciate that a "protein" can be a complete protein chain as produced by a cell (with or without a signal sequence), or can be a functional portion thereof. Those of ordinary skill will further appreciate that a protein can sometimes include more than one protein chain, for example linked by one or more disulfide bonds or associated by other means. Proteins may contain L-amino acids, D-amino acids, or both and may contain any of a variety of amino acid modifications or analogs known in the art. Useful modifications include, e.g., addition of a chemical entity such as a carbohydrate group, a phosphate group, a farnesyl group, an isofarnesyl group, a fatty acid group, an amide group, a terminal acetyl group, a linker for conjugation, functionalization, or other modification (e.g., alpha amidation), etc. In certain embodiments, the modifications of the protein lead to a more stable protein (e.g., greater half-life in vivo). These modifications may include cyclization of the protein, the incorporation of D-amino acids, etc. None of the modifications should substantially interfere with the desired biological activity of the protein. In certain embodiments, the modifications of the protein lead to a more biologically active protein. In some embodiments, proteins may comprise natural amino acids, non-natural amino acids, synthetic amino acids, amino acid analogs, and combinations thereof.

Reprogramming factor: As used herein, the term "reprogramming factor" refers to a factor that, alone or in combination with other factors, can change the state of a cell from a somatic, differentiated state into a pluripotent stem cell state. Non-limiting examples of reprogramming factors include a protein (e.g., a transcription factor), a peptide, a nucleic acid, or a small molecule. Known reprogramming factors that are useful for cell reprogramming include, but are not limited to Oct4, Sox2, Klf4, and c-myc. Similarly, a programming factor may be used to modulate cell differentiation, for example, to facilitate or induce cell differentiation towards a desired lineage.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Therapeutically effective amount: As used herein, the term "therapeutically effective amount" means an amount of an agent to be delivered (e.g., nucleic acid, protein, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules. Examples of transcription factors include, but are not limited to, Sp1, NF1, CCAAT, GATA, HNF, PIT-1, MyoD, Myf5, Hox, Winged Helix, SREBP, p53, CREB, AP-1, Mef2, STAT, R-SMAD, NF-κB, Notch, TUBBY, and NFAT.

Treating: As used herein, the term "treating" refers to partially or completely preventing, and/or reducing incidence of one or more symptoms or features of a particular disease or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, or condition for the purpose of decreasing the risk of developing more severe effects associated with the disease, or condition.

Vector: As used herein, "vector" refers to a nucleic acid molecule which can transport another nucleic acid to which it has been linked. In some embodiment, vectors can achieve extra-chromosomal replication and/or expression of nucleic acids to which they are linked in a host cell such as a eukaryotic and/or prokaryotic cell. Vectors capable of directing the expression of operatively linked genes are referred to herein as "expression vectors."

The term "Cas9" or "Cas9 protein" refers to an RNA-guided nuclease comprising a Cas9 protein, or a variant thereof (e.g., a protein comprising an active, inactive, or altered DNA cleavage domain of Cas9, and/or the gRNA binding domain of Cas9). A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (mc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA into a single RNA species. See, e.g., Jinek M., Chylinski K., Fonfara I., Hauer M., Doudna J. A., Charpentier E. *Science* 337:816-821 (2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain.

A nuclease-inactivated Cas9 protein may interchangeably be referred to as a "dCas9" protein (for nuclease-"dead" Cas9). Methods for generating a Cas9 protein (or a variant thereof) having an inactive DNA cleavage domain are known (See, e.g., Jinek et al., *Science*. 337:816-821(2012); Qi et al., "Repurposing CRISPR as an RNA-Guided Platform for Sequence-Specific Control of Gene Expression" (2013) *Cell*. 28; 152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H841A completely inactivate the nuclease activity of *S. pyogenes* Cas9 (Jinek et al., *Science*. 337:816-821(2012); Qi et al., *Cell*. 28; 152(5):1173-83 (2013). In some embodiments, proteins comprising variants of Cas9 are provided. For example, in some embodiments, a protein comprises one of two Cas9 domains: (1) the gRNA binding domain of Cas9; or (2) the DNA cleavage domain of Cas9. In some embodiments, proteins comprising Cas9 or variants thereof are referred to as "Cas9 variants." A Cas9 variant shares homology to Cas9, or a variant thereof. For example a Cas9 variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to wild type Cas9. In some embodiments, the Cas9 variant comprises a variant of Cas9 (e.g., a gRNA binding domain or a DNA-cleavage domain), such that the variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to the corresponding variant of wild type Cas9. In some embodiments, wild type Cas9 corresponds to Cas9 from *Streptococcus pyogenes* (NCBI Reference Sequence: NC_017053.1, SEQ ID NO:1 (nucleotide); SEQ ID NO:2 (amino acid)).

```
                                              (SEQ ID NO: 1)
ATGGATAAGAAATACTCAATAGGCTTAGATATCGGCACAAATAGCGTCG

GATGGGCGGTGATCACTGATGATTATAAGGTTCCGTCTAAAAAGTTCAA

GGTTCTGGGAAATACAGACCGCCACAGTATCAAAAAAAATCTTATAGGG

GCTCTTTTATTTGGCAGTGGAGAGACAGCGGAAGCGACTCGTCTCAAAC

GGACAGCTCGTAGAAGGTATACACGTCGGAAGAATCGTATTTGTTATCT
```

```
                        -continued
ACAGGAGATTTTTTCAAATGAGATGGCGAAAGTAGATGATAGTTTCTTT

CATCGACTTGAAGAGTCTTTTTTGGTGGAAGAAGACAAGAAGCATGAAC

GTCATCCTATTTTTGGAAATATAGTAGATGAAGTTGCTTATCATGAGAA

ATATCCAACTATCTATCATCTGCGAAAAAAATTGGCAGATTCTACTGAT

AAAGCGGATTTGCGCTTAATCTATTTGGCCTTAGCGCATATGATTAAGT

TTCGTGGTCATTTTTTGATTGAGGGAGATTTAAATCCTGATAATAGTGA

TGTGGACAAACTATTTATCCAGTTGGTACAAATCTACAATCAATTATTT

GAAGAAACCCTATTAACGCAAGTAGAGTAGATGCTAAAGCGATTCTTT

CTGCACGATTGAGTAAATCAAGACGATTAGAAAATCTCATTGCTCAGCT

CCCCGGTGAGAAGAGAAATGGCTTGTTTGGGAATCTCATTGCTTTGTCA

TTGGGATTGACCCCTAATTTTAAATCAAATTTTGATTGGCAGAAGATG

CTAAATTACAGCTTTCAAAAGATACTTACGATGATGATTTAGATAATTT

ATTGGCGCAAATTGGAGATCAATATGCTGATTTGTTTTTGGCAGCTAAG

AATTTATCAGATGCTATTTTACTTTCAGATATCCTAAGAGTAAATAGTG

AAATAACTAAGGCTCCCCTATCAGCTTCAATGATTAAGCGCTACGATGA

ACATCATCAAGACTTGACTCTTTTAAAAGCTTTAGTTCGACAACAACTT

CCAGAAAAGTATAAAGAAATCTTTTTTGATCAATCAAAAAACGGATATG

CAGGTTATATTGATGGGGAGCTAGCCAAGAAGAATTTTATAAATTTAT

CAAACCAATTTTAGAAAAAATGGATGGTACTGAGGAATTATTGGTGAAA

CTAAATCGTGAAGATTTGCTGCGCAAGCAACGGACCTTTGACAACGGCT

CTATTCCCCATCAAATTCACTTGGGTGAGCTGCATGCTATTTTGAGAAG

ACAAGAAGACTTTTATCCATTTTTAAAAGACAATCGTGAGAAGATTGAA

AAAATCTTGACTTTTCGAATTCCTTATTATGTTGGTCCATTGGCGCGTG

GCAATAGTCGTTTTGCATGGATGACTCGGAAGTCTGAAGAAACAATTAC

CCCATGGAATTTTGAAGAAGTTGTCGATAAAGGTGCTTCAGCTCAATCA

TTTATTGAACGCATGACAAACTTTGATAAAAATCTTCCAAATGAAAAG

TACTACCAAAACATAGTTTGCTTTATGAGTATTTTACGGTTTATAACGA

ATTGACAAAGGTCAAATATGTTACTGAGGGAATGCGAAAACCAGCATTT

CTTTCAGGTGAACAGAAGAAAGCCATTGTTGATTTACTCTTCAAAACAA

ATCGAAAAGTAACCGTTAAGCAATTAAAAGAAGATTATTTCAAAAAAAT

AGAATGTTTTGATAGTGTTGAAATTTCAGGAGTTGAAGATAGATTTAAT

GCTTCATTAGGCGCCTACCATGATTTGCTAAAAATTATTAAAGATAAAG

ATTTTTTGGATAATGAAGAAAATGAAGATATCTTAGAGGATATTGTTTT

AACATTGACCTTATTTGAAGATAGGGGGATGATTGAGGAAAGACTTAAA

ACATATGCTCACCTCTTTGATGATAAGGTGATGAAACAGCTTAAACGTC

GCCGTTATACTGGTTGGGGACGTTTGTCTCGAAAATTGATTAATGGTAT

TAGGGATAAGCAATCTGGCAAAACAATATTAGATTTTTTGAAATCAGAT

GGTTTTGCCAATCGCAATTTTATGCAGCTGATCCATGATGATAGTTTGA

CATTTAAAGAAGATATTCAAAAAGCACAGGTGTCTGGACAAGGCCATAG

TTTACATGAACAGATTGCTAACTTAGCTGGCAGTCCTGCTATTAAAAAA

GGTATTTTACAGACTGTAAAAATTGTTGATGAACTGGTCAAAGTAATGG
```

-continued

```
GGCATAAGCCAGAAAATATCGTTATTGAAATGGCACGTGAAAATCAGAC
AACTCAAAAGGGCCAGAAAAATTCGCGAGAGCGTATGAAACGAATCGAA
GAAGGTATCAAAGAATTAGGAAGTCAGATTCTTAAAGAGCATCCTGTTG
AAAATACTCAATTGCAAATGAAAAGCTCTATCTCTATTATCTACAAAA
TGGAAGAGACATGTATGTGGACCAAGAATTAGATATTAATCGTTTAAGT
GATTATGATGTCGATCACATTGTTCCACAAAGTTTCATTAAAGACGATT
CAATAGACAATAAGGTACTAACGCGTTCTGATAAAAATCGTGGTAAATC
GGATAACGTTCCAAGTGAAGAAGTAGTCAAAAAGATGAAAAACTATTGG
AGACAACTTCTAAACGCCAAGTTAATCACTCAACGTAAGTTTGATAATT
TAACGAAAGCTGAACGTGGAGGTTTGAGTGAACTTGATAAAGCTGGTTT
TATCAAACGCCAATTGGTTGAAACTCGCCAAATCACTAAGCATGTGGCA
CAAATTTTGGATAGTCGCATGAATACTAAATACGATGAAAATGATAAAC
TTATTCGAGAGGTTAAAGTGATTACCTTAAAATCTAAATTAGTTTCTGA
CTTCCGAAAAGATTTCCAATTCTATAAAGTACGTGAGATTAACAATTAC
CATCATGCCCATGATGCGTATCTAAATGCCGTCGTTGGAACTGCTTTGA
TTAAGAAATATCCAAAACTTGAATCGGAGTTTGTCTATGGTGATTATAA
AGTTTATGATGTTCGTAAAATGATTGCTAAGTCTGAGCAAGAAATAGGC
AAAGCAACCGCAAAATATTTCTTTTACTCTAATATCATGAACTTCTTCA
AAACAGAAATTACACTTGCAAATGGAGAGATTCGCAAACGCCCTCTAAT
CGAAACTAATGGGGAAACTGGAGAAATTGTCTGGGATAAAGGGCGAGAT
TTTGCCACAGTGCGCAAAGTATTGTCCATGCCCCAAGTCAATATTGTCA
AGAAAACAGAAGTACAGACAGGCGGATTCTCCAAGGAGTCAATTTTACC
AAAAAGAAATTCGGACAAGCTTATTGCTCGTAAAAAGACTGGGATCCA
AAAAAATATGGTGGTTTTGATAGTCCAACGGTAGCTTATTCAGTCCTAG
TGGTTGCTAAGGTGGAAAAAGGGAAATCGAAGAAGTTAAAATCCGTTAA
AGAGTTACTAGGGATCACAATTATGGAAAGAAGTTCCTTTGAAAAAAAT
CCGATTGACTTTTTAGAAGCTAAAGGATATAAGGAAGTTAAAAAAGACT
TAATCATTAAACTACCTAAATATAGTCTTTTTGAGTTAGAAAACGGTCG
TAAACGGATGCTGGCTAGTGCCGGAGAATTACAAAAAGGAAATGAGCTG
GCTCTGCCAAGCAAATATGTGAATTTTTTATATTTAGCTAGTCATTATG
AAAAGTTGAAGGGTAGTCCAGAAGATAACGAACAAAAACAATTGTTTGT
GGAGCAGCATAAGCATTATTTAGATGAGATTATTGAGCAAATCAGTGAA
TTTTCTAAGCGTGTTATTTTAGCAGATGCCAATTTAGATAAAGTTCTTA
GTGCATATAACAAACATAGAGACAAACCAATACGTGAACAAGCAGAAAA
TATTATTCATTTATTTACGTTGACGAATCTTGGAGCTCCCGCTGCTTTT
AAATATTTTGATACAACAATTGATCGTAAACGATATACGTCTACAAAAG
AAGTTTTAGATGCCACTCTTATCCATCAATCCATCACTGGTCTTTATGA
AACACGCATTGATTTGAGTCAGCTAGGAGGTGACTGA
```

(SEQ ID NO: 2)
MDKK<u>YSIGLDIGTNSVGWAVITDDYKVPSKKFKVLGNTDRHSIKKNLI</u>

<u>GALLFGSGET</u>AEATRLKRTARRRYTRRKNRICYLQEIFSNEMAKVDDS

FFHRLEESFLVEEDKKHERHPIFGNIVDEVAYHEKYPTIYHLRKKLAD

STDKADLRLIYLALAHMIKFRGHFLIEGDLNPDNSDVDKLFIQLVQIY

NQLFEENPINASRVDAKAILSARLSKSRRLENLIAQLPGEKRNGLFGN

LIALSLGLTPNFKSNFDLAEDAKLQLSKDTYDDDLDNLLAQIGDQYAD

LFLAAKNLSDAILLSDILRVNSEITKAPLSASMIKRYDEHHQDLTLLK

ALVRQQLPEKYKEIFFDQSKNGYAGYIDGGASQEEFYKFIKPILEKMD

GTEELLVKLNREDLLRKQRTFDNGSIPHQIHLGELHAILRRQEDFYPF

LKDNREKIEKILTFRIPYYVGPLARGNSRFAWMTRKSEETITPWNFEE

VVDKGASAQSFIERMTNFDKNLPNEKVLPKHSLLYEYFTVYNELTKVK

YVTEGMRKPAFLSGEQKKAIVDLLFKTNRKVTVKQLKEDYFKKIECFD

SVEISGVEDRFNASLGAYHDLLKIIKDKDFLDNEENEDILEDIVLTLT

LFEDRGMIEERLKTYAHLFDDKVMKQLKRRRYTGWGRLSRKLINGIRD

KQSGKTILDFLKSDGFANRNFMQLIHDDSLTFKEDIQKAQVSGQG<u>HSL</u>

<u>HEQIANLAGSPAIKKGILQTVKIVDELVKVMGHKPENIVIEMARENQTT</u>

<u>QKGQKNSRERMKRIEEGIKELGSQILKEHPVENTQLQNEKLYLYYLQN</u>

<u>GRDMYVDQELDINRLSDYDVDHIVPQSFIKDDSIDNKVLTRSDKNRGK</u>

<u>SDNVPSEEVVKKMKNYWRQLLNAKLITQRKFDNLTKAERG</u>==GLSELDKA==

==GFIKRQLVETRQITKHVAQILDSRMNTKYDENDKLIREVKVITLKSKL==

==VSDFRKDFQFYKVREINNYHHAHDAYLNAVVGTALIKKYPKLESEFVY==

==GDYKVYDVRKMIAKSEQEIGKATAKYFFYSNIMNFFKTEITLANGEIR==

==KRPLIETNGETGEIVWDKGRDFATVRKVLSMPQVNIVKKTEVQTGGFS==

KESILPKRNSDKLIARKKDWDPKKYGGFDSPTVAYSVLVVAKVEKGKS

KKLKSVKELLGITIMERSSFEKNPIDFLEAKGYKEVKKDLIIKLPKYS

LFELENGRKRMLASAGELQKGNELALPSKYVNFLYLASHYEKLKGSPE

DNEQKQLFVEQHKHYLDEIIEQISEFSKRVILADANLDKVLSAYNKHR

DKPIREQAENIIHLFTLTNLGAPAAFKYFDTTIDRKRYTSTKEVLDAT

LIHQSITGLYETRIDLSQLGGD (single underline: HNH domain; double underline: RuvC domain)

In some embodiments, wild type Cas9 corresponds to, or comprises SEQ ID NO:3 (nucleotide) and/or SEQ ID NO: 4 (amino acid):

```
                                                  (SEQ ID NO: 3)
ATGGATAAAAAGTATTCTATTGGTTTAGACATCGGCACTAATTCCGTTGG

ATGGGCTGTCATAACCGATGAATACAAAGTACCTTCAAAGAAATTTAAGG

TGTTGGGGAACACAGACCGTCATTCGATTAAAAAGAATCTTATCGGTGCC

CTCCTATTCGATAGTGGCGAAACGGCAGAGGCGACTCGCCTGAAACGAAC

CGCTCGGAGAAGGTATACACGTCGCAAGAACCGAATATGTTACTTACAAG

AAATTTTAGCAATGAGATGGCCAAAGTTGACGATTCTTCTTTCCACCGT

TTGGAAGAGTCCTTCCTTGTCGAAGAGGACAAGAAACATGAACGGCACCC

CATCTTTGGAAACATAGTAGATGAGGTGGCATATCATGAAAAGTACCCAA

CGATTTATCACCTCAGAAAAAAGCTAGTTGACTCAACTGATAAAGCGGAC
```

-continued

CTGAGGTTAATCTACTTGGCTCTTGCCCATATGATAAAGTTCCGTGGGCA

CTTTCTCATTGAGGGTGATCTAAATCCGGACAACTCGGATGTCGACAAAC

TGTTCATCCAGTTAGTACAAACCTATAATCAGTTGTTTGAAGAGAACCCT

ATAAATGCAAGTGGCGTGGATGCGAAGGCTATTCTTAGCGCCCGCCTCTC

TAAATCCCGACGGCTAGAAAACCTGATCGCACAATTACCCGGAGAGAAGA

AAAATGGGTTGTTCGGTAACCTTATAGCGCTCTCACTAGGCCTGACACCA

AATTTTAAGTCGAACTTCGACTTAGCTGAAGATGCCAAATTGCAGCTTAG

TAAGGACACGTACGATGACGATCTCGACAATCTACTGGCACAAATTGGAG

ATCAGTATGCGGACTTATTTTTGGCTGCCAAAAACCTTAGCGATGCAATC

CTCCTATCTGACATACTGAGAGTTAATACTGAGATTACCAAGGCGCCGTT

ATCCGCTTCAATGATCAAAAGGTACGATGAACATCACCAAGACTTGACAC

TTCTCAAGGCCCTAGTCCGTCAGCAACTGCCTGAGAAATATAAGGAAATA

TTCTTTGATCAGTCGAAAAACGGGTACGCAGGTTATATTGACGGCGGAGC

GAGTCAAGAGGAATTCTACAAGTTTATCAAACCCATATTAGAGAAGATGG

ATGGGACGGAAGAGTTGCTTGTAAAACTCAATCGCGAAGATCTACTGCGA

AAGCAGCGGACTTTCGACAACGGTAGCATTCCACATCAAATCCACTTAGG

CGAATTGCATGCTATACTTAGAAGGCAGGAGGATTTTTATCCGTTCCTCA

AAGACAATCGTGAAAGATTGAGAAAATCCTAACCTTTCGCATACCTTAC

TATGTGGGACCCCTGGCCCGAGGGAACTCTCGGTTCGCATGGATGACAAG

AAAGTCCGAAGAAACGATTACTCCATGGAATTTTGAGGAAGTTGTCGATA

AAGGTGCGTCAGCTCAATCGTTCATCGAGAGGATGACCAACTTTGACAAG

AATTTACCGAACGAAAAGTATTGCCTAAGCACAGTTTACTTTACGAGTA

TTTCACAGTGTACAATGAACTCACGAAAGTTAAGTATGTCACTGAGGGCA

TGCGTAAACCCGCCTTTCTAAGCGGAGAACAGAAGAAAGCAATAGTAGAT

CTGTTATTCAAGACCAACCGCAAAGTGACAGTTAAGCAATTGAAAGAGGA

CTACTTTAAGAAAATTGAATGCTTCGATTCTGTCGAGATCTCCGGGGTAG

AAGATCGATTTAATGCGTCACTTGGTACGTATCATGACCTCCTAAAGATA

ATTAAAGATAAGGACTTCCTGGATAACGAAGAGAATGAAGATATCTTAGA

AGATATAGTGTTGACTCTTACCCTCTTTGAAGATCGGGAAATGATTGAGG

AAAGACTAAAAACATACGCTCACCTGTTCGACGATAAGGTTATGAAACAG

TTAAAGAGGCGTCGCTATACGGGCTGGGGACGATTGTCGCGGAAACTTAT

CAACGGGATAAGAGACAAGCAAAGTGGTAAAACTATTCTCGATTTTCTAA

AGAGCGACGGCTTCGCCAATAGGAACTTTATGCAGCTGATCCATGATGAC

TCTTTAACCTTCAAAGAGGATATACAAAAGGCACAGGTTTCCGGACAAGG

GGACTCATTGCACGAACATATTGCGAATCTTGCTGGTTCGCCAGCCATCA

AAAAGGGCATACTCCAGACAGTCAAAGTAGTGGATGAGCTAGTTAAGGTC

ATGGGACGTCACAAACCGGAAAACATTGTAATCGAGATGGCACGCGAAAA

TCAAACGACTCAGAAGGGGCAAAAAAACAGTCGAGAGCGGATGAAGAGAA

TAGAAGAGGGTATTAAAGAACTGGCAGCCAGATCTTAAAGGAGCATCCT

GTGGAAAATACCCAATTGCAGAACGAGAAACTTTACCTCTATTACCTACA

-continued

AAATGGAAGGGACATGTATGTTGATCAGGAACTGGACATAAACCGTTTAT

CTGATTACGACGTCGATCACATTGTACCCCAATCCTTTTTGAAGGACGAT

TCAATCGACAATAAAGTGCTTACACGCTCGGATAAGAACCGAGGGAAAAG

TGACAATGTTCCAAGCGAGGAAGTCGTAAAGAAAATGAAGAACTATTGGC

GGCAGCTCCTAAATGCGAAACTGATAACGCAAAGAAAGTTCGATAACTTA

ACTAAAGCTGAGAGGGTGGCTTGTCTGAACTTGACAAGGCCGGATTTAT

TAAACGTCAGCTCGTGGAAACCCGCCAAATCACAAAGCATGTTGCACAGA

TACTAGATTCCCGAATGAATACGAAATACGACGAGAACGATAAGCTGATT

CGGGAAGTCAAAGTAATCACTTTAAAGTCAAAATTGGTGTCGGACTTCAG

AAAGGATTTTCAATTCTATAAAGTTAGGGAGATAAATAACTACCACCATG

CGCACGACGCTTATCTTAATGCCGTCGTAGGGACCGCACTCATTAAGAAA

TACCCGAAGCTAGAAAGTGAGTTTGTGTATGGTGATTACAAAGTTTATGA

CGTCCGTAAGATGATCGCGAAAAGCGAACAGGAGATAGGCAAGGCTACAG

CCAAATACTTCTTTTATTCTAACATTATGAATTTCTTTAAGACGGAAATC

ACTCTGGCAAACGGAGAGATACGCAAACGACCTTTAATTGAAACCAATGG

GGAGACAGGTGAAATCGTATGGGATAAGGGCCGGGACTTCGCGACGGTGA

GAAAAGTTTTGTCCATGCCCCAAGTCAACATAGTAAAGAAAACTGAGGTG

CAGACCGGAGGGTTTTCAAAGGAATCGATTCTTCCAAAAAGGAATAGTGA

TAAGCTCATCGCTCGTAAAAAGGACTGGGACCCGAAAAAGTACGGTGGCT

TCGATAGCCCTACAGTTGCCTATTCTGTCCTAGTAGTGGCAAAAGTTGAG

AAGGGAAAATCCAAGAAACTGAAGTCAGTCAAAGAATTATTGGGGATAAC

GATTATGGAGCGCTCGTCTTTTGAAAAGAACCCCATCGACTTCCTTGAGG

CGAAAGGTTACAAGGAAGTAAAAAAGGATCTCATAATTAAACTACCAAAG

TATAGTCTGTTTGAGTTAGAAAATGGCCGAAAACGGATGTTGGCTAGCGC

CGGAGAGCTTCAAAAGGGGAACGAACTCGCACTACCGTCTAAATACGTGA

ATTTCCTGTATTTAGCGTCCCATTACGAGAAGTTGAAAGGTTCACCTGAA

GATAACGAACAGAAGCAACTTTTTGTTGAGCAGCACAAACATTATCTCGA

CGAAATCATAGAGCAAATTTCGGAATTCAGTAAGAGAGTCATCCTAGCTG

ATGCCAATCTGGACAAAGTATTAAGCGCATACAACAAGCACAGGGATAAA

CCCATACGTGAGCAGGCGGAAAATATTATCCATTTGTTTACTCTTACCAA

CCTCGGCGCTCCAGCCGCATTCAAGTATTTTGACACAACGATAGATCGCA

AACGATACACTTCTACCAAGGAGGTGCTAGAGCGACACTGATTCACCAA

TCCATCACGGGATTATATGAAACTCGGATAGATTTGTCACAGCTTGGGGG

TGACGGATCCCCCAAGAAGAAGAGGAAAGTCTCGAGCGACTACAAAGACC

ATGACGGTGATTATAAAGATCATGACATCGATTACAAGGATGACGATGAC

AAGGCTGCAGGA (SEQ ID NO: 4)
MDKK<u>YSIGLAIGTNSVGWAVITDEYKVPSKKFKVLGNTDRHSIKKNLIGA
LLFDSGETA</u>EATRLKRTARRRYTRRKNRICYLQEIFSNEMAKVDDSFF

HRLEESFLVEEDKKHERHPIFGNIVDEVAYHEKYPTIYHLRKKLVDST

DKADLRLIYLALAHMIKFRGHFLIEGDLNPDNSDVDKLFIQLVQTYNQ

-continued
LFEENPINASGVDAKAILSARLSKSRRLENLIAQLPGEKKNGLFGNLI

ALSLGLTPNFKSNFDLAEDAKLQLSKDTYDDDLDNLLAQIGDQYADLF

LAAKNLSDAILLSDILRVNTEITKAPLSASMIKRYDEHHQDLTLLKAL

VRQQLPEKYKEIFFDQSKNGYAGYIDGGASQEEFYKFIKPILEKMDGT

EELLVKLNREDLLRKQRTFDNGSIPHQIHLGELHAILRRQEDFYPFLK

DNREKIEKILTFRIPYYVGPLARGNSRFAWMTRKSEETITPWNFEEVV

DKGASAQSFIERMTNFDKNLPNEKVLPKHSLLYEYFTVYNELTKVKYV

TEGMRKPAFLSGEQKKAIVDLLFKTNRKVTVKQLKEDYFKKIECFDSV

EISGVEDRFNASLGTYHDLLKIIKDKDFLDNEENEDILEDIVLTLTLF

EDREMIEERLKTYAHLFDDKVMKQLKRRRYTGWGRLSRKLINGIRDKQ

SGKTILDFLKSDGFANRNFMQLIHDDSLTFKEDIQKAQVSGQGDSLHE

HIANLAGSPAIKKGILQTVKVVDELVKVMGRHKPENIVIEMARENQTT

QKGQKNSRERMKRIEEGIKELGSQILKEHPVENTQLQNEKLYLYYLQN

GRDMYVDQELDINRLSDYDVDHIVPQSFLKDDSIDNKVLTRSDKNRGK

SDNVPSEEVVKKMKNYWRQLLNAKLITQRKFDNLTKAERGGLSELDKA

GFIKRQLVETRQITKHVAQILDSRMNTKYDENDKLIREVKVITLKSKL

VSDFRKDFQFYKVREINNYHHAHDAYLNAVVGTALIKKYPKLESEFVY

GDYKVYDVRKMIAKSEQEIGKATAKYFFYSNIMNFFKTEITLANGEIR

KRPLIETNGETGEIVWDKGRDFATVRKVLSMPQVNIVKKTEVQTGGFS

KESILPKRNSDKLIARKKDWDPKKYGGFDSPTVAYSVLVVAKVEKGKS

KKLKSVKELLGITIMERSSFEKNPIDFLEAKGYKEVKKDLIIKLPKYS

LFELENGRKRMLASAGELQKGNELALPSKYVNFLYLASHYEKLKGSPE

DNEQKQLFVEQHKHYLDEIIEQISEFSKRVILADANLDKVLSAYNKHR

DKPIREQAENIIHLFTLTNLGAPAAFKYFDTTIDRKRYTSTKEVLDAT

LIHQSITGLYETRIDLSQLGGD
(single underline: HNH domain; double underline: RuvC domain)

In some embodiments, dCas9 corresponds to, or comprises in part or in whole, a Cas9 amino acid sequence having one or more mutations that inactivate the Cas9 nuclease activity. For example, in some embodiments, a dCas9 domain comprises D10A and/or H820A mutation. dCas9 (D10A and H840A):

dCas9 (D10A and H840A):
(SEQ ID NO: 5)
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKA

DLRLIYLALAHMIKFRGHFLIEGDLNPDNSDVDKLFIQLVQTYNQLFEEN

PINASGVDAKAILSARLSKSRRLENLIAQLPGEKKNGLFGNLIALSLGLT

PNFKSNFDLAEDAKLQLSKDTYDDDLDNLLAQIGDQYADLFLAAKNLSDA

ILLSDILRVNTEITKAPLSASMIKRYDEHHQDLTLLKALVRQQLPEKYKE

IFFDQSKNGYAGYIDGGASQEEFYKFIKPILEKMDGTEELLVKLNREDLL

RKQRTFDNGSIPHQIHLGELHAILRRQEDFYPFLKDNREKIEKILTFRIP

-continued
YYVGPLARGNSRFAWMTRKSEETITPWNFEEVVDKGASAQSFIERMTNFD

KNLPNEKVLPKHSLLYEYFTVYNELTKVKYVTEGMRKPAFLSGEQKKAIV

DLLFKTNRKVTVKQLKEDYFKKIECFDSVEISGVEDRFNASLGTYHDLLK

IIKDKDFLDNEENEDILEDIVLTLTLFEDREMIEERLKTYAHLFDDKVMK

QLKRRRYTGWGRLSRKLINGIRDKQSGKTILDFLKSDGFANRNFMQLIHD

DSLTFKEDIQKAQVSGQGDSLHEHIANLAGSPAIKKGILQTVKVVDELVK

VMGRHKPENIVIEMARENQTTQKGQKNSRERMKRIEEGIKELGSQILKEH

PVENTQLQNEKLYLYYLQNGRDMYVDQELDINRLSDYDVDAIVPQSFLKD

DSIDNKVLTRSDKNRGKSDNVPSEEVVKKMKNYWRQLLNAKLITQRKFDN

LTKAERGGLSELDKAGFIKRQLVETRQITKHVAQILDSRMNTKYDENDKL

IREVKVITLKSKLVSDFRKDFQFYKVREINNYHHAHDAYLNAVVGTALIK

KYPKLESEFVYGDYKVYDVRKMIAKSEQEIGKATAKYFFYSNIMNFFKTE

ITLANGEIRKRPLIETNGETGEIVWDKGRDFATVRKVLSMPQVNIVKKTE

VQTGGFSKESILPKRNSDKLIARKKDWDPKKYGGFDSPTVAYSVLVVAKV

EKGKSKKLKSVKELLGITIMERSSFEKNPIDFLEAKGYKEVKKDLIIKLP

KYSLFELENGRKRMLASAGELQKGNELALPSKYVNFLYLASHYEKLKGSP

EDNEQKQLFVEQHKHYLDEIIEQISEFSKRVILADANLDKVLSAYNKHRD

KPIREQAENIIHLFTLTNLGAPAAFKYFDTTIDRKRYTSTKEVLDATLIH

QSITGLYETRIDLSQLGGD
(single underline: HNH domain; double underline: RuvC domain)

In other embodiments, dCas9 variants having mutations other than D10A and H820A are provided, which e.g., result in nuclease inactivated Cas9 (dCas9). Such mutations, by way of example, include other amino acid substitutions at D10 and H820, or other substitutions within the nuclease domains of Cas9 (e.g., substitutions in the HNH nuclease subdomain and/or the RuvC1 subdomain). In some embodiments, variants or homologues of dCas9 (e.g., variants of SEQ ID NO: 5) are provided which are at least about 70% identical, at least about 80% identical, at least about 90% identical, at least about 95% identical, at least about 98% identical, at least about 99% identical, at least about 99.5% identical, or at least about 99.9% to SEQ ID NO:5. In some embodiments, variants of dCas9 (e.g., variants of SEQ ID NO: 5) are provided having amino acid sequences which are shorter, or longer than SEQ ID NO: 5, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

In some embodiments, Cas9 fusion proteins as provided herein comprise the full-length amino acid of a Cas9 protein, e.g., one of the sequences provided above. In other embodiments, however, fusion proteins as provided herein do not comprise a full-length Cas9 sequence, but only a fragment thereof. For example, in some embodiments, a Cas9 fusion protein provided herein comprises a Cas9 fragment, wherein the fragment binds crRNA and tracrRNA or sgRNA, but does not comprise a functional nuclease domain, e.g., in that it comprises only a truncated version of a nuclease domain or no nuclease domain at all. Exemplary amino acid sequences of suitable Cas9 domains and Cas9 fragments are provided herein, and additional suitable sequences of Cas9 domains and fragments will be apparent to those of skill in the art.

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisI* (NCBI Ref: NC_018721.1); *Streptococcus thermophilus* (NCBI Ref: YP_820832.1); *Listeria innocua* (NCBI Ref: NP_472073.1); *Campylobacter jejuni* (NCBI Ref: YP_002344900.1); or *Neisseria. meningitidis* (NCBI Ref: YP_002342100.1).

The term "deaminase" refers to an enzyme that catalyzes a deamination reaction. In some embodiments, the deaminase is a cytidine deaminase, catalyzing the hydrolytic deamination of cytidine or deoxycytidine to uracil or deoxyuracil, respectively.

The terms "RNA-programmable nuclease" and "RNA-guided nuclease" are used interchangeably herein and refer to a nuclease that forms a complex with (e.g., binds or associates with) one or more RNA molecule that is not a target for cleavage. In some embodiments, an RNA-programmable nuclease, when in a complex with an RNA, may be referred to as a nuclease:RNA complex. RNA-programmable nucleases include Cas9 nucleases. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeably to refer to guide RNAs that exist as either single molecules or as two or more molecules. Typically, gRNAs that exist as single RNA species comprise two domains: (1) a domain that shares homology to a target nucleic acid (e.g., and directs binding of a Cas9 complex to the target); and (2) a domain that binds a Cas9 protein. The gRNA comprises a nucleotide sequence that complements a target site, which mediates binding of the nuclease/RNA complex to said target site and providing the sequence specificity of the nuclease:RNA complex.

The term "recombinase," as used herein, refers to a site-specific enzyme that mediates the recombination of DNA between recombinase recognition sequences, which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, φC31, TP901, TG1, φBT1, R4, φRV1, φFC1, MR11, A118, U153, and gp29. Examples of tyrosine recombinases include, without limitation, Cre, FLP, R, Lambda, HK101, HK022, and pSAM2. The serine and tyrosine recombinase names stem from the conserved nucleophilic amino acid residue that the recombinase uses to attack the DNA and which becomes covalently linked to the DNA during strand exchange. Recombinases have numerous applications, including the creation of gene knockouts/knock-ins and gene therapy applications. See, e.g., Brown et al., "Serine recombinases as tools for genome engineering." Methods. 2011; 53(4):372-9; Hirano et al., "Site-specific recombinases as tools for heterologous gene integration." Appl. Microbiol. Biotechnol. 2011; 92(2):227-39; Chavez and Calos, "Therapeutic applications of the ΦC31 integrase system." Curr. Gene Ther. 2011; 11(5):375-81; Turan and Bode, "Site-specific recombinases: from tag-and-target- to tag-and-exchange-based genomic modifications." FASEB J. 2011; 25(12):4088-107; Venken and Bellen, "Genome-wide manipulations of *Drosophila melanogaster* with transposons, Flp recombinase, and ΦC31 integrase." Methods Mol. Biol. 2012; 859:203-28; Murphy, "Phage recombinases and their applications." Adv. Virus Res. 2012; 83:367-414; Zhang et al., "Conditional gene manipulation: Cre-ating a new biological era." J. Zhejiang Univ. Sci. B. 2012; 13(7): 511-24; Karpenshif and Bernstein, "From yeast to mammals: recent advances in genetic control of homologous recombination." DNA Repair (Amst). 2012; 1; 11(10):781-8; the entire contents of each are hereby incorporated by reference in their entirety. The recombinases provided herein are not meant to be exclusive examples of recombinases that can be used in embodiments of the invention. The methods and compositions of the invention can be expanded by mining databases for new orthogonal recombinases or designing synthetic recombinases with defined DNA specificities (See, e.g., Groth et al., "Phage integrases: biology and applications." J. Mol. Biol. 2004; 335, 667-678; Gordley et al., "Synthesis of programmable integrases." Proc. Natl. Acad. Sci. USA. 2009; 106, 5053-5058; the entire contents of each are hereby incorporated by reference in their entirety). Other examples of recombinases that are useful in the methods and compositions described herein are known to those of skill in the art, and any new recombinase that is discovered or generated is expected to be able to be used in the different embodiments of the invention. In some embodiments, a recombinase (or catalytic domain thereof) is fused to a Cas9 protein (e.g., dCas9).

The term "recombine" or "recombination," in the context of a nucleic acid modification (e.g., a genomic modification), is used to refer to the process by which two or more nucleic acid molecules, or two or more regions of a single nucleic acid molecule, are modified by the action of a recombinase protein. Recombination can result in, inter alia, the insertion, inversion, excision, or translocation of a nucleic acid sequence, e.g., in or between one or more nucleic acid molecules.

The term "WW domain" as described herein, is a protein domain having two basic residues at the C-terminus that mediates protein-protein interactions with short proline-rich or proline-containing motifs. The WW domain possessing the two basic C-terminal amino acid residues may have the ability to associate with short proline-rich or proline-containing motifs (i.e., a PPXY (SEQ ID NO: 75) motif). WW domains bind a variety of distinct peptide ligands including motifs with core proline-rich sequences, such as PPXY (SEQ ID NO: 75), which is found in AARDC1. A WW domain may be a 30-40 amino acid protein interaction domain with two signature tryptophan residues spaced by 20-22 amino acids. The three-dimensional structure of WW domains shows that they generally fold into a three-stranded, antiparallel β sheet with two ligand-binding grooves.

WW domains are found in many eukaryotes and are present in approximately 50 human proteins (Bork, P. & Sudol, M. The WW domain: a signaling site in dystrophin? Trends Biochem Sci 19, 531-533 (1994)). WW domains may be present together with several other interaction domains, including membrane targeting domains, such as C2 in the NEDD4 family proteins, the phosphotyrosinebinding (PTB) domain in FE65 protein, FF domains in CA150 and FBPI1, and pleckstrin homology (PH) domains in PLEKHA5. WW domains are also linked to a variety of catalytic domains, including HECT E3 protein-ubiquitin ligase domains in NEDD4 family proteins, rotomerase or peptidyl prolyisomerase domains in Pin1, and Rho GAP domains in ArhGAP9 and ArhGAP12.

In the instant disclosure, the WW domain may be a WW domain that naturally possesses two basic amino acids at the C-terminus, for example a WW domain or WW domain variant may be from the human ubiquitin ligase WWP1, WWP2, Nedd4-1, Nedd4-2, Smurf1, Smurf2, ITCH, NEDL1, or NEDL2. Exemplary amino acid sequences of WW domain containing proteins (WW domains underlined) are listed below. It should be appreciated that any of the WW domains or WW domain variants of the exemplary proteins may be used in the invention, described herein, and are not meant to be limiting.

```
Human WWP1 amino acid sequence (uniprot.org/uniprot/Q9H0M0). The four
underlined WW domains correspond to amino acids 349-382( WW1),
381-414 (WW2), 456-489 (WW3), and 496-529 (WW4).
                                                       (SEQ ID NO: 6)
          MATASPRSDT SNNHSGRLQL QVTVSSAKLK RKKNWFGTAI YTEVVVDGEI    50

TKTAKSSSSS NPKWDEQLTV NVTPQTTLEF QVWSHRTLKA DALLGKATID   100

LKQALLIHNR KLERVKEQLK LSLENKNGIA QTGELTVVLD GLVIEQENIT   150

NCSSSPTIEI QENGDALHEN GEPSARTTAR LAVEGTNGID NHVPTSTLVQ   200

NSCCSYVVNG DNTPSSPSQV AARPKNTPAP KPLASEPADD TVNGESSSFA   250

PTDNASVTGT PVVSEENALS PNCTSTTVED PPVQEILTSS ENNECIPSTS   300

AELESEARSI LEPDTSNSRS SSAFEAAKSR QPDGCMDPVR QQSGNANTET   350

LPSGWEQRKD PHGRTYYVDH NTRTTTWERP QPLPPGWERR VDDRRRVYYV   400

DHNTRTTTWQ RPTMESVRNF EQWQSQRNQL QGAMQQFNQR YLYSASMLAA   450

ENDPYGPLPP GWEKRVDSTD RVYFVNHNTK TTQWEDPRTQ GLQNEEPLPE   500

GWEIRYTREG VRYFVDHNTR TTTFKDPRNG KSSVTKGGPQ IAYERGFRWK   550

LAHFRYLCQS NALPSHVKIN VSRQTLFEDS FQQIMALKPY DLRRRLYVIF   600

RGEEGLDYGG LAREWFFLLS HEVLNPMYCL FEYAGKNNYC LQINPASTIN   650

PDHLSYFCFI GRFIAMALFH GKFIDTGFSL PFYKRMLSKK LTIKDLESID   700

TEFYNSLIWI RDNNIEECGL EMYFSVDMEI LGKVTSHDLK LGGSNILVTE   750

ENKDEYIGLM TEWRFSRGVQ EQTKAFLDGF NEVVPLQWLQ YFDEKELEVM   800

LCGMQEVDLA DWQRNTVYRH YTRNSKQIIW FWQFVKETDN EVRMRLLQFV   850

TGTCRLPLGG FAELMGSNGP QKFCIEKVGK DTWLPRSHTC FNRLDLPPYK   900

SYEQLKEKLL FAIEETEGFG QE                                922

WW1 (349-382):
                                                      (SEQ ID NO: 36)
ETLPSGWEQRKDPHGRTYYVDHNTRTTTWERPQP.

WW2 (381-414):
                                                      (SEQ ID NO: 37)
QPLPPGWERRVDDRRRVYYVDHNTRTTTWQRPTM.

WW3 (456-489):
                                                      (SEQ ID NO: 38)
ENDPYGPLPPGWEKRVDSTDRVYFVNHNTKTTQWEDPRT.

WW4 (496-529):
                                                      (SEQ ID NO: 39)
EPLPEGWEIRYTREGVRYFVDHNTRTTTFKDPRN.

Human WWP2 amino acid sequence (uniprot.org/uniprot/O00308). The four
underlined WW domains correspond to amino acids 300-333 (WW1),
330-363 (WW2), 405-437 (WW3), and 444-547 (WW4).
                                                       (SEQ ID NO: 7)
          MASASSSRAG VALPFEKSQL TLKVVSAKPK VHNRQPRINS YVEVAVDGLP    50

SETKKTGKRI GSSELLWNEI IILNVTAQSH LDLKVWSCHT LRNELLGTAS   100

VNLSNVLKNN GGKMENMQLT LNLQTENKGS VVSGGELTIF LDGPTVDLGN   150

VPNGSALTDG SQLPSRDSSG TAVAPENRHQ PPSTNCFGGR SRTHRHSGAS   200
```

```
ARTTPATGEQ SPGARSRHRQ PVKNSGHSGL ANGTVNDEPT TATDPEEPSV      250

VGVTSPPAAP LSVTPNPNTT SLPAPATPAE GEEPSTSGTQ QLPAAAQAPD      300

ALPAGWEQRE LPNGRVYYVD HNTKTTTWER PLPPGWEKRT DPRGRFYYVD      350

HNTRTTTWQR PTAEYVRNYE QWQSQRNQLQ GAMQHFSQRF LYQSSSASTD      400

HDPLGPLPPG WEKRQDNGRV YYVNHNTRTT QWEDPRTQGM IQEPALPPGW      450

EMKYTSEGVR YFVDHNTRTT TFKDPRPGFE SGTKQGSPGA YDRSFRWKYH      500

QFRFLCHSNA LPSHVKISVS RQTLFEDSFQ QIMNMKPYDL RRRLYIIMRG      550

EEGLDYGGIA REWFFLLSHE VLNPMYCLFE YAGKNNYCLQ INPASSINPD      600

HLTYFRFIGR FIAMALYHGK FIDTGFTLPF YKRMLNKRPT LKDLESIDPE      650

FYNSIVWIKE NNLEECGLEL YFIQDMEILG KVTTHELKEG GESIRVTEEN     700

KEEYIMLLTD WRFTRGVEEQ TKAFLDGFNE VAPLEWLRYF DEKELELMLC      750

GMQEIDMSDW QKSTIYRHYT KNSKQIQWFW QVVKEMDNEK RIRLLQFVTG      800

TCRLPVGGFA ELIGSNGPQK FCIDKVGKET WLPRSHTCFN RLDLPPYKSY      850

EQLREKLLYA IEETEGFGQE                                      870
```

WW1 (300-333):
(SEQ ID NO: 40)
DALPAGWEQRELPNGRVYYVDTTNTKITTWERPLP.

WW2 (330-363):
(SEQ ID NO: 41)
PLPPGWEKRT DPRGRFYYVDHNTRTTTWQRPTA.

WW3 (405-437):
(SEQ ID NO: 42)
HDPLGPLPPGWEKRQDNGRVYYVNHNTRTTQWEDPRT.

WW4 (444-477):
(SEQ ID NO: 43)
PALPPGWEMKYTSEGVRYFVDHNTRTTTFKDPRP.

Human Nedd4-1 amino acid sequence (uniprot.org/uniprot/P46934). The
four underlined WW domains correspond to amino acids 610-643 (WW1),
767-800 (WW2), 840-873 (WW3), and 892-925 (WW4).
(SEQ ID NO: 8)

```
MAQSLRLHFA ARRSNTYPLS ETSGDDLDSH VHMCFKRPTR ISTSNVVQMK       50

LTPRQTALAP LIKENVQSQE RSSVPSSENV NKKSSCLQIS LQPTRYSGYL      100

QSSNVLADSD DASFTCILKD GIYSSAVVDN ELNAVNDGHL VSSPAICSGS      150

LSNFSTSDNG SYSSNGSDFG SCASITSGGS YTNSVISDSS SYTFPPSDDT      200

FLGGNLPSDS TSNRSVPNRN TTPCEIFSRS TSTDPFVQDD LEHGLEIMKL      250

PVSRNTKIPL KRYSSLVIFP RSPSTTRPTS PTSLCTLLSK GSYQTSHQFI      300

ISPSEIAHNE DGTSAKGFLS TAVNGLRLSK TICTPGEVRD IRPLHRKGSL      350

QKKIVLSNNT PRQTVCEKSS EGYSCVSVHF TQRKAATLDC ETTNGDCKPE      400

MSEIKINSDS EYIKLMHRTS ACLPSSQNVD CQININGELE RPHSQMNKNH      450

GILRRSISLG GAYPNISCLS SLKHNCSKGG PSQLLIKFAS GNEGKVDNLS      500

RDSNRDCTNE LSNSCKTRDD FLGQVDVPLY PLPTENPRLE RPYTFKDFVL      550

HPRSHKSRVK GYLRLKMTYL PKTSGSEDDN AEQAEELEPG WVVLDQPDAA      600

CHLQQQQEPS PLPPGWEERQ DILGRTYYVN HESRRTQWKR PTPQDNLTDA      650

ENGNIQLQAQ RAFTTRRQIS EETESVDNRE SSENWEIIRE DEATMYSNQA      700

FPSPPPSSNL DVPTHLAEEL NARLTIFGNS AVSQPASSSN HSSRRGSLQA      750

YTFEEQPTLP VLLPTSSGLP PGWEEKQDER GRSYYVDHNS RTTTWTKPTV      800
```

```
QATVETSQLT SSQSSAGPQS QASTSDSGQQ VTQPSEIEQG FLPKGWEVRH      850
APNGRPFFID HNTKTTTWED PRLKIPAHLR GKTSLDTSND LGPLPPGWEE      900
RTHTDGRIFY INHNIKRTQW EDPRLENVAI TGPAVPYSRD YKRKYEFFRR      950
KLKKQNDIPN KFEMKLRRAT VLEDSYRRIM GVKRADFLKA RLWIEEDGEK     1000
GLDYGGVARE WFFLISKEMF NPYYGLFEYS ATDNYTLQIN PNSGLCNEDH     1050
LSYFKFIGRV AGMAVYHGKL LDGFFIRPFY KMMLHKPITL HDMESVDSEY     1100
YNSLRWILEN DPTELDLRFI IDEELFGQIH QHELKNGGSE IVVTNKNKKE     1150
YIYLVIQWRF VNRIQKQMAA FKEGFFELIP QDLIKIFDEN ELELLMCGLG     1200
DVDVNDWREH TKYKNGYSAN HQVIQWFWKA VLMMDSEKRI RLLQFVTGTS     1250
RVPMNGFAEL YGSNGPQSFT VEQWGTPEKL PRAHTCFNRL DLPPYESFEE     1300
LWDKLQMAIE NTQGFDGVD                                      1319

WW1 (610-643):
                                                (SEQ ID NO: 44)
SPLPPGWEERQDILGRTYYVNHESRRTQWKRPTP.

WW2 (767-800):
                                                (SEQ ID NO: 45)
SGLPPGWEEKQDERGRSYYVDHNSRTTTWTKPTV.

WW3 (840-873):
                                                (SEQ ID NO: 46)
GFLPKGWEVRHAPNGRPFFIDHNTKTTTWEDPRL.

WW4 (892-925):
                                                (SEQ ID NO: 47)
GPLPPGWEERTHTDGRIFYINHNIKRTQWEDPRL.

Human Nedd4-2 amino acid sequence (>gi|21361472|ref|NP_056092.2|  E3
ubiquitin-protein ligase NEDD4-like isoform 3 [Homo sapiens]). The
four underlined WW domains correspond to amino acids 198-224 (WW1),
368-396 (WW2), 480-510 (WW3), and 531-561 (WW4).
                                                (SEQ ID NO: 9)
MATGLGEPVYGLSEDEGESRILRVKVVSGIDLAKKDIFGASDPYVKLSLYVADENRELA

LVQTKTIKKTLNPKWNEEFYFRVNPSNHRLLFEVFDENRLTRDDFLGQVDVPLSHLPTE

DPTMERPYTFKDFLLRPRSHKSRVKGFLRLKMAYMPKNGGQDEENSDQRDDMEHGWE

VVDSNDSASQHQEELPPPPLPPGWEEKVDNLGRTYYVNHNNRTTQWHRPSLMDVSSES

DNNIRQINQEAAHRRFRSRRHISEDLEPEPSEGGDVPEPWETISEEVNIAGDSLGLALPPPP

ASPGSRTSPQELSEELSRRLQITPDSNGEQFSSLIQREPSSRLRSCSVTDAVAEQGHLPPPS

VAYVHTTPGLPSGWEERKDAKGRTYYVNHNNRTTTWTRPIMQLAEDGASGSATNSNN

HLIEPQIRRPRSLSSPTVTLSAPLEGAKDSPVRRAVKDTLSNPQSPQPSPYNSPKPQHKVT

QSFLPPGWEMRIAPNGRPFFIDHNTKTTTWEDPRLKFPVHMRSKTSLNPNDLGPLPPGW

EERIFILDGRTFYIDHNSKITQWEDPRLQNPAITGPAVPYSREFKQKYDYFRKKLKKPADI

PNRFEMKLHRNNIFEESYRRIMSVKRPDVLKARLWIEFESEKGLDYGGVAREWFFLLSK

EMFNPYYGLFEYSATDNYTLQINPNSGLCNEDHLSYFTFIGRVAGLAVFHGKLLDGFFIR

PFYKMMLGKQITLNDMESVDSEYYNSLKWILENDPTELDLMFCIDEENFGQTYQVDLKP

NGSEIMVTNENKREYIDLVIQWRFVNRVQKQMNAFLEGFTELLPIDLIKIFDENELELLM

CGLGDVDVNDWRQHSIYKNGYCPNHPVIQWFWKAVLLMDAEKRIRLLQFVTGTSRVP

MNGFAELYGSNGPQLFTIEQWGSPEKLPRAHTCFNRLDLPPYETFEDLREKLLMAVENA

QGFEGVD
```

WW1 (198-224):
(SEQ ID NO: 61)
GWEEKVDNLGRTYYVNHNNRTTQWHRP.

WW2 (368-396):
(SEQ ID NO: 62)
PSGWEERKDAKGRTYYVNHNNRTTTWTRP.

WW3 (480-510):
(SEQ ID NO: 63)
PPGWEMRIAPNGRPFFIDHNTKTTTWEDPRL.

WW4 (531-561):
(SEQ ID NO: 64)
PPGWEERIFILDGRTFYIDHNSKITQWEDPRL.

Human Smurf1 amino acid sequence (uniprot.org/uniprot/Q9HCE7). The two underlined WW domains correspond to amino acids 234-267 (WW1), and 306-339 (WW2).

(SEQ ID NO: 10)

| | | |
|---|---|---|
| MSNPGTRRNG SSIKIRLTVL CAKNLAKKDF FRLPDPFAKI VVDGSGQCHS | 50 |
| TDTVKNTLDP KWNQHYDLYV GKTDSITISV WNHKKIHKKQ GAGFLGCVRL | 100 |
| LSNAISRLKD TGYQRLDLCK LNPSDTDAVR GQIVVSLQTR DRIGTGGSVV | 150 |
| DCRGLLENEG TVYEDSGPGR PLSCFMEEPA PYTDSTGAAA GGGNCRFVES | 200 |
| PSQDQRLQAO RLRNPDVRGS LQTPQNRPHG HQSPELPEGY EQRTTVQGQV | 250 |
| YFLHTQTGVS TWHDPRIPSP SGTIPGGDAA FLYEFLLQGH TSEPRDLNSV | 300 |
| NCDELGPLPP GWEVRSTVSG RIYFVDHNNR TTQFTDPRLH HIMNHQCQLK | 350 |
| EPSQPLPLPS EGSLEDEELP AQRYERDLVQ KLKVLRHELS LQQPQAGHCR | 400 |
| IEVSREEIFE ESYRQIMKPR PKDLKKRLMV KFRGEEGLDY GGVAREWLYL | 450 |
| LCHEMLNPYY GLFQYSTDNI YMLQINPDSS INPDHLSYFH FVGRIMGLAV | 500 |
| FHGHYINGGF TVPFYKQLLG KPIQLSDLES VDPELHKSLV WILENDITPV | 550 |
| LDHTFCVEHN AFGRILQHEL KPNGRNVPVT EENKKEYVRL YVNWRFMRGI | 600 |
| EAQFLALQKG FNELIPQHLL KPFDQKELEL IIGGLDKIDL NDWKSNTRLK | 650 |
| HCVADSNIVR WFWQAVETFD EERRARLLQF VTGSTRVPLQ GFKALQGSTG | 700 |
| AAGPRLFTIH LIDANTDNLP KAHTCFNRID IPPYESYEKL YEKLLTAVEE | 750 |
| TCGFAVE | 757 |

WW1 (234-267):
(SEQ ID NO: 48)
PELPEGYEQRTTVQGQVYFLHTQTGVSTWHDPRI.

WW2 (306-339):
(SEQ ID NO: 49)
GPLPPGWEVRSTVSGRIYFVDHNNRTTQFTDPRL.

Human Smurf2 amino acid sequence (uniprot.org/uniprot/Q9HAU4). The three underlined WW domains correspond to amino acids 157-190 (WW1), 251-284 (WW2), and 297-330 (WW3).

(SEQ ID NO: 11)

| | | |
|---|---|---|
| MSNPGGRRNG PVKLRLTVLC AKNLVKKDFF RLPDPFAKVV VDGSGQCHST | 50 |
| DTVKNTLDPK WNQHYDLYIG KSDSVTISVW NHKKIHKKQG AGFLGCVRLL | 100 |
| SNAINRLKDT GYQRLDLCKL GPNDNDTVRG QIVVSLQSRD RIGTGGQVVD | 150 |
| CSRLFDNDLP DGWEERRTAS GRIQYLNHIT RTTQWERPTR PASEYSSPGR | 200 |
| PLSCFVDENT PISGTNGATC GQSSDPRLAE RRVRSQRHRN YMSRTHLHTP | 250 |
| PDLPEGYEQR TTQQGQVYFL HTQTGVSTWH DPRVPRDLSN INCEELGPLP | 300 |
| PGWEIRNTAT GRVYFVDHNN RTTQFTDPRL SANLHLVLNR QNQLKDQQQQ | 350 |
| QVVSLCPDDT ECLTVPRYKR DLVQKLKILR QELSQQQPQA GHCRIEVSRE | 400 |

```
EIFEESYRQV MKMRPKDLWK RLMIKFRGEE GLDYGGVARE WLYLLSHEML      450

NPYYGLFQYS RDDIYTLQIN PDSAVNPEHL SYFHFVGRIM GMAVFHGHYI      500

DGGFTLPFYK QLLGKSITLD DMELVDPDLH NSLVWILEND ITGVLDHTFC      550

VEHNAYGEII QHELKPNGKS IPVNEENKKE YVRLYVNWRF LRGIEAQFLA      600

LQKGFNEVIP QHLLKTFDEK ELELIICGLG KIDVNDWKVN TRLKHCTPDS      650

NIVKWFWKAV EFFDEERRAR LLQFVTGSSR VPLQGFKALQ GAAGPRLFTI      700

HQIDACTNNL PKAHTCFNRI DIPPYESYEK LYEKLLTAIE ETCGFAVE       748
```

WW1 (157-190):
(SEQ ID NO: 50)
NDLPDGWEERRTASGRIQYLNHITRTTQWERPTR.

WW2 (251-284):
(SEQ ID NO: 51)
PDLPEGYEQRTTQQGQVYFLHTQTGVSTWHDPRV.

WW3 (297-330):
(SEQ ID NO: 52)
GPLPPGWEIRNTATGRVYFVDHNNRTTQFTDPRL.

Human ITCH amino acid sequence (uniprot.org/uniprot/Q96J02). The four
underlined WW domains correspond to amino acids 326-359 (WW1),
358-391 (WW2), 438-471 (WW3), and 478-511 (WW4).

(SEQ ID NO: 12)
```
MSDSGSQLGS MGSLTMKSQL QITVISAKLK ENKKNWFGPS PYVEVTVDGQ       50

SKKTEKCNNT NSPKWKQPLT VIVTPVSKLH FRVWSHQTLK SDVLLGTAAL      100

DIYETLKSNN MKLEEVVVTL QLGGDKEPTE TIGDLSICLD GLQLESEVVT      150

NGETTCSENG VSLCLPRLEC NSAISAHCNL CLPGLSDSPI SASRVAGFTG      200

ASQNDDGSRS KDETRVSTNG SDDPEDAGAG ENRRVSGNNS PSLSNGGFKP      250

SRPPRPSRPP PPTPRRPASV NGSPSATSES DGSSTGSLPP TNTNTNTSEG      300

ATSGLIIPLT ISGGSGPRPL NPVTQAPLPP GWEQRVDQHG RVYYVDHVEK      350

RTTWDRPEPL PPGWERRVDN MGRIYYVDHF TRTTTWQRPT LESVRNYEQW      400

QLQRSQLQGA MQQFNQRFIY GNQDLFATSQ SKEFDPLGPL PPGWEKRTDS      450

NGRVYFVNHN TRITQWEDPR SQGQLNEKPL PEGWEMRFTV DGIPYFVDHN      500

RRTTTYIDPR TGKSALDNGP QIAYVRDFKA KVQYFRFWCQ QLAMPQHIKI      550

TVTRKTLFED SFQQIMSFSP QDLRRRLWVI FPGEEGLDYG GVAREWFFLL      600

SHEVLNPMYC LFEYAGKDNY CLQINPASYI NPDHLKYFRF IGRFIAMALF      650

HGKFIDTGFS LPFYKRILNK PVGLKDLESI DPEFYNSLIW VKENNIEECD      700

LEMYFSVDKE ILGEIKSHDL KPNGGNILVT EENKEEYIRM VAEWRLSRGV      750

EEQTQAFFEG FNEILPQQYL QYFDAKELEV LLCGMQEIDL NDWQRHAIYR      800

HYARTSKQIM WFWQFVKEID NEKRMRLLQF VTGTCRLPVG GFADLMGSNG      850

PQKFCIEKVG KENWLPRSHT CFNRLDLPPY KSYEQLKEKL LFAIEETEGF      900

GQE                                                        903
```

ITCH WW1 (326-359):
(SEQ ID NO: 53)
APLPPGWEQRVDQHGRVYYVDHVEKRTTWDRPEP.

ITCH WW2 (358-391):
(SEQ ID NO: 54)
EPLPPGWERRVDNMGRIYYVDHFTRTTTWQRPTL.

ITCH WW3 (438-471):
(SEQ ID NO: 55)
GPLPPGWEKRTDSNGRVYFVNHNTRITQWEDPRS.

ITCH WW4 (478-511):

-continued (SEQ ID NO: 56)
KPLPEGWEMRFTVDGIPYFVDHNRRTTTYIDPRT.

Human NEDL1 amino acid sequence (uniprot.org/uniprot/Q76N89). The two underlined WW domains correspond to amino acids 829-862 (WW1), and 1018-1051 (WW2).

(SEQ ID NO: 13)

| | | | | |
|---|---|---|---|---|
| MLLHLCSVKN | LYQNRFLGLA | AMASPSRNSQ | SRRRCKEPLR | YSYNPDQFHN | 50 |
| MDLRGGPHDG | VTIPRSTSDT | DLVTSDSRST | LMVSSSYYSI | GHSQDLVIHW | 100 |
| DIKEEVDAGD | WIGMYLIDEV | LSENFLDYKN | RGVNGSHRGQ | IIWKIDASSY | 150 |
| FVEPEIKICF | KYYHGVSGAL | RATTPSVTVK | NSAAPIFKSI | GADETVQGQG | 200 |
| SRRLISFSLS | DFQAMGLKKG | MFFNPDPYLK | ISIQPGKHSI | FPALPHHGQR | 250 |
| RRSKIIGNTV | NPIWQAEQFS | FVSLPTDVLE | IEVKDKFAKS | RPIIKRFLGK | 300 |
| LSMPVQRLLE | RHAIGDRVVS | YTLGRRLPTD | HVSGQLQFRF | EITSSIHPDD | 350 |
| EEISLSTEPE | SAQIQDSPMN | NLMESGSGEP | RSEAPESSES | WKPEQLGEGS | 400 |
| VPDGPGNQSI | ELSRPAEEAA | VITEAGDQGM | VSVGPEGAGE | LLAQVQKDIQ | 450 |
| PAPSAEELAE | QLDLGEEASA | LLLEDGEAPA | STKEEPLEEE | ATTQSRACRE | 500 |
| EEEKEQEEEG | DVSTLEQGEG | RLQLRASVKR | KSRPCSLPVS | ELETVIASAC | 550 |
| GDPETPRTHY | IRIHTLLHSM | PSAQGCSAAE | EEDGAEEEST | LKDSSEKDGL | 600 |
| SEVDTVAADP | SALEEDREEP | EGATPGTAHP | GHSGGHFPSL | ANGAAQDGDT | 650 |
| HPSTGSESDS | SPRQGGDHSC | EGCDASCCSP | SCYSSSCYST | SCYSSSCYSA | 700 |
| SCYSPSCYNG | NRFASHTRFS | SVDSAKISES | TVFSSQDDEE | EENSAFESVP | 750 |
| DSMQSPELDP | ESTNGAGPWQ | DELAAPSGHV | ERSPEGLESP | VAGPSNRREG | 800 |
| ECPILHNSQP | VSQLPSLRPE | HHHYPTIDEP LPPNWEARID | SHGRVFYVDH | 850 |
| VNRTTTWQRP TAAATPDGMR | RSGSIQQMEQ | LNRRYQNIQR | TIATERSEED | 900 |
| SGSQSCEQAP | AGGGGGGGSD | SEAESSQSSL | DLRREGSLSP | VNSQKITLLL | 950 |
| QSPAVKFITN | PEFFTVLHAN | YSAYRVFTSS | TCLKHMILKV | RRDARNFERY | 1000 |
| QHNRDLVNFI | NMFADTRLEL PRGWEIKTDQ QGKSFFVDHN SRATTFIDPR | 1050 |
| IPLQNGRLPN | HLTRHQHLQR | LRSYSAGEAS | EVSRNRGASL | LARPGHSLVA | 1100 |
| AIRSQHQHES | LPLAYNDKIV | AFLRQPNIFE | MLQERQPSLA | RNHTLREKIH | 1150 |
| YIRTEGNHGL | EKLSCDADLV | ILLSLFEEEI | MSYVPLQAAF | HPGYSFSPRC | 1200 |
| SPCSSPQNSP | GLQRASARAP | SPYRRDFEAK | LRNFYRKLEA | KGFGQGPGKI | 1250 |
| KLIIRRDHLL | EGTFNQVMAY | SRKELQRNKL | YVTFVGEEGL | DYSCPSREFF | 1300 |
| FLLSQELFNP | YYGLFEYSAN | DTYTVQISPM | SAFVENHLEW | FRFSCRILGL | 1350 |
| ALIHQYLLDA | FFTRPFYKAL | LRLPCDLSDL | EYLDEEFHQS | LQWMKDNNIT | 1400 |
| DILDLTFTVN | EEVFGQVTER | ELKSGGANTQ | VTEKNKKEYI | ERMVKWRVER | 1450 |
| GVVQQTEALV | RGFYEVVDSR | LVSVFDAREL | ELVIAGTAEI | DLNDWRNNTE | 1500 |
| YRGCYHDGHL | VIRWFWAAVE | RFNNEQRLRL | LQFVTGTSSV | PYEGFAALRG | 1550 |
| SNGLRRFCIE | KWGKITSLPR | AHTCFNRLDL | PPYPSYSMLY | EKLLTAVEET | 1600 |
| STFGLE | | | | | 1606 |

WW1 (829-862):

(SEQ ID NO: 57)
PLPPNWEARIDSHGRVFYVDHVNRTTTWQRPTA.

WW2 (1018-1051):

(SEQ ID NO: 58)
LELPRGWEIKTDQQGKSFFVDHNSRATTFIDPRI.

-continued

Human NEDL2 amino acid sequence (uniprot.org/uniprot/Q9P2P5). The two underlined WW domains correspond to amino acids 807-840(WW1), and 985-1018 (WW2).

(SEQ ID NO: 14)

```
MASSAREHLL FVRRRNPQMR YTLSPENLQS LAAQSSMPEN MTLQRANSDT      50
DLVTSESRSS LTASMYEYTL GQAQNLIIFW DIKEEVDPSD WIGLYHIDEN     100
SPANFWDSKN RGVTGTQKGQ IVWRIEPGPY FMEPEIKICF KYYHGISGAL     150
RATTPCITVK NPAVMMGAEG MEGGASGMLH SRKLVSFTLS DLRAVGLKKG     200
MFFNPDPYLK MSIQPGKKSS FPTCAHHGQE RRSTIISNTT NPIWHREKYS     250
FFALLTDVLE IEIKDKFAKS RPIIKRFLGK LTIPVQRLLE RQAIGDQMLS     300
YNLGRRLPAD HVSGYLQFKV EVTSSVHEDA SPEAVGTILG VNSVNGDLGS     350
PSDDEDMPGS HHDSQVCSNG PVSEDSAADG TPKHSFRTSS TLEIDTEELT     400
STSSRTSPPR GRQDSLNDYL DAIEHNGHSR PGTATCSERS MGASPKLRSS     450
FPTDTRLNAM LHIDSDEEDH EFQQDLGYPS SLEEEGGLIM FSRASRADDG     500
SLTSQTKLED NPVENEEAST HEAASFEDKP ENLPELAESS LPAGPAPEEG     550
EGGPEPQPSA DQGSAELCGS QEVDQPTSGA DTGTSDASGG SRRAVSETES     600
LDQGSEPSQV SSETEPSDPA RTESVSEAST RPEGESDLEC ADSSCNESVT     650
TQLSSVDTRC SSLESARFPE TPAFSSQEEE DGACAAEPTS SGPAEGSQES     700
VCTAGSLPVV QVPSGEDEGP GAESATVPDQ EELGEVWQRR GSLEGAAAAA     750
ESPPQEEGSA GEAQGTCEGA TAQEEGATGG SQANGHQPLR SLPSVRQDVS     800
RYQRVDEALP PNWEARIDSH GRIFYVDHVN RTTTWQRPTA PPAPQVLQRS     850
NSIQQMEQLN RRYQSIRRTM TNERPEENTN AIDGAGEEAD FHQASADFRR     900
ENILPHSTSR SRITLLLQSP PVKFLISPEF FTVLHSNPSA YRMFTNNTCL     950
KHMITKVRRD THHFERYQHN RDLVGFLNMF ANKQLELPRG WEMKHDHQGK    1000
AFFVDHNSRT TTFIDPRLPL QSSRPTSALV HRQHLTRQRS HSAGEVGEDS    1050
RHAGPPVLPR PSSTFNTVSR PQYQDMVPVA YNDKIVAFLR QPNIFEILQE    1100
RQPDLTRNHS LREKIQFIRT EGTPGLVRLS SDADLVMLLS LFEEEIMSYV    1150
PPHALLHPSY CQSPRGSPVS SPQNSPGTQR ANARAPAPYK RDFEAKLRNF    1200
YRKLETKGYG QGPGKLKLII RRDHLLEDAF NQIMGYSRYD LQRNKLYVTF    1250
VCEEGLDYSG PSREFFFLVS RELFNPYYGL FEYSANDTYT VQISPMSAFV    1300
DNHHEWFRFS GRILGLALIH QYLLDAFFTR PFYKALLRIL CDLSDLEYLD    1350
EEFHQSLQWM KDNDIHDILD LTFTVNEEVF GQITERELKP GGANIPVTEK    1400
NKKEYIERMV KWRIERGVVQ QTESLVRGFY EVVDARLVSV FDARELELVI    1450
AGTAEIDLSD WRNNTEYRGG YHDNHIVIRW FWAAVERFNN EQRLRLLQFV    1500
TGTSSIPYEG FASLRGSNGP RRFCVEKWGK ITALPRAHTC FNRLDLPPYP    1550
SFSMLYEKLL TAVEETSTFG LE                                 1572

WW1 (807-840):
                                                    (SEQ ID NO: 59)
EALPPNWEARIDSHGRIFYVDHVNRTTTWQRPTA.

WW2 (985-1018):
                                                    (SEQ ID NO: 60)
LELPRGWEMKHDHQGKAFFVDHNSRTTTFIDPRL.
```

In some embodiments, the WW domain comprises a WW domain or WW domain variant from the amino acid sequence (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14). In other embodiments, the WW domain consists of a WW domain or WW domain variant from the amino acid sequence (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14). In another embodiment, the WW domain consists essentially of a WW domain or WW domain variant from the amino acid sequence (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14). Consists essentially of means that a domain, peptide or polypeptide consists essentially of an amino acid sequence when such an amino acid sequence is present with only a few additional amino acid residues, for example, from about 1 to about 10 or so additional residues, typically from 1 to about 5 additional residues in the domain, peptide or polypeptide.

Alternatively, the WW domain may be a WW domain that has been modified to include two basic amino acids at the C-terminus of the domain. Techniques are known in the art and are described in the art, for example, in Sambrook et al. ((2001) *Molecular Cloning: a Laboratory Manual*, 3rd ed., Cold Spring Harbour Laboratory Press). Thus, a skilled person could readily modify an existing WW domain that does not normally have two C-terminal basic residues so as to include two basic residues at the C-terminus.

Basic amino acids are amino acids that possess a side-chain functional group that has a pKa of greater than 7 and include lysine, arginine, and histidine, as well as basic amino acids that are not included in the twenty α-amino acids commonly included in proteins. The two basic amino acids at the C-terminus of the WW domain may be the same basic amino acid or may be different basic amino acids. In one embodiment, the two basic amino acids are two arginines.

The term WW domain also includes variants of a WW domain provided that any such variant possesses two basic amino acids at its C-terminus and maintains the ability of the WW domain to associate with the PPXY (SEQ ID NO: 75) motif. A variant of such a WW domain refers to a WW domain which retains the ability to associate with the PPXY (SEQ ID NO: 75) motif (i.e., the PPXY (SEQ ID NO: 75) motif of ARRDC1) and that has been mutated at one or more amino acids, including point, insertion or deletion mutations, but still retains the ability to associate with the PPXY (SEQ ID NO: 75) motif. A variant or derivative therefore includes deletions, including truncations and fragments; insertions and additions, for example conservative substitutions, site-directed mutants and allelic variants; and modifications, including one or more non-amino acyl groups (e.g., sugar, lipid, etc.) covalently linked to the peptide and post-translational modifications. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

The WW domain may be part of a longer protein. Thus, the protein, in various different embodiments, comprises the WW domain, consists of the WW domain or consists essentially of the WW domain, as defined herein. The polypeptide may be a protein that includes a WW domain as a functional domain within the protein sequence. In one embodiment, the polypeptide is a Cas9 protein. In other embodiments, the polypeptide comprises the sequence set forth in (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14), consists of (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14), or consists essentially of (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14).

The term "target site," as used herein in the context of functional effector proteins that bind a nucleic acid molecule, such as nucleases and transcriptional activators or repressors, refers to a sequence within a nucleic acid molecule that is bound and acted upon by the effector protein, e.g., cleaved by the nuclease or transcriptionally activated or repressed by the transcriptional activator or repressor, respectively. A target site may be single-stranded or double-stranded. In the context of RNA-guided (e.g., RNA-programmable) nucleases (e.g., a protein dimer comprising a Cas9 gRNA binding domain and an active Cas9 DNA cleavage domain), a target site typically comprises a nucleotide sequence that is complementary to the gRNA of the RNA-programmable nuclease, and a protospacer adjacent motif (PAM) at the 3' end adjacent to the gRNA-complementary sequence. For the RNA-guided nuclease Cas9, the target site may be, in some embodiments, 20 base pairs plus a 3 base pair PAM (e.g., NNN, wherein N represents any nucleotide). Typically, the first nucleotide of a PAM can be any nucleotide, while the two downstream nucleotides are specified depending on the specific RNA-guided nuclease.

Exemplary target sites for RNA-guided nucleases, such as Cas9, are known to those of skill in the art and include, without limitation, NNG, NGN, NAG, and NGG, wherein N represents any nucleotide. In addition, Cas9 nucleases from different species (e.g., *S. thermophilus* instead of *S. pyogenes*) recognizes a PAM that comprises the sequence NGGNG. Additional PAM sequences are known, including, but not limited to, NNAGAAW and NAAR (see, e.g., Esvelt and Wang, Molecular Systems Biology, 9:641 (2013), the entire contents of which are incorporated herein by reference). For example, the target site of an RNA-guided nuclease, such as, e.g., Cas9, may comprise the structure [NZ]-[PAM], where each N is, independently, any nucleotide, and Z is an integer between 1 and 50, inclusive. In some embodiments, Z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, Z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, Z is 20. In some embodiments, "target site" may also refer to a sequence within a nucleic acid molecule that is bound but not cleaved by a nuclease. For example, certain embodiments described herein provide proteins comprising an inactive (or inactivated) Cas9 DNA cleavage domain. Such proteins (e.g., when also including a Cas9 RNA binding domain) are able to bind the target site specified by the gRNA, however because the DNA cleavage site is inactivated, the target site is not cleaved by the particular protein. However, such proteins as described herein are typically associated with another protein (e.g., a nuclease or transcription factor) or molecule that mediates cleavage of the nucleic acid molecule. In some embodiments, the sequence actually cleaved will depend on the protein (e.g., nuclease) or molecule that mediates cleavage of the nucleic acid molecule, and in some cases, for example, will relate to the proximity or distance from which the inactivated Cas9 protein(s) is/are bound.

DETAILED DESCRIPTION OF CERTAIN EMBODIMENTS OF THE INVENTION

The instant disclosure relates to the discovery that a Cas9:WW domain fusion protein along with a guide RNA sequence (gRNA) can be loaded into ARMMs. Furthermore, fusion of the WW domain to Cas9 nuclease does not interfere with Cas9 nuclease function. As described in more detail herein, cargo proteins (e.g. Cas9 nuclease; Oct4, Sox2, c-Myc, or KLF4 reprogramming factor; or therapeutic protein) may be fused to one or more WW domains or WW domain variant s to facilitate their incorporation into ARMMs which may be used to deliver the fusion proteins into a target cell.

Microvesicles with WW Domain Containing Cargo Proteins

Some aspects of this invention provide arrestin domain-containing protein 1 (ARRDC1)-mediated microvesicles (ARMMs) containing a cargo protein that is fused to a WW domain. Such ARMMs typically include a lipid bilayer and an ARRDC1 protein or variant thereof. In some embodiments, the cargo protein is fused to a WW domain that associates with the PPXY (SEQ ID NO: 75) (where x=any amino acid) domain of ARRDC1 which may facilitate loading of the cargo protein into an ARMM. In some embodiments, the cargo protein is a Cas9 protein or Cas9 variant. In some embodiments the Cas9 protein or variant is a fusion protein. For example, the Cas9 protein or Cas9 variant may be fused to one or more WW domains to facilitate loading into an ARMM. In some embodiments, the Cas9 fusion protein or Cas9 variant is fused to one or more nuclear localization sequences (NLSs) to facilitate translocation of the Cas9 fusion protein into the nucleus of a target cell. In certain embodiments the Cas9 variant is a Cas9 protein or Cas9 protein variant comprising an active or inactive DNA cleavage domain of Cas9 or a partially inactive DNA cleavage domain (e.g., a Cas9 "nickase"), and/or the gRNA binding domain of Cas9. It should be appreciated that any number of proteins known in the art can be fused to one or more WW domains to generate a cargo protein that can be loaded into an ARMM, for example, a reprogramming factor (e.g., Oct4, Sox2, c-Myc, or KLF4) may be fused to one or more WW domains to facilitate loading of one or more reprogramming factors into an ARMM. In some embodiments, the cargo protein is a therapeutic protein (e.g., a transcription factor, a tumor suppressor, a developmental regulator, a growth factor, a metastasis suppressor, a pro-apoptotic protein, a zinc finger nuclease, or a recombinase) that is fused to one or more WW domains. In other embodiments, an ARMM further includes a non-cargo protein, such as a TSG101 protein or variant thereof to facilitate the release of ARMMs. The TSG101 protein interacts with ARRDC1, which results in relocation of TSG101 from endosomes to the plasma membrane and mediates the release of microvesicles that contain TSG101, ARRDC1, and other cellular components, including, for example, cargo proteins and nucleic acids (i.e., gRNAs).

ARRDC1

ARRDC1 is a protein that comprises a PSAP (SEQ ID NO: 74) and a PPXY (SEQ ID NO: 75) motif, also referred to herein as a PSAP (SEQ ID NO: 74) and PPXY (SEQ ID NO: 75) motif, respectively, in its C-terminus, and interacts with TSG101 as shown herein. Exemplary, non-limiting ARRDC1 protein sequences are provided herein, and additional, suitable ARRDC1 protein variants according to aspects of this invention are known in the art. It will be appreciated by those of skill in the art that this invention is not limited in this respect. Exemplary ARRDC1 sequences include the following (PSAP (SEQ ID NO: 74) and PPXY (SEQ ID NO: 75) motifs are marked):

```
>gi|22748653|ref|NP_689498.1| arrestin domain-containing protein 1 [Homo sapiens]
                                                                  (SEQ ID NO: 15)
MGRVQLFEISLSHGRVVYSPGEPLAGTVRVRLGAPLPFRAIRVTCIGSCGVSNKANDTA

WVVEEGYFNSSLSLADKGSLPAGEHSFPFQFLLPATAPTSFEGPFGKIVHQVRAAIHTPRF

SKDHKCSLVFYILSPLNLNSIPDIEQPNVASATKKFSYKLVKTGSVVLTASTDLRGYVVG

QALQLHADVENQSGKDTSPVVASLLQKVSYKAKRWIHDVRTIAEVEGAGVKAWRRAQ

WHEQILVPALPQSALPGCSLIHIDYYLQVSLKAPEATVTLPVFIGNIAVNHAPVSPRPGLG

LPPGAPPLVV[PSAP]PQEEAEAEAAAGGPHFLDPVFLSTKSHSQRQPLLATLSSVPGAPEPC

PQDGSPASHPLHPPLCISTGATVPYFAEGSGGPVPTTSTLIL[PPEY]SSWGYPYEAPPSYEQS

CGGVEPSLTPES

>gi|244798004|ref|NP_001155957.1| arrestin domain-containing protein 1 isoform a
[Mus musculus]
                                                                  (SEQ ID NO: 16)
MGRVQLFEIRLSQGRVVYGPGEPLAGTVHLRLGAPLPFRAIRVTCMGSCGVSTKANDG

AWVVEESYFNSSLSLADKGSLPAGEHNFPFQFLLPATAPTSFEGPFGKIVHQVRASIDTPR

FSKDHKCSLVFYILSPLNLNSIPDIEQPNVASTTKKFSYKLVKTGNVVLTASTDLRGYVV

GQVLRLQADIENQSGKDTSPVVASLLQKVSYKAKRWIYDVRTIAEVEGTGVKAWRRAQ

WQEQILVPALPQSALPGCSLIHIDYYLQVSMKAPEATVTLPLFVGNIAVNQTPLSPCPGR
```

ESSPGTLSLVVPSAPPQEEAEAVASGPHFSDPVSLSTKSHSQQQPLSAPLGSVSVTTTEPW

VQVGSPARHSLHPPLCISIGATVPYFAEGSAGPVPTTSALILPPEYSSWGYPYEAPPSYEQ

SCGAAGTDLGLIPGS

>gi|244798112|ref|NP_848495.2| arrestin domain-containing protein 1 isoform b [Mus musculus]
(SEQ ID NO: 17)
MGRVQLFEIRLSQGRVVYGPGEPLAGTVHLRLGAPLPFRAIRVTCMGSCGVSTKANDG

AWVVEESYFNSSLSLADKGSLPAGEHNFPFQFLLPATAPTSFEGPFGKIVHQVRASIDTPR

FSKDHKCSLVFYILSPLNLNSIPDIEQPNVASTTKKFSYKLVKTGNVVLTASTDLRGYVV

GQVLRLQADIENQSGKDTSPVVASLLQVSYKAKRWIYDVRTIAEVEGTGVKAWRRAQ

WQEQILVPALPQSALPGCSLIHIDYYLQVSMKAPEATVTLPLFVGNIAVNQTPLSPCPGR

ESSPGTLSLVVPSAPPQEEAEAVASGPHFSDPVSLSTKSHSQQQPLSAPLGSVSVTTTEPW

VQVGSPARHSLHPPLCISIGATVPYFAEGSAGPVPTTSALILPPEYSSWGYPYEAPPSYEQ

SCGAAGTDLGLIPGS

WW Domain Containing Cargo Proteins

Figure 2:
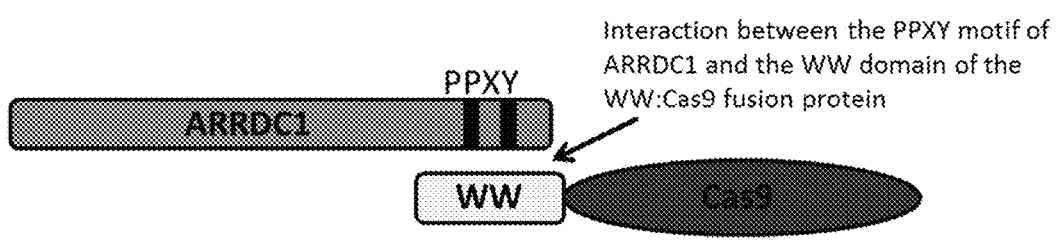
FIG. 2 is a schematic of an ARRDC1 protein containing a PPXY (SEQ ID NO: 75) motif that binds a WW domain fused to a Cas9 protein.

Aspects of the disclosure relate to ARMMs comprising a cargo protein associated with at least one WW domain. In some aspects, fusion proteins are provided that comprise a cargo protein with at least one WW domain. In some aspects, expression constructs are provided that encode a cargo protein associated with at least one WW domain. The WW domain of a cargo protein may associate with the PPXY (SEQ ID NO: 75) motif of ARRDC1, or variant thereof, to facilitate association with or inclusion of the cargo protein into an ARMM. A schematic representation of a Cas9 cargo protein fused to a WW domain that associates with the PPXY (SEQ ID NO: 75) motif of ARRDC1 can be seen in FIG. 2. In some embodiments, the cargo protein is fused to at least one, at least two, at least three, at least four, at least five, at least six, at least seven, at least eight, at least nine, at least ten, or more WW domains. The WW domain may be derived from a WW domain of the ubiquitin ligase WWP1, WWP2, Nedd4-1, Nedd4-2, Smurf1, Smurf2, ITCH, NEDL1, or NEDL2 (FIG. 1). For example, the WW domain may comprise a WW domain or WW domain variant from the amino acid sequence set forth in (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14). In certain embodiments, the cargo proteins may comprise two WW domains or WW domain variants from the human ITCH protein having the amino acid sequence:

(SEQ ID NO: 18)
PLPPGWEQRVDQHGRVYYVDHVEKRTTWDRPEPLPPGWERRVDNMGRIY
YVDHFTRTTTWQRPTL.

In other embodiments, the cargo proteins may comprise four WW domains or WW domain variants from the human ITCH protein having the amino acid sequence:

(SEQ ID NO: 19)
PLPPGWEQRVDQHGRVYYVDHVEKRTTWDRPEPLPPGWERRVDNMGRIY
YVDHFTRTTTWQRPTLESVRNYEQWQLQRSQLQGAMQQFNQRFIYGNQD

LFATSQSKEFDPLGPLPPGWEKRTDSNGRVYFVNHNTRITQWEDPRSQG

QLNEKPLPEGWEMRFTVDGIPYFVDHNRRTTTYIDPRT.

The cargo proteins, described herein, that are fused to at least one WW domain or WW domain variant are non-naturally occurring, that is, they do not exist in nature.

In some embodiments, one or more WW domains may be fused to the N-terminus of a cargo protein. In other embodiments, one or more WW domains may be fused to the C-terminus or the N-terminus of a cargo protein. In yet other embodiments, one or more WW domains may be inserted into a cargo protein. It should be appreciated that the WW domains may be configured in any number of ways to maintain function of the cargo protein, which can be tested by methods known to one of ordinary skill in the art.

The cargo protein of the inventive microvesicles may be a protein comprising at least one WW domain. For example, the cargo protein may be a WW domain containing protein or a protein fused to at least one WW domain. In some embodiments, the cargo protein may be a Cas9 protein or Cas9 variant fused to at least one WW domain. In some embodiments, the cargo protein may be a recombinant cargo protein. For example the recombinant cargo protein may be a Cas9 protein, or Cas9 variant, fused to at least one nuclear localization sequence (NLS). A NLS, as referred to herein, is an amino acid sequence that facilitates the import of a protein into the cell nucleus by nuclear transport. In some embodiments, a NLS is fused to the N-terminus of a Cas9 protein, or Cas9 variant. In some embodiments, a NLS is fused to the C-terminus of Cas9 protein, or Cas9 variant. In some embodiments, Cas9 is fused to at least one, at least two, at least three, at least four, at least five, at least six, at least seven, at least eight, at least nine, at least ten, or more nuclear localization sequences (NLSs). In certain embodiments, one NLS is fused to the N-terminus, and one NLS is fused to the C-terminus of the Cas9 protein to create a recombinant NLS:Cas9:NLS fusion protein. In certain embodiments, the Cas9 protein, or Cas9 variant, fused to at least one NLS may also be fused to at least one WW domain. It should be appreciated that, as described above, the WW domains may be configured in any number of ways such that the Cas9 protein or Cas9 variant may be loaded into an ARMM for delivery to a target cell and translocate into the nucleus of the target cell to perform its nuclease function. In certain embodiments, one or more WW domains are fused to the N-terminus of a recombinant NLS:Cas9:NLS fusion protein. In certain embodiments, one or more WW domains are fused to the C-terminus of a recombinant NLS:Cas9: NLS fusion protein. In certain embodiments, the cargo protein comprises the sequence (SEQ ID NO: 65) or (SEQ ID NO: 66). In certain embodiments, the cargo protein consists of the sequence (SEQ ID NO: 65) or (SEQ ID NO: 66). In certain embodiments, the cargo protein consists essentially of (SEQ ID NO: 65) or (SEQ ID NO: 66).

The following amino acid sequences are exemplary Cas9 cargo protein sequences that have either 2 WW domains (SEQ ID NO: 65) or 4 WW domains (SEQ ID NO: 66), which were cloned into the AgeI site of the pX330 plasmid (Addgene).

```
                                          (SEQ ID NO: 65)
MPLPPGWEQRVDQHGRVYYVDHVEKRITWDRPEPLPPGWERRVDNMGRIY

YVDHFIRITTWQRPTLIGATMDYKDHDGDYKDHDIDYKDDDDKMAPKKKR

KVGIHGVPAADKKYSIGLDIGINSVGWAVITDEYKVPSKKFKVLGNIDRH

SIKKNLIGALLFDSGETAEATRLKRTARRRYTRRKNRICYLQEIFSNEMA

KVDDSFFHRLEESFLVEEDKKHERHPIFGNIVDEVAYHEKYPTIYHLRKK

LVDSTDKADLRLIYLALAHMIKFRGHFLIEGDLNPDNSDVDKLFIQLVQT

YNQLFEENPINASGVDAKAILSARLSKSRRLENLIAQLPGEKKNGLFGNL

IALSLGLIPNEKSNFDLAEDAKLQLSKDTYDDDLDNLLAQIGDQYADLFL

AAKNLSDAILLSDILRVNTEITKAPLSASMIKRYDEHHQDLILLKALVRQ

QLPEKYKEIFFDQSKNGYAGYIDGGASQEEFYKFIKPILEKMDGTEELLV

KLNREDLLRKQRTFDNGSIPHQIHLGELHAILRRQEDFYPFLKDNREKIE

KILTFRIPYYVGPLARGNSRFAWMTRKSEETITPWNFEEVVDKGASAQSF

IERMINFDKNLPNEKVLPKHSLLYEYFTVYNELTKVKYVTEGMRKPAFLS

GEQKKAIVDLLFKINRKVIVKQLKEDYFKKIECFDSVEISGVEDRFNASL

GTYHDLLKIIKDKDFLDNEENEDILEDIVLILTLFEDREMIEERLKTYAH

LFDDKVMKQLKRRRYTGWGRLSRKLINGIRDKQSGKTILDFLKSDGFANR

NFMQLIHDDSLIFKEDIQKAQVSGQGDSLHEHIANLAGSPAIKKGILQTV

KVVDELVKVMGRHKPENIVIEMARENQTTQKGQKNSRERMKRIEEGIKEL

GSQILKEHPVENTQLQNEKLYLYYLQNGRDMYVDQELDINRLSDYDVDHI

VPQSFLKDDSIDNKVLIRSDKNRGKSDNVPSEEVVKKMKNYWRQLLNAKL

ITQRKFDNLIKAERGGLSELDKAGFIKRQLVETRQIIKHVAQILDSRMNI

KYDENDKLIREVKVITLKSKLVSDFRKDFQFYKVREINNYHHAHDAYLNA

VVGIALIKKYPKLESEFVYGDYKVYDVRKMIAKSEQEIGKATAKYFFYSN

IMNFFKTEITLANGEIRKRPLIETNGETGEIVWDKGRDFATVRKVLSMPQ

VNIVKKTEVQTGGFSKESILPKRNSDKLIARKKDWDPKKYGGFDSPIVAY

SVLVVAKVEKGKSKKLKSVKELLGITIMERSSFEKNPIDFLEAKGYKEVK

KDLIIKLPKYSLFELENGRKRMLASAGELQKGNELALPSKYVNFLYLASH

YEKLKGSPEDNEQKQLFVEQHKHYLDEIIEQISEFSKRVILADANLDKVL

SAYNKHRDKPIREQAENIIHLFTLINLGAPAAFKYFDTTIDRKRYISTKE

VLDATLIHQSITGLYETRIDLSQLGGDKRPAATKKAGQAKKKK (SEQ ID NO: 66)
MPLPPGWEQRVDQHGRVYYVDHVEKRITWDRPEPLPPGWERRVDNMGRIY

YVDHFIRITTWQRPTLESVRNYEQWQLQRSQLQGAMQQFNQRFIYGNQDL

FATSQSKEFDPLGPLPPGWEKRIDSNGRVYFVNHNTRITQWEDPRSQGQL

NEKPLPEGWEMRFTVDGIPYFVDHNRRITTYIDPRIGGGIGATMDYKDHD

GDYKDHDIDYKDDDDKMAPKKKRKVGIHGVPAADKKYSIGLDIGINSVGW

AVITDEYKVPSKKFKVLGNIDRHSIKKNLIGALLFDSGETAEATRLKRTA

RRRYTRRKNRICYLQEIFSNEMAKVDDSFFHRLEESFLVEEDKKHERHPI

FGNIVDEVAYHEKYPTIYHLRKKLVDSTDKADLRLIYLALAHMIKFRGHF

LIEGDLNPDNSDVDKLFIQLVQTYNQLFEENPINASGVDAKAILSARLSK

SRRLENLIAQLPGEKKNGLFGNLIALSLGLIPNEKSNFDLAEDAKLQLSK

DTYDDDLDNLLAQIGDQYADLFLAAKNLSDAILLSDILRVNTEITKAPLS

ASMIKRYDEHHQDLILLKALVRQQLPEKYKEIFFDQSKNGYAGYIDGGAS

QEEFYKFIKPILEKMDGTEELLVKLNREDLLRKQRTFDNGSIPHQIHLGE

LHAILRRQEDFYPFLKDNREKIEKILTFRIPYYVGPLARGNSRFAWMTRK

SEETITPWNFEEVVDKGASAQSFIERMINFDKNLPNEKVLPKHSLLYEYF

TVYNELTKVKYVTEGMRKPAFLSGEQKKAIVDLLFKINRKVIVKQLKEDY

FKKIECFDSVEISGVEDRFNASLGTYHDLLKIIKDKDFLDNEENEDILED

IVLILTLFEDREMIEERLKTYAHLFDDKVMKQLKRRRYTGWGRLSRKLIN

GIRDKQSGKTILDFLKSDGFANRNFMQLIHDDSLIFKEDIQKAQVSGQGD

SLHEHIANLAGSPAIKKGILQTVKVVDELVKVMGRHKPENIVIEMARENQ

TTQKGQKNSRERMKRIEEGIKELGSQILKEHPVENTQLQNEKLYLYYLQN

GRDMYVDQELDINRLSDYDVDHIVPQSFLKDDSIDNKVLIRSDKNRGKSD

NVPSEEVVKKMKNYWRQLLNAKLITQRKFDNLIKAERGGLSELDKAGFIK

RQLVETRQIIKHVAQILDSRMNIKYDENDKLIREVKVITLKSKLVSDFRK

DFQFYKVREINNYHHAHDAYLNAVVGIALIKKYPKLESEFVYGDYKVYDV

RKMIAKSEQEIGKATAKYFFYSNIMNFFKTEITLANGEIRKRPLIETNGE

TGEIVWDKGRDFATVRKVLSMPQVNIVKKTEVQTGGFSKESILPKRNSDK

LIARKKDWDPKKYGGFDSPIVAYSVLVVAKVEKGKSKKLKSVKELLGITI

MERSSFEKNPIDFLEAKGYKEVKKDLIIKLPKYSLFELENGRKRMLASAG

ELQKGNELALPSKYVNFLYLASHYEKLKGSPEDNEQKQLFVEQHKHYLDE

IIEQISEFSKRVILADANLDKVLSAYNKHRDKPIREQAENIIHLFTLINL

GAPAAFKYFDTTIDRKRYISTKEVLDATLIHQSITGLYETRIDLSQLGGD

KRPAATKKAGQAKKKK
```

The microvesicles described herein may further comprise a nucleic acid. In some embodiments, the microvesicles may comprise at least one guide RNA (gRNA), which may be associated, for example, with a nuclease or a nickase. As one example, a gRNA may be associated with a Cas9 cargo protein or Cas9 variant cargo protein. The gRNA may comprise a nucleotide sequence that complements a target site, which mediates binding of the nuclease/RNA complex to said target site and providing the sequence specificity of the nuclease:RNA complex. In certain embodiments, the gRNA comprises a nucleotide sequence that is complementary to any target known in the art. For example the gRNA may comprise a nucleotide sequence that is complementary to a therapeutic target (e.g., APOC3, alpha 1 antitrypsin, HBV or HIV). In certain embodiments the gRNA comprises the sequence complementary to enhanced green fluorescent protein (EGFP). For example the gRNA sequence may be encoded by the nucleic acid sequence set forth in SEQ ID NO: 69.

The following is an exemplary nucleic acid sequence that encodes a guide RNA (gRNA) that targets EGFP. The EGFP target sequence is underlined below.

(SEQ ID NO: 69)
ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGACCTA

CGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACAACAGCCACAAC

GTCTATATCATGGCCGACAAGCAGAAGAACGGCATCAAGGTGAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAG

TSG101

In certain embodiments, the inventive microvesicles further comprise TSG101. Tumor susceptibility gene 101, also referred to herein as TSG101, is a protein encoded by this gene belongs to a group of apparently inactive homologs of ubiquitin-conjugating enzymes. The protein contains a coiled-coil domain that interacts with stathmin, a cytosolic phosphoprotein implicated in tumorigenesis. TSG101 is a protein that comprises a UEV domain, and interacts with ARRDC1. Exemplary, non-limiting TSG101 protein sequences are provided herein, and additional, suitable TSG101 protein sequences, isoforms, and variants according to aspects of this invention are known in the art. It will be appreciated by those of skill in the art that this invention is not limited in this respect. Exemplary TSG101 sequences include the following:

>gi|5454140|ref|NP_006283.1| tumor susceptibility gene 101 protein [Homo sapiens]
(SEQ ID NO: 20)
MAVSESQLKKMVSKYKYRDLTVRETVNVITLYKDLKPVLDSYVFNDGSS

RELMNLTGTIPVRYRGNTYNIPICLWLLDTYPYNPPICFVKPTSSMTIK

TGKHVDANGKIYLPYLHEWKHPQSDLLGLIQVMIVVFGDEPPVFSRPIS

ASYPPYQATGPPNTSYMPGMPGGISPYPSGYPPNPSGYPGCPYPPGGPY

PATTSSQYPSQPPVTTVGPSRDGTISEDTIRASLISAVSDKLRWRMKEE

MDRAQAELNALKRTEEDLKKGHQKLEEMVTRLDQEVAEVDKNIELLKKK

DEELSSALEKMENQSENNDIDEVIIPTAPLYKQILNLYAEENAIEDTIF

YLGEALRRGVIDLDVFLKHVRLLSRKQFQLRALMQKARKTAGLSDLY

>gi|11230780|ref|NP_068684.1| tumor susceptibility gene 101 protein [Mus musculus]
(SEQ ID NO: 21)
MAVSESQLKKMMSKYKYRDLTVRQTVNVIAMYKDLKPVLDSYVFNDGSS

RELVNLTGTIPVRYRGNIYNIPICLWLLDTYPYNPPICFVKPTSSMTIK

TGKHVDANGKIYLPYLHDWKHPRSELLELIQIMIVIFGEEPPVFSRPTV

SASYPPYTATGPPNTSYMPGMPSGISAYPSGYPPNPSGYPGCPYPPAGP

YPATTSSQYPSQPPVTTVGPSRDGTISEDTIRASLISAVSDKLRWRMKE

EMDGAQAELNALKRTEEDLKKGHQKLEEMVTRLDQEVAEVDKNIELLKK

KDEELSSALEKMENQSENNDIDEVIIPTAPLYKQILNLYAEENAIEDTI

FYLGEALRRGVIDLDVFLKHVRLLSRKQFQLRALMQKARKTAGLSDLY

>gi|48374087|ref|NP_853659.2| tumor susceptibility gene 101 protein [Rattus norvegicus]
(SEQ ID NO: 22)
MAVSESQLKKMMSKYKYRDLTVRQTVNVIAMYKDLKPVLDSYVFNDGSSR

ELVNLTGTIPVRYRGNIYNIPICLWLLDTYPYNPPICFVKPTSSMTIKTG

KHVDANGKIYLPYLHDWKHPRSELLELIQIMIVIFGEEPPVFSRPTVSAS

YPPYTAAGPPNTSYLPSMPSGISAYPSGYPPNPSGYPGCPYPPAGPYPAT

TSSQYPSQPPVTTAGPSRDGTISEDTIRASLISAVSDKLRWRMKEEMDGA

QAELNALKRTEEDLKKGHQKLEEMVTRLDQEVAEVDKNIELLKKKDEELS

SALEKMENQSENNDIDEVIIPTAPLYKQILNLYAEENAIEDTIFYLGEAL

RRGVIDLDVFLKHVRLLSRKQFQLRALMQKARKTAGLSDLY

The UEV domain in these sequences includes amino acids 1-145 (underlined in the sequences above). The structure of UEV domains is known to those of skill in the art (see, e.g., Owen Pornillos et al., Structure and functional interactions of the Tsg101 UEV domain, *EMBO J.* 2002 May 15; 21(10): 2397-2406, the entire contents of which are incorporated herein by reference).

Cas9 Cargo Proteins Fused to ARRDC1 or TSG101

In some aspects, microvesicles, e.g., ARMMs, are provided that comprise an ARRDC1 protein, or variant thereof, fused to a Cas9 protein or Cas9 variant. In some aspects, microvesicles are provided that comprise a TSG101 protein, or variant thereof, fused to a Cas9 protein. In some aspects, fusion proteins are provided that comprise an ARRDC1 protein, or variant thereof, fused to a Cas9 protein and/or a TSG101 protein, or variant thereof, fused to a Cas9 protein. In some aspects, expression constructs are provided that encode an ARRDC1 protein, or variant thereof, fused to a Cas9 cargo protein and/or a TSG101 protein, or variant thereof, fused to a Cas9 cargo protein. In some embodiments, the ARRDC1 protein variant is a C-terminal ARRDC1 protein variant. In some embodiments, the ARRDC1 protein variant has a PSAP (SEQ ID NO: 74) motif and at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 contiguous amino acids of the ARRCD1 sequence. In some embodiments, the TSG101 protein variant comprises a TSG101 UEV domain. In some embodiments, the TSG101 protein variant comprises the UEV domain and comprises at least 150, at least 160, at least 170, at least 180, at least 190, at least 200, at least 210, at least 220, at least 230, at least 240, at least 250, at least 260, at least 270, at least 280, at least 290, or at least 300 contiguous amino acids of the TSG101 sequence.

Some aspects of this invention provide ARRDC1 fusion proteins that comprise an ARRDC1 protein or a variant thereof, and a Cas9 protein, or Cas9 variant, associated with the ARRDC1 protein or variant thereof. In some embodiments the Cas9 protein is covalently linked to the ARRDC1 protein, or variant thereof. The Cas9 protein, for example, may be covalently linked to the N-terminus, the C-terminus, or within the amino acid sequence of the ARRDC1 protein. In some embodiments, the ARRDC1 variant comprises a PSAP (SEQ ID NO: 74) motif or domain (comprising the amino acid sequence PSAP (SEQ ID NO: 74)). In some embodiments, the ARRDC1 protein variant comprises the PSAP (SEQ ID NO: 74) motif and at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 contiguous amino acids of the ARRCD1 sequence.

Some aspects of this invention provide TSG101 fusion proteins, comprising an TSG101 protein, or a variant thereof, and a Cas9 protein, or Cas9 variant, associated with the TSG101 protein or variant thereof. In some embodiments the Cas9 protein is covalently linked to the TSG101 protein or variant thereof. The Cas9 protein, for example, may be covalently linked to the N-terminus, the C-terminus, or within the amino acid sequence of the TSG101 protein. In some embodiments, the TSG101 variant comprises a UEV domain. UEV domains are well known to those of skill in the art, and exemplary UEV domains are described herein (e.g., the 145 N-terminal amino acids of the human, rat, and mouse TSG101 protein sequence provided herein). Additional UEV domain sequences will be apparent to those of skill in the art, and the invention is not limited in this respect. In some embodiments, the TSG101 protein variant comprises the UEV domain and at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 contiguous amino acids of the TSG101 sequence.

In certain embodiments, the Cas9 protein or Cas9 variant is fused to the C-terminus of the ARRDC1 protein or protein variant, or to the C-terminus of the TSG101 protein or protein variant. The Cas9 protein or Cas9 variant may also be fused to the N terminus of the ARRDC1 protein or protein variant, or to the N terminus of the TSG101 protein or protein variant. In some embodiments, the Cas9 protein or Cas9 variant may be within the ARRDC1 or TSG101 protein or variants thereof.

In certain embodiments, the Cas9 protein is associated with an ARRDC1 protein, an ARRDC1 variant, a TSG101 protein, or a TSG101 variant via a covalent bond. In some embodiments, the Cas9 protein is associated with the ARRDC1 protein, the ARRDC1 protein variant, the TSG101 protein, or the TSG101 protein variant via a linker. In some embodiments, the linker is a cleavable linker, for example, the linker may contain a protease recognition site. The protease recognition site of the linker may be recognized by a protease expressed in a target cell, resulting in the Cas9 protein fused to the ARRDC1 protein or variant thereof or the TSG101 protein variant thereof being released into the cytoplasm of the target cell upon uptake of the ARMM. A person skilled in the art would appreciate that any number of linkers may be used to fuse the Cas9 protein or Cas9 variant to the ARRDC1 protein or variant thereof or the TSG101 protein or variant thereof.

The linker may be cleavable or uncleavable. In some embodiments, the linker comprises an amide, ester, ether, carbon-carbon, or disulfide bond, although any covalent bond in the chemical art may be used. In some embodiments, the linker comprises a labile bond, cleavage of which results in separation of the cargo protein from the ARRDC1 protein, an ARRDC1 variant, a TSG101 protein, or a TSG101 variant. In some embodiments, the linker is cleaved under conditions found in the target cell (e.g., a specific pH, a reductive environment, or the presence of a cellular enzyme). In some embodiments, the linker is cleaved by a cellular enzyme. In some embodiments, the cellular enzyme is a cellular protease or a cellular esterase. In some embodiments, the cellular protease is a cytoplasmic protease, an endosomal protease, or an endosomal esterase. In some embodiments, the cellular enzyme is specifically expressed in a target cell or cell type, resulting in preferential or specific release of the functional cargo protein or peptide in the target cell or cell type. The target sequence of the protease may be engineered into the linker between the Cas9 fusion protein and the ARRDC1 protein or the TSG101 protein or variant thereof. The target cell may be any cell type found in a subject, including normal and pathologic or diseased cells, and the linker is cleaved by an enzyme or based on a characteristic specific for the target cell. In some embodiments, the linker comprises an amino acid sequence chosen from the group including, but not limited to, AGVF (SEQ ID NO: 77), GFLG (SEQ ID NO: 78), FK, AL, ALAL (SEQ ID NO: 79), or ALALA (SEQ ID NO: 80). Other suitable linkers will be apparent to those of skill in the art. In some embodiments, the linker is a cleavable linker. In some embodiments, the linker comprises a protease recognition site. In certain embodiments, the linker is a UV-cleavable moiety. Suitable linkers, for example, linkers comprising a protease recognition site, or linkers comprising a UV cleavable moiety are known to those of skill in the art. In some embodiments, the Cas9 fusion protein is associated with the ARRDC1 protein or variant thereof, or the TSG101 protein or variant thereof, via a sortase reaction, and the linker comprises an LPXTG (SEQ ID NO: 76) motif. Methods and reagents for conjugating proteins according to some aspects of this invention to proteins are known to those of skill in the art. Accordingly, suitable methods for conjugating and Cas9 fusion proteins to be included in an ARMM to an ARRDC1 protein or variant thereof or a TSG101 protein or variant thereof will be apparent to those of skill in the art based on this disclosure.

Any of the linkers, described herein, may be fused to the C-terminus of the ARRDC1 protein or variant thereof and the N-terminus of the Cas9 protein or Cas9 variant, thereby linking the ARRDC1 protein or variant thereof to the Cas9 protein or Cas9 variant. In other embodiments, the linker may be fused to the C-terminus of the Cas9 protein Cas9 variant and the N-terminus of the ARRDC1 protein or variant thereof. Similarly, the linker may be fused to the C-terminus of the TSG101 protein or variant thereof and the N-terminus of the Cas9 protein or Cas9 variant, thereby linking the TSG101 protein or variant thereof to the Cas9 protein or Cas9 variant. In other embodiments, the linker may be fused to the C-terminus of the Cas9 protein Cas9 variant and the N-terminus of the TSG101 protein or variant thereof.

The Cas9 protein or Cas9 variant associated with an ARRDC1 protein, an ARRDC1 protein variant, a TSG101 protein, or a TSG101 protein variant, may further include a nuclear localization sequence (NLS). In some embodiments, the Cas9 fusion protein is fused to at least one NLS. In some embodiments, one or more nuclear localization sequences (NLSs) are fused to the N-terminus of Cas9. In some embodiments, one or more NLSs are fused to the C-terminus of Cas9. In some embodiments, Cas9 is fused to at least one, at least two, at least three, at least four, at least five, at least six, at least seven, at least eight, at least nine, at least ten, or more NLSs. It should be appreciated that one or more NLSs may be fused to Cas9 to allow translocation of Cas9 fusion protein into the nucleus of a target cell. In some embodiments, the Cas9 protein fused to at least one NLS is associated with ARRDC1, an ARRDC1 protein variant, a TSG101 protein, or a TSG101 protein variant via a linker. In some embodiments, the linker contains a protease recognition site. In other embodiments, the linker contains a UV-cleavable moiety. In some embodiments, the protease recognition site is recognized by a protease expressed in a target cell, resulting in the Cas9 protein fused to at least one NLS being released from the ARRDC1 protein or variant thereof or the TSG101 protein or variant thereof into the cytoplasm, where it may translocate into the nucleus upon uptake of the ARMM.

Expression Constructs

Some aspects of this invention provide expression constructs that encode any of the Cas9 fusion proteins, ARRDC1 fusion proteins, TSG101 fusion proteins, or cargo fusion proteins described herein. In some embodiments, the expression constructs described herein may further encode a guide RNA (gRNA). It should be appreciated that the gRNA may be expressed under the control of the same promoter sequence or a different promoter sequence as any of the fusion proteins described herein. In some embodiments, an expression construct encoding a gRNA may be co-expressed with any of the expression constructs described herein.

In some embodiments, the expression constructs described herein may further encode a gene product or gene products that induce or facilitate the generation of ARMMs in cells harboring such a construct. In some embodiments, the expression constructs encode an ARRDC1 protein, or variant thereof, and/or a TSG101 protein, or variant thereof. In some embodiments, overexpression of either or both of these gene products in a cell increase the production of ARMMs in the cell, thus turning the cell into a microvesicle producing cell. In some embodiments, such an expression construct comprises at least one restriction or recombination site that allows in-frame cloning of a Cas9 sequence to be fused, either at the C-terminus, or at the N-terminus of the encoded ARRDC1 and/or TSG101 protein or variant thereof.

In some embodiments, the expression construct comprises (a) a nucleotide sequence encoding an ARRDC1 protein, or variant thereof, operably linked to a heterologous promoter, and (b) a restriction site or a recombination site positioned adjacent to the ARRDC1-encoding nucleotide sequence allowing for the insertion of a Cas9 or Cas9 variant sequence in frame with the ARRDC1-encoding nucleotide sequence. Some aspects of this invention provide an expression construct comprising (a) a nucleotide sequence encoding a TSG101 protein, or variant thereof, operably linked to a heterologous promoter, and (b) a restriction site or a recombination site positioned adjacent to the TSG101-encoding nucleotide sequence allowing for the insertion of a Cas9 or Cas9 variant sequence in frame with the TSG101-encoding nucleotide sequence.

The expression constructs may encode a cargo protein fused to at least one WW domain. In some embodiments, the expression constructs encode a Cas9 protein, or variant thereof, fused to at least one WW domain, or variant thereof. Any of the expression constructs, described herein, may encode any WW domain or variant thereof. For example, the expression constructs may comprise any nucleotide sequence capable of encoding a WW domain or variant thereof from the poly peptide sequence (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); (SEQ ID NO: 14); (SEQ ID NO: 18) or (SEQ ID NO: 19).

The expression constructs, described herein, may comprise any nucleic acid sequence capable of encoding a WW domain or variant thereof. For example a nucleic acid sequence encoding a WW domain or WW domain variant may be from the human ubiquitin ligase WWP1, WWP2, Nedd4-1, Nedd4-2, Smurf1, Smurf2, ITCH, NEDL1, or NEDL2. Exemplary nucleic acid sequences of WW domain containing proteins are listed below. It should be appreciated that any of the nucleic acids encoding WW domains or WW domain variants of the exemplary proteins may be used in the invention, described herein, and are not meant to be limiting.

```
Human WWP1 nucleic acid sequence
(uniprot.org/uniprot/Q9H0M0).
                                    (SEQ ID NO: 23)
GAATTCGCGGCCGCGTCGACCGCTTCTGTG

GCCACGGCAGATGAAACAGAAAGGCTAAAG

AGGGCTGGAGTCAGGGGACTTCTCTTCCAC

CAGCTTCACGGTGATGATATGGCATCTGCC

AGCTCTAGCCGGGCAGGAGTGGCCCTGCCT

TTTGAGAAGTCTCAGCTCACTTTGAAAGTG

GTGTCCGCAAAGCCCAAGGTGCATAATCGT

CAACCTCGAATTAACTCCTACGTGGAGGTG

GCGGTGGATGGACTCCCCAGTGAGACCAAG

AAGACTGGGAAGCGCATTGGGAGCTCTGAG

CTTCTCTGGAATGAGATCATCATTTTGAAT

GTCACGGCACAGAGTCATTTAGATTTAAAG

GTCTGGAGCTGCCATACCTTGAGAAATGAA

CTGCTAGGCACCGCATCTGTCAACCTCTCC

AACGTCTTGAAGAACAATGGGGGCAAAATG
```

GAGAACATGCAGCTGACCCTGAACCTGCAG

ACGGAGAACAAAGGCAGCGTTGTCTCAGGC

GGAAAACTGACAATTTTCCTGGACGGGCCA

ACTGTTGATCTGGGAAATGTGCCTAATGGC

AGTGCCCTGACAGATGGATCACAGCTGCCT

TCGAGAGACTCCAGTGGAACAGCAGTAGCT

CCAGAGAACCGGCACCAGCCCCCAGCACA

AACTGCTTTGGTGGAAGATCCCGGACGCAC

AGACATTCGGGTGCTTCAGCCAGAACAACC

CCAGCAACCGGCGAGCAAAGCCCCGGTGCT

CGGAGCCGGCACCGCCAGCCCGTCAAGAAC

TCAGGCCACAGTGGCTTGGCCAATGGCACA

GTGAATGATGAACCCACAACAGCCACTGAT

CCCGAAGAACCTTCCGTTGTTGGTGTGACG

TCCCCACCTGCTGCACCCTTGAGTGTGACC

CCGAATCCCAACACGACTTCTCTCCCTGCC

CCAGCCACACCGGCTGAAGGAGAGGAACCC

AGCACTTCGGGTACACAGCAGCTCCCAGCG

GCTGCCCAGGCCCCCGACGCTCTGCCTGCT

GGATGGAACAGCGAGAGCTGCCCAACGGA

CGTGTCTATTATGTTGACCACAATACCAAG

ACCACCACCTGGGAGCGGCCCCTTCCTCCA

GGCTGGGAAAAACGCACAGATCCCCGAGGC

AGGTTTTACTATGTGGATCACAATACTCGG

ACCACCACCTGGCAGCGTCCGACCGCGGAG

TACGTGCGCAACTATGAGCAGTGGCAGTCG

CAGCGGAATCAGCTCCAGGGGGCCATGCAG

CACTTCAGCCAAAGATTCCTATACCAGTTT

TGGAGTGCTTCGACTGACCATGATCCCCTG

GGCCCCCTCCCTCCTGGTTGGGAGAAAAGA

CAGGACAATGGACGGGTGTATTACGTGAAC

CATAACACTCGCACGACCCAGTGGGAGGAT

CCCCGGACCCAGGGGATGATCCAGGAACCA

GCTTTGCCCCCAGGATGGGAGATGAAATAC

ACCAGCGAGGGGTGCGATACTTTGTGGAC

CACAATACCCGCACCACCACCTTTAAGGAT

CCTCGCCCGGGGTTTGAGTCGGGGACGAAG

CAAGGTTCCCCTGGTGCTTATGACCGCAGT

TTTCGGTGGAAGTATCACCAGTTCCGTTTC

CTCTGCCATTCAAATGCCCTACCTAGCCAC

GTGAAGATCAGCGTTTCCAGGCAGACGCTT

TTCGAAGATTCCTTCCAACAGATCATGAAC

ATGAAACCCTATGACCTGCGCCGCCGGCTT

TACATCATCATGCGTGGCGAGGAGGGCCTG

GACTATGGGGCATCGCCAGAGAGTGGTTT

TTCCTCCTGTCTCACGAGGTGCTCAACCCT

ATGTATTGTTTATTTGAATATGCCGGAAAG

AACAATTACTGCCTGCAGATCAACCCCGCC

TCCTCCATCAACCCGGACCACCTCACCTAC

TTTCGCTTTATAGGCAGATTCATCGCCATG

GCGCTGTACCATGGAAAGTTCATCGACACG

GGCTTCACCCTCCCTTTCTACAAGCGGATG

CTCAATAAGAGACCAACCCTGAAAGACCTG

GAGTCCATTGACCCTGAGTTCTACAACTCC

ATTGTCTGGATCAAAGAGAACAACCTGGAA

GAATGTGGCCTGGAGCTGTACTTCATCCAG

GACATGGAGATACTGGGCAAGGTGACGACC

CACGAGCTGAAGGAGGGCGGCGAGAGCATC

CGGGTCACGGAGGAGAACAAGGAAGAGTAC

ATCATGCTGCTGACTGACTGGCGTTTCACC

CGAGGCGTGGAAGAGCAGACCAAAGCCTTC

CTGGATGGCTTCAACGAGGTGGCCCCGCTG

GAGTGGCTGCGCTACTTTGACGAGAAAGAG

CTGGAGCTGATGCTGTGCGGCATGCAGGAG

ATAGACATGAGCGACTGGCAGAAGAGCACC

ATCTACCGGCACTACACCAAGAACAGCAAG

CAGATCCAGTGGTTCTGGCAGGTGGTGAAG

GAGATGGACAACGAGAAGAGGATCCGGCTG

CTGCAGTTTGTCACCGGTACCTGCCGCCTG

CCCGTCGGGGGATTTGCCGAACTCATCGGT

AGCAACGGACCACAGAAGTTTTGCATTGAC

AAAGTTGGCAAGGAAACCTGGCTGCCCAGA

AGCCACACCTGCTTCAACCGTCTGGATCTT

CCACCCTACAAGAGCTACGAACAGCTGAGA

GAGAAGCTGCTGTATGCCATTGAGGAGACC

GAGGGCTTTGGACAGGAGTAACCGAGGCCG

CCCCTCCCACGCCCCCAGCGCACATGTAG

TCCTGAGTCCTCCCTGCCTGAGAGGCCACT

GGCCCCGCAGCCCTTGGGAGGCCCCCGTGG

ATGTGGCCCTGTGTGGGACCACACTGTCAT

CTCGCTGCTGGCAGAAAAGCCTGATCCCAG

GAGGCCCTGCAGTTCCCCCGACCCGCGGAT
GGCAGTCTGGAATAAAGCCCCCTAGTTGCC
TTTGGCCCCACCTTTGCAAAGTTCCAGAGG
GCTGACCCTCTCTGCAAAACTCTCCCCTGT
CCTCTAGACCCCACCCTGGGTGTATGTGAG
TGTGCAAGGGAAGGTGTTGCATCCCCAGGG
GCTGCCGCAGAGGCCGGAGACCTCCTGGAC
TAGTTCGGCGAGGAGACTGGCCACTGGGGG
TGGCTGTTCGGGACTGAGAGCGCCAAGGGT
CTTTGCCAGCAAAGGAGGTTCTGCCTGTAA
TTGAGCCTCTCTGATGATGGAGATGAAGTG
AAGGTCTGAGGGACGGGCCCTGGGGCTAGG
CCATCTCTGCCTGCCTCCCTAGCAGGCGCC
AGCGGTGGAGGCTGAGTCGCAGGACACATG
CCGGCCAGTTAATTCATTCTCAGCAAATGA
AGGTTTGTCTAAGCTGCCTGGGTATCCACG
GGACAAAAACAGCAAACTCCCTCCAGACTT
TGTCCATGTTATAAACTTGAAAGTTGGTTG
TTGTTTGTTAGGTTTGCCAGGTTTTTTTGT
TTACGCCTGCTGTCACTTTCCTGTC

Human WWP2 nucleic acid sequence
(uniprot.org/uniprot/O00308).
(SEQ ID NO: 24)
GAATTCGCGGCCGCGTCGACCGCTTCTGTG
GCCACGGCAGATGAAACAGAAAGGCTAAAG
AGGGCTGGAGTCAGGGGACTTCTCTTCCAC
CAGCTTCACGGTGATGATATGGCATCTGCC
AGCTCTAGCCGGGCAGGAGTGGCCCTGCCT
TTTGAGAAGTCTCAGCTCACTTTGAAAGTG
GTGTCCGCAAAGCCCAAGGTGCATAATCGT
CAACCTCGAATTAACTCCTACGTGGAGGTG
GCGGTGGATGGACTCCCCAGTGAGACCAAG
AAGACTGGGAAGCGCATTGGGAGCTCTGAG
CTTCTCTGGAATGAGATCATCATTTTGAAT
GTCACGGCACAGAGTCATTTAGATTTAAAG
GTCTGGAGCTGCCATACCTTGAGAAATGAA
CTGCTAGGCACCGCATCTGTCAACCTCTCC
AACGTCTTGAAGAACAATGGGGGCAAAATG
GAGAACATGCAGCTGACCCTGAACCTGCAG
ACGGAGAACAAAGGCAGCGTTGTCTCAGGC
GGAAAACTGACAATTTTCCTGGACGGGCCA
ACTGTTGATCTGGGAAATGTGCCTAATGGC AGTGCCCTGACAGATGGATCACAGCTGCCT
TCGAGAGACTCCAGTGGAACAGCAGTAGCT
CCAGAGAACCGGCACCAGCCCCCCAGCACA
AACTGCTTTGGTGGAAGATCCCGGACGCAC
AGACATTCGGGTGCTTCAGCCAGAACAACC
CCAGCAACCGGCGAGCAAAGCCCCGGTGCT
CGGAGCCGGCACCGCCAGCCCGTCAAGAAC
TCAGGCCACAGTGGCTTGGCCAATGGCACA
GTGAATGATGAACCCACAACAGCCACTGAT
CCCGAAGAACCTTCCGTTGTTGGTGTGACG
TCCCCACCTGCTGCACCCTTGAGTGTGACC
CCGAATCCCAACACGACTTCTCTCCCTGCC
CCAGCCACACCGGCTGAAGGAGAGGAACCC
AGCACTTCGGGTACACAGCAGCTCCCAGCG
GCTGCCCAGGCCCCCGACGCTCTGCCTGCT
GGATGGGAACAGCGAGAGCTGCCCAACGGA
CGTGTCTATTATGTTGACCACAATACCAAG
ACCACCACCTGGGAGCGGCCCCTTCCTCCA
GGCTGGGAAAAACGCACAGATCCCCGAGGC
AGGTTTTACTATGTGGATCACAATACTCGG
ACCACCACCTGGCAGCGTCCGACCGCGGAG
TACGTGCGCAACTATGAGCAGTGGCAGTCG
CAGCGGAATCAGCTCCAGGGGGCCATGCAG
CACTTCAGCCAAAGATTCCTATACCAGTTT
TGGAGTGCTTCGACTGACCATGATCCCCTG
GGCCCCCTCCCTCCTGGTTGGGAGAAAAGA
CAGGACAATGGACGGGTGTATTACGTGAAC
CATAACACTCGCACGACCCAGTGGGAGGAT
CCCCGGACCCAGGGGATGATCCAGGAACCA
GCTTTGCCCCCAGGATGGGAGATGAAATAC
ACCAGCGAGGGGTGCGATACTTTGTGGAC
CACAATACCCGCACCACCACCTTTAAGGAT
CCTCGCCCGGGGTTTGAGTCGGGGACGAAG
CAAGGTTCCCCTGGTGCTTATGACCGCAGT
TTTCGGTGGAAGTATCACCAGTTCCGTTTC
CTCTGCCATTCAAATGCCCTACCTAGCCAC
GTGAAGATCAGCGTTTCCAGGCAGACGCTT
TTCGAAGATTCCTTCCAACAGATCATGAAC
ATGAAACCCTATGACCTGCGCCGCCGGCTT
TACATCATCATGCGTGGCGAGGAGGGCCTG -continued

```
GACTATGGGGGCATCGCCAGAGAGTGGTTT
TTCCTCCTGTCTCACGAGGTGCTCAACCCT
ATGTATTGTTTATTTGAATATGCCGGAAAG
AACAATTACTGCCTGCAGATCAACCCCGCC
TCCTCCATCAACCCGGACCACCTCACCTAC
TTTCGCTTTATAGGCAGATTCATCGCCATG
GCGCTGTACCATGGAAAGTTCATCGACACG
GGCTTCACCCTCCCTTTCTACAAGCGGATG
CTCAATAAGAGACCAACCCTGAAAGACCTG
GAGTCCATTGACCCTGAGTTCTACAACTCC
ATTGTCTGGATCAAAGAGAACAACCTGGAA
GAATGTGGCCTGGAGCTGTACTTCATCCAG
GACATGGAGATACTGGGCAAGGTGACGACC
CACGAGCTGAAGGAGGGCGGCGAGAGCATC
CGGGTCACGGAGGAGAACAAGGAAGAGTAC
ATCATGCTGCTGACTGACTGGCGTTTCACC
CGAGGCGTGGAAGAGCAGACCAAAGCCTTC
CTGGATGGCTTCAACGAGGTGGCCCCGCTG
GAGTGGCTGCGCTACTTTGACGAGAAAGAG
CTGGAGCTGATGCTGTGCGGCATGCAGGAG
ATAGACATGAGCGACTGGCAGAAGAGCACC
ATCTACCGGCACTACACCAAGAACAGCAAG
CAGATCCAGTGGTTCTGGCAGGTGGTGAAG
GAGATGGACAACGAGAAGAGGATCCGGCTG
CTGCAGTTTGTCACCGGTACCTGCCGCCTG
CCCGTCGGGGGATTTGCCGAACTCATCGGT
AGCAACGGACCACAGAAGTTTTGCATTGAC
AAAGTTGGCAAGGAAACCTGGCTGCCCAGA
AGCCACACCTGCTTCAACCGTCTGGATCTT
CCACCCTACAAGAGCTACGAACAGCTGAGA
GAGAAGCTGCTGTATGCCATTGAGGAGACC
GAGGGCTTTGGACAGGAGTAACCGAGGCCG
CCCCTCCCACGCCCCCAGCGCACATGTAG
TCCTGAGTCCTCCCTGCCTGAGAGGCCACT
GGCCCCGCAGCCCTTGGGAGGCCCCCGTGG
ATGTGGCCCTGTGTGGGACCACACTGTCAT
CTCGCTGCTGGCAGAAAAGCCTGATCCCAG
GAGGCCCTGCAGTTCCCCCGACCCGCGGAT
GGCAGTCTGGAATAAAGCCCCCTAGTTGCC
TTTGGCCCCACCTTTGCAAAGTTCCAGAGG
GCTGACCCTCTCTGCAAAACTCTCCCCTGT
CCTCTAGACCCCACCCTGGGTGTATGTGAG
TGTGCAAGGGAAGGTGTTGCATCCCCAGGG
GCTGCCGCAGAGGCCGGAGACCTCCTGGAC
TAGTTCGGCGAGGAGACTGGCCACTGGGGG
TGGCTGTTCGGGACTGAGAGCGCCAAGGGT
CTTTGCCAGCAAAGGAGGTTCTGCCTGTAA
TTGAGCCTCTCTGATGATGGAGATGAAGTG
AAGGTCTGAGGGACGGGCCCTGGGGCTAGG
CCATCTCTGCCTGCCTCCCTAGCAGGCGCC
AGCGGTGGAGGCTGAGTCGCAGGACACATG
CCGGCCAGTTAATTCATTCTCAGCAAATGA
AGGTTTGTCTAAGCTGCCTGGGTATCCACG
GGACAAAAACAGCAAACTCCCTCCAGACTT
TGTCCATGTTATAAACTTGAAAGTTGGTTG
TTGTTTGTTAGGTTTGCCAGGTTTTTTTGT
TTACGCCTGCTGTCACTTTCCTGTC
```

Human Nedd4-1 nucleic acid sequence (uniprot.org/uniprot/P46934).
(SEQ ID NO: 25)

```
ACAGTTGCCTGCCCTGGGCGGGGCGAGCG
CGTCCGGTTTGCTGGAAGCGTTCGGAAATG
GCAACTTGCGCGGTGGAGGTGTTCGGGCTC
CTGGAGGACGAGGAAAATTCACGAATTGTG
AGAGTAAGAGTTATAGCCGGAATAGGCCTT
GCCAAGAAGGATATATTGGGAGCTAGTGAT
CCTTACGTGAGAGTGACGTTATATGACCCA
ATGAATGGAGTTCTTACAAGTGTGCAAACA
AAAACCATTAAAAAGAGTTTGAATCCAAAG
TGGAATGAAGAAATATTATTCAGAGTTCAT
CCTCAGCAGCACCGGCTTCTTTTTGAAGTG
TTTGACGAAAACCGATTGACAAGAGATGAT
TTCCTAGGTCAAGTGGATGTTCCACTTTAT
CCATTACCGACAGAAAATCCAAGATTGGAG
AGACCATATACATTTAAGGATTTGTTCTT
CATCCAAGAAGTCACAAATCAAGAGTTAAA
GGTTATCTGAGACTAAAAATGACTTATTTA
CCTAAAACCAGTGGCTCAGAAGATGATAAT
GCAGAACAGGCTGAGGAATTAGAGCCTGGC
TGGGTTGTTTTGGACCAACCAGATGCTGCT
TGCCATTTGCAGCAACAACAAGAACCTTCT
CCTCTACCTCCAGGGTGGGAAGAGAGGCAG
GATATCCTTGGAAGGACCTATTATGTAAAC
```

-continued

CATGAATCTAGAAGAACACAGTGGAAAAGA
CCAACCCCTCAGGACAACCTAACAGATGCT
GAGAATGGCAACATTCAACTGCAAGCACAA
CGTGCATTTACCACCAGGCGGCAGATATCC
GAGGAAACAGAAAGTGTTGACAACCAAGAG
TCTTCCGAGAACTGGGAAATTATAAGAGAA
GATGAAGCCACCATGTATAGCAGCCAGGCC
TTCCCATCACCTCCACCGTCAAGTAACTTG
GATGTTCCAACTCATCTTGCAGAAGAATTG
AATGCCAGACTCACCATTTTTGGAAATTCA
GCCGTGAGCCAGCCAGCATCGAGCTCAAAT
CATTCCAGCAGAAGAGGCAGCTTACAAGCC
TATACTTTTGAGGAACAACCTACACTTCCT
GTGCTTTTGCCTACTTCATCTGGATTACCA
CCAGGTTGGGAAGAAAAACAAGATGAAAGA
GGAAGATCATATTATGTAGATCACAATTCC
AGAACGACTACTTGGACAAAGCCCACTGTA
CAGGCCACAGTGGAGACCAGTCAGCTGACC
TCAAGCCAGAGTTCTGCAGGCCCTCAATCA
CAAGCCTCCACCAGTGATTCAGGCCAGCAG
GTGACCCAGCCATCTGAAATTGAGCAAGGA
TTCCTTCCTAAAGGCTGGGAAGTCCGGCAT
GCACCAAATGGGAGGCCTTTCTTTATTGAC
CACAACACTAAAACCACCACCTGGGAAGAT
CCAAGATTGAAAATTCCAGCCCATCTGAGA
GGAAAGACATCACTTGATACTTCCAATGAT
CTAGGGCCTTTACCTCCAGGATGGGAAGAG
AGAACTCACACAGATGGAAGAATCTTCTAC
ATAAATCACAATATAAAAAGAACACAATGG
GAAGATCCTCGGTTGGAGAATGTAGCAATA
ACTGGACCAGCAGTGCCCTACTCCAGGGAT
TACAAAAGAAAGTATGAGTTCTTCCGAAGA
AAGTTGAAGAAGCAGAATGACATTCCAAAC
AAATTTGAAATGAAACTTCGCCGAGCAACT
GTTCTTGAAGACTCTTACCGGAGAATTATG
GGTGTCAAGAGAGCAGACTTCCTGAAGGCT
CGACTGTGGATTGAGTTTGATGGTGAAAAG
GGATTGGATTATGGAGGAGTTGCCAGAGAA
TGGTTCTTCCTGATCTCAAAGGAAATGTTT
AACCCTTATTATGGGTTGTTTGAATATTCT

-continued

GCTACGGACAATTATACCCTACAGATAAAT
CCAAACTCTGGATTGTGTAACGAAGATCAC
CTCTCTTACTTCAAGTTTATTGGTCGGGTA
GCTGGAATGGCAGTTTATCATGGCAAACTG
TTGGATGGTTTTTTCATCCGCCCATTTTAC
AAGATGATGCTTCACAAACCAATAACCCTT
CATGATATGGAATCTGTGGATAGTGAATAT
TACAATTCCCTAAGATGGATTCTTGAAAAT
GACCCAACAGAATTGGACCTCAGGTTTATC
ATAGATGAAGAACTTTTTGGACAGACACAT
CAACATGAGCTGAAAAATGGTGGATCAGAA
ATAGTTGTCACCAATAAGAACAAAAAGGAA
TATATTTATCTTGTAATACAATGGCGATTT
GTAAACCGAATCCAGAAGCAAATGGCTGCT
TTTAAAGAGGGATTCTTTGAACTAATACCA
CAGGATCTCATCAAAATTTTTGATGAAAAT
GAACTAGAGCTTCTTATGTGTGGACCGGGA
GATGTTGATGTGAATGACTGGAGGGAACAT
ACAAAGTATAAAAATGGCTACAGTGCAAAT
CATCAGGTTATACAGTGGTTTTGGAAGGCT
GTTTTAATGATGGATTCAGAAAAAAGAATA
AGATTACTTCAGTTTGTCACTGGCACATCT
CGGGTGCCTATGAATGGATTTGCTGAACTA
TACGGTTCAAATGGACCACAGTCATTTACA
GTTGAACAGTGGGGTACTCCTGAAAAGCTG
CCAAGAGCTCATACCTGTTTTAATCGCCTG
GACTTGCCACCTTATGAATCATTTGAAGAA
TTATGGGATAAACTTCAGATGGCAATTGAA
AACACCCAGGGCTTTGATGGAGTTGATTAG
ATTACAAATAACAATCTGTAGTGTTTTTAC
TGCCATAGTTTTATAACCAAAATCTTGACT
TAAAATTTTCCGGGGAACTACTAAAATGTG
GCCACTGAGTCTTCCCAGATCTTGAAGAAA
ATCATATAAAAAGCATTTGAAGAAATAGTA
CGAC

Human Nedd4-2 nucleic acid sequence
(>gi|345478679|ref|NM_015277.5| Homo
sapiens neural precursor cell expressed,
developmentally down-regulated 4-like,
E3 ubiquitin protein ligase (NEDD4L),
transcript variant d, mRNA).
(SEQ ID NO: 26)
ATGGCGACCGGGCTCGGGGAGCCGGTCTATGG
ACTTTCCGAAGACGAGGGAGAGTCCCGTATTCTCA

```
GAGTAAAAGTTGTTTCTGGAATTGATCTCGCCAAA
AAGGACATCTTTGGAGCCAGTGATCCGTATGTGAA
ACTTTCATTGTACGTAGCGGATGAGAATAGAGAAC
TTGCTTTGGTCCAGACAAAAACAATTAAAAAGACA
CTGAACCCAAAATGGAATGAAGAATTTTATTTCAG
GGTAAACCCATCTAATCACAGACTCCTATTTGAAG
TATTTGACGAAAATAGACTGACACGAGACGACTTC
CTGGGCCAGGTGGACGTGCCCCTTAGTCACCTTCC
GACAGAAGATCCAACCATGGAGCGACCCTATACAT
TTAAGGACTTTCTCCTCAGACCAAGAAGTCATAAG
TCTCGAGTTAAGGGATTTTTGCGATTGAAAATGGC
CTATATGCCAAAAAATGGAGGTCAAGATGAAGAAA
ACAGTGACCAGAGGGATGACATGGAGCATGGATGG
GAAGTTGTTGACTCAAATGACTCGGCTTCTCAGCA
CCAAGAGGAACTTCCTCCTCCTCCTCTGCCTCCCG
GGTGGGAAGAAAAAGTGGACAATTTAGGCCGAACT
TACTATGTCAACCAACAACCGGACCACTCAGTG
GCACAGACCAAGCCTGATGGACGTGTCCTCGGAGT
CGGACAATAACATCAGACAGATCAACCAGGAGGCA
GCACACCGGCGCTTCCGCTCCCGCAGGCACATCAG
CGAAGACTTGGAGCCCGAGCCCTCGGAGGGCGGGG
ATGTCCCCGAGCCTTGGGAGACCATTTCAGAGGAA
GTGAATATCGCTGGAGACTCTCTCGGTCTGGCTCT
GCCCCCACCACCGGCCTCCCCAGGATCTCGGACCA
GCCCTCAGGAGCTGTCAGAGGAACTAAGCAGAAGG
CTTCAGATCACTCCAGACTCCAATGGGGAACAGTT
CAGCTCTTTGATTCAAAGAGAACCCTCCTCAAGGT
TGAGGTCATGCAGTGTCACCGACGCAGTTGCAGAA
CAGGGCCATCTACCACCGCCATCAGTGGCCTATGT
ACATACCACGCCGGGTCTGCCTTCAGGCTGGGAAG
AAAGAAAAGATGCTAAGGGGCGCACATACTATGTC
AATCATAACAATCGAACCACAACTTGGACTCGACC
TATCATGCAGCTTGCAGAAGATGGTGCGTCCGGAT
CAGCCACAAACAGTAACAACCATCTAATCGAGCCT
CAGATCCGCCGGCCTCGTAGCCTCAGCTCGCCAAC
AGTAACTTTATCTGCCCCGCTGGAGGGTGCCAAGG
ACTCACCCGTACGTCGGGCTGTGAAAGACACCCTT
TCCAACCCACAGTCCCCACAGCCATCACCTTACAA
CTCCCCCAAACCACAACACAAAGTCACACAGAGCT
TCTTGCCACCCGGCTGGGAAATGAGGATAGCGCCA
AACGGCCGGCCCTTCTTCATTGATCATAACACAAA
GACTACAACCTGGGAAGATCCACGTTTGAAATTTC
CAGTACATATGCGGTCAAAGACATCTTTAAACCCC
AATGACCTTGGCCCCCTTCCTCCTGGCTGGGAAGA
AAGAATTCACTTGGATGGCCGAACGTTTTATATTG
ATCATAATAGCAAAATTACTCAGTGGGAAGACCCA
AGACTGCAGAACCCAGCTATTACTGGTCCGGCTGT
CCCTTACTCCAGAGAATTTAAGCAGAAATATGACT
ACTTCAGGAAGAAATTAAAGAAACCTGCTGATATC
CCCAATAGGTTTGAAATGAAACTTCACAGAAATAA
CATATTTGAAGAGTCCTATCGGAGAATTATGTCCG
TGAAAAGACCAGATGTCCTAAAAGCTAGACTGTGG
ATTGAGTTTGAATCAGAGAAAGGTCTTGACTATGG
GGGTGTGGCCAGAGAATGGTTCTTCTTACTGTCCA
AAGAGATGTTCAACCCCTACTACGGCCTCTTTGAG
TACTCTGCCACGGACAACTACACCCTTCAGATCAA
CCCTAATTCAGGCCTCTGTAATGAGGATCATTTGT
CCTACTTCACTTTTATTGGAAGAGTTGCTGGTCTG
GCCGTATTTCATGGGAAGCTCTTAGATGGTTTCTT
CATTAGACCATTTTACAAGATGATGTTGGGAAAGC
AGATAACCCTGAATGACATGGAATCTGTGGATAGT
GAATATTACAACTCTTTGAAATGGATCCTGGAGAA
TGACCCTACTGAGCTGGACCTCATGTTCTGCATAG
ACGAAGAAAACTTTGGACAGACATATCAAGTGGAT
TTGAAGCCCAATGGGTCAGAAATAATGGTCACAAA
TGAAAACAAAAGGGAATATATCGACTTAGTCATCC
AGTGGAGATTTGTGAACAGGGTCCAGAAGCAGATG
AACGCCTTCTTGGAGGGATTCACAGAACTACTTCC
TATTGATTTGATTAAAATTTTTGATGAAAATGAGC
TGGAGTTGCTCATGTGCGGCCTCGGTGATGTGGAT
GTGAATGACTGGAGACAGCATTCTATTTACAAGAA
CGGCTACTGCCCAAACCACCCCGTCATTCAGTGGT
TCTGGAAGGCTGTGCTACTCATGGACGCCGAAAAG
CGTATCCGGTTACTGCAGTTTGTCACAGGGACATC
GCGAGTACCTATGAATGGATTTGCCGAACTTTATG
GTTCCAATGGTCCTCAGCTGTTTACAATAGAGCAA
TGGGGCAGTCCTGAGAAACTGCCCAGAGCTCACAC
ATGCTTTAATCGCCTTGACTTACCTCCATATGAAA
CCTTTGAAGATTTACGAGAGAAACTTCTCATGGCC
GTGGAAAATGCTCAAGGATTTGAAGGGGTGGATTA
A
```

Human Smurf1 nucleic acid sequence
(uniprot.org/uniprot/Q9HCE7).
(SEQ ID NO: 27)

ATGTCGAACCCCGGGACACGCAGGAACGGC

TCCAGCATCAAGATCCGTCTGACAGTGTTA

TGTGCCAAGAACCTTGCAAAGAAAGACTTC

TTCAGGCTCCCTGACCCTTTTGCAAAGATT

GTCGTGGATGGGTCTGGGCAGTGCCACTCA

ACCGACACTGTGAAAAACACATTGGACCCA

AAGTGGAACCAGCACTATGATCTATATGTT

GGGAAAACGGATTCGATAACCATTAGCGTG

TGGAACCATAAGAAAATTCACAAGAAACAG

GGAGCTGGCTTCCTGGGCTGTGTGCGGCTG

CTCTCCAATGCCATCAGCAGATTAAAAGAT

ACCGGATACCAGCGTTTGGATCTATGCAAA

CTAAACCCCTCAGATACTGATGCAGTTCGT

GGCCAGATAGTGGTCAGTTTACAGACACGA

GACAGAATAGGAACCGGCGGCTCGGTGGTG

GACTGCAGAGGACTGTTAGAAAATGAAGGA

ACGGTGTATGAAGACTCCGGGCCTGGGAGG

CCGCTCAGCTGCTTCATGGAGGAACCAGCC

CCTTACACAGATAGCACCGGTGCTGCTGCT

GGAGGAGGGAATTGCAGGTTCGTGGAGTCC

CCAAGTCAAGATCAAAGACTTCAGGCACAG

CGGCTTCGAAACCCTGATGTGCGAGGTTCA

CTACAGACGCCCCAGAACCGACCACACGGC

CACCAGTCCCCGGAACTGCCCGAAGGCTAC

GAACAAAGAACAACAGTCCAGGGCCAAGTT

TACTTTTTGCATACACAGACTGGAGTTAGC

ACGTGGCACGACCCCAGGATACCAAGTCCC

TCGGGGACCATTCCTGGGGAGATGCAGCT

TTTCTATACGAATTCCTTCTACAAGGCCAT

ACATCTGAGCCCAGAGACCTTAACAGTGTG

AACTGTGATGAACTTGGACCACTGCCGCCA

GGCTGGGAAGTCAGAAGTACAGTTTCTGGG

AGGATATATTTTGTAGATCATAATAACCGA

ACAACCCAGTTTACAGACCCAAGGTTACAC

CACATCATGAATCACCAGTGCCAACTCAAG

GAGCCCAGCCAGCCGCTGCCACTGCCCAGT

GAGGGCTCTCTGGAGGACGAGGAGCTTCCT

GCCCAGAGATACGAAAGAGATCTAGTCCAG

AAGCTGAAAGTCCTCAGACACGAACTGTCG

CTTCAGCAGCCCCAAGCTGGTCATTGCCGC

ATCGAAGTGTCCAGAGAAGAAATCTTTGAG

GAGTCTTACCGCCAGATAATGAAGATGCGA

CCGAAAGACTTGAAAAAACGGCTGATGGTG

AAATTCCGTGGGGAAGAAGGTTTGGATTAC

GGTGGTGTGGCCAGGGAGTGGCTTTACTTG

CTGTGCCATGAAATGCTGAATCCTTATTAC

GGGCTCTTCCAGTATTCTACGGACAATATT

TACATGTTGCAAATAAATCCGGATTCTTCA

ATCAACCCCGACCACTTGTCTTATTTCCAC

TTTGTGGGGCGGATCATGGGGCTGGCTGTG

TTCCATGGACACTACATCAACGGGGGCTTC

ACAGTGCCCTTCTACAAGCAGCTGCTGGGG

AAGCCCATCCAGCTCTCAGATCTGGAATCT

GTGGACCCAGAGCTGCATAAGAGCTTGGTG

TGGATCCTAGAGAACGACATCACGCCTGTA

CTGGACCACACCTTCTGCGTGGAACACAAC

GCCTTCGGGCGGATCCTGCAGCATGAACTG

AAACCCAATGGCAGAAATGTGCCAGTCACA

GAGGAGAATAAGAAAGAATACGTCCGGTTG

TATGTAAACTGGAGGTTTATGAGAGGAATC

GAAGCCCAGTTCTTAGCTCTGCAGAAGGGG

TTCAATGAGCTCATCCCTCAACATCTGCTG

AAGCCTTTTGACCAGAAGGAACTGGAGCTG

ATCATAGGCGGCCTGGATAAAATAGACTTG

AACGACTGGAAGTCGAACACGCGGCTGAAG

CACTGTGTGGCCGACAGCAACATCGTGCGG

TGGTTCTGGCAAGCGGTGGAGACGTTCGAT

GAAGAAAGGAGGGCCAGGCTCCTGCAGTTT

GTGACTGGGTCCACGCGAGTCCCGCTCCAA

GGCTTCAAGGCTTTGCAAGGTTCTACAGGC

GCGGCAGGGCCCCGGCTGTTCACCATCCAC

CTGATAGACGCGAACACAGACAACCTTCCG

AAGGCCCATACCTGCTTTAACCGGATCGAC

ATTCCACCATATGAGTCCTATGAGAAGCTC

TACGAGAAGCTGCTGACAGCCGTGGAGGAG

ACCTGCGGGTTTGCTGTGGAGTGA

Human Smurf2 nucleic acid sequence
(uniprot.org/uniprot/Q9HAU4).
(SEQ ID NO: 28)

ATGTCTAACCCCGGACGCCGGAGGAACGGG

CCCGTCAAGCTGCGCGCCTGACAGTACTCTGT

```
GCAAAAAACCTGGTGAAAAAGGATTTTTC
CGACTTCCTGATCCATTTGCTAAGGTGGTG
GTTGATGGATCTGGGCAATGCCATTCTACA
GATACTGTGAAGAATACGCTTGATCCAAAG
TGGAATCAGCATTATGACCTGTATATTGGA
AAGTCTGATTCAGTTACGATCAGTGTATGG
AATCACAAGAAGATCCATAAGAAACAAGGT
GCTGGATTTCTCGGTTGTGTTCGTCTTCTT
TCCAATGCCATCAACCGCCTCAAAGACACT
GGTTATCAGAGGTTGGATTTATGCAAACTC
GGGCCAAATGACAATGATACAGTTAGAGGA
CAGATAGTAGTAAGTCTTCAGTCCAGAGAC
CGAATAGGCACAGGAGGACAAGTTGTGGAC
TGCAGTCGTTTATTTGATAACGATTTACCA
GACGGCTGGGAAGAAAGGAGAACCGCCTCT
GGAAGAATCCAGTATCTAAACCATATAACA
AGAACTACGCAATGGGAGCGCCCAACACGA
CCGGCATCCGAATATTCTAGCCCTGGCAGA
CCTCTTAGCTGCTTTGTTGATGAGAACACT
CCAATTAGTGGAACAAATGGTGCAACATGT
GGACAGTCTTCAGATCCCAGGCTGGCAGAG
AGGAGAGTCAGGTCACAACGACATAGAAAT
TACATGAGCAGAACACATTTACATACTCCT
CCAGACCTACCAGAAGGCTATGAACAGAGG
ACAACGCAACAAGGCCAGGTGTATTTCTTA
CATACACAGACTGGTGTGAGCACATGGCAT
GATCCAAGAGTGCCCAGGGATCTTAGCAAC
ATCAATTGTGAAGAGCTTGGTCCATTGCCT
CCTGGATGGGAGATCCGTAATACGGCAACA
GGCAGAGTTTATTTCGTTGACCATAACAAC
AGAACAACACAATTTACAGATCCTCGGCTG
TCTGCTAACTTGCATTTAGTTTTAAATCGG
CAGAACCAATTGAAAGACCAACAGCAACAG
CAAGTGGTATCGTTATGTCCTGATGACACA
GAATGCCTGACAGTCCCAAGGTACAAGCGA
GACCTGGTTCAGAAACTAAAAATTTTGCGG
CAAGAACTTTCCCAACAACAGCCTCAGGCA
GGTCATTGCCGCATTGAGGTTTCCAGGGAA
GAGATTTTTGAGGAATCATATCGACAGGTC
ATGAAAATGAGACCAAAAGATCTCTGGAAG
CGATTAATGATAAAATTTCGTGGAGAAGAA
GGCCTTGACTATGGAGGCGTTGCCAGGGAA
TGGTTGTATCTCTTGTCACATGAAATGTTG
AATCCATACTATGGCCTCTTCCAGTATTCA
AGAGATGATATTTATACATTGCAGATCAAT
CCTGATTCTGCAGTTAATCCGGAACATTTA
TCCTATTTCCACTTTGTTGGACGAATAATG
GGAATGGCTGTGTTTCATGGACATTATATT
GATGGTGGTTTCACATTGCCTTTTTATAAG
CAATTGCTTGGGAAGTCAATTACCTTGGAT
GACATGGAGTTAGTAGATCCGGATCTTCAC
AACAGTTTAGTGTGGATACTTGAGAATGAT
ATTACAGGTGTTTTGGACCATACCTTCTGT
GTTGAACATAATGCATATGGTGAAATTATT
CAGCATGAACTTAAACCAAATGGCAAAGT
ATCCCTGTTAATGAAGAAAATAAAAAAGAA
TATGTCAGGCTCTATGTGAACTGGAGATTT
TTACGAGGCATTGAGGCTCAATTCTTGGCT
CTGCAGAAAGGATTAATGAAGTAATTCCA
CAACATCTGCTGAAGACATTTGATGAGAAG
GAGTTAGAGCTCATTATTTGTGGACTTGGA
AAGATAGATGTTAATGACTGGAAGGTAAAC
ACCCGGTTAAAACACTGTACACCAGACAGC
AACATTGTCAAATGGTTCTGGAAAGCTGTG
GAGTTTTTTGATGAAGAGCGACGAGCAAGA
TTGCTTCAGTTTGTGACAGGATCCTCTCGA
GTGCCTCTGCAGGGCTTCAAAGCATTGCAA
GGTGCTGCAGGCCCGAGACTCTTTACCATA
CACCAGATTGATGCCTGCACTAACAACCTG
CCGAAAGCCCACACTTGCTTCAATCGAATA
GACATTCCACCCTATGAAAGCTATGAAAAG
CTATATGAAAGCTGCTAACAGCCATTGAA
GAAACATGTGGATTTGCTGTGGAATGA
```

Human ITCH nucleic acid sequence
(uniprot.org/uniprot/Q96J02).
(SEQ ID NO: 29)

```
GGAGTCGCCGCCGCCCCGAGTTCCGGTACC
ATGCATTTCACGGTGGCCTTGTGGAGACAA
CGCCTTAACCCAAGGAAGTGACTCAAACTG
TGAGAACTCCAGGTTTTCCAACCTATTGGT
GGTATGTCTGACAGTGGATCACAACTTGGT
TCAATGGGTAGCCTCACCATGAAATCACAG
CTTCAGATCACTGTCATCTCAGCAAAACTT
```

```
AAGGAAAATAAGAAGAATTGGTTTGGACCA
AGTCCTTACGTAGAGGTCACAGTAGATGGA
CAGTCAAAGAAGACAGAAAAATGCAACAAC
ACAAACAGTCCCAAGTGGAAGCAACCCCTT
ACAGTTATCGTTACCCCTGTGAGTAAATTA
CATTTTCGTGTGTGGAGTCACCAGACACTG
AAATCTGATGTTTTGTTGGGAACTGCTGCA
TTAGATATTTATGAAACATTAAAGTCAAAC
AATATGAAACTTGAAGAAGTAGTTGTGACT
TTGCAGCTTGGAGGTGACAAAGAGCCAACA
GAGACAATAGGAGACTTGTCAATTTGTCTT
GATGGGCTACAGTTAGAGTCTGAAGTTGTT
ACCAATGGTGAAACTACATGTTCAGAAAGT
GCTTCTCAGAATGATGATGGCTCCAGATCC
AAGGATGAAACAAGAGTGAGCACAAATGGA
TCAGATGACCCTGAAGATGCAGGAGCTGGT
GAAAATAGGAGAGTCAGTGGGAATAATTCT
CCATCACTCTCAAATGGTGGTTTTAAACCT
TCTAGACCTCCAAGACCTTCACGACCACCA
CCACCCACCCCACGTAGACCAGCATCTGTC
AATGGTTCACCATCTGCCACTTCTGAAAGT
GATGGGTCTAGTACAGGCTCTCTGCCGCCG
ACAAATACAAATACAAATACATCTGAAGGA
GCAACATCTGGATTAATAATTCCTCTTACT
ATATCTGGAGGCTCAGGCCCTAGGCCATTA
AATCCTGTAACTCAAGCTCCCTTGCCACCT
GGTTGGGAGCAGAGAGTGGACCAGCACGGG
CGAGTTTACTATGTAGATCATGTTGAGAAA
AGAACAACATGGGATAGACCAGAACCTCTA
CCTCCTGGCTGGGAACGGCGGGTTGACAAC
ATGGGACGTATTTATTATGTTGACCATTTC
ACAAGAACAACAACGTGGCAGAGGCCAACA
CTGGAATCCGTCCGGAACTATGAACAATGG
CAGCTACAGCGTAGTCAGCTTCAAGGAGCA
ATGCAGCAGTTTAACCAGAGATTCATTTAT
GGGAATCAAGATTTATTTGCTACATCACAA
AGTAAAGAATTTGATCCTCTTGGTCCATTG
CCACCTGGATGGGAGAAGAGAACAGACAGC
AATGGCAGAGTATATTTCGTCAACCACAAC
ACACGAATTACACAATGGGAAGACCCCAGA
AGTCAAGGTCAATTAAATGAAAAGCCCTTA
CCTGAAGGTTGGGAAATGAGATTCACAGTG
GATGGAATTCCATATTTTGTGGACCACAAT
AGAAGAACTACCACCTATATAGATCCCCGC
ACAGGAAAATCTGCCCTAGACAATGGACCT
CAGATAGCCTATGTTCGGGACTTCAAAGCA
AAGGTTCAGTATTTCCGGTTCTGGTGTCAG
CAACTGGCCATGCCACAGCACATAAAGATT
ACAGTGACAAGAAAAACATTGTTTGAGGAT
TCCTTTCAACAGATAATGAGCTTCAGTCCC
CAAGATCTGCGAAGACGTTTGTGGGTGATT
TTTCCAGGAGAAGAAGGTTTAGATTATGGA
GGTGTAGCAAGAGAATGGTTCTTTCTTTTG
TCACATGAAGTGTTGAACCCAATGTATTGC
CTGTTTGAATATGCAGGGAAGGATAACTAC
TGCTTGCAGATAAACCCCGCTTCTTACATC
AATCCAGATCACCTGAAATATTTTCGTTTT
ATTGGCAGATTTATTGCCATGGCTCTGTTC
CATGGGAAATTCATAGACACGGGTTTTTCT
TTACCATTCTATAAGCGTATCTTGAACAAA
CCAGTTGGACTCAAGGATTTAGAATCTATT
GATCCAGAATTTTACAATTCTCTCATCTGG
GTTAAGGAAAACAATATTGAGGAATGTGAT
TTGGAAATGTACTTCTCCGTTGACAAAGAA
ATTCTAGGTGAAATTAAGAGTCATGATCTG
AAACCTAATGGTGGCAATATTCTTGTAACA
GAAGAAAATAAAGAGGAATACATCAGAATG
GTAGCTGAGTGGAGGTTGTCTCGAGGTGTT
GAAGAACAGACACAAGCTTTCTTTGAAGGC
TTTAATGAAATTCTTCCCCAGCAATATTTG
CAATACTTTGATGCAAAGGAATTAGAGGTC
CTTTTATGTGGAATGCAAGAGATTGATTTG
AATGACTGGCAAAGACATGCCATCTACCGT
CATTATGCAAGGACCAGCAAACAAATCATG
TGGTTTTGGCAGTTTGTTAAAGAAATTGAT
AATGAGAAGAGAATGAGACTTCTGCAGTTT
GTTACTGGAACCTGCCGATTGCCAGTAGGA
GGATTTGCTGATCTCATGGGGAGCAATGGA
CCACAGAAATTCTGCATTGAAAAAGTTGGG
AAAGAAAATTGGCTACCCAGAAGTCATACC
TGTTTTAATCGCCTGGACCTGCCACCATAC
```

-continued

AAGAGCTATGAGCAACTGAAGGAAAAGCTG

TTGTTTGCCATAGAAGAAACAGAAGGATTT

GGACAAGAGTAACTTCTGAGAACTTGCACC

ATGAATGGGCAAGAACTTATTTGCAATGTT

TGTCCTTCTCTGCCTGTTGCACATCTTGTA

AAATTGGACAATGGCTCTTTAGAGAGTTAT

CTGAGTGTAAGTAAATTAATGTTCTCATTT

AAAAAAAAAAAAAAAAAA

Human NEDL1 nucleic acid sequence
(uniprot.org/uniprot/Q76N89).
(SEQ ID NO: 30)
GCGCATCAGGCGCTGTTGTTGGAGCCGGAA

CACCGTGCGACTCTGACCGAACCGGCCCCC

TCCTCGCGCACACACTCGCCGAGCCGCGCG

CGCCCCTCCGCCGTGACAGTGGCCGTGGCC

TCCGCTCTCTCGGGGCACCCGGCAGCCAGA

GCGCAGCGAGAGCGGGCGGTCGCCAGGGTC

CCCTCCCCAGCCAGTCCCAGGCGCCCGGTG

CACTATGCGGGCACGTGCGCCCCCCAGCT

CTAATCTGCGCGCTGACAGGAGCATGATCT

GTGCCCAGGCCAGGGCTGCCAAGGAATTGA

TGCGCGTACACGTGGTGGGTCATTATGCTG

CTACACCTGTGTAGTGTGAAGAATCTGTAC

CAGAACAGGTTTTTAGGCCTGGCCGCCATG

GCGTCTCCTTCTAGAAACTCCCAGAGCCGA

CGCCGGTGCAAGGAGCCGCTCCGATACAGC

TACAACCCCGACCAGTTCCACAACATGGAC

CTCAGGGGCGGCCCCCACGATGGCGTCACC

ATTCCCCGCTCCACCAGCGACACTGACCTG

GTCACCTCGGACAGCCGCTCCACGCTCATG

GTCAGCAGCTCCTACTATTCCATCGGGCAC

TCTCAGGACCTGGTCATCCACTGGGACATA

AAGGAGGAAGTGGACGCTGGGGACTGGATT

GGCATGTACCTCATTGATGAGGTCTTGTCC

GAAAACTTTCTGGACTATAAAAACCGTGGA

GTCAATGGTTCTCATCGGGGCCAGATCATC

TGGAAGATCGATGCCAGCTCGTACTTTGTG

GAACCTGAAACTAAGATCTGCTTCAAATAC

TACCATGGAGTGAGTGGGGCCCTGCGAGCA

ACCACCCCCAGTGTCACGGTCAAAAACTCG

GCAGCTCCTATTTTTAAAAGCATTGGTGCT

GATGAGACCGTCCAAGGACAAGGAAGTCGG

AGGCTGATCAGCTTCTCTCTCTCAGATTTC

CAAGCCATGGGGTTGAAGAAAGGGATGTTT

TTCAACCCAGACCCTTATCTGAAGATTTCC

ATTCAGCCTGGGAAACACAGCATCTTCCCC

GCCCTCCCTCACCATGGACAGGAGAGGAGA

TCCAAGATCATAGGCAACACCGTGAACCCC

ATCTGGCAGGCCGAGCAATTCAGTTTTGTG

TCCTTGCCCACTGACGTGCTGGAAATTGAG

GTGAAGGACAAGTTTGCCAAGAGCCGCCCC

ATCATCAAGCGCTTCTTGGGAAAGCTGTCG

ATGCCCGTTCAAAGACTCCTGGAGAGACAC

GCCATAGGGGATAGGGTGGTCAGCTACACA

CTTGGCCGCAGGCTTCCAACAGATCATGTG

AGTGGACAGCTGCAATTCCGATTTGAGATC

ACTTCCTCCATCCACCCAGATGATGAGGAG

ATTTCCCTGAGTACCGAGCCTGAGTCAGCC

CAAATTCAGGACAGCCCCATGAACAACCTG

ATGGAAAGCGGCAGTGGGGAACCTCGGTCT

GAGGCACCAGAGTCCTCTGAGAGCTGGAAG

CCAGAGCAGCTGGGTGAGGGCAGTGTCCCC

GATGGTCCAGGGAACCAAAGCATAGAGCTT

TCCAGACCAGCTGAGGAAGCAGCAGTCATC

ACGGAGGCAGGAGACCAGGGCATGGTCTCT

GTGGGACCTGAAGGGGCTGGGGAGCTCCTG

GCCCAGGTGCAAAAGGACATCCAGCCTGCC

CCCAGTGCAGAAGAGCTGGCCGAGCAGCTG

GACCTGGGTGAGGAGGCATCAGCACTGCTG

CTGGAAGACGGTGAAGCCCCAGCCAGCACC

AAGGAGGAGCCCTTGGAGGAGGAAGCAACG

ACCCAGAGCCGGGCTGGAAGGGAAGAAGAG

GAGAAGGAGCAGGAGGAGGAGGGAGATGTG

TCTACCCTGGAGCAGGGAGAGGGCAGGCTG

CAGCTGCGGGCCTCGGTGAAGAGAAAAAGC

AGGCCCTGCTCCTTGCCTGTGTCCGAGCTG

GAGACGGTGATCGCGTCAGCCTGCGGGGAC

CCCGAGACCCCGCGGACACACTACATCCGC

ATCCACACCCTGCTGCACAGCATGCCCTCC

GCCCAGGGCGGCAGCGCGGCAGAGGAGGAG

GACGGCGCGGAGGAGGAGTCCACCCTCAAG

GACTCCTCGGAGAAGGATGGGCTCAGCGAG

-continued

```
GTGGACACGGTGGCCGCTGACCCGTCTGCC
CTGGAAGAGGACAGAGAAGAGCCCGAGGGG
GCTACTCCAGGCACGGCGCACCCTGGCCAC
TCCGGGGCCACTTCCCCAGCCTGGCCAAT
GGCGCGGCCCAGGATGGCGACACGCACCCC
AGCACCGGGAGCGAGAGCGACTCCAGCCCC
AGGCAAGGCGGGGACCACAGTTGCGAGGGC
TGTGACGCGTCCTGCTGCAGCCCCTCGTGC
TACAGCTCCTCGTGCTACAGCACGTCCTGC
TACAGCAGCTCGTGCTACAGCGCCTCGTGC
TACAGCCCCTCCTGCTACAACGGCAACAGG
TTCGCCAGCCACACGCGCTTCCCTCCGTG
GACAGCGCCAAGATCTCCGAGAGCACGGTC
TTCTCCTCGCAAGACGACGAGGAGGAGGAG
AACAGCGCGTTCGAGTCGGTACCCGACTCC
ATGCAGAGCCCTGAGCTGGACCCGGAGTCC
ACGAACGGCGCTGGGCCGTGGCAAGACGAG
CTGGCCGCCCCTAGCGGGCACGTGGAAAGA
AGCCCGGAAGGTCTGGAATCCCCGTGGCA
GGTCCAAGCAATCGGAGAGAAGACTGGGAA
GCTCGAATTGACAGCCACGGGCGGGTCTTT
TATGTGGACCACGTGAACCGCACAACCACC
TGGCAGCGTCCGACGGCAGCAGCCACCCCG
GATGGCATGCGGAGATCGGGGTCCATCCAG
CAGATGGAGCAACTCAACAGGCGGTATCAA
AACATTCAGCGAACCATTGCAACAGAGAGG
TCCGAAGAAGATTCTGGCAGCCAAAGCTGC
GAGCAAGCCCCAGCAGGAGGAGGCGGAGGT
GGAGGGAGTGACTCAGAAGCCGAATCTTCC
CAGTCCAGCTTAGATCTAAGGAGAGAGGGG
TCACTTTCTCCAGTGAACTCACAAAAAATC
ACCTTGCTGCTGCAGTCCCCAGCGGTCAAG
TTCATCACCAACCCCGAGTTCTTCACTGTG
CTACACGCCAATTATAGTGCCTACCGAGTC
TTCACCAGTAGCACCTGCTTAAAGCACATG
ATTCTGAAAGTCCGACGGGATGCTCGCAAT
TTTGAACGCTACCAGCACAACCGGGACTTG
GTGAATTTCATCAACATGTTCGCAGACACT
CGGCTGGAACTGCCCCGGGGCTGGGAGATC
AAAACGGACCAGCAGGGAAAGTCTTTTTTC
GTGGACCACAACAGTCGAGCTACCACTTTC
```

-continued

```
ATTGACCCCCGAATCCCTCTTCAGAACGGT
CGTCTTCCCAATCATCTAACTCACCGACAG
CACCTCCAGAGGCTCCGAAGTTACAGCGCC
GGAGAGGCCTCAGAAGTTTCTAGAAACAGA
GGAGCCTCTTTACTGGCCAGGCCAGGACAC
AGCTTAGTAGCTGCTATTCGAAGCCAACAT
CAACATGAGTCATTGCCACTGGCATATAAT
GACAAGATTGTGGCATTTCTTCGCCAGCCA
AACATTTTTGAAATGCTGCAAGAGCGTCAG
CCAAGCTTAGCAAGAAACCACACACTCAGG
GAGAAAATCCATTACATTCGGACTGAGGGT
AATCACGGGCTTGAGAAGTTGTCCTGTGAT
GCGGATCTGGTCATTTTGCTGAGTCTCTTT
GAAGAAGAGATTATGTCCTACGTCCCCCTG
CAGGCTGCCTTCCACCCTGGGTATAGCTTC
TCTCCCCGATGTTCACCCTGTTCTTCACCT
CAGAACTCCCCAGGTTTACAGAGAGCCAGT
GCAAGAGCCCCTTCCCCCTACCGAAGAGAC
TTTGAGGCCAAGCTCCGCAATTTCTACAGA
AAACTGGAAGCCAAAGGATTTGGTCAGGGT
CCGGGGAAAATTAAGCTCATTATTCGCCGG
GATCATTTGTTGGAGGGAACCTTCAATCAG
GTGATGGCCTATTCGCGGAAAGAGCTCCAG
CGAAACAAGCTCTACGTCACCTTTGTTGGA
GAGGAGGGCCTGGACTACAGTGGCCCCTCG
CGGGAGTTCTTCTTCCTTCTGTCTCAGGAG
CTCTTCAACCCTTACTATGGACTCTTTGAG
TACTCGGCAAATGATACTTACACGGTGCAG
ATCAGCCCCATGTCCGCATTTGTAGAAAAC
CATCTTGAGTGGTTCAGGTTTAGCGGTCGC
ATCCTGGGTCTGGCTCTGATCCATCAGTAC
CTTCTTGACGCTTTCTTCACGAGGCCCTTC
TACAAGGCACTCCTGAGACTGCCCTGTGAT
TTGAGTGACCTGGAATATTTGGATGAGGAA
TTCCACCAGAGTTTGCAGTGGATGAAGGAC
AACAACATCACAGACATCTTAGACCTCACT
TTCACTGTTAATGAAGAGGTTTTTGGACAG
GTCACGGAAAGGGAGTTGAAGTCTGGAGGA
GCCAACACACAGGTGACGGAGAAAAACAAG
AAGGAGTACATCGAGCGCATGGTGAAGTGG
```

-continued
CGGGTGGAGCGCGGCGTGGTACAGGAGACC

GAGGCGCTGGTGCGCGGCTTCTACGAGGTT

GTAGACTCGAGGCTGGTGTCCGTGTTTCAT

GCCAGGGAGCTGGAGCTGGTGATAGCTGGC

ACCGCGGAAATCGACCTAAATGACTGGCGG

AATAACACTGAGTACCGGGGAGGTTACCAC

GATGGGCATCTTGTGATCCGCTGGTTCTGG

GCTGCGGTGGAGCGCTTCAATAATGAGCAG

AGGCTGAGATTACTGCAGTTTGTCACGGGA

ACATCCAGCGTGCCCTACGAAGGCTTCGCA

GCCCTCCGTGGGAGCAATGGGCTTCGGCGC

TTCTGCATAGAAATGGGGGAAAATTACT

TCTCTCCCCAGGGCACACACATGCTTCAAC

CGACTGGATCTTCCACCGTATCCCTCGTAC

TCCATGTTGTATGAAAAGCTGTTAACAGCA

GTAGAGGAAACCAGCACCTTTGGACTTGAG

TGAGGACATGGAACCTCGCCTGACATTTTC

CTGGCCAGTGACATCACCCTTCCTGGGATG

ATCCCCTTTTCCCTTTCCCTTAATCAACTC

TCCTTTGATTTTGGTATTCCATGATTTTTA

TTTTCAAAC

Human NEDL2 nucleic acid sequence
(uniprot.org/uniprot/Q9P2P5).
(SEQ ID NO: 31)
AGAGTTCCATCAGAGCCTGCAGTGGATGAA

AGACAATGATATCCATGACATCCTAGACCT

CACGTTCACTGTGAACGAAGAAGTATTTGG

GCAGATAACTGAACGAGAATTAAAGCCAGG

GGGTGCCAATATCCCAGTTACAGAGAAGAA

CAAGAAGGAGTACATCGAGAGGATGGTGAA

GTGGAGGATTGAGAGGGGTGTTGTACAGCA

AACAGAGAGCTTAGTGCGTGGCTTCTATGA

GGTGGTGGATGCCAGGCTGGTATCTGTTTT

TGATGCAAGAGAACTGGAATTGGTCATCGC

AGGCACAGCTGAAATAGACCTAAGTGATTG

GAGAAACAACACAGAATATAGAGGAGGATA

CCATGACAATCATATTGTAATTCGGTGGTT

CTGGGCTGCAGTGGAAAGATTCAACAATGA

ACAACGACTAAGGTTGTTACAGTTTGTTAC

AGGCACATCCAGCATTCCCTATGAAGGATT

TGCTTCACTCCGAGGGAGTAACGGCCCAAG

AAGATTCTGTGTGGAGAAATGGGGGAAAAT

-continued
CACTGCTCTTCCCAGAGCGCATACATGTTT

TAACCGTCTGGATCTGCCTCCCTACCCATC

CTTTTCCATGCTTTATGAAAAACTGTTGAC

AGCAGTTGAAGAAACCAGTACTTTTGGACT

TGAGTGACCTGGAAGCTGAATGCCCATCTC

TGTGGACAGGCAGTTTCAGAAGCTGCCTTC

TAGAAGAATGATTGAACATTGGAAGTTTCA

AGAGGATGCTTCCTTTAGGATAAAGCTACG

TGCTGTTGTTTTCCAGGAACAAGTGCTCTG

TCACATTTGGGGACTGGAGATGAGTCCTCT

TGGAAGGATTTGGGTGAGCTTGATGCCCAG

GGAACAACCCAACCGTCTTTCAATCAACAG

TTCTTGACTGCCAAACTTTTTCCATTTGTT

ATGTTCCAAGACAAAGATGAACCCATACAT

GATCAGCTCCACGGTAATTTTTAGGGACTC

AGGAGAATCTTGAAACTTACCCTTGAACGT

GGTTCAAGCCAAACTGGCAGCATTTGGCCC

AATCTCCAAATTAGAGCAAGTTAAATAATA

TAATAAAAGTAAATATATTTCCTGAAAGTA

CATTCATTTAAGCCCTAAGTTATAACAGAA

TATTCATTTCTTGCTTATGAGTGCCTGCAT

GGTGTGCACCATAGGTTTCCGCTTTCATGG

GACATGAGTGAAAATGAAACCAAGTCAATA

TGAGGTACCTTTACAGATTTGCAATAAGAT

GGTCTGTGACAATGTATATGCAAGTGGTAT

GTGTGTAATTATGGCTAAAGACAAACCATT

ATTCAGTGAATTACTAATGACAGATTTTAT

GCTTTATAATGCATGAAAACAATTTTAAAA

TAACTAGCAATTAATCACAGCATATCAGGA

AAAAGTACACAGTGAGTTCTGTTTATTTTT

TGTAGGCTCATTATGTTTATGTTCTTTAAG

ATGTATATAAGAACCTACTTATCATGCTGT

ATGTATCACTCATTCCATTTTCATGTTCCA

TGCATACTCGGGCATCATGCTAATATGTAT

CCTTTTAAGCACTCTCAAGGAAACAAAAGG

GCCTTTTATTTTTATAAAGGTAAAAAAAAT

TCCCCAAATATTTTGCACTGAATGTACCAA

AGGTGAAGGGACATTACAATATGACTAACA

GCAACTCCATCACTTGAGAAGTATAATAGA

AAATAGCTTCTAAATCAAACTTCCTTCACA

GTGCCGTGTCTACCACTACAAGGACTGTGC

-continued

```
ATCTAAGTAATAATTTTTTAAGATTCACTA
TATGTGATAGTATGATATGCATTTATTTAA
AATGCATTAGACTCTCTTCCATCCATCAAA
TACTTTACAGGATGGCATTTAATACAGATA
TTTCGTATTTCCCCCACTGCTTTTTATTTG
TACAGCATCATTAAACACTAAGCTCAGTTA
AGGAGCCATCAGCAACACTGAAGAGATCAG
TAGTAAGAATTCCATTTTCCCTCATCAGTG
AAGACACCACAAATTGAAACTCAGAACTAT
ATTTCTAAGCCTGCATTTTCACTGATGCAT
AATTTTCTTATTAATATTAAGAGACAGTTT
TTCTATGGCATCTCCAAAACTGCATGACAT
CACTAGTCTTACTTCTGCTTAATTTTATGA
GAAGGTATTCTTCATTTTAATTGCTTTTGG
GATTACTCCACATCTTTGTTTATTTCTTGA
CTAATCAGATTTTCAATAGAGTGAAGTTAA
ATTGGGGGTCATAAAAGCATTGGATTGACA
TATGGTTTGCCAGCCTATGGGTTTACAGGC
ATTGCCCAAACATTTCTTTGAGATCTATAT
TTATAAGCAGCCATGGAATTCCTATTATGG
GATGTTGGCAATCTTACATTTTATAGAGGT
CATATGCATAGTTTTCATAGGTGTTTTGTA
AGAACTGATTGCTCTCCTGTGAGTTAAGCT
ATGTTTACTACTGGGACCCTCAAGAGGAAT
ACCACTTATGTTACACTCCTGCACTAAAGG
CACGTACTGCAGTGTGAAGAAATGTTCTGA
AAAAGGGTTATAGAAATCTGGAAATAAGAA
AGGAAGAGCTCTCTGTATTCTATAATTGGA
AGAGAAAAAAGAAAAACTTTTAACTGGAA
ATGTTAGTTTGTACTTATTGATCATGAATA
CAAGTATATATTTAATTTTGCAAAAAAAAA
AAAAAAAAAAAAAG
```

In certain embodiments, the nucleic acids may encode cargo proteins having two WW domains or WW domain variants from the human ITCH protein having the nucleic acid sequence:

(SEQ ID NO: 32)
```
CCCTTGCCACCTGGTTGGGAGCAGAGAGTGGACCAGCACGGGCGAGTTTA
CTATGTAGATCATGTTGAGAAAAGAACAACATGGGATAGACCAGAACCTC
TACCTCCTGGCTGGGAACGGCGGGTTGACAACATGGGACGTATTTATTAT
GTTGACCATTTCACAAGAACAACAACGTGGCAGAGGCCAACACTG.
```

In other embodiments, the nucleic acids may encode cargo proteins having four WW domains or WW domain variants from the human ITCH protein having the nucleic acid sequence:

(SEQ ID NO: 33)
```
CCCTTGCCACCTGGTTGGGAGCAGAGAGGGACCAGCACGGGCGAGTTTA
CTATGTAGATCATGTTGAGAAAAGAACAACATGGGATAGACCAGAACCTC
TACCTCCTGGCTGGGAACGGCGGGTTGACAACATGGGACGTATTTATTAT
GTTGACCATTTCACAAGAACAACAACGTGGCAGAGGCCAACACTGGAATC
CGTCCGGAACTATGAACAATGGCAGCTACAGCGTAGTCAGCTTCAAGGAG
CAATGCAGCAGTTTAACCAGAGATTCATTTATGGGAATCAAGATTTATTT
GCTACATCACAAAGTAAAGAATTTGATCCTCTTGGTCCATTGCCACCTGG
ATGGGAGAAGAGAACAGACAGCAATGGCAGAGTATATTTCGTCAACCACA
ACACACGAATTACACAATGGGAAGACCCCAGAAGTCAAGGTCAATTAAAT
GAAAAGCCCTTACCTGAAGGTTGGGAAATGAGATTCACAGTGGATGGAAT
TCCATATTTTGTGGACCACAATAGAAGAACTACCACCTATATAGATCCCC
GCACA.
```

The nucleic acid constructs that encode the cargo proteins, described herein, that are fused to at least one WW domain or WW domain variant are non-naturally occurring, that is, they do not exist in nature.

In some embodiments the expression constructs comprise a nucleic acid sequence encoding a WW domain, or variant thereof from the nucleic acid sequence (SEQ ID NO: 23); (SEQ ID NO: 24); (SEQ ID NO: 25); (SEQ ID NO: 26); (SEQ ID NO: 27); (SEQ ID NO: 28); (SEQ ID NO: 29); (SEQ ID NO: 30); (SEQ ID NO: 31); (SEQ ID NO: 32) or (SEQ ID NO: 33). In certain embodiments, the expression constructs encode a fusion protein comprising a WW domain or multiple WW domains, a nuclear localization sequence (NLS), and a Cas9 protein or variant thereof. In certain embodiments, the expression constructs comprise the nucleic acid sequence (SEQ ID NO: 67) or (SEQ ID NO: 68). In certain embodiments, the expression constructs consist of the nucleic acid sequence (SEQ ID NO: 67) or (SEQ ID NO: 68). In certain embodiments, the expression constructs consist essentially of the nucleic acid sequence (SEQ ID NO: 67) or (SEQ ID NO: 68).

The following nucleic acid sequences encode exemplary Cas9 cargo protein sequences that have either 2 WW domains (SEQ ID NO: 65) or 4 WW domains (SEQ ID NO: 66), which were cloned into the AgeI site of the pX330 plasmid (Addgene).

(SEQ ID NO: 67)
```
ATGCCCTTGCCACCTGGTTGGGAGCAGAGAGTGGACCAGCACGGGCGAGT
TTACTATGTAGATCATGTTGAGAAAAGAACAACATGGGATAGACCAGAAC
CTCTACCTCCTGGCTGGGAACGGCGGGTTGACAACATGGGACGTATTTAT
TATGTTGACCATTTCACAAGAACAACAACGTGGCAGAGGCCAACACTGAC
CGGTGCCACCATGGACTATAAGGACACGACGGAGACTACAAGGATCATGA
TATTGATTACAAAGACGATGACGATAAGATGGCCCCAAAGAAGAAGCGGA
AGGTCGGTATCCACGGAGTCCCAGCAGCCGACAAGAAGTACAGCATCGGC
```

```
CTGGACATCGGCACCAACTCTGTGGGCTGGGCCGTGATCACCGACGAGTA
CAAGGTGCCCAGCAAGAAATTCAAGGTGCTGGGCAACACCGACCGGCACA
GCATCAAGAAGAACCTGATCGGAGCCCTGCTGTTCGACAGCGGCGAAACA
GCCGAGGCCACCCGGCTGAAGAGAACCGCCAGAAGAAGATACACCAGACG
GAAGAACCGGATCTGCTATCTGCAAGAGATCTTCAGCAACGAGATGGCCA
AGGTGGACGACAGCTTCTTCCACAGACTGGAAGAGTCCTTCCTGGTGGAA
GAGGATAAGAAGCACGAGCGGCACCCCATCTTCGGCAACATCGTGGACGA
GGTGGCCTACCACGAGAAGTACCCCACCATCTACCACCTGAGAAAGAAAC
TGGTGGACAGCACCGACAAGGCCGACCTGCGGCTGATCTATCTGGCCCTG
GCCCACATGATCAAGTTCCGGGGCCACTTCCTGATCGAGGGCGACCTGAA
CCCCGACAACAGCGACGTGGACAAGCTGTTCATCCAGCTGGTGCAGACCT
ACAACCAGCTGTTCGAGGAAAACCCCATCAACGCCAGCGGCGTGGACGCC
AAGGCCATCCTGTCTGCCAGACTGAGCAAGAGCAGACGGCTGGAAAATCT
GATCGCCCAGCTGCCCGGCGAGAAGAAGAATGGCCTGTTCGGAAACCTGA
TTGCCCTGAGCCTGGGCCTGACCCCCAACTTCAAGAGCAACTTCGACCTG
GCCGAGGATGCCAAACTGCAGCTGAGCAAGGACACCTACGACGACGACCT
GGACAACCTGCTGGCCCAGATCGGCGACCAGTACGCCGACCTGTTTCTGG
CCGCCAAGAACCTGTCCGACGCCATCCTGCTGAGCGACATCCTGAGAGTG
AACACCGAGATCACCAAGGCCCCCCTGAGCGCCTCTATGATCAAGAGATA
CGACGAGCACCACCAGGACCTGACCCTGCTGAAAGCTCTCGTGCGGCAGC
AGCTGCCTGAGAAGTACAAAGAGATTTTCTTCGACCAGAGCAAGAACGGC
TACGCCGGCTACATTGACGGCGGAGCCAGCCAGGAAGAGTTCTACAAGTT
CATCAAGCCCATCCTGGAAAAGATGGACGGCACCGAGGAACTGCTCGTGA
AGCTGAACAGAGAGGACCTGCTGCGGAAGCAGCGGACCTTCGACAACGGC
AGCATCCCCCACCAGATCCACCTGGGAGAGCTGCACGCCATTCTGCGGCG
GCAGGAAGATTTTTACCCATTCCTGAAGGACAACCGGGAAAAGATCGAGA
AGATCCTGACCTTCCGCATCCCCTACTACGTGGGCCCTCTGGCCAGGGGA
AACAGCAGATTCGCCTGGATGACCAGAAAGAGCGAGGAAACCATCACCCC
CTGGAACTTCGAGGAAGTGGTGGACAAGGGCGCTTCCGCCCAGAGCTTCA
TCGAGCGGATGACCAACTTCGATAAGAACCTGCCCAACGAGAAGGTGCTG
CCCAAGCACAGCCTGCTGTACGAGTACTTCACCGTGTATAACGAGCTGAC
CAAAGTGAAATACGTGACCGAGGGAATGAGAAAGCCCGCCTTCCTGAGCG
GCGAGCAGAAAAGGCCATCGTGGACCTGCTGTTCAAGACCAACCGGAAA
GTGACCGTGAAGCAGCTGAAAGAGGACTACTTCAAGAAAATCGAGTGCTT
CGACTCCGTGGAAATCTCCGGCGTGGAAGATCGGTTCAACGCCTCCCTGG
GCACATACCACGATCTGCTGAAAATTATCAAGGACAAGGACTTCCTGGAC
AATGAGGAAAACGAGGACATTCTGGAAGATATCGTGCTGACCCTGACACT
GTTTGAGGACAGAGAGATGATCGAGGAACGGCTGAAAACCTATGCCCACC
TGTTCGACGACAAAGTGATGAAGCAGCTGAAGCGGCGGAGATACACCGGC
TGGGGCAGGCTGAGCCGGAAGCTGATCAACGGCATCCGGGACAAGCAGTC
```

```
CGGCAAGACAATCCTGGATTTCCTGAAGTCCGACGGCTTCGCCAACAGAA
ACTTCATGCAGCTGATCCACGACGACAGCCTGACCTTTAAAGAGGACATC
CAGAAAGCCCAGGTGTCCGGCCAGGGCGATAGCCTGCACGAGCACATTGC
CAATCTGGCCGGCAGCCCCGCCATTAAGAAGGGCATCCTGCAGACAGTGA
AGGTGGTGGACGAGCTCGTGAAAGTGATGGGCCGGCACAAGCCCGAGAAC
ATCGTGATCGAAATGGCCAGAGAGAACCAGACCACCCAGAAGGGACAGAA
GAACAGCCGCGAGAGAATGAAGCGGATCGAAGAGGGCATCAAAGAGCTGG
GCAGCCAGATCCTGAAAGAACACCCCGTGGAAAACACCCAGCTGCAGAAC
GAGAAGCTGTACCTGTACTACCTGCAGAATGGGCGGGATATGTACGTGGA
CCAGGAACTGGACATCAACCGGCTGTCCGACTACGATGTGGACCATATCG
TGCCTCAGAGCTTTCTGAAGGACGACTCCATCGACAACAAGGTGCTGACC
AGAAGCGACAAGAACCGGGGCAAGAGCGACAACGTGCCCTCCGAAGAGGT
CGTGAAGAAGATGAAGAACTACTGGCGGCAGCTGCTGAACGCCAAGCTGA
TTACCCAGAGAAAGTTCGACAATCTGACCAAGGCCGAGAGAGGCGGCCTG
AGCGAACTGGATAAGGCCGGCTTCATCAAGAGACAGCTGGTGGAAACCCG
GCAGATCACAAAGCACGTGGCACAGATCCTGGACTCCCGGATGAACACTA
AGTACGACGAGAATGACAAGCTGATCCGGGAAGTGAAAGTGATCACCCTG
AAGTCCAAGCTGGTGTCCGATTTCCGGAAGGATTTCCAGTTTTACAAAGT
GCGCGAGATCAACAACTACCACCACGCCCACGACGCCTACCTGAACGCCG
TCGTGGGAACCGCCCTGATCAAAAAGTACCCTAAGCTGGAAAGCGAGTTC
GTGTACGGCGACTACAAGGTGTACGACGTGCGGAAGATGATCGCCAAGAG
CGAGCAGGAAATCGGCAAGGCTACCGCCAAGTACTTCTTCTACAGCAACA
TCATGAACTTTTTCAAGACCGAGATTACCCTGGCCAACGGCGAGATCCGG
AAGCGGCCTCTGATCGAGACAAACGGCGAAACCGGGGAGATCGTGTGGGA
TAAGGGCCGGGATTTTGCCACCGTGCGGAAAGTGCTGAGCATGCCCCAAG
TGAATATCGTGAAAAAGACCGAGGTGCAGACAGGCGGCTTCAGCAAAGAG
TCTATCCTGCCCAAGAGGAACAGCGATAAGCTGATCGCCAGAAAGAAGGA
CTGGGACCCTAAGAAGTACGGCGGCTTCGACAGCCCCACCGTGGCCTATT
CTGTGCTGGTGGTGGCCAAAGTGGAAAAGGGCAAGTCCAAGAAACTGAAG
AGTGTGAAAGAGCTGCTGGGGATCACCATCATGGAAAGAAGCAGCTTCGA
GAAGAATCCCATCGACTTTCTGGAAGCCAAGGGCTACAAAGAAGTGAAAA
AGGACCTGATCATCAAGCTGCCTAAGTACTCCCTGTTCGAGCTGGAAAAC
GGCCGGAAGAGAATGCTGGCCTCTGCCGGCGAACTGCAGAAGGGAAACGA
ACTGGCCCTGCCCTCCAAATATGTGAACTTCCTGTACCTGGCCAGCCACT
ATGAGAAGCTGAAGGGCTCCCCCGAGGATAATGAGCAGAAACAGCTGTTT
GTGGAACAGCACAAGCACTACCTGGACGAGATCATCGAGCAGATCAGCGA
GTTCTCCAAGAGAGTGATCCTGGCCGACGCTAATCTGGACAAAGTGCTGT
CCGCCTACAACAAGCACCGGGATAAGCCCATCAGAGAGCAGGCCGAGAAT
ATCATCCACCTGTTTACCCTGACCAATCTGGGAGCCCCTGCCGCCTTCAA
GTACTTTGACACCACCATCGACCGGAAGAGGTACACCAGCACCAAAGAGG
TGCTGGACGCCACCCTGATCCACCAGAGCATCACCGGCCTGTACGAGACA
```

CGGATCGACCTGTCTCAGCTGGGAGGCGACAAAAGGCCGGCGGCCACGAA

AAAGGCCGGCCAGGCAAAAAAGAAAAG (SEQ ID NO: 68)
ATGCCCTTGCCACCTGGTTGGGAGCAGAGAGTGGACCAGCACGGGCGAGT

TTACTATGTAGATCATGTTGAGAAAAGAACAACATGGGATAGACCAGAAC

CTCTACCTCCTGGCTGGGAACGGCGGGTTGACAACATGGGACGTATTTAT

TATGTTGACCATTTCACAGAACAACAACGTGGCAGAGGCCAACACTGGAA

TCCGTCCGGAACTATGAACAATGGCAGCTACAGCGTAGTCAGCTTCAAGG

AGCAATGCAGCAGTTTAACCAGAGATTCATTTATGGGAATCAAGATTTAT

TTGCTACATCACAAAGTAAAGAATTTGATCCTCTTGGTCCATTGCCACCT

GGATGGGAGAAGAGAACAGACAGCAATGGCAGAGTATATTTCGTCAACCA

CAACACACGAATTACACAATGGGAAGACCCCAGAAGTCAAGGTCAATTAA

ATGAAAAGCCCTTACCTGAAGGTTGGGAAATGAGATTCACAGTGGATGGA

ATTCCATATTTTGTGGACCACAATAGAAGAACTACCACCTATATAGATCC

CCGCACAGGCGGAGGAACCGGTGCCACCATGGACTATAAGGACCACGACG

GAGACTACAAGGATCATGATATTGATTACAAAGACGATGACGATAAGATG

GCCCCAAAGAAGAAGCGGAAGGTCGGTATCCACGGAGTCCCAGCAGCCGA

CAAGAAGTACAGCATCGGCCTGGACATCGGCACCAACTCTGTGGGCTGGG

CCGTGATCACCGACGAGTACAAGGTGCCCAGCAAGAAATTCAAGGTGCTG

GGCAACACCGACCGGCACAGCATCAAGAAGAACCTGATCGGAGCCCTGCT

GTTCGACAGCGGCGAAACAGCCGAGGCCACCCGGCTGAAGAGAACCGCCA

GAAGAAGATACACCAGACGGAAGAACCGGATCTGCTATCTGCAAGAGATC

TTCAGCAACGAGATGGCCAAGGTGGACGACAGCTTCTTCCACAGACTGGA

AGAGTCCTTCTTGGTGGAAGAGGATAAGAAGCACGAGCGGCACCCCATCTT

CGGCAACATCGTGGACGAGGTGGCCTACCACGAGAAGTACCCCACCATCT

ACCACCTGAGAAAGAAACTGGTGGACAGCACCGACAAGGCCGACCTGCGG

CTGATCTATCTGGCCCTGGCCCACATGATCAAGTTCCGGGGCCACTTCCT

GATCGAGGGCGACCTGAACCCCGACAACAGCGACGTGGACAAGCTGTTCA

TCCAGCTGGTGCAGACCTACAACCAGCTGTTCGAGGAAAACCCCATCAAC

GCCAGCGGCGTGGACGCCAAGGCCATCCTGTCTGCCAGACTGAGCAAGAG

CAGACGGCTGGAAAATCTGATCGCCCAGCTGCCCGGCGAGAAGAAGAATG

GCCTGTTCGGAAACCTGATTGCCCTGAGCCTGGGCCTGACCCCCAACTTC

AAGAGCAACTTCGACCTGGCCGAGGATGCCAAACTGCAGCTGAGCAAGGA

CACCTACGACGACGACCTGGACAACCTGCTGGCCCAGATCGGCGACCAGT

ACGCCGACCTGTTTCTGGCCGCCAAGAACCTGTCCGACGCCATCCTGCTG

AGCGACATCCTGAGAGTGAACACCGAGATCACCAAGGCCCCCCTGAGCGC

CTCTATGATCAAGAGATACGACGAGCACCACCAGGACCTGACCCTGCTGA

AAGCTCTCGTGCGGCAGCAGCTGCCTGAGAAGTACAAAGAGATTTTCTTC

GACCAGAGCAAGAACGGCTACGCCGGCTACATTGACGGCGGAGCCAGCCA

GGAAGAGTTCTACAAGTTCATCAAGCCCATCCTGGAAAAGATGGACGGCA

CCGAGGAACTGCTCGTGAAGCTGAACAGAGAGGACCTGCTGCGGAAGCAG

CGGACCTTCGACAACGGCAGCATCCCCCACCAGATCCACCTGGGAGAGCT

GCACGCCATTCTGCGGCGGCAGGAAGATTTTTACCCATTCCTGAAGGACA

ACCGGGAAAAGATCGAGAAGATCCTGACCTTCCGCATCCCCTACTACGTG

GGCCCTCTGGCCAGGGGAAACAGCAGATTCGCCTGGATGACCAGAAAGAG

CGAGGAAACCATCACCCCCTGGAACTTCGAGGAAGTGGTGGACAAGGGCG

CTTCCGCCCAGAGCTTCATCGAGCGGATGACCAACTTCGATAAGAACCTG

CCCAACGAGAAGGTGCTGCCCAAGCACAGCCTGCTGTACGAGTACTTCAC

CGTGTATAACGAGCTGACCAAAGTGAAATACGTGACCGAGGGAATGAGAA

AGCCCGCCTTCCTGAGCGGCGAGCAGAAAAAGGCCATCGTGGACCTGCTG

TTCAAGACCAACCGGAAAGTGACCGTGAAGCAGCTGAAAGAGGACTACTT

CAAGAAAATCGAGTGCTTCGACTCCGTGGAAATCTCCGGCGTGGAAGATC

GGTTCAACGCCTCCCTGGGCACATACCACGATCTGCTGAAAATTATCAAG

GACAAGGACTTCCTGGACAATGAGGAAAACGAGGACATTCTGGAAGATAT

CGTGCTGACCCTGACACTGTTTGAGGACAGAGAGATGATCGAGGAACGGC

TGAAAACCTATGCCCACCTGTTCGACGACAAAGTGATGAAGCAGCTGAAG

CGGCGGAGATACACCGGCTGGGGCAGGCTGAGCCGGAAGCTGATCAACGG

CATCCGGGACAAGCAGTCCGGCAAGACAATCCTGGATTTCCTGAAGTCGA

CGGCTTCGCCAACAGAAACTTCATGCAGCTGATCCACGACGACAGCCTGA

CCTTTAAAGAGGACATCCAGAAAGCCCAGGTGTCCGGCCAGGGCGATAGC

CTGCACGAGCACATTGCCAATCTGGCCGGCAGCCCCGCCATTAAGAAGGG

CATCCTGCAGACAGTGAAGGTGGTGGACGAGCTCGTGAAAGTGATGGGCC

GGCACAAGCCCGAGAACATCGTGATCGAAATGGCCAGAGAGAACCAGACC

ACCCAGAAGGGACAGAAGAACAGCCGCGAGAGAATGAAGCGGATCGAAGA

GGGCATCAAAGAGCTGGGCAGCCAGATCCTGAAAGAACACCCCGTGGAAA

ACACCCAGCTGCAGAACGAGAAGCTGTACCTGTACTACCTGCAGAATGGG

CGGGATATGTACGTGGACCAGGAACTGGACATCAACCGGCTGTCCGACTA

CGATGTGGACCATATCGTGCCTCAGAGCTTTCTGAAGGACGACTCCATCG

ACAACAAGGTGCTGACCAGAAGCGACAAGAACCGGGGCAAGAGCGACAAC

GTGCCCTCCGAAGAGGTCGTGAAGAAGATGAAGAACTACTGGCGGCAGCT

GCTGAACGCCAAGCTGATTACCCAGAGAAAGTTCGACAATCTGACCAAGG

CCGAGAGAGGCGGCCTGAGCGAACTGGATAAGGCCGGCTTCATCAAGAGA

CAGCTGGTGGAAACCCGGCAGATCACAAAGCACGTGGCACAGATCCTGGA

CTCCCGGATGAACACTAAGTACGACGAGAATGACAAGCTGATCCGGGAAG

TGAAAGTGATCACCCTGAAGTCCAAGCTGGTGTCCGATTTCCGGAAGGAT

TTCCAGTTTTACAAAGTGCGCGAGATCAACAACTACCACCACGCCCACGA

CGCCTACCTGAACGCCGTCGTGGGAACCGCCCTGATCAAAAAGTACCCTA

AGCTGGAAAGCGAGTTCGTGTACGGCGACTACAAGGTGTACGACGTGCGG

AAGATGATCGCCAAGAGCGAGCAGGAAATCGGCAAGGCTACCGCCAAGTA

CTTCTTCTACGCAACATCATGAACTTTTTCAAGACCGAGATTACCCTGGC

CAACGGCGAGATCCGGAAGCGGCCTCTGATCGAGACAAACGGCGAAACCG

-continued
```
GGGAGATCGTGTGGGATAAGGGCCGGGATTTTGCCACCGTGCGGAAAGTG

CTGAGCATGCCCCAAGTGAATATCGTAAAAAGACCGAGGTGCAGACAGGC

GGCTTCAGCAAAGAGTCTATCCTGCCCAAGAGGAACAGCGATAAGCTGAT

CGCCAGAAAGAAGGACTGGGACCCTAAGAAGTACGGGGCTTCGACAGCCC

CACCGTGGCCTATTCTGTGCTGGTGGTGGCCAAAGTGGAAAAGGGCAAGT

CCAAGAAACTGAAGAGTGTGAAAGAGCTGCTGGGGATCACCATCATGGAA

AGAAGCAGCTTCGAGAAGAATCCCATCGACTTTCTGGAAGCCAAGGGCTA

CAAAGAAGTGAAAAAGGACCTGATCATCAAGCTGCCTAAGTACTCCCTGT

TCGAGCTGGAAAACGGCCGGAAGAGAATGCTGGCCTCTGCCGGCGAACTG

CAGAAGGGAAACGAACTGGCCCTGCCCTCCAAATATGTGAACTTCCTGTA

CCTGGCCAGCCACTATGAGAAGCTGAAGGGCTCCCCCGAGGATAATGAGC

AGAAACAGCTGTTTGTGGAACAGCACAAGCACTACCTGGACGAGATCATC

GAGCAGATCAGCGAGTTCTCCAAGAGAGTGATCCTGGCCGACGCTAATCT

GGACAAAGTGCTGTCCGCCTACAACAAGCACCGGGATAAGCCCATCAGAG

AGCAGGCCGAGAATATCATCCACCTGTTTACCCTGACCAATCTGGGAGCC

CCTGCCGCCTTCAAGTACTTTGACACCACCATCGACCGGAAGAGGTACAC

CAGCACCAAAGAGGTGCTGGACGCCACCCTGATCCACCAGAGCATCACCG

GCCTGTACGAGACACGGATCGACCTGTCTCAGCTGGGAGGCGACAAAAGG

CCGGCGGCCACGAAAAAGGCCGGCCAGGCAAAAAGAAAAAG
```

Nucleic acids encoding any of the fusion proteins, described herein, may be in any number of nucleic acid "vectors" known in the art. As used herein, a "vector" means any nucleic acid or nucleic acid-bearing particle, cell, or organism capable of being used to transfer a nucleic acid into a host cell. The term "vector" includes both viral and nonviral products and means for introducing the nucleic acid into a cell. A "vector" can be used in vitro, ex vivo, or in vivo. Non-viral vectors include plasmids, cosmids, artificial chromosomes (e.g., bacterial artificial chromosomes or yeast artificial chromosomes) and can comprise liposomes, electrically charged lipids (cytofectins), DNA-protein complexes, and biopolymers, for example. Viral vectors include retroviruses, lentiviruses, adeno-associated virus, pox viruses, baculovirus, reoviruses, vaccinia viruses, herpes simplex viruses, Epstein-Barr viruses, and adenovirus vectors, for example. Vectors can also comprise the entire genome sequence or recombinant genome sequence of a virus. A vector can also comprise a portion of the genome that comprises the functional sequences for production of a virus capable of infecting, entering, or being introduced to a cell to deliver nucleic acid therein.

Expression of any of the fusion proteins, described herein, may be controlled by any regulatory sequence (e.g. a promoter sequence) known in the art. Regulatory sequences, as described herein, are nucleic acid sequences that regulate the expression of a nucleic acid sequence. A regulatory or control sequence may include sequences that are responsible for expressing a particular nucleic acid (i.e. a Cas9 cargo protein) or may include other sequences, such as heterologous, synthetic, or partially synthetic sequences. The sequences can be of eukaryotic, prokaryotic or viral origin that stimulate or repress transcription of a gene in a specific or non-specific manner and in an inducible or non-inducible manner. Regulatory or control regions may include origins of replication, RNA splice sites, introns, chimeric or hybrid introns, promoters, enhancers, transcriptional termination sequences, poly A sites, locus control regions, signal sequences that direct the polypeptide into the secretory pathways of the target cell, and introns. A heterologous regulatory region is not naturally associated with the expressed nucleic acid it is linked to. Included among the heterologous regulatory regions are regulatory regions from a different species, regulatory regions from a different gene, hybrid regulatory sequences, and regulatory sequences that do not occur in nature, but which are designed by one of ordinary skill in the art.

The term operably linked refers to an arrangement of sequences or regions wherein the components are configured so as to perform their usual or intended function. Thus, a regulatory or control sequence operably linked to a coding sequence is capable of affecting the expression of the coding sequence. The regulatory or control sequences need not be contiguous with the coding sequence, so long as they function to direct the proper expression or polypeptide production. Thus, for example, intervening untranslated but transcribed sequences can be present between a promoter sequence and the coding sequence and the promoter sequence can still be considered operably linked to the coding sequence. A promoter sequence, as described herein, is a DNA regulatory region a short distance from the 5' end of a gene that acts as the binding site for RNA polymerase. The promoter sequence may bind RNA polymerase in a cell and/or initiate transcription of a downstream (3' direction) coding sequence. The promoter sequence may be a promoter capable of initiating transcription in prokaryotes or eukaryotes. Some non-limiting examples of eukaryotic promoters include the cytomegalovirus (CMV) promoter, the chicken β-actin (CBA) promoter, and a hybrid form of the CBA promoter (CBh).

In certain embodiments, the Cas9 cargo protein is expressed from the pX330 plasmid (Addgene). An exemplary nucleic acid sequence of the pX330 plasmid with the 5' AgeI cloning site underlined (single underline) and the 3' EcoRI cloning site underlined (double underlined) is shown as (SEQ ID NO: 34). Any of the nucleic acids encoding the WW domains or WW domain variants, described herein, may be cloned, in frame, with the sequence encoding Cas9 from SEQ ID NO: 34. For example, the two ITCH WW domains or the four ITCH WW domains encoded in the nucleic acid sequences (SEQ ID NO: 32), or (SEQ ID NO: 33) may be cloned into the 5' AgeI cloning site or the 3' EcoRI cloning site. It should be appreciated that a nucleic acid encoding any of the WW domains or WW domain variants, described herein, may be cloned into the Cas9 sequence of (SEQ ID NO: 34) and the examples provided are not meant to be limiting.

(SEQ ID NO: 34)
```
  1    gagggcctat tcccatgat  tccttcatat ttgcatatac gatacaaggc tgttagagag
 61    ataattggaa ttaatttgac tgtaaacaca aagatattag tacaaaatac gtgacgtaga
121    aagtaataat ttcttgggta gtttgcagtt ttaaaattat gttttaaaat ggactatcat
```

-continued

```
 181   atgcttaccg taacttgaaa gtatttcgat ttcttggctt tatatatctt GTGGAAAGGA
 241   CGAAACACCg gGTCTTCgaG AAGACctgtt ttagagctaG AAAtagcaag ttaaaataag
 301   gctagtccgt tatcaacttg aaaaagtggc accgagtcgg tgcTTTTTTg ttttagagct
 361   agaaatagca agttaaaata aggctagtcc gtTTTTagcg cgtgcgccaa ttctgcagac
 421   aaatggctct agaggtaccc gttacataac ttacggtaaa tggcccgcct ggctgaccgc
 481   ccaacgaccc ccgcccattg acgtcaatag taacgccaat agggactttc cattgacgtc
 541   aatgggtgga gtatttacgg taaactgccc acttggcagt acatcaagtg tatcatatgc
 601   caagtacgcc ccctattgac gtcaatgacg gtaaatggcc cgcctggcat tGtgcccagt
 661   acatgacctt atgggacttt cctacttggc agtacatcta cgtattagtc atcgctatta
 721   ccatggtcga ggtgagcccc acgttctgct tcactctccc catctccccc cctccccac
 781   ccccaattttt gtatttattt attttttaat tattttgtgc agcgatgggg gcggggggg
 841   ggggggggcg cgcgccaggc ggggcgggc ggggcgaggg gcggggcggg gcgaggcgga
 901   gaggtgcggc ggcagccaat cagagcggcg cgctccgaaa gtttccttt atggcgaggc
 961   ggcggcggcg gcggccctat aaaaagcgaa gcgcgcggcg ggcgggagtc gctgcgacgc
1021   tgccttcgcc ccgtgccccg ctccgccgcc gcctcgcgcc gcccgccccg gctctgactg
1081   accgcgttac tcccacaggt gagcgggcgg gacggccctt ctcctccggg ctgtaattag
1141   ctgagcaaga ggtaagggtt taagggatgg ttggttggtg gggtattaat gtttaattac
1201   ctggagcacc tgcctgaaat cactttttttt caggttGGac cggtgccacc ATGGACTATA
1261   AGGACCACGA CGGAGACTAC AAGGATCATG ATATTGATTA CAAAGACGAT GACGATAAGA
1321   TGGCCCCAAA GAAGAAGCGG AAGGTCGGTA TCCACGGAGT CCCAGCAGCC GACAAGAAGT
1381   ACAGCATCGG CCTGGACATC GGCACCAACT CTGTGGGCTG GGCCGTGATC ACCGACGAGT
1441   ACAAGGTGCC CAGCAAGAAA TTCAAGGTGC TGGGCAACAC CGACCGGCAC AGCATCAAGA
1501   AGAACCTGAT CGGAGCCCTG CTGTTCGACA GCGGCGAAAC AGCCGAGGCC ACCCGGCTGA
1561   AGAGAACCGC CAGAAGAAGA TACACCAGAC GGAAGAACCG GATCTGCTAT CTGCAAGAGA
1621   TCTTCAGCAA CGAGATGGCC AAGGTGGACG ACAGCTTCTT CCACAGACTG GAAGAGTCCT
1681   TCCTGGTGGA AGAGGATAAG AAGCACGAGC GGCACCCCAT CTTCGGCAAC ATCGTGGACG
1741   AGGTGGCCTA CCACGAGAAG TACCCCACCA TCTACCACCT GAGAAAGAAA CTGGTGGACA
1801   GCACCGACAA GGCCGACCTG CGGCTGATCT ATCTGGCCCT GGCCCACATG ATCAAGTTCC
1861   GGGGCCACTT CCTGATCGAG GGCGACCTGA ACCCCGACAA CAGCGACGTG GACAAGCTGT
1921   TCATCCAGCT GGTGCAGACC TACAACCAGC TGTTCGAGGA AAACCCCATC AACGCCAGCG
1981   GCGTGGACGC CAAGGCCATC CTGTCTGCCA GACTGAGCAA GAGCAGACGG CTGGAAAATC
2041   TGATCGCCCA GCTGCCCGGC GAGAAGAAGA ATGGCCTGTT CGGAAACCTG ATTGCCCTGA
2101   GCCTGGGCCT GACCCCCAAC TTCAAGAGCA ACTTCGACCT GGCCGAGGAT GCCAAACTGC
2161   AGCTGAGCAA GGACACCTAC GACGACGACC TGGACAACCT GCTGGCCCAG ATCGGCGACC
2221   AGTACGCCGA CCTGTTTCTG GCCGCCAAGA ACCTGTCCGA CGCCATCCTG CTGAGCGACA
2281   TCCTGAGAGT GAACACCGAG ATCACCAAGG CCCCCCTGAG CGCCTCTATG ATCAAGAGAT
2341   ACGACGAGCA CCACCAGGAC CTGACCCTGC TGAAAGCTCT CGTGCGGCAG CAGCTGCCTG
2401   AGAAGTACAA AGAGATTTTC TTCGACCAGA GCAAGAACGG CTACGCCGGC TACATTGACG
2461   GCGGAGCCAG CCAGGAAGAG TTCTACAAGT TCATCAAGCC CATCCTGGAA AAGATGGACG
2521   GCACCGAGGA ACTGCTCGTG AAGCTGAACA GAGAGGACCT GCTGCGGAAG CAGCGGACCT
```

-continued

```
2581  TCGACAACGG CAGCATCCCC CACCAGATCC ACCTGGGAGA GCTGCACGCC ATTCTGCGGC
2641  GGCAGGAAGA TTTTTACCCA TTCCTGAAGG ACAACCGGGA AAAGATCGAG AAGATCCTGA
2701  CCTTCCGCAT CCCCTACTAC GTGGGCCCTC TGGCCAGGGG AAACAGCAGA TTCGCCTGGA
2761  TGACCAGAAA GAGCGAGGAA ACCATCACCC CCTGGAACTT CGAGGAAGTG GTGGACAAGG
2821  GCGCTTCCGC CCAGAGCTTC ATCGAGCGGA TGACCAACTT CGATAAGAAC CTGCCCAACG
2881  AGAAGGTGCT GCCCAAGCAC AGCCTGCTGT ACGAGTACTT CACCGTGTAT AACGAGCTGA
2941  CCAAAGTGAA ATACGTGACC GAGGGAATGA GAAAGCCCGC CTTCCTGAGC GGCGAGCAGA
3001  AAAAGGCCAT CGTGGACCTG CTGTTCAAGA CCAACCGGAA AGTGACCGTG AAGCAGCTGA
3061  AAGAGGACTA CTTCAAGAAA ATCGAGTGCT TCGACTCCGT GGAAATCTCC GGCGTGGAAG
3121  ATCGGTTCAA CGCCTCCCTG GGCACATACC ACGATCTGCT GAAAATTATC AAGGACAAGG
3181  ACTTCCTGGA CAATGAGGAA AACGAGGACA TTCTGGAAGA TATCGTGCTG ACCCTGACAC
3241  TGTTTGAGGA CAGAGAGATG ATCGAGGAAC GGCTGAAAAC CTATGCCCAC CTGTTCGACG
3301  ACAAAGTGAT GAAGCAGCTG AAGCGGCGGA GATACACCGG CTGGGGCAGG CTGAGCCGGA
3361  AGCTGATCAA CGGCATCCGG GACAAGCAGT CCGGCAAGAC AATCCTGGAT TTCCTGAAGT
3421  CCGACGGCTT CGCCAACAGA AACTTCATGC AGCTGATCCA CGACGACAGC CTGACCTTTA
3481  AAGAGGACAT CCAGAAAGCC CAGGTGTCCG GCCAGGGCGA TAGCCTGCAC GAGCACATTG
3541  CCAATCTGGC CGGCAGCCCC GCCATTAAGA AGGGCATCCT GCAGACAGTG AAGGTGGTGG
3601  ACGAGCTCGT GAAAGTGATG GGCCGGCACA AGCCCGAGAA CATCGTGATC GAAATGGCCA
3661  GAGAGAACCA GACCACCCAG AAGGGACAGA AGAACAGCCG CGAGAGAATG AAGCGGATCG
3721  AAGAGGGCAT CAAAGAGCTG GGCAGCCAGA TCCTGAAAGA ACACCCCGTG GAAAACACCC
3781  AGCTGCAGAA CGAGAAGCTG TACCTGTACT ACCTGCAGAA TGGGCGGGAT ATGTACGTGG
3841  ACCAGGAACT GGACATCAAC CGGCTGTCCG ACTACGATGT GGACCATATC GTGCCTCAGA
3901  GCTTTCTGAA GGACGACTCC ATCGACAACA AGGTGCTGAC CAGAAGCGAC AAGAACCGGG
3961  GCAAGAGCGA CAACGTGCCC TCCGAAGAGG TCGTGAAGAA GATGAAGAAC TACTGGCGGC
4021  AGCTGCTGAA CGCCAAGCTG ATTACCCAGA GAAAGTTCGA CAATCTGACC AAGGCCGAGA
4081  GAGGCGGCCT GAGCGAACTG GATAAGGCCG GCTTCATCAA GAGACAGCTG GTGGAAACCC
4141  GGCAGATCAC AAAGCACGTG GCACAGATCC TGGACTCCCG GATGAACACT AAGTACGACG
4201  AGAATGACAA GCTGATCCGG GAAGTGAAAG TGATCACCCT GAAGTCCAAG CTGGTGTCCG
4261  ATTTCCGGAA GGATTTCCAG TTTTACAAAG TGCGCGAGAT CAACAACTAC CACCACGCCC
4321  ACGACGCCTA CCTGAACGCC GTCGTGGGAA CCGCCCTGAT CAAAAAGTAC CCTAAGCTGG
4381  AAAGCGAGTT CGTGTACGGC GACTACAAGG TGTACGACGT GCGGAAGATG ATCGCCAAGA
4441  GCGAGCAGGA AATCGGCAAG GCTACCGCCA AGTACTTCTT CTACAGCAAC ATCATGAACT
4501  TTTTCAAGAC CGAGATTACC CTGGCCAACG GCGAGATCCG GAAGCGGCCT CTGATCGAGA
4561  CAAACGGCGA AACCGGGGAG ATCGTGTGGG ATAAGGGCCG GGATTTTGCC ACCGTGCGGA
4621  AAGTGCTGAG CATGCCCCAA GTGAATATCG TGAAAAAGAC CGAGGTGCAG ACAGGCGGCT
4681  TCAGCAAAGA GTCTATCCTG CCCAAGAGGA ACAGCGATAA GCTGATCGCC AGAAAGAAGG
4741  ACTGGGACCC TAAGAAGTAC GGCGGCTTCG ACAGCCCCAC CGTGGCCTAT TCTGTGCTGG
4801  TGGTGGCCAA AGTGGAAAAG GGCAAGTCCA AGAAACTGAA GAGTGTGAAA GAGCTGCTGG
4861  GGATCACCAT CATGGAAAGA AGCAGCTTCG AGAAGAATCC CATCGACTTT CTGGAAGCCA
4921  AGGGCTACAA AGAAGTGAAA AAGGACCTGA TCATCAAGCT GCCTAAGTAC TCCCTGTTCG
4981  AGCTGGAAAA CGGCCGGAAG AGAATGCTGG CCTCTGCCGG CGAACTGCAG AAGGGAAACG
```

```
5041   AACTGGCCCT GCCCTCCAAA TATGTGAACT TCCTGTACCT GGCCAGCCAC TATGAGAAGC
5101   TGAAGGGCTC CCCCGAGGAT AATGAGCAGA ACAGCTGTT TGTGGAACAG CACAAGCACT
5161   ACCTGGACGA GATCATCGAG CAGATCAGCG AGTTCTCCAA GAGAGTGATC CTGGCCGACG
5221   CTAATCTGGA CAAAGTGCTG TCCGCCTACA ACAAGCACCG GGATAAGCCC ATCAGAGAGC
5281   AGGCCGAGAA TATCATCCAC CTGTTTACCC TGACCAATCT GGGAGCCCCT GCCGCCTTCA
5341   AGTACTTTGA CACCACCATC GACCGGAAGA GGTACACCAG CACCAAAGAG GTGCTGGACG
5401   CCACCCTGAT CCACCAGAGC ATCACCGGCC TGTACGAGAC ACGGATCGAC CTGTCTCAGC
5461   TGGGAGGCGA CAAAAGGCCG GCGGCCACGA AAAAGGCCGG CCAGGCAAAA AAGAAAAAGt
5521   aagaattcCT AGAGCTCGCT GATCAGCCTC GACTGTGCCT TCTAGTTGCC AGCCATCTGT
5581   TGTTTGCCCC TCCCCCGTGC CTTCCTTGAC CCTGGAAGGT GCCACTCCCA CTGTCCTTTC
5641   CTAATAAAAT GAGGAAATTG CATCGCATTG TCTGAGTAGG TGTCATTCTA TTCTGGGGGG
5701   TGGGGTGGGG CAGGACAGCA AGGGGGAGGA TTGGGAAGAg AATAGCAGGC ATGCTGGGGA
5761   gcggccgcag gaaccectag tgatggagtt ggccactccc tctctgcgcg ctcgctcgct
5821   cactgaggcc gggcgaccaa aggtcgcccg acgcccgggc tttgcccggg cggcctcagt
5881   gagcgagcga gcgcgcagct gcctgcaggg gcgcctgatg cggtattttc tccttacgca
5941   tctgtgcggt atttcacacc gcatacgtca aagcaaccat agtacgcgcc ctgtagcggc
6001   gcattaagcg cggcgggtgt ggtggttacg cgcagcgtga ccgctacact tgccagcgcc
6061   ctagcgcccg ctcctttcgc tttcttccct cctttctcg ccacgttcgc cggctttccc
6121   cgtcaagctc taaatcgggg gctcccttta gggttccgat ttagtgcttt acggcacctc
6181   gaccccaaaa aacttgattt gggtgatggt tcacgtagtg ggccatcgcc ctgatagacg
6241   gttttcgcc ctttgacgtt ggagtccacg ttctttaata gtggactctt gttccaaact
6301   ggaacaacac tcaaccctat ctcgggctat tctttgatt tataagggat tttgccgatt
6361   tcggcctatt ggttaaaaaa tgagctgatt taacaaaaat ttaacgcgaa ttttaacaaa
6421   atattaacgt ttacaatttt atggtgcact ctcagtacaa tctgctctga tgccgcatag
6481   ttaagccagc cccgacaccc gccaacaccc gctgacgcgc cctgacgggc ttgtctgctc
6541   ccggcatccg cttacagaca agctgtgacc gtctccggga gctgcatgtg tcagaggttt
6601   tcaccgtcat caccgaaacg cgcgagacga agggcctcg tgatacgcct attttatag
6661   gttaatgtca tgataataat ggtttcttag acgtcaggtg cacttttcg gggaaatgtg
6721   cgcggaaccc ctatttgttt attttctaa atacattcaa atatgtatcc gctcatgaga
6781   caataaccct gataaatgct tcaataatat tgaaaaagga agagtatgag tattcaacat
6841   ttccgtgtcg cccttattcc cttttttgcg gcattttgcc ttcctgtttt tgctcaccca
6901   gaaacgctgg tgaaagtaaa agatgctgaa gatcagttgg gtgcacgagt gggttacatc
6961   gaactggatc tcaacagcgg taagatcctt gagagtttc gccccgaaga acgttttcca
7021   atgatgagca cttttaaagt tctgctatgt ggcgcggtat tatcccgtat tgacgccggg
7081   caagagcaac tcggtcgccg catacactat tctcagaatg acttggttga gtactcacca
7141   gtcacagaaa agcatcttac ggatggcatg acagtaagag aattatgcag tgctgccata
7201   accatgagtg ataacactgc ggccaactta cttctgacaa cgatcggagg accgaaggag
7261   ctaaccgctt ttttgcacaa catgggggat catgtaactc gccttgatcg ttgggaaccg
7321   gagctgaatg aagccatacc aaacgacgag cgtgacacca cgatgcctgt agcaatggca
7381   acaacgttgc gcaaactatt aactggcgaa ctacttactc tagcttcccg gcaacaatta
```

```
-continued
7441   atagactgga tggaggcgga taaagttgca ggaccacttc tgcgctcggc ccttccggct 7501   ggctggttta ttgctgataa atctggagcc ggtgagcgtg gaagccgcgg tatcattgca 7561   gcactggggc cagatggtaa gccctcccgt atcgtagtta tctacacgac ggggagtcag 7621   gcaactatgg atgaacgaaa tagacagatc gctgagatag gtgcctcact gattaagcat 7681   tggtaactgt cagaccaagt ttactcatat atactttaga ttgatttaaa acttcatttt 7741   taatttaaaa ggatctaggt gaagatcctt tttgataatc tcatgaccaa aatcccttaa 7801   cgtgagtttt cgttccactg agcgtcagac cccgtagaaa agatcaaagg atcttcttga 7861   gatccttttt ttctgcgcgt aatctgctgc ttgcaaacaa aaaaaccacc gctaccagcg 7921   gtggtttgtt tgccggatca agagctacca actcttttc cgaaggtaac tggcttcagc 7981   agagcgcaga taccaaatac tgtccttcta gtgtagccgt agttaggcca ccacttcaag 8041   aactctgtag caccgcctac atacctcgct ctgctaatcc tgttaccagt ggctgctgcc 8101   agtggcgata agtcgtgtct taccgggttg gactcaagac gatagttacc ggataaggcg 8161   cagcggtcgg gctgaacggg gggttcgtgc acacagccca gcttggagcg aacgacctac 8221   accgaactga gatacctaca gcgtgagcta tgagaaagcg ccacgcttcc cgaagggaga 8281   aaggcggaca ggtatccggt aagcggcagg gtcggaacag gagagcgcac gagggagctt 8341   ccaggggaa  acgcctggta tctttatagt cctgtcgggt ttcgccacct ctgacttgag 8401   cgtcgatttt tgtgatgctc gtcaggggg  cggagcctat ggaaaaacgc cagcaacgcg 8461   gcctttttac ggttcctggc cttttgctgg cctttgctc  acatgt
```

Cells Producing Microvesicles Containing Cargo Proteins

A microvesicle-producing cell of the present invention may be a cell containing any of the expression constructs or any of the cargo proteins described herein. For example, an inventive microvesicle-producing cell may contain one or more recombinant expression constructs encoding (1) an ARRDC1 protein, or PSAP (SEQ ID NO: 74) motif-containing variant thereof, and (2) a cargo protein fused to at least one WW domain, or variant thereof, under the control of a heterologous promoter. In certain embodiments, the expression construct in the microvesicle producing cell encodes a cargo protein with one or more WW domains or variants thereof. In some embodiments, the expression construct encodes a Cas9 cargo protein or variant thereof fused to one or more WW domains or variants thereof. In some embodiments, the expression construct encodes a Cas9 cargo protein or variant thereof fused to at least one WW domain and at least one NLS. In some embodiments, the expression construct further encodes a guide RNA (gRNA). In some embodiments, the expression construct further encodes a TSG101 protein, or a TSG101 protein variant. It should be appreciated that the ARMMs produced by such a microvesicle producing cell typically comprise the WW domain containing cargo proteins encoded by the expression constructs described herein.

Another inventive microvesicle-producing cell may contain a recombinant expression construct encoding (1) an ARRDC1 protein, or a PSAP (SEQ ID NO: 74) motif-containing variant thereof, linked to (2) a Cas9 cargo protein, or variant thereof, under the control of a heterologous promoter. Some aspects of this invention provide a microvesicle-producing cell that comprises a recombinant expression construct encoding (1) a TSG101 protein, or a UEV domain-containing variant thereof, linked to (2) a Cas9 cargo protein or variant thereof, under the control of a heterologous promoter.

Any of the expression constructs, described herein, may be stably inserted into the genome of the cell. In some embodiments, the expression construct is maintained in the cell, but not inserted into the genome of the cell. In some embodiments, the expression construct is in a vector, for example, a plasmid vector, a cosmid vector, a viral vector, or an artificial chromosome. In some embodiments, the expression construct further comprises additional sequences or elements that facilitate the maintenance and/or the replication of the expression construct in the microvesicle-producing cell, or that improve the expression of the fusion protein in the cell. Such additional sequences or elements may include, for example, an origin of replication, an antibiotic resistance cassette, a polyA sequence, and/or a transcriptional isolator. Some expression constructs suitable for the generation of microvesicle producing cells according to aspects of this invention are described elsewhere herein. Methods and reagents for the generation of additional expression constructs suitable for the generation of microvesicle producing cells according to aspects of this invention will be apparent to those of skill in the art based on the present disclosure. In some embodiments, the microvesicle producing cell is a mammalian cell, for example, a mouse cell, a rat cell, a hamster cell, a rodent cell, or a nonhuman primate cell. In some embodiments, the microvesicle producing cell is a human cell.

One skilled in the art may employ conventional techniques, such as molecular or cell biology, virology, microbiology, and recombinant DNA techniques. Exemplary techniques are explained fully in the literature. For example, one may rely on the following general texts to make and use the invention: Sambrook et al., Molecular Cloning: A Laboratory Manual, Second Edition (1989) Cold Spring Harbor Laboratory Press, Cold Spring Harbor, N.Y., and Sambrook et al. Third Edition (2001); DNA Cloning: A Practical Approach, Volumes I and II (D. N. Glover ed. 1985);

Oligonucleotide Synthesis (M. J. Gaited. 1984); Nucleic Acid Hybridization (B. D. Hames & S. J. Higgins eds. (1985)); Transcription And Translation Hames & Higgins, eds. (1984); Animal Cell Culture (R I. Freshney, ed. (1986)); Immobilized Cells And Enzymes (IRL Press, (1986)); Gennaro et al. (eds.) Remington's Pharmaceutical Sciences, 18th edition; B. Perbal, A Practical Guide To Molecular Cloning (1984); F. M. Ausubel et al. (eds.), Current Protocols in Molecular Biology, John Wiley & Sons, Inc. (updates through 2001), Coligan et al. (eds.), Current Protocols in Immunology, John Wiley & Sons, Inc. (updates through 2001); W. Paul et al. (eds.) Fundamental Immunology, Raven Press; E. J. Murray et al. (ed.) Methods in Molecular Biology: Gene Transfer and Expression Protocols, The Humana Press Inc. (1991)(especially vol. 7); and J. E. Celis et al., Cell Biology: A Laboratory Handbook, Academic Press (1994).

Delivery of ARMMs Containing Cargo Proteins

The inventive microvesicles (e.g., ARMMs) containing a cargo protein, described herein, may further have a targeting moiety. The targeting moiety may be used to target the delivery of ARMMs to specific cell types, resulting in the release of the contents of the ARMM into the cytoplasm of the specific targeted cell type. A targeting moiety may selectively bind an antigen of the target cell. For example, the targeting moiety may be a membrane-bound immunoglobulin, an integrin, a receptor, a receptor ligand, an aptamer, a small molecule, or a variant thereof. Any number of cell surface proteins may also be included in an ARMM to facilitate the binding of an ARMM to a target cell and/or to facilitate the uptake of an ARMM into a target cell. Integrins, receptor tyrosine kinases, G-protein coupled receptors, and membrane-bound immunoglobulins suitable for use with embodiments of this invention will be apparent to those of skill in the art and the invention is not limited in this respect. For example, in some embodiments, the integrin is an $\alpha1\beta1$, $\alpha2\beta1$, $\alpha4\beta1$, $\alpha5\beta1$, $\alpha6\beta1$, $\alpha L\beta2$, $\alpha M\beta2$, $\alpha IIb\beta3$, $\alpha V\beta3$, $\alpha V\beta5$, $\alpha V\beta6$, or a $\alpha6\beta4$ integrin. In some embodiments, the receptor tyrosine kinase is a an EGF receptor (ErbB family), insulin receptor, PDGF receptor, FGF receptor, VEGF receptor, HGF receptor, Trk receptor, Eph receptor, AXL receptor, LTK receptor, TIE receptor, ROR receptor, DDR receptor, RET receptor, KLG receptor, RYK receptor, or MuSK receptor. In some embodiments, the G-protein coupled receptor is a rhodopsin-like receptor, the secretin receptor, metabotropic glutamate/pheromone receptor, cyclic AMP receptor, frizzled/smoothened receptor, CXCR4, CCR5, or beta-adrenergic receptor.

Any number of membrane-bound immunoglobulins, known in the art, may be used as targeting moieties to target the delivery of ARMMs containing a cargo protein to any number of target cell types. In certain embodiments, the membrane-bound immunoglobulin targeting moiety binds a tumor associated or tumor specific antigen. Some non-limiting examples of tumor antigens include, CA19-9, c-met, PD-1, CTLA-4, ALK, AFP, EGFR, Estrogen receptor (ER), Progesterone receptor (PR), HER2/neu, KIT, B-RAF, S100, MAGE, Thyroglobulin, MUC-1, and PSMA (Bigbee W., et al. "Tumor markers and immunodiagnosis.", *Cancer Medicine*. 6th ed. Hamilton, Ontario, Canada: BC Decker Inc., 2003; Andriole G, et al. "Mortality results from a randomized prostate-cancer screening trial.", *New England Journal of Medicine*, 360(13):1310-1319, 2009; Schroder F H, et al. "Screening and prostate-cancer mortality in a randomized European study." *New England Journal of Medicine*, 360(13):1320-1328, 2009; Buys S S, et al. "Effect of screening on ovarian cancer mortality: the Prostate, Lung, Colorectal and Ovarian (PLCO) Cancer Screening Randomized Controlled Trial.", *JAMA*, 305(22):2295-2303, 2011; Cramer D W et al. "Ovarian cancer biomarker performance in prostate, lung, colorectal, and ovarian cancer screening trial specimens." *Cancer Prevention Research*, 4(3):365-374, 2011; Roy D M, et al. "Candidate prognostic markers in breast cancer: focus on extracellular proteases and their inhibitors.", *Breast Cancer*. July 3; 6:81-91, 2014; Tykodi S S. et al. "PD-1 as an emerging therapeutic target in renal cell carcinoma: current evidence." *Onco Targets Ther*. July 25; 7:1349-59, 2014; and Weinberg R A. *The Biology of Cancer*, Garland Science, Taylor & Francis Group LLC, New York, N.Y., 2007; the entire contents of each are incorporated herein by reference).

In certain embodiments, the membrane-bound immunoglobulin targeting moiety binds to an antigen of a specific cell type. The cell type may be a stem cell, such as a pluripotent stem cell. Some non-limiting examples of antigens specific to pluripotent stem cells include Oct4 and Nanog, which were the first proteins identified as essential for both early embryo development and pluripotency maintenance in embryonic stem cells (Nichols J, et al. "Formation of pluripotent stem cells in the mammalian embryo depends on the POU transcription factor Oct4.", *Cell*. 95:379-91, 1998; the contents of which are hereby incorporated by reference). In addition to Oct4, Sox2 and Nanog, many other pluripotent stem cell markers have been identified, including Sal14, Dax1, Essrb, Tbx3, Tcl1, Rif1, Nac1 and Zfp281 (Loh Y, et al. "The Oct4 and Nanog transcription network regulates pluripotency in mouse embryonic stem cells.", *Nat Genet*. 38:431-40, 2006). The membrane-bound immunoglobulin targeting moiety may also bind to an antigen of a differentiated cell type. For example, the targeting moiety may bind to an antigen specific for a lung epithelial cell to direct the delivery of ARMM cargo proteins to lung epithelial cells. As a non-limiting example, a membrane-bound immunoglobulin targeting moiety may bind to the alveolar epithelial type 1 cell specific protein $RTI_{40}$ or $HTI_{56}$ to deliver cargo proteins to alveolar epithelial type 1 cells (McElroy M C et al. "The use of alveolar epithelial type I cell-selective markers to investigate lung injury and repair.", *European Respiratory Jorunal* 24:4, 664-673, 2004; the entire contents of which are hereby incorporated by reference). As another example, the targeting moiety may bind a mucin, such as muc5ac, or muc5b. It should be appreciated that the examples of antigens provided in this application are not limiting and the targeting moiety may be any moiety capable of binding any cellular antigen known in the art.

Some aspects of this invention relate to the recognition that ARMMs are taken up by target cells, and ARMM uptake results in the release of the contents of the ARMM into the cytoplasm of the target cells. In some embodiments, the fusion protein is an agent that affects a desired change in the target cell, for example, a change in cell survival, proliferation rate, a change in differentiation stage, a change in a cell identity, a change in chromatin state, a change in the transcription rate of one or more genes, a change in the transcriptional profile, or a post-transcriptional change in gene compression of the target cell. It will be understood by those of skill in the art, that the agent to be delivered will be chosen according to the desired effect in the target cell.

The genome of the target cell may be edited by a nuclease delivered to the cell via a strategy or method disclosed herein, e.g., by a RNA-programmable nuclease (e.g., Cas9), a TALEN, or a zinc-finger nuclease, or a plurality or combination of such nucleases. Some non-limiting aspects of this invention relate to the recognition that ARMMs can be used to deliver a cargo protein fused to at least one WW domain, or variant thereof, or a Cas9 fusion protein in ARMMs to the target cell or a population of target cells, for example, by contacting the target cell with ARMMs comprising the fusion protein to be delivered. Accordingly, some aspects of this invention provide ARMMs that comprise a fusion protein, for example, a Cas9 protein, or variant thereof, fused to a WW domain, an ARRDC1 protein, or variant thereof, or a TSG101 protein or variant thereof.

Using any of the nucleases, described herein, or any of the nucleases known in the art, a single- or double-strand break may be introduced at a specific site within the genome of a target cell by the nuclease, resulting in a disruption of the targeted genomic sequence. In some embodiments, the targeted genomic sequence is a nucleic acid sequence within the coding region of a gene. In some embodiments, the strand break introduced by the nuclease leads to a mutation within the target gene that impairs the expression of the encoded gene product. In some embodiments, a nucleic acid is co-delivered to the cell with the nuclease. In some embodiments, the nucleic acid comprises a sequence that is identical or homologous to a sequence adjacent to the nuclease target site. In some such embodiments, the strand break effected by the nuclease is repaired by the cellular DNA repair machinery to introduce all or part of the co-delivered nucleic acid into the cellular DNA at the break site, resulting in a targeted insertion of the co-delivered nucleic acid, or part thereof. In some embodiments, the insertion results in the disruption or repair of a pathogenic allele. In some embodiments, the insertion is detected by a suitable assay, e.g., a DNA sequencing assay, a southern blot assay, or an assay for a reporter gene encoded by the co-delivered nucleic acid, e.g., a fluorescent protein or resistance to an antibiotic. In some embodiments, the nucleic acid is co-delivered by association to a supercharged protein. In some embodiments, the supercharged protein is also associated to the functional effector protein, e.g., the nuclease. In some embodiments, the delivery of a nuclease to a target cell results in a clinically or therapeutically beneficial disruption of the function of a gene.

In some embodiments, cells from a subject are obtained and a nuclease is delivered to the cells by a system or method provided herein ex vivo. In some embodiments, the treated cells are selected for those cells in which a desired nuclease-mediated genomic editing event has been effected. In some embodiments, treated cells carrying a desired genomic mutation or alteration are returned to the subject they were obtained from.

Methods for engineering, generation, and isolation of nucleases targeting specific sequences, e.g., Cas9, TALE, or zinc finger nucleases, and editing cellular genomes at specific target sequences, are well known in the art (see, e.g., Mani et al., Biochemical and Biophysical Research Communications 335:447-457, 2005; Perez et al., Nature Biotechnology 26:808-16, 2008; Kim et al., Genome Research, 19:1279-88, 2009; Urnov et al., Nature 435:646-51, 2005; Carroll et al., Gene Therapy 15:1463-68, 2005; Lombardo et al., Nature Biotechnology 25:1298-306, 2007; Kandavelou et al., Biochemical and Biophysical Research Communications 388:56-61, 2009; and Hockemeyer et al., Nature Biotechnology 27(9):851-59, 2009, as well as the reference recited in the respective section for each nuclease). The skilled artisan will be able to ascertain suitable methods for use in the context of the present disclosure based on the guidance provided herein.

As another example, to augment the differentiation stage of a target cell, for example, to reprogram a differentiated target cell into an embryonic stem cell-like stage, the cell is contacted, in some embodiments, with ARMMs with reprogramming factors, for example, Oct4, Sox2, c-Myc, and/or KLF4 that are fused to at least one WW domain, or variant thereof. Similarly, to affect the change in the chromatin state of a target cell, the cell is contacted, in some embodiments, with ARMMs containing a chromatin modulator, for example, a DNA methyltransferase, or a histone deacetylase fused to at least one WW domain, or variant thereof. For another example, if survival of the target cell is to be diminished, the target cell, in some embodiments, is contacted with ARMMs comprising a cytotoxic agent, for example, a cytotoxic protein fused to at least one WW domain or variant thereof. Additional agents suitable for inclusion into ARMMs and for a ARMM-mediated delivery to a target cell or target cell population will be apparent to those skilled in the art, and the invention is not limited in this respect.

In some embodiments, the ARMMs comprising a cargo protein fused to a WW domain, or variant thereof, or a Cas9 protein, or variant thereof, are provided that further include a detectable label. Such ARMMs allow for the labeling of a target cell without genetic manipulation. Detectable labels suitable for direct delivery to target cells are known in the art, and include, but are not limited to, fluorescent proteins, fluorescent dyes, membrane-bound dyes, and enzymes, for example, membrane-bound or cytosolic enzymes, catalyzing the reaction resulting in a detectable reaction product. Detectable labels suitable according to some aspects of this invention further include membrane-bound antigens, for example, membrane-bound ligands that can be detected with commonly available antibodies or antigen binding agents.

In some embodiments, ARMMs are provided that comprise a WW domain containing protein or a fusion protein comprising a WW domain or variant thereof to be delivered to a target cell. In some embodiments, the fusion protein is or comprises a transcription factor, a transcriptional repressor, a fluorescent protein, a kinase, a phosphatase, a protease, a ligase, a chromatin modulator, or a recombinase. In some embodiments, the protein is a therapeutic protein. In some embodiments the protein is a protein that affects a change in the state or identity of a target cell. For example, in some embodiments, the protein is a reprogramming factor. Suitable transcription factors, transcriptional repressors, fluorescent proteins, kinases, phosphatases, proteases, ligases, chromatin modulators, recombinases, and reprogramming factors may be fused to one or more WW domains to facilitate their incorporation into ARMMs and their function may be tested by any methods that are known to those skilled in the art, and the invention is not limited in this respect.

Methods for isolating the ARMMs described herein are also provided. One exemplary method includes collecting the culture medium, or supernatant, of a cell culture comprising microvesicle-producing cells. In some embodiments, the cell culture comprises cells obtained from a subject, for example, cells suspected to exhibit a pathological phenotype, for example, a hyperproliferative phenotype. In some embodiments, the cell culture comprises genetically engineered cells producing ARMMs, for example, cells expressing a recombinant ARMM protein, for example, a recombinant ARRDC1 or TSG101 protein, such as an ARRDC1 or TSG101 protein fused to a Cas9 protein or variant thereof. In some embodiments, the supernatant is pre-cleared of cellular debris by centrifugation, for example, by two consecutive centrifugations of increasing G value (e.g., 500 G and 2000 G). In some embodiments, the method comprises passing the supernatant through a 0.2 μm filter, eliminating all large pieces of cell debris and whole cells. In some embodiments, the supernatant is subjected to ultracentrifugation, for example, at 120,000 G for 2 hours, depending on the volume of centrifugate. The pellet obtained comprises microvesicles. In some embodiments, exosomes are depleted from the microvesicle pellet by staining and/or sorting (e.g., by FACS or MACS) using an exosome marker as described herein. Isolated or enriched ARMMs can be suspended in culture media or a suitable buffer, as described herein.

Methods of Microvesicle-Mediated Delivery of Cargo Proteins

Some aspects of this invention provide a method of delivering an agent, for example, a cargo protein fused to a WW domain (e.g., a Cas9 protein fused to a WW domain) to a target cell. The target cell can be contacted with an ARMM in different ways. For example, a target cell may be contacted directly with an ARMM as described herein, or with an isolated ARMM from a microvesicle producing cell. The contacting can be done in vitro by administering the ARMM to the target cell in a culture dish, or in vivo by administering the ARMM to a subject. Alternatively, the target cell can be contacted with a microvesicle producing cell as described herein, for example, in vitro by co-culturing the target cell and the microvesicle producing cell, or in vivo by administering a microvesicle producing cell to a subject harboring the target cell. Accordingly, the method may include contacting the target cell with a microvesicle, for example, an ARMM containing any of the cargo proteins to be delivered, as described herein. The target cell may be contacted with a microvesicle-producing cell, as described herein, or with an isolated microvesicle that has a lipid bilayer, an ARRDC1 protein or variant thereof, and a cargo protein.

It should be appreciated that the target cell may be of any origin. For example, the target cell may be a human cell. The target cell may be a mammalian cell. Some non-limiting examples of a mammalian cell include a mouse cell, a rat cell, hamster cell, a rodent cell, and a nonhuman primate cell. It should also be appreciated that the target cell may be of any cell type. For example the target cell may be a stem cell, which may include embryonic stem cells, induced pluripotent stem cells (iPS cells), fetal stem cells, cord blood stem cells, or adult stem cells (i.e., tissue specific stem cells). In other cases, the target cell may be any differentiated cell type found in a subject. In some embodiments, the target cell is a cell in vitro, and the method includes administering the microvesicle to the cell in vitro, or co-culturing the target cell with the microvesicle-producing cell in vitro. In some embodiments, the target cell is a cell in a subject, and the method comprises administering the microvesicle or the microvesicle-producing cell to the subject. In some embodiments, the subject is a mammalian subject, for example, a rodent, a mouse, a rat, a hamster, or a non-human primate. In some embodiments, the subject is a human subject.

In some embodiments, the target cell is a pathological cell. In some embodiments, the target cell is a cancer cell. In some embodiments, the microvesicle is associated with a binding agent that selectively binds an antigen on the surface of the target cell. In some embodiments, the antigen of the target cell is a cell surface antigen. In some embodiments, the binding agent is a membrane-bound immunoglobulin, an integrin, a receptor, or a receptor ligand. Suitable surface antigens of target cells, for example of specific target cell types, e.g. cancer cells, are known to those of skill in the art, as are suitable binding agents that specifically bind such antigens. Methods for producing membrane-bound binding agents, for example, membrane-bound immunoglobulin, for example, membrane-bound antibodies or antibody fragments that specifically bind a surface antigen expressed on the surface of cancer cells, are also known to those of skill in the art. The choice of the binding agent will depend, of course, on the identity or the type of target cell. Cell surface antigens specifically expressed on various types of cells that can be targeted by ARMMs comprising membrane-bound binding agents will be apparent to those of skill in the art. It will be appreciated that the present invention is not limited in this respect.

Co-Culture Systems

Some aspects of this invention provide in vitro cell culture systems having at least two types of cells: microvesicle producing cells, and target cells that take up the microvesicles produced. Accordingly, in the co-culture systems provided herein, there is a shuffling of the contents of the microvesicles (e.g., ARMMs) to the target cells. Such co-culture systems allow for the expression of a gene product or multiple gene products generated by the microvesicle producing cells in the target cells without genetic manipulation of the target cells.

In some embodiments, a co-culture system is provided that comprises (a) a microvesicle-producing cell population having a recombinant expression construct encoding (i) an ARRDC1 protein, or variant thereof fused to a Cas9 protein or variant thereof under the control of a heterologous promoter, and/or (ii) a TSG101 protein or variant thereof fused to a Cas9 protein variant thereof under the control of a heterologous promoter, and/or (iii) a cargo protein fused to a WW domain; and (b) a target cell population. In some embodiments, the ARRDC1 variant comprises a PSAP (SEQ ID NO: 74) motif, and/or the TSG101 variant comprises a UEV domain. In some embodiments, the expression construct further encodes a guide RNA (gRNA) which may comprise a nucleotide sequence that complements a target site to mediate binding of a nuclease (e.g., a Cas9 nuclease) to a target site thereby providing the sequence specificity of the nuclease:RNA complex. In some embodiments, the host cell comprises a plurality of expression constructs encoding a plurality of ARRDC1:Cas9 fusion proteins and/or TSG101:Cas9 fusion proteins and/or cargo proteins fused to a WW domain.

One exemplary application of a co-culture system as provided herein is the programming or reprogramming of a target cell without genetic manipulation. For example, in some embodiments, the target cell is a differentiated cell, for example, a fibroblast cell. In some embodiments, the microvesicle producing cells are feeder cells or non-proliferating cells. In some embodiments, the microvesicle producing cells produce ARMMs comprising a reprogramming factor fused to one or more WW domains, or a plurality of reprogramming factors that are fused to one or more WW domains. In some embodiments, co-culture of the differentiated target cells with the microvesicle producing cells results in the reprogramming of the differentiated target cells to an embryonic state. In some embodiments, co-culture of the differentiated target cells with the microvesicle producing cells results in the programming, or trans-differentiation, of the target cells to a differentiated cell states that is different from the original cell state of the target cells.

Another exemplary application of a co-culture system, as provided herein, is the directed differentiation of embryonic stem cells. In some embodiments, the target cells are undifferentiated embryonic stem cells, and the microvesicle producing cells express one or more differentiation factors fused to one or more WW domains, for example, signaling molecules or transcription factors that trigger or facilitate the differentiation of the embryonic stem cells into differentiated cells of a desired lineage, for example neuronal cells, or mesenchymal cells.

Yet another exemplary application of a co-culture system, as provided herein, is the maintenance of stem cells, for example, of embryonic stem cells or of adult stem cells in an undifferentiated state. In some such embodiments, the microvesicle producing cells express signaling molecules and/or transcription factors fused to one or more WW domains that promote stem cell maintenance and/or inhibit stem cell differentiation. The microvesicle producing cells may create a microenvironment for the stem cells that mimics a naturally occurring stem cell niche.

The microvesicle-producing cell of a culture system may be a cell of any type or origin that is capable of producing any of the ARMMs described herein. For example, the microvesicle-producing cell may be a mammalian cell, examples of which include but are not limited to, a cell from a rodent, a mouse, a rat, a hamster, or a non-human primate. The microvesicle-producing cell may also be from a human. One non-limiting example of a microvesicle-producing cell capable of producing an ARMM is a human embryonic kidney 293T cell. The microvesicle-producing cell may be a proliferating or a non-proliferating cell. In some embodiments, the microvesicle-producing cell is a feeder cell which supports the growth of other cells in the culture. Feeder cells may provide attachment substrates, nutrients, or other factors that are needed for the growth of cells in culture.

The target cell of the culture system can be a cell of any type or origin, which may be contacted with an ARMM from any of the microvesicle-producing cells, described herein. For example, the target cell may be a mammalian cell, examples of which include but are not limited to, a cell from a rodent, a mouse, a rat, a hamster, or a non-human primate. The target cell may also be from a human. The target cell may be from an established cell line (e.g., a 293T cell), or a primary cell cultured ex vivo (e.g., cells obtained from a subject and grown in culture). Target cells may be hematologic cells (e.g., hematopoietic stem cells, leukocytes, thrombocytes or erythrocytes), or cells from solid tissues, such as liver cells, kidney cells, lung cells, heart cells bone cells, skin cells, brain cells, or any other cell found in a subject. Cells obtained from a subject can be contacted with an ARMM from a microvesicle-producing cell and subsequently re-introduced into the same or another subject. In some embodiments, the target cell is a stem cell. The stem cell may be a totipotent stem cell that can differentiate into embryonic and extraembryonic cell types. The stem cell may also be a pluripotent stem cell, a multipotent stem cell, an oligopotent stem cell or a unipotent stem cell. In other embodiments, the target cell is a differentiated cell.

Method of Gene Editing

Some aspects of the invention provide methods for gene editing by contacting a target cell with ARMMs that contain any of the RNA-programmable fusion proteins (i.e. Cas9 fusion proteins) described herein. Other aspects of the invention provide methods for gene editing by contacting a target cell with a microvesicle-producing cell comprising a recombinant expression construct encoding any of the RNA-programmable fusion proteins described herein. The RNA-guided or RNA-programmable fusion protein may be delivered to a target cell by any of the systems or methods provided herein. For example, the RNA-programmable fusion protein may contain a Cas9 nuclease, or variants thereof, one or more WW domains, or variants thereof, or optionally one or more NLSs which may be delivered to a target cell by the systems or methods provided herein.

In some embodiments, the RNA-programmable nuclease includes any of the Cas9 fusion proteins described herein. Because RNA-programmable nucleases (i.e., Cas9) use RNA:DNA hybridization to determine target DNA cleavage sites, these proteins are able to cleave, in principle, any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. Science 339, 819-823 (2013); Mali, P. et al. RNA-guided human genome engineering via Cas9. Science 339, 823-826 (2013); Hwang, W. Y. et al. Efficient genome editing in zebrafish using a CRISPR-Cas system. Nature biotechnology 31, 227-229 (2013); Jinek, M. et al. RNA-programmed genome editing in human cells. eLife 2, e00471 (2013); Dicarlo, J. E. et al. Genome engineering in *Saccharomyces cerevisiae* using CRISPR-Cas systems. Nucleic acids research (2013); Jiang, W. et al. RNA-guided editing of bacterial genomes using CRISPR-Cas systems. Nature biotechnology 31, 233-239 (2013); the entire contents of each of which are incorporated herein by reference).

Some aspects of this disclosure provide fusion proteins that have an RNA-guided or RNA-programmable fusion protein (i.e., a Cas9 protein, or Cas9 variant) that can bind to a gRNA, which, in turn, binds a target nucleic acid sequence; and a DNA-editing domain. Some non-limiting examples of DNA-editing domains include, but are not limited to, nucleases, nickases, recombinases or deaminases. As one example, a deaminase domain that can deaminate a nucleobase, such as, for example, cytidine is fused to an RNA-guided or RNA-programmable fusion protein. In some embodiments, the deaminase is fused to any of the Cas9 fusion proteins, described herein. The deamination of a nucleobase by a deaminase can lead to a point mutation at the respective residue, which is referred to herein as nucleic acid editing. Cargo proteins having a Cas9 protein or Cas9 variant, a DNA editing domain, and a protein capable of facilitating the incorporation of the cargo protein into an ARMM (e.g., a WW domain, an ARRDC1 protein, or a TSG101 protein) can thus be used for the targeted editing of nucleic acid sequences. It should be appreciated that any number of DNA editing domains (e.g., nucleases, nickases, recombinases and deaminases) known in the art may be fused to an (i) RNA-guided or RNA-programmable fusion protein (e.g., Cas9 or a Cas9 variant), and (ii) one or more WW domains or WW domain variants, or (iii) an ARRDC1 protein, or variant thereof, or (iv) a TSG101 protein, or variant thereof. Such fusion proteins are useful for targeted editing of DNA in vitro, e.g., for the generation of mutant cells or animals; for the introduction of targeted mutations, e.g., for the correction of genetic defects in cells ex vivo, e.g., in cells obtained from a subject that are subsequently re-introduced into the same or another subject; and for the introduction of targeted mutations, e.g., the correction of genetic defects or the introduction of deactivating mutations in disease-associated genes in a subject. It should also be appreciated that any of the cargo proteins, described herein, are useful for targeted editing of DNA in vivo, e.g., for the generation of mutant cells in a subject. Delivery of ARMMs containing any of the fusion proteins, described herein, may be administered to a subject by any of the methods or systems, described herein.

The methods of gene editing, described herein, may result in the correction of a genetic defect, e.g., in the correction of a point mutation that leads to a loss of function in a gene product. In some embodiments, the genetic defect is associated with a disease or disorder, e.g., a lysosomal storage disorder or a metabolic disease, such as, for example, type I diabetes. In some embodiments, the methods provided herein are used to introduce a deactivating point mutation into a gene or allele that encodes a gene product that is associated with a disease or disorder. For example, in some embodiments, methods are provided herein that employ an RNA-guided or RNA-programmable fusion protein (i.e., a Cas9 protein, or Cas9 variant) fused to a DNA editing cargo protein and at least one WW domain, or variant thereof, or an ARRDC1 protein, or variant thereof, or a TSG101 protein, or variant thereof, to introduce a deactivating point mutation into an oncogene. A deactivating mutation may, in some embodiments, generate a premature stop codon in a coding sequence, which results in the expression of a truncated gene product, e.g., a truncated protein lacking a function of the full-length protein.

The purpose of the methods provide herein may be used to restore the function of a dysfunctional gene via genome editing. The cargo proteins provided herein can be validated for gene editing-based human therapeutics in vitro, e.g., by correcting a disease-associated mutation in human cell culture. It will be understood by the skilled artisan that the cargo proteins provided herein, e.g., the fusion proteins comprising a Cas9 protein or Cas9 variant, a nucleic acid editing domain, and at least one WW domain or an ARRDC1 protein or a TSG101 protein, can be used to correct any single point T>C or A>G mutation. For example, deamination of the mutant C back to U corrects the mutation, and in the latter case, deamination of the C that is base-paired with the mutant G, followed by a round of replication, corrects the mutation.

An exemplary disease-relevant mutation that can be corrected by the instantly provided cargo proteins in vitro or in vivo is the H1047R (A3140G) polymorphism in the PIK3CA protein. The phosphoinositide-3-kinase, catalytic alpha subunit (PIK3CA) protein acts to phosphorylate the 3-OH group of the inositol ring of phosphatidylinositol. The PIK3CA gene has been found to be mutated in many different carcinomas, and thus it is considered to be a very potent oncogene (Lee J W et al. "PIK3CA gene is frequently mutated in breast carcinomas and hepatocellular carcinomas.", *Oncogene*. 2005; 24(8):1477-80; the entire contents of which are hereby incorporated by reference). In fact, the A3140G mutation is present in several NCI-60 cancer cell lines such as the HCT116, SKOV3, and T47D cell lines, which are readily available from the American Type Culture Collection (ATCC) (Ikediobi O N et al. "Mutation analysis of 24 known cancer genes in the NCI-60 cell line set.", *Mol Cancer Ther.* 2006; 5(11):2606-12).

In some embodiments, a cell carrying a mutation to be corrected, e.g., a cell carrying a point mutation resulting in a H1047R or A3140G substitution in the PIK3CA protein are contacted with an ARRM containing (i) a Cas9 protein or Cas9 variant fused to (ii) at least one WW domain or variant thereof, or an ARRDC1 protein or variant thereof, or a TSG101 protein or variant thereof, (iii) a deaminase fusion protein and an appropriately designed gRNA targeting the fusion protein to the respective mutation site in the encoding PIK3CA gene. Control experiments can be performed where the gRNAs are designed to target the fusion proteins to non-C residues that are within the PIK3CA gene. Genomic DNA of the treated cells can be extracted and the relevant sequence of the PIK3CA genes PCR amplified and sequenced to assess the activities of the fusion proteins in human cell culture.

It will be understood that the example of correcting point mutations in PIK3CA is provided for illustration purposes, and is not meant to limit the instant disclosure. The skilled artisan will understand that the instantly disclosed DNA-editing cargo proteins, described herein, can be used to correct other point mutations and mutations associated with other cancers and with diseases other than cancer.

The successful correction of mutations in disease-associated genes and alleles using any of the ARMMs or fusion proteins, described herein, opens up new strategies for gene correction with applications in disease therapeutics and gene study. Site-specific nucleotide modification proteins like the disclosed Cas9 variants fused to DNA-editing domains and at least one WW protein or an ARRDC1 protein or a TSG101 protein also have applications in "reverse" gene therapy, where certain gene functions are purposely suppressed or abolished. In these cases, site-specifically mutating Trp (TGG), Gln (CAA and CAG), or Arg (CGA) residues to premature stop codons (TAA, TAG, TGA) can be used to abolish protein function in vitro, ex vivo, or in vivo.

The instant disclosure provides methods for the treatment of a subject diagnosed with a disease associated or caused by a mutation that can be corrected by any of the DNA editing cargo proteins provided herein. For example, in some embodiments, a method is provided that comprises administering to a subject having such a disease, (e.g., a cancer associated with a PIK3CA point mutation) as described above, an effective amount of ARMMs containing any of the cargo proteins, described herein, that corrects the point mutation or introduces a deactivating mutation into the disease-associated gene. It should be appreciated that the inventive ARMMs may be used to target the delivery of any of the cargo proteins, described herein, to any target cell, described herein. In some embodiments, the disease is a neoplastic disease. In some embodiments, the disease is a metabolic disease. In some embodiments, the disease is a lysosomal storage disease. Other diseases that can be treated by correcting a mutation or introducing a deactivating mutation into a disease-associated gene will be known to those of skill in the art, and the disclosure is not limited in this respect.

In some embodiments, the genome of the target cell is edited by a nuclease delivered to the target cell via a system or method disclosed herein, e.g., by delivering any of the Cas9 fusion proteins using any of the ARMMs or ARMM producing cells described herein. In some embodiments, a single- or double-strand break is introduced at a specific site within the genome of a target cell by a Cas9 protein, resulting in a disruption of the targeted genomic sequence. In some embodiments, the targeted genomic sequence is a nucleic acid sequence within the coding region of a gene. In some embodiments, the targeted genomic sequence is a nucleic acid sequence outside the coding region of a gene, for example, the targeted genomic sequence may be within the promoter region of a gene. In some embodiments, the strand break introduced by the nuclease leads to a mutation within the target gene that impairs the expression of the encoded gene product.

A nucleic acid (e.g., a gRNA) may be associated with an RNA-guided protein (e.g., a Cas9 protein, or Cas9 variant) fused to a DNA editing domain and at least one WW domain, or variant thereof, or an ARRDC1 protein, or variant thereof, or a TSG101 protein, or variant thereof. Typically, a gRNA contains a nucleotide sequence that complements a target site, which mediates binding of the protein:RNA complex to a target site and providing the sequence specificity of the protein:RNA complex. Accordingly, a nucleic acid (e.g., a gRNA) may be co-expressed with any of the cargo proteins, described herein, in order to confer target sequence specificity to any of the RNA-guided fusion proteins, described herein. As one non-limiting example, a Cas9 variant fused to a WW domain may be co-expressed in a cell with a gRNA such that the gRNA associates with the Cas9 fusion protein and the Cas9 fusion protein, in complex with the gRNA, is loaded into an ARMM. In some embodiments, the nucleic acid has a sequence that is identical or homologous to a sequence adjacent to the nuclease target site. In some such embodiments, the strand break effected by the nuclease is repaired by the cellular DNA repair machinery to introduce all or part of the co-delivered nucleic acid into the cellular DNA at the break site, resulting in a targeted insertion of the co-delivered nucleic acid, or part thereof. In some embodiments, the insertion results in the disruption or repair of a pathogenic allele.

In certain embodiments, a catalytically inactive Cas9 fusion protein is used to activate or repress gene expression by fusing the inactive enzyme (that retains its gRNA-binding ability) to known regulatory domains. Cas9 variants that can be used to control gene expression have been described in detail, for example, in U.S. patent application number U.S. Ser. No. 14/216,655, filed on Mar. 17, 2014 (published as US20140273226 A1) by Wu F. et al., entitled Crispr/cas systems for genomic modification and gene modulation, and in PCT application number PCT/US2013/074736, filed on Dec. 12, 2013 (published as WO2014093655 A2) by Zhang F. et al., entitled Engineering and optimization of systems, methods and compositions for sequence manipulation with functional domains; the entire contents of each are incorporated herein by reference. For example, a catalytically inactive Cas9 fusion protein may be fused to a transcriptional activator (e.g. VP64). In certain embodiments, any of the Cas9 fusion proteins described herein may be when fused to a transcriptional activator to up-regulating gene transcription of targeted genes to enhance expression. In some embodiments, a catalytically inactive Cas9 fusion protein may be fused to a transcriptional repressor (e.g. KRAB). In certain embodiments, any of the Cas9 fusion proteins described herein may be fused to a transcriptional repressor to down-regulate gene transcription of targeted genes to reduce expression. In some embodiments, the delivery of a nuclease to a target cell results in a clinically or therapeutically beneficial disruption or enhancement of the function of a gene. It should be appreciated that the methods described herein are not meant to be limiting and may include any method of using Cas9 that is well known in the art.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Example 1: Loading of WW Domain Containing Fusion Proteins into ARMMs

Introduction

Safe and efficient delivery of protein molecules into cells and tissues remains an unsolved problem in the art. The use of ARMMs as a protein delivery system may provide advantages over current delivery methods such as transfection or viral infection. For example, ARMMs are generated via an endogenous budding pathway that is mimicked by viruses and therefore has an intrinsic potential to deliver genetic materials and signaling molecules. In addition, ARMMs are unlikely to elicit a strong immune response as they may be produced by endogenous mechanisms. Furthermore, ARMMs may be targeted to specific recipient cells/tissues by incorporating antibodies or other types of molecules that recognize cell/tissue specific markers.

Targeted editing of nucleic acid sequences, for example, the introduction of a specific modification into genomic DNA, is a highly promising approach for the study of gene function and also has the potential to provide new therapies for human genetic diseases. An ideal nucleic acid editing technology possesses three characteristics: (1) high efficiency of installing the desired modification; (2) minimal off-target activity; and (3) the ability to be programmed to edit precisely any site in a given nucleic acid, e.g., any site within the human genome. Current genome engineering tools, including engineered zinc finger nucleases (ZFNs), transcription activator like effector nucleases (TALENs), and most recently, the RNA-guided DNA endonuclease Cas9 affect sequence-specific DNA cleavage in a genome. This programmable cleavage can result in mutation of the DNA at the cleavage site via nonhomologous end joining (NHEJ) or replacement of the DNA surrounding the cleavage site via homology-directed repair (HDR).

Engineered gRNA sequences can be co-expressed in a cell with Cas9 proteins to precisely edit target genome sequences. However, current delivery methods such as transfection or viral infection are not adequate for efficiently delivering Cas9, or other cargo proteins, to target cells in a subject. Accordingly, the ability of Cas9 fusion proteins to (i) load into ARMMs and (ii) perform RNA-guided genome editing is demonstrated.

Results

Figure 3:
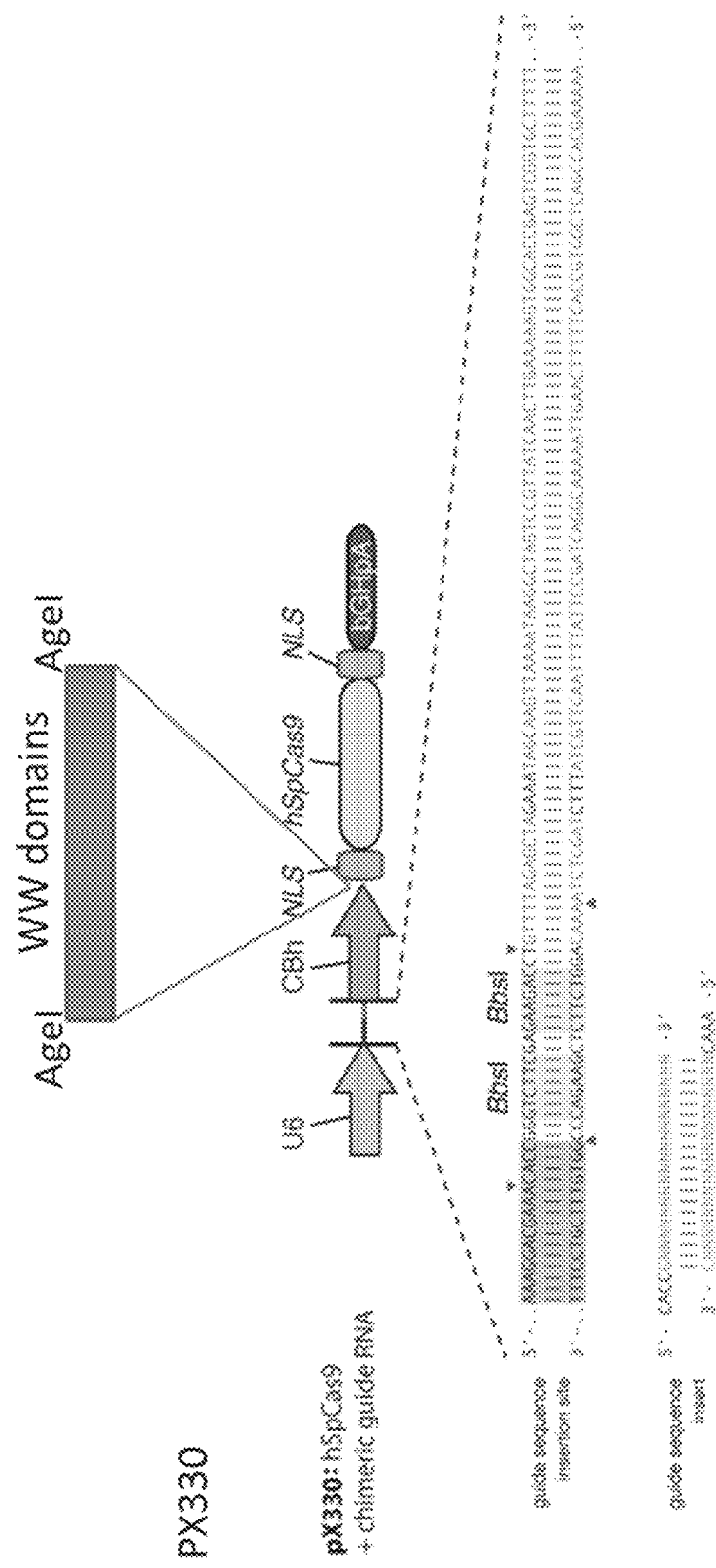
FIG. 3 is a schematic of the PX330 plasmid (top) which expresses a humanized *Streptococcus pyogenes* Cas9 protein with nuclear localization sequences (NLSs). The schematic shows that one or more WW domains may be fused toward the N-terminus of the fusion protein using the AgeI restriction site. Additionally, one or more WW domains may be fused toward the N-terminus of the fusion protein using the AgeI restriction site (not shown), which is located between the CBh promoter and the first NLS. The schematic also shows the guide sequence insertion site (bottom), which is under the control of the U6 promoter. A guide sequence (e.g., a gRNA) may be cloned into the plasmid using the BbsI restriction site.

Two WW domains from ITCH (SEQ ID NO: 32) or Four WW domains from ITCH (SEQ ID NO: 33) were cloned into the AgeI site of the pX330 Cas9 construct (SEQ ID NO: 34) (Addgene) placing the WW domains at the N-terminus of the encoded Cas9 fusion protein (FIG. 3). Notably, the pX330 Cas9 fusion protein contains an N-terminal FLAG epitope tag. 293T cells at ~60% confluency in 6-well plates were transfected with the following plasmids using the Turbofect transfection reagent:

(1) 0.5 µg GFP (pEGFP-N1)+0.5 µg Cas9 (px330)
(2) 0.5 µg GFP (pEGFP-N1)+0.5 µg 2WW-Cas9 (px330+2WW)
(3) 0.5 µg GFP (pEGFP-N1)+0.5 µg 4WW-Cas9 (px330+4WW)
(4) 0.5 µg ARRDC1-GFP (pEGFP-N1+ARRDC1)+0.5 µg Cas9 (px330)
(5) 0.5 µg ARRDC1-GFP (pEGFP-N1+ARRDC1)+0.5 µg 2WW-Cas9 (px330+2WW)
(6) 0.5 µg ARRDC1-GFP (pEGFP-N1+ARRDC1)+0.5 µg 4WW-Cas9 (px330+4WW)

After transfection for 12 hours, culture medium was changed with fresh culture medium. About 48 hours post transfection, conditioned media were collected, and ARMMs were purified and lysed in ~20 μl of lysis buffer. Cells were washed with PBS and lysed in ~200 μl of lysis buffer per well. For Western blotting, 7 μg of total protein per cell lysate sample was used; 15 μl of ARMMs lysate per sample was used.

Figure 5:
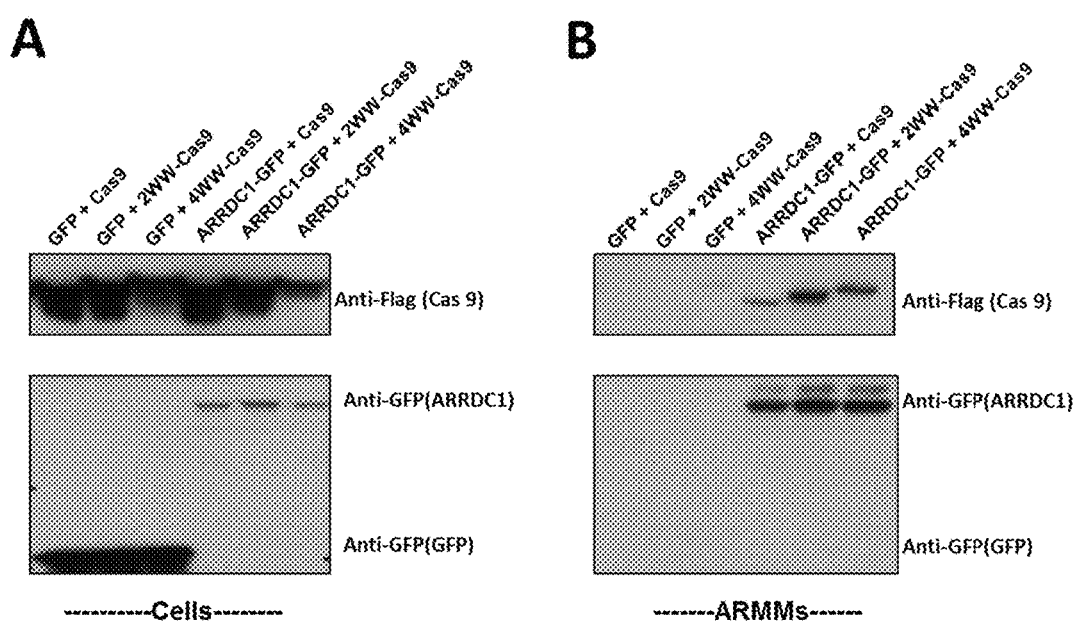
FIG. 5 provides Western blots shows that WW-Cas9 is incorporated into ARMMs. (A) Western blotting result of samples from the total cell lysates. 293T cells were transfected with 2 protein-expressing plasmids. Lane 1: GFP and Cas9; lane 2: GFP and 2WW-Cas9; lane 3: GFP and 4WW-Cas9; lane 4: ARRDC1-GFP and Cas9; lane 5: ARRDC1-GFP and 2WW-Cas9; lane 6: ARRDC1-GFP and 4WW-Cas9; The upper panel shows the Western blotting result using antibody against the FLAG-tag, which is fused to the Cas9 protein. The lower panel shows the Western blotting result using anti-GFP antibody. Western blotting result of samples of purified ARMMs from condition media (B) of transfected 293T cells. The order of the lanes is the same as in (A). The 2WW-Cas9 and 4WW-Cas9 fusion proteins are efficiently incorporated into ARMMs when ARRDC1-GFP is expressed in the microvesicle-producing 293T cells.

FIG. 5 shows that Cas9, 2WW-Cas9, and 4WW-Cas9 were expressed in 293T cells as evidenced by Western blot detection by Anti-FLAG. Additionally, ARRDC1-GFP expression was detected by Western blot, using an Anti-GFP antibody, in cells transfected with ARRDC1-GFP as expected (FIG. 5A, lanes 4-6). ARMMs from the 293T cells transfected with the plasmids, listed above, were collected and tested for the presence of ARRDC1 and the Cas9 fusion proteins (Cas9, 2WW-Cas9, and 4WW-Cas9). Little or no Cas9 was detected in ARMMs produced by cells that either did not express ARRDC1-GFP or expressed Cas9 that was not fused to a WW domain (FIG. 5B, lanes 1-4). However, both 2WW-Cas9 and 4WW-Cas9 were efficiently incorporated into ARMMs along with ARRDC1-GFP (FIG. 5B, lanes 5 and 6) demonstrating that Cas9 fused to two or four WW domains can be efficiently delivered into ARMMs when ARRDC1 is expressed in microvesicle-producing cells.

Figure 6:
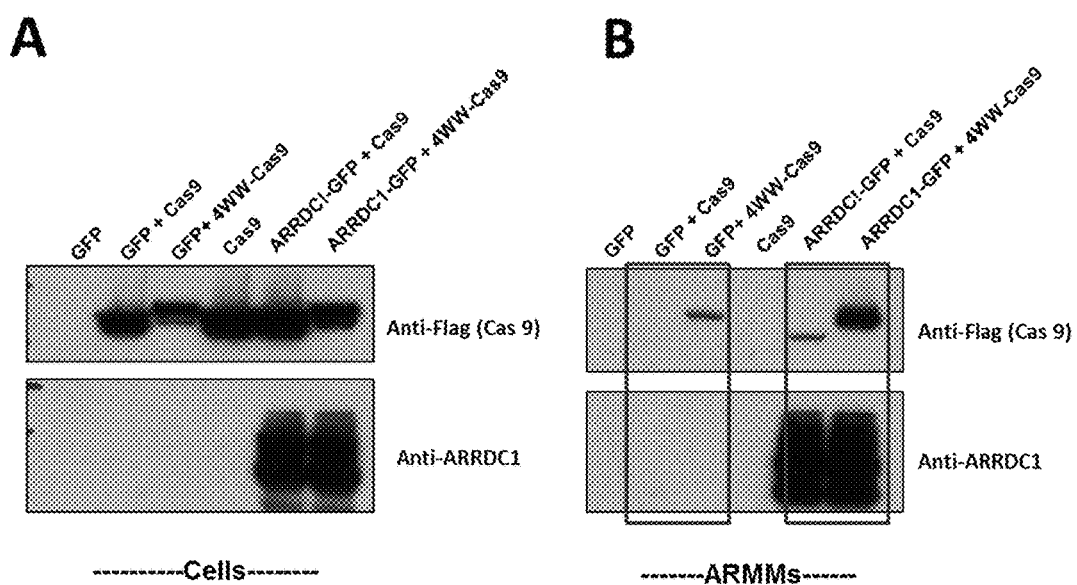
FIG. 6 provides representative Western blots showing that little to no Cas9 fusion protein is released from ARRDC1-null cells, but exogenous ARRDC1 expression facilitated the incorporation of Cas9 into ARMMs. Western blotting results of samples from the total cell lysates (A) of 293T ARRDC1-null cells transfected with the following plasmids: GFP and empty vector DNA (lane 1); GFP and Cas9 (lane 2); GFP and 4WW-Cas9 (lane 3); empty vector and Cas9 (lane 4); ARRDC1-GFP and Cas9 (lane 5); ARRDC1-GFP and 4WW-Cas9 (lane 6); The upper panel shows the Western blotting result using antibody against the Flag-tag, which is fused to the Cas9 protein. The lower panel shows the Western blotting result using anti-GFP antibody. The Western blotting result of samples of purified ARMMs (B) from condition media of transfected 293T cells has the same order of the lanes as in (A). The results demonstrate that ARRDC1 is both necessary and sufficient for the incorporation of a WW-Cas9 fusion protein into ARMMs.

FIG. 6 shows that no, or little, Cas9 is released from ARRDC1-null cells, but exogenous ARRDC1 expression rescued the incorporation of WW-Cas9 into ARMMs. 293T cells null for ARRDC1 (ARRDC1-KO) were transfected with following combination of plasmids:

(1) 0.5 μg GFP (pEGFP-N1)+0.5 μg control DNA
(2) 0.5 μg GFP (pEGFP-N1)+0.5 μg Cas9 (px330)
(3) 0.5 μg GFP (pEGFP-N1)+0.5 μg 4WW-Cas9 (px330+4WW)
(4) 0.5 μg control DNA+0.5 μg Cas9 (px330)
(5) 0.5 μg ARRDC1-GFP (pEGFP-N1+ARRDC1)+0.5 μg Cas9 (px330)
(6) 0.5 μg ARRDC1-GFP (pEGFP-N1+ARRDC1)+0.5 μg 4WW-Cas9 (px330+4WW)

After transfection for 12 hours, culture medium was changed with fresh culture medium. About 48 hours post transfection, conditioned media were collected, and ARMMs were purified and lysed in ~20 μl of lysis buffer. Cells were washed with PBS and lysed in ~200 μl of lysis buffer per well. For Western blotting, 7 μg of total protein per cell lysate sample was used; 15 μl of ARMMs lysate per sample was used.

Figure 4:
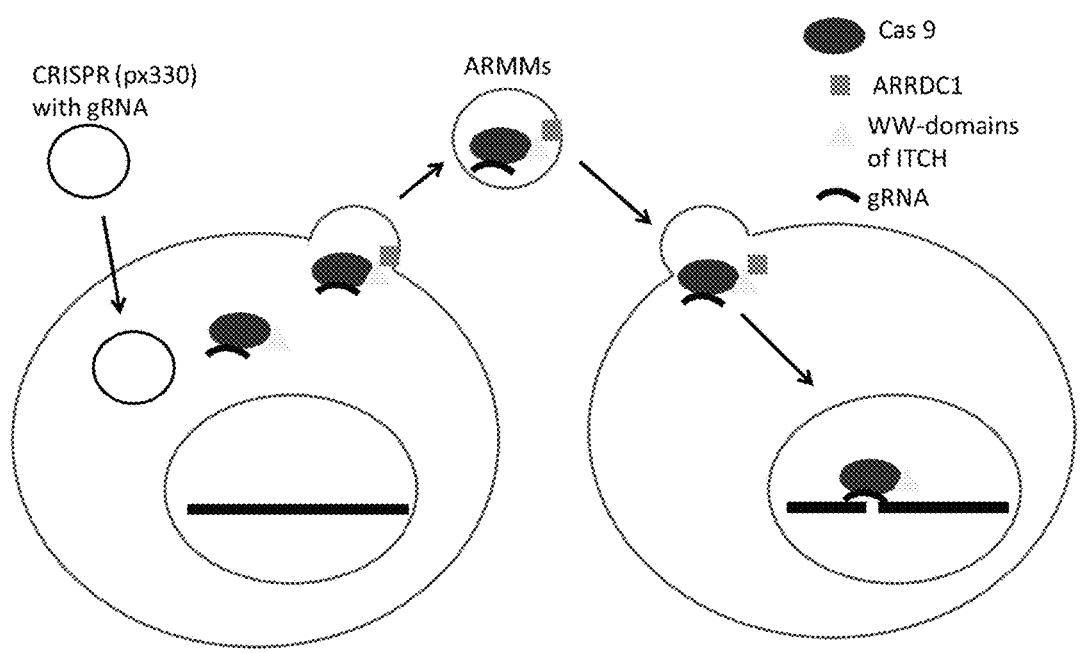
FIG. 4 is a schematic demonstrating the production of an ARMM in a microvesicle-producing cell that contains a Cas9:WW domain fusion protein, which associates with a gRNA and the ARRDC1 protein of the ARMM to facilitate the loading of the Cas9:WW domain fusion protein into the ARMM. The gRNA may be co-expressed with the Cas9 and thus co-incorporated into ARMMs (left). The ARMM may then be delivered to a target cell (right), where the Cas9:WW domain fusion protein is released into the cytoplasm of the target cell. The Cas9:WW domain fusion protein may then translocate into the nucleus, which may be facilitated by one or more NLSs, to perform a gene editing function.

Expression of the Cas9, 4WW-Cas9 and ARRDC1-GFP constructs was detected in 293T cells null for ARRDC1 as evidenced by Western Blot (FIG. 6A). Western blots of isolated ARMMs showed that the 4WW-Cas9 fusion protein was efficiently loaded onto ARMMs when ARRDC1-GFP was exogenously expressed in 293T cells (FIG. 6B, lane 6). Only small amounts of 4WW-Cas9 were observed in ARMMs produced from cells that do not express ARRDC1 (FIG. 6B, lane 3). Additionally, only small amounts of Cas9, not fused to a WW domain, were observed in cells exogenously expressing ARRDC1 (FIG. 6B, lane 5). Accordingly, these results demonstrate that ARRDC1 facilitates the loading of WW domain-containing fusion proteins (e.g., a 4WW-Cas9 fusion protein) into ARMMs, which may be used to deliver the fusion protein to a target cell. A schematic of this process can be seen in FIG. 4.

As stated above, directing Cas9 activity, or Cas9 variant activity, to a specific nucleic acid sequence (e.g., a genomic sequence) requires association with a guide sequence (e.g., a gRNA). Therefore, the ability to incorporate a gRNA into ARMMs was tested. To do this, 293T cells were co-transfected with the plasmids (listed below) using 1.5 μl of turbofect and 1 ml medium. Notably, an anti-GFP gRNA sequence was also expressed from the px330 construct (Addgene) under the U6 promoter to determine whether it can be incorporated into ARMMs.

(1) 1 μg control DNA
(2) 0.5 μg control DNA+0.5 μg 2WW-Cas9 (px330+2WW)
(3) 0.5 μg HA-ARRDC1+0.5 μg 2WW-Cas9 (px330+2WW)

Figure 7:
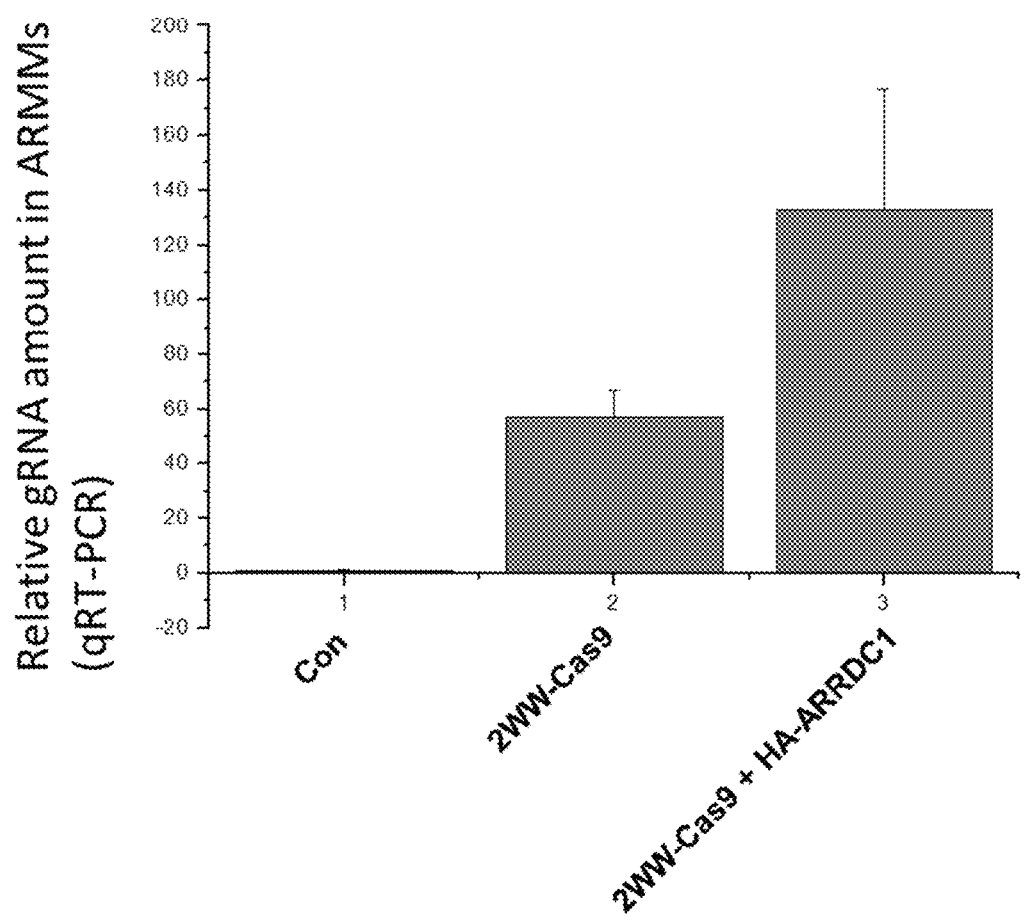
FIG. 7 is a graph showing that a guide RNA (gRNA) is also incorporated into ARMMs. 293T cells were transfected with either control DNA (bar 1), or 2WW-Cas9 (bar 2), or 2WW-Cas9 and HA-ARRDC1 (bar 3). 2WW-Cas9 was constructed in a PX330 backbone, which contains the gRNA coding sequences. ARMMs were collected from the condition media of the transfected cells 48 hours post transfection. RNAs were extracted from purified ARMMs. qRT-PCR was done to measure gRNA expression. Values of GAPDH gene expression were used for normalization.

ARMMs produced from 293T cells transfected with either control DNA (FIG. 7, bar 1), or 2WW-Cas9 (FIG. 7, bar 2), or 2WW-Cas9 and HA-ARRDC1 (FIG. 7, bar 3) were collected from the condition media 48 hours post transfection. RNAs were extracted from purified ARMMs to measure the amount of gRNA using qRT-PCR. Values of GAPDH gene expression were used for normalization. The data demonstrates that the gRNA was also efficiently incorporated into ARMMs when a WW domain-Cas9 fusion protein was co-expressed with ARRDC1 in the microvesicle producing cells (FIG. 7, bar 3). While the Cas9-WW domain fusion proteins and gRNAs were capable of being efficiently loaded into ARMMs, it was important to determine whether the Cas9-WW domain fusion proteins maintained their genome-editing function.

Figure 8:
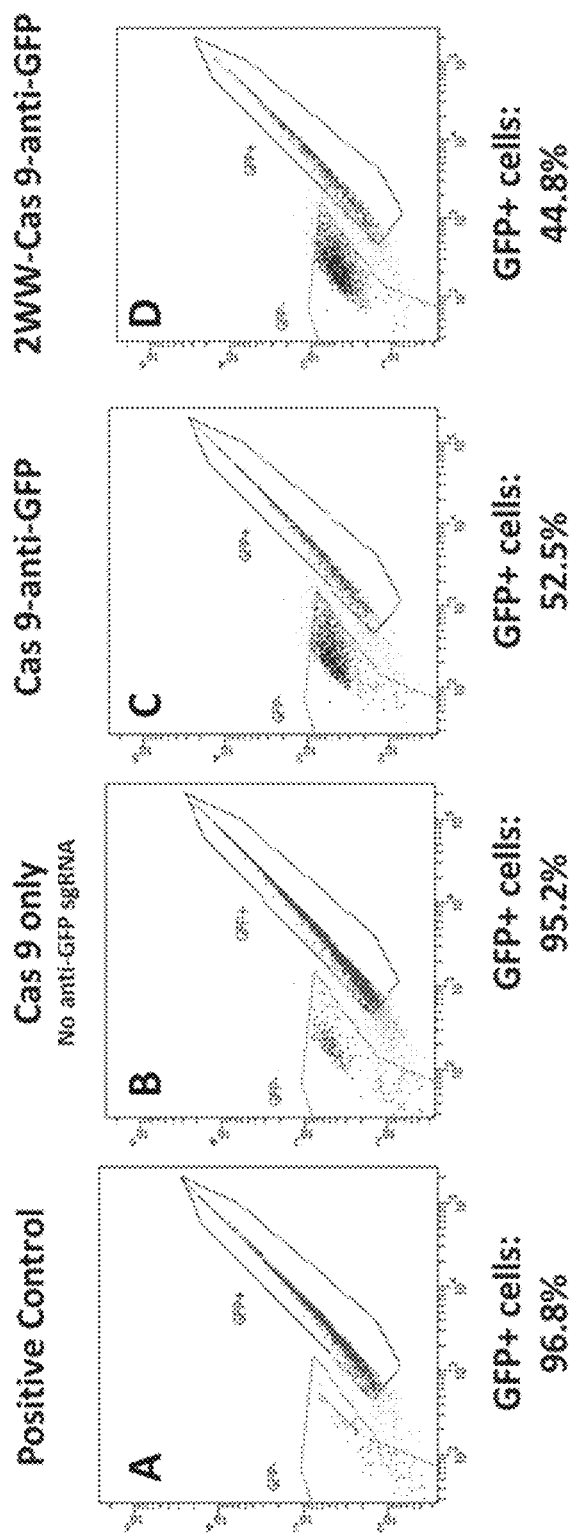
FIG. 8 shows representative fluorescence activated cell sorting (FACS) data showing WW-fused Cas9 is as effective as unmodified Cas9 in genome-editing. 293T-EGFP cells were transfected with different DNA constructs. 48 hours post transfection GFP signal was examined in transfected cells by flow cytometry. (A) Cells were transfected with control DNA. (B) Cells were transfected with Cas9. (C) Cells were transfected with Cas9-anti-GFP, which contains gRNA targeting the GFP gene. (D) Cells were transfected with 2WW-Cas9-anti-GFP, which contains gRNA targeting the GFP gene and in which the Cas9 is fused to first two WW domains of the ITCH protein.

To determine whether 2WW-Cas9 was able to perform its genome-editing function, 293T cells expressing enhanced green fluorescent protein (EGFP) were transfected (1.5 ul of Turbofect in 100 μl Medium to mix, then in 1 ml cell medium for 12 h transfection) with 1 μg of the DNA constructs listed below. Following transfection, GFP signal was examined by flow cytometry to determine whether 2WW-Cas9 associated with an anti-GFP gRNA sequence (FIG. 8D) was able to decrease GFP signal comparatively to Cas9 with an anti-GFP gRNA sequence (FIG. 8C).

(A) Control DNA,
(B) Cas9 (px330);
(C) Cas9-antiGFP (px330 containing the anti-GFP gRNA sequence)
(D) 2WW-Cas9-anti-GFP (px330+2WW, and containing the anti-GFP sgRNA sequence)

Expression of Cas9 without an anti-GFP gRNA (FIG. 8B) did not decrease GFP signal as compared to the control (FIG. 8A) as expected. Importantly, the 2WW-Cas9 protein associated with the anti-GFP gRNA sequence (FIG. 8D) was able to prevent/decrease GFP expression in GFP expressing 293T cells at an efficiency comparable to that of Cas9 protein associated with the anti-GFP gRNA sequence (FIG. 8C). These results demonstrate that WW-fused Cas9 is at least as effective as unmodified Cas9 in genome-editing.

Figure 9:
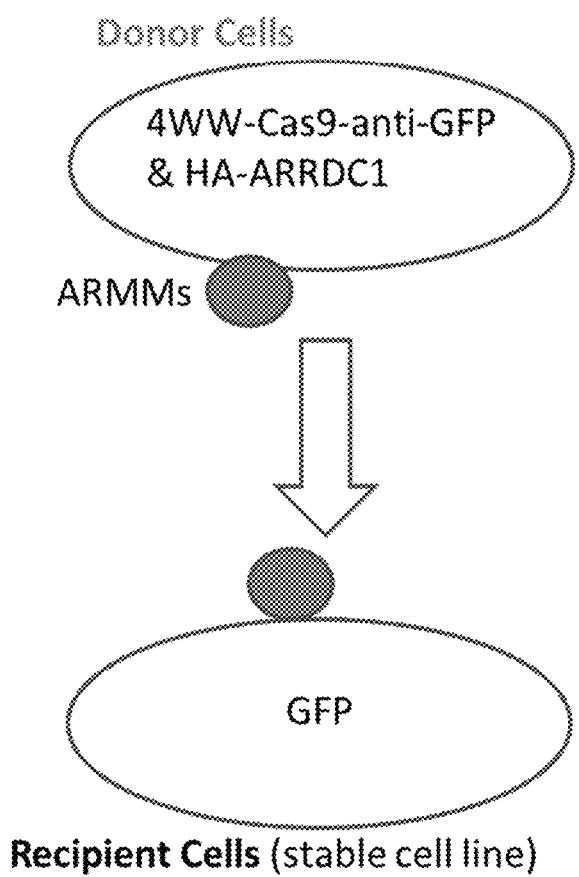
FIG. 9 is a schematic representation of how the efficiency of WW-Cas9 in ARMMs in decreasing gene expression of recipient cells may be tested. In this representation (A), the microvesicle-producing "donor cells" express 4WW-Cas9, a gRNA that targets GFP (4WW-Cas9-anti-GFP), and an HA tagged ARRDC1 protein (HA-ARRDC1). The ARMMs produced by the donor cell are administered to GFP expressing "recipient cells" and the amount of GFP expression in the recipient cell may be measured by flow cytometry (B) to determine the efficiency of preventing gene expression or even sort the cells using fluorescence-activated cell sorting (FACS).
Figure 9:
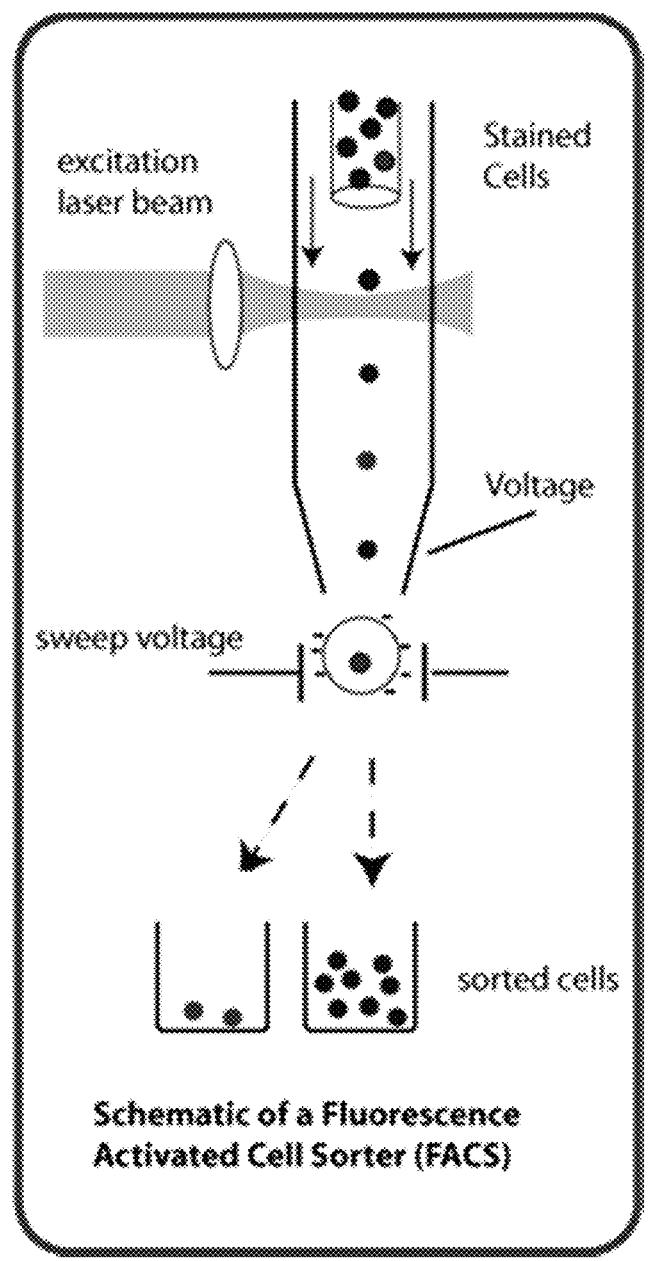

It should be appreciated that the experiments laid out in FIGS. 5-8 can be used to test (i) the ability to load any cargo protein into an ARMM, (ii) the ability to load any gRNA into an ARMM, and (iii) the ability of any WW-fused Cas9 protein, or Cas9 variant, to perform a genome-editing or expression altering function. Furthermore, the ability of ARMMs to deliver their cargo proteins into a recipient cell can be tested, for example by isolating ARMMs containing a WW-fused Cas9 protein associated with an anti-GFP gRNA, and administering the ARMMs to a target cell expressing GFP (FIG. 9A). The GFP signal of the GFP expressing target cells may be measured using flow cytometry to determine whether the GFP signal is altered (FIG. 9B), thus determining whether the ARMMs were able to deliver their cargo proteins into the target cells.

REFERENCES

1. Hurley J H, Boura E, Carlson L A, & Rozycki B (2010) Membrane budding. Cell 143:875-887.

2. Thery C, Ostrowski M, & Segura E (2009) Membrane vesicles as conveyors of immune responses. Nat Rev Immunol 9:581-593.
3. Henne W M, Buchkovich N J, & Emr S D (2011) The ESCRT pathway. Dev Cell 21:77-91.
4. Katzmann D J, Odorizzi G, & Emr S D (2002) Receptor downregulation and multivesicular-body sorting. Nat Rev Mol Cell Biol 3:893-905.
5. Babst M, Odorizzi G, Estepa E J, & Emr S D (2000) Mammalian tumor susceptibility gene 101 (TSG101) and the yeast homologue, Vps23p, both function in late endosomal trafficking. Traffic 1:248-258.
6. Lu Q, Hope L W, Brasch M, Reinhard C, & Cohen S N (2003) TSG101 interaction with HRS mediates endosomal trafficking and receptor down-regulation. Proc Natl Acad Sci USA 100:7626-7631.
7. Pornillos O, Alam S L, Davis D R, & Sundquist W I (2002) Structure of the Tsg101 UEV domain in complex with the PTAP motif of the HIV-1 p6 protein. Nat Struct Biol 9:812-817.
8. Pornillos O, Alam S L, Rich R L, Myszka D G, Davis D R, & Sundquist W I (2002) Structure and functional interactions of the Tsg101 UEV domain. EMBO J 21:2397-2406.
9. Sundquist W I, Schubert H L, Kelly B N, Hill G C, Holton J M, & Hill C P (2004) Ubiquitin recognition by the human TSG101 protein. Mol Cell 13:783-789.
10. Bache K G, Brech A, Mehlum A, & Stenmark H (2003) Hrs regulates multivesicular body formation via ESCRT recruitment to endosomes. J Cell Biol 162:435-442.
11. Pornillos O, Higginson D S, Stray K M, Fisher R D, Garrus J E, Payne M, He G P, Wang H E, Morham S G, & Sundquist W I (2003) HIV Gag mimics the Tsg101-recruiting activity of the human Hrs protein. J Cell Biol 162:425-434.
12. von Schwedler U K, Stuchell M, Muller B, Ward D M, Chung H Y, Morita E, Wang H E, Davis T, He G P, Cimbora D M, et al. (2003) The protein network of HIV budding. Cell 114:701-713.
13. Hurley J H & Stenmark H (2011) Molecular mechanisms of ubiquitin-dependent membrane traffic. Annu Rev Biophys 40:119-142.
14. Schorey J S & Bhatnagar S (2008) Exosome function: from tumor immunology to pathogen biology. Traffic 9:871-881.
15. Thery C, Zitvogel L, & Amigorena S (2002) Exosomes: composition, biogenesis and function. Nat Rev Immunol 2:569-579.
16. Bieniasz P D (2009) The cell biology of HIV-1 virion genesis. Cell Host Microbe 5:550-558.
17. Demirov D G & Freed E O (2004) Retrovirus budding. Virus Res 106:87-102.
18. Morita E & Sundquist W I (2004) Retrovirus budding. Annu Rev Cell Dev Biol 20:395-425.
19. Garrus J E, von Schwedler U K, Pornillos O W, Morham S G, Zavitz K H, Wang H E, Wettstein D A, Stray K M, Cote M, Rich R L, et al. (2001) Tsg101 and the vacuolar protein sorting pathway are essential for HIV-1 budding. Cell 107:55-65.
20. VerPlank L, Bouamr F, LaGrassa T J, Agresta B, Kikonyogo A, Leis J, & Carter C A (2001) Tsg101, a homologue of ubiquitin-conjugating (E2) enzymes, binds the L domain in HIV type 1 Pr55(Gag). Proc Natl Acad Sci USA 98:7724-7729.
21. Martin-Serrano J, Zang T, & Bieniasz P D (2001) HIV-1 and Ebola virus encode small peptide motifs that recruit Tsg101 to sites of particle assembly to facilitate egress. Nat Med 7:1313-1319.
22. Martin-Serrano J, Zang T, & Bieniasz P D (2003) Role of ESCRT-I in retroviral budding. J Virol 77:4794-4804.
23. Demirov D G, Ono A, Orenstein J M, & Freed E O (2002) Overexpression of the N-terminal domain of TSG101 inhibits HIV-1 budding by blocking late domain function. Proc Natl Acad Sci USA 99:955-960.
24. Gottlinger H G, Dorfman T, Sodroski J G, & Haseltine W A (1991) Effect of mutations affecting the p6 gag protein on human immunodeficiency virus particle release. Proc Natl Acad Sci USA 88:3195-3199.
25. Huang M, Orenstein J M, Martin M A, & Freed E O (1995) p6Gag is required for particle production from full-length human immunodeficiency virus type 1 molecular clones expressing protease. J Virol 69:6810-6818.
26. Freed E O & Mouland A J (2006) The cell biology of HIV-1 and other retroviruses. Retrovirology 3:77.
27. Martin-Serrano J & Neil S J Host factors involved in retroviral budding and release. Nat Rev Microbiol 9:519-531.
28. Rauch S & Martin-Serrano J (2011) Multiple interactions between the ESCRT machinery and arrestin-related proteins: implications for PPXY-dependent budding. J Virol 85:3546-3556.
29. Ono A & Freed E O (2004) Cell-type-dependent targeting of human immunodeficiency virus type 1 assembly to the plasma membrane and the multivesicular body. J Virol 78:1552-1563.
30. Pisitkun T, Shen R F, & Knepper M A (2004) Identification and proteomic profiling of exosomes in human urine. Proc Natl Acad Sci USA 101:13368-13373.
31. Welton J L, Khanna S, Giles P J, Brennan P, Brewis I A, Staffurth J, Mason M D, & Clayton A (2010) Proteomics analysis of bladder cancer exosomes. Mol Cell Proteomics 9:1324-1338.
32. Mathivanan S, Lim J W, Tauro B J, Ji H, Moritz R L, & Simpson R J (2009) Proteomics analysis of A33 immunoaffinity-purified exosomes released from the human colon tumor cell line LIM1215 reveals a tissue-specific protein signature. Mol Cell Proteomics 9:197-208.
33. Razi M & Futter C E (2006) Distinct roles for Tsg101 and Hrs in multivesicular body formation and inward vesiculation. Mol Biol Cell 17:3469-3483.
34. Hammarstedt M & Garoff H (2004) Passive and active inclusion of host proteins in human immunodeficiency virus type 1 gag particles during budding at the plasma membrane. J Virol 78:5686-5697.
35. Babst M (2005) A protein's final ESCRT. Traffic 6:2-9.
36. Scott A, Chung H Y, Gonciarz-Swiatek M, Hill G C, Whitby F G, Gaspar J, Holton J M, Viswanathan R, Ghaffarian S, Hill C P, et al. (2005) Structural and mechanistic studies of VPS4 proteins. EMBO J 24:3658-3669.
37. Alvarez C E (2008) On the origins of arrestin and rhodopsin. BMC Evol Biol 8:222.
38. Lefkowitz R J & Shenoy S K (2005) Transduction of receptor signals by beta-arrestins. Science 308:512-517.
39. Draheim K M, Chen H B, Tao Q, Moore N, Roche M, & Lyle S (2010) ARRDC3 suppresses breast cancer progression by negatively regulating integrin beta4. Oncogene 29:5032-5047.

40. Nabhan J F, Pan H, & Lu Q (2010) Arrestin domain-containing protein 3 recruits the NEDD4 E3 ligase to mediate ubiquitination of the beta2-adrenergic receptor. EMBO Rep 11:605-611.
41. Chantry A (2011) WWP2 ubiquitin ligase and its isoforms: new biological insight and promising disease targets. Cell Cycle 10:2437-2439.
42. Rotin D & Kumar S (2009) Physiological functions of the HECT family of ubiquitin ligases. Nat Rev Mol Cell Biol 10:398-409.
43. Denzer K, Kleijmeer M J, Heijnen H F, Stoorvogel W, & Geuze H J (2000) Exosome: from internal vesicle of the multivesicular body to intercellular signaling device. J Cell Sci 113 Pt 19:3365-3374.
44. Komada M & Soriano P (1999) Hrs, a FYVE finger protein localized to early endosomes, is implicated in vesicular traffic and required for ventral folding morphogenesis. Genes Dev 13:1475-1485.
45. Ono A, Demirov D, & Freed E O (2000) Relationship between human immunodeficiency virus type 1 Gag multimerization and membrane binding. J Virol 74:5142-5150.
46. Fujii K, Hurley J H, & Freed E O (2007) Beyond Tsg101: the role of Alix in 'ESCRTing' HIV-1. Nat Rev Microbiol 5:912-916.
47. Wehman A M, Poggioli C, Schweinsberg P, Grant B D, & Nance J (2011) The P4-ATPase TAT-5 Inhibits the Budding of Extracellular Vesicles in C. elegans Embryos. Curr Biol 21:1951-1959.
48. Skog J, Wurdinger T, van Rijn S, Meijer D H, Gainche L, Sena-Esteves M, Curry W T, Jr., Carter B S, Krichevsky A M, & Breakefield X O (2008) Glioblastoma microvesicles transport RNA and proteins that promote tumour growth and provide diagnostic biomarkers. Nat Cell Biol 10:1470-1476.
49. Valadi H, Ekstrom K, Bossios A, Sjostrand M, Lee J J, & Lotvall J O (2007) Exosome-mediated transfer of mRNAs and microRNAs is a novel mechanism of genetic exchange between cells. Nat Cell Biol 9:654-659.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. An arrestin domain-containing protein 1 (ARRDC1)-mediated microvesicle (ARMM), comprising:
   (i) a lipid bilayer and an ARRDC1 protein, and
   (ii) a cargo protein, wherein the cargo protein is linked to the ARRDC1 protein via one or more WW domains, and wherein the cargo protein is a transcription factor, a tumor suppressor, a developmental regulator, a growth factor, a metastasis suppressor, a pro-apoptotic protein, a nuclease, a recombinase, or a reprogramming factor.

2. The microvesicle of claim 1, wherein the cargo protein is linked to the ARRDC1 protein via two, three, four or five WW domains.

3. The microvesicle of claim 1, wherein one or more of the WW domains is a WW domain of the ubiquitin ligase WWP1, WWP2, Nedd4-1, Nedd4-2, Smurf1, Smurf2, ITCH, NEDL1 or NEDL2.

4. The microvesicle of claim 1, wherein one or more of the WW domains comprises any one of the amino acid sequences selected from the group consisting of (SEQ ID NO: 36), (SEQ ID NO: 37), (SEQ ID NO: 38), (SEQ ID NO: 39), (SEQ ID NO: 40), (SEQ ID NO: 41), (SEQ ID NO: 42), (SEQ ID NO: 43), (SEQ ID NO: 44), (SEQ ID NO: 45), (SEQ ID NO: 46), (SEQ ID NO: 47), (SEQ ID NO: 48), (SEQ ID NO: 49), (SEQ ID NO: 50), (SEQ ID NO: 51), (SEQ ID NO: 52), (SEQ ID NO: 53), (SEQ ID NO: 54), (SEQ ID NO: 55), (SEQ ID NO: 56), (SEQ ID NO: 57), (SEQ ID NO: 58), (SEQ ID NO: 59), (SEQ ID NO: 60), (SEQ ID NO: 61), (SEQ ID NO: 62), (SEQ ID NO: 63), and (SEQ ID NO: 64).

5. The microvesicle of claim 1, wherein the cargo protein is a recombinant protein.

6. The microvesicle of claim 1, wherein the one or more WW domains are fused to the N-terminus of the cargo protein.

7. The microvesicle of claim 1, wherein the one or more WW domains are fused to the C-terminus of the cargo protein.

8. The microvesicle of claim 1, wherein the ARRDC1 protein comprises any one of the ARRDC1 amino acid sequences set forth in SEQ ID NOs: 15-17.

9. A method of delivering a cargo protein to a target cell, the method comprising
   contacting the target cell with the microvesicle of claim 1.

10. The method of claim 9, wherein the target cell is a cell in vitro, and wherein the method comprises administering the microvesicle to the cell in vitro.

11. The method of claim 9, wherein the target cell is a cell in a subject; and wherein the method comprises administering the microvesicle to the subject.

12. The method of claim 11, wherein the subject is a human subject.

13. The microvesicle of claim 1, wherein the cargo protein is a transcription factor selected from the group consisting of Sp1, NF1, CCAAT, GATA, HNF, PIT-1, MyoD, Myf5, Hox, Winged Helix, SREBP, p53, CREB, AP-1, Mef2, STAT, R-SMAD, NF-κB, Notch, TUBBY, and NFAT.

14. The microvesicle of claim 1, wherein the cargo protein is a tumor suppressor or a metastasis suppressor selected from the group consisting of p53, retinoblastoma protein (Rb), BRCA1, BRCA2, PTEN, APC, CD95, ST7, ST14, BRMS1, CRSP3, DRG1, KAI1, KISS1, NM23, TIMP-family proteins, and BCL-2 family proteins.

15. The microvesicle of claim 1, wherein the cargo protein is a pro-apoptotic protein, and wherein the pro-apoptotic protein is a caspase.

16. The microvesicle of claim 1, wherein the cargo protein is a reprogramming factor selected from the group consisting of Oct4, Sox2, Klf4, and c-myc.

17. The microvesicle of claim 1, wherein the cargo protein is a growth factor selected from the group consisting of EGF, EPO, FGF, G-CSF, GM-CSF, HGF, HDGF, IGF, PDGF, TPO, TGF-α, TGF-β, VEGF, BMP-family growth factors, and GDF-family growth factors.

18. The microvesicle of claim 1, wherein the cargo protein is a nuclease selected from the group consisting of TALE nucleases, and zinc finger nucleases.

19. The microvesicle of claim 1, wherein the cargo protein is recombinase selected from the group consisting of Cre, Dre, and FLP.

20. The microvesicle of claim 1 further comprising a targeting moiety selected from the group consisting of a membrane-bound immunoglobulins, integrins, receptors, and receptor ligands.

* * * * *

SEQUENCE LISTING

<160> NUMBER OF SEQ ID NOS: 80

<210> SEQ ID NO 1
<211> LENGTH: 4104
<212> TYPE: DNA
<213> ORGANISM: Streptococcus pyogenes

<400> SEQUENCE: 1

```
atggataaga aatactcaat aggcttagat atcggcacaa atagcgtcgg atgggcggtg      60
atcactgatg attataaggt tccgtctaaa aagttcaagg ttctgggaaa tacagaccgc     120
cacagtatca aaaaaaatct tataggggct ctttttatttg gcagtggaga gacagcggaa    180
gcgactcgtc tcaaacggac agctcgtaga aggtatacac gtcggaagaa tcgtatttgt    240
tatctacagg agatttttc aaatgagatg gcgaaagtag atgatagttt ctttcatcga     300
cttgaagagt cttttttggt ggaagaagac aagaagcatg aacgtcatcc tattttttgga   360 aatatagtag atgaagttgc ttatcatgag aaatatccaa ctatctatca tctgcgaaaa    420
aaattggcag attctactga taaagcggat ttgcgcttaa tctatttggc cttagcgcat    480
atgattaagt ttcgtggtca ttttttgatt gagggagatt aaatcctga taatagtgat     540 gtggacaaac tatttatcca gttggtacaa atctacaatc aattatttga agaaaaccct    600
attaacgcaa gtagagtaga tgctaaagcg attctttctg cacgattgag taaatcaaga    660
cgattagaaa atctcattgc tcagctcccc ggtgagaaga gaaatggctt gtttgggaat    720
ctcattgctt tgtcattggg attgaccct aattttaaat caaattttga tttggcagaa    780
gatgctaaat tacagctttc aaaagatact tacgatgatg atttagataa tttattggcg   840
caaattggag atcaatatgc tgatttgttt ttggcagcta agaatttatc agatgctatt    900
ttactttcag atatcctaag agtaaatagt gaaataacta aggctcccct atcagcttca    960
atgattaagc gctacgatga acatcatcaa gacttgactc ttttaaaagc tttagttcga   1020
caacaacttc cagaaaagta taaagaaatc tttttttgatc aatcaaaaaa cggatatgca   1080
ggttatattg atgggggagc tagccaagaa gaatttttata aatttatcaa accaatttta   1140
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat    1260 gctatttttga agacaaga agacttttat ccattttaa aagacaatcg tgagaagatt    1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aggtgctttc agctcaatca tttattgaac gcatgacaaa ctttgataaa    1500
aatcttccaa atgaaaaagt actaccaaaa catagtttgc tttatgagta ttttacggtt   1560
tataacgaat tgacaaaggt caaatatgtt actgagggaa tgcgaaaacc agcatttctt   1620
tcaggtgaac agaagaaagc cattgttgat ttactcttca aaacaaatcg aaaagtaacc    1680
gttaagcaat aaaagaaga ttatttcaaa aaatagaat gttttgatag tgttgaaatt    1740
tcaggagttg aagatagatt taatgcttca ttaggcgcct accatgattt gctaaaaatt    1800
attaaagata agatttttttt ggataatgaa gaaatgaag atatcttaga ggatattgtt    1860
ttaacattga cctatttga agataggggg atgattgagg aaagacttaa acatatgct    1920 cacctctttg atgataaggt gatgaaacag cttaaacgtc gccgttatac tggttgggga   1980
cgtttgtctc gaaaattgat taatggtatt agggataagc aatctggcaa acaatatta    2040 gatttttttga aatcagatgg ttttgccaat cgcaattttta tgcagctgat ccatgatgat    2100
```

-continued

```
agtttgacat ttaaagaaga tattcaaaaa gcacaggtgt ctggacaagg ccatagttta   2160
catgaacaga ttgctaactt agctggcagt cctgctatta aaaaaggtat tttacagact   2220
gtaaaaattg ttgatgaact ggtcaaagta atggggcata agccagaaaa tatcgttatt   2280
gaaatggcac gtgaaaatca gacaactcaa aagggccaga aaaattcgcg agagcgtatg   2340
aaacgaatcg aagaaggtat caaagaatta ggaagtcaga ttcttaaaga gcatcctgtt   2400
gaaaatactc aattgcaaaa tgaaaagctc tatctctatt atctacaaaa tggaagagac   2460
atgtatgtgg accaagaatt agatattaat cgtttaagtg attatgatgt cgatcacatt   2520
gttccacaaa gtttcattaa agacgattca atagacaata aggtactaac gcgttctgat   2580
aaaaatcgtg gtaaatcgga taacgttcca agtgaagaag tagtcaaaaa gatgaaaaac   2640
tattggagac aacttctaaa cgccaagtta atcactcaac gtaagtttga taatttaacg   2700
aaagctgaac gtggaggttt gagtgaactt gataaagctg gttttatcaa acgccaattg   2760
gttgaaactc gccaaatcac taagcatgtg gcacaaattt tggatagtcg catgaatact   2820
aaatacgatg aaaatgataa acttattcga gaggttaaag tgattacctt aaaatctaaa   2880
ttagtttctg acttccgaaa agatttccaa ttctataaag tacgtgagat taacaattac   2940
catcatgccc atgatgcgta tctaaatgcc gtcgttggaa ctgctttgat taagaaatat   3000
ccaaaacttg aatcggagtt tgtctatggt gattataaag tttatgatgt tcgtaaaatg   3060
attgctaagt ctgagcaaga aataggcaaa gcaaccgcaa atatttctt ttactctaat   3120
atcatgaact tcttcaaaac agaaattaca cttgcaaatg gagagattcg caaacgccct   3180
ctaatcgaaa ctaatgggga aactggagaa attgtctggg ataaagggcg agattttgcc   3240
acagtgcgca aagtattgtc catgccccaa gtcaatattg tcaagaaaac agaagtacag   3300
acaggcggat tctccaagga gtcaatttta ccaaaaagaa attcggacaa gcttattgct   3360
cgtaaaaaag actgggatcc aaaaaaatat ggtggttttg atagtccaac ggtagcttat   3420
tcagtcctag tggttgctaa ggtggaaaaa gggaaatcga agaagttaaa atccgttaaa   3480
gagttactag ggatcacaat tatggaagaa agttcctttg aaaaaaatcc gattgacttt   3540
ttagaagcta aaggatataa ggaagttaaa aaagacttaa tcattaaaact acctaaatat   3600
agtcttttg agttagaaaa cggtcgtaaa cggatgctgg ctagtgccgg agaattacaa   3660
aaaggaaatg agctggctct gccaagcaaa tatgtgaatt ttttatattt agctagtcat   3720
tatgaaaagt tgaagggtag tccagaagat aacgaacaaa aacaattgtt tgtggagcag   3780
cataagcatt atttagatga gattattgag caaatcagtg aattttctaa gcgtgttatt   3840
ttagcagatg ccaatttaga taaagttctt agtgcatata acaaacatag agacaaacca   3900
atacgtgaac aagcagaaaa tattattcat ttatttacgt tgacgaatct ggagctccc    3960
gctgctttta aatattttga tacaacaatt gatcgtaaac gatatacgtc tacaaaagaa   4020
gttttagatg ccactcttat ccatcaatcc atcactggtc tttatgaaac acgcattgat   4080
ttgagtcagc taggaggtga ctga                                          4104
```

<210> SEQ ID NO 2
<211> LENGTH: 1367
<212> TYPE: PRT
<213> ORGANISM: Streptococcus pyogenes

<400> SEQUENCE: 2

```
Met Asp Lys Lys Tyr Ser Ile Gly Leu Asp Ile Gly Thr Asn Ser Val
1               5                   10                  15
```

```
Gly Trp Ala Val Ile Thr Asp Asp Tyr Lys Val Pro Ser Lys Lys Phe
             20                  25                  30
Lys Val Leu Gly Asn Thr Asp Arg His Ser Ile Lys Lys Asn Leu Ile
             35                  40                  45
Gly Ala Leu Leu Phe Gly Ser Gly Glu Thr Ala Glu Ala Thr Arg Leu
             50                  55                  60
Lys Arg Thr Ala Arg Arg Arg Tyr Thr Arg Arg Lys Asn Arg Ile Cys
 65              70                  75                  80
Tyr Leu Gln Glu Ile Phe Ser Asn Glu Met Ala Lys Val Asp Asp Ser
                 85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
                115                 120                 125
His Glu Lys Tyr Pro Thr Ile Tyr His Leu Arg Lys Lys Leu Ala Asp
                130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Ile Tyr
                180                 185                 190
Asn Gln Leu Phe Glu Glu Asn Pro Ile Asn Ala Ser Arg Val Asp Ala
                195                 200                 205
Lys Ala Ile Leu Ser Ala Arg Leu Ser Lys Ser Arg Arg Leu Glu Asn
                210                 215                 220
Leu Ile Ala Gln Leu Pro Gly Glu Lys Arg Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
                290                 295                 300
Ile Leu Arg Val Asn Ser Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
```

```
Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Ala Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Gly Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly His Ser Leu
705                 710                 715                 720

His Glu Gln Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
            740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
            770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Ile Lys Asp
            835                 840                 845

Asp Ser Ile Asp Asn Lys Val Leu Thr Arg Ser Asp Lys Asn Arg Gly
```

```
                    850               855               860
Lys Ser Asp Asn Val Pro Ser Glu Glu Val Val Lys Lys Met Lys Asn
865                 870               875                 880

Tyr Trp Arg Gln Leu Leu Asn Ala Lys Leu Ile Thr Gln Arg Lys Phe
                885               890                 895

Asp Asn Leu Thr Lys Ala Glu Arg Gly Gly Leu Ser Glu Leu Asp Lys
                900               905               910

Ala Gly Phe Ile Lys Arg Gln Leu Val Glu Thr Arg Gln Ile Thr Lys
            915               920               925

His Val Ala Gln Ile Leu Asp Ser Arg Met Asn Thr Lys Tyr Asp Glu
            930               935               940

Asn Asp Lys Leu Ile Arg Glu Val Lys Val Ile Thr Leu Lys Ser Lys
945                 950               955                 960

Leu Val Ser Asp Phe Arg Lys Asp Phe Gln Phe Tyr Lys Val Arg Glu
                965               970               975

Ile Asn Asn Tyr His His Ala His Asp Ala Tyr Leu Asn Ala Val Val
                980               985               990

Gly Thr Ala Leu Ile Lys Lys Tyr  Pro Lys Leu Glu Ser  Glu Phe Val
            995              1000             1005

Tyr Gly  Asp Tyr Lys Val Tyr  Asp Val Arg Lys Met  Ile Ala Lys
    1010             1015             1020

Ser Glu  Gln Glu Ile Gly Lys  Ala Thr Ala Lys Tyr  Phe Phe Tyr
    1025             1030             1035

Ser Asn  Ile Met Asn Phe Phe  Lys Thr Glu Ile Thr  Leu Ala Asn
    1040             1045             1050

Gly Glu  Ile Arg Lys Arg Pro  Leu Ile Glu Thr Asn  Gly Glu Thr
    1055             1060             1065

Gly Glu  Ile Val Trp Asp Lys  Gly Arg Asp Phe Ala  Thr Val Arg
    1070             1075             1080

Lys Val  Leu Ser Met Pro Gln  Val Asn Ile Val Lys  Lys Thr Glu
    1085             1090             1095

Val Gln  Thr Gly Gly Phe Ser  Lys Glu Ser Ile Leu  Pro Lys Arg
    1100             1105             1110

Asn Ser  Asp Lys Leu Ile Ala  Arg Lys Lys Asp Trp  Asp Pro Lys
    1115             1120             1125

Lys Tyr  Gly Gly Phe Asp Ser  Pro Thr Val Ala Tyr  Ser Val Leu
    1130             1135             1140

Val Val  Ala Lys Val Glu Lys  Gly Lys Ser Lys Lys  Leu Lys Ser
    1145             1150             1155

Val Lys  Glu Leu Leu Gly Ile  Thr Ile Met Glu Arg  Ser Ser Phe
    1160             1165             1170

Glu Lys  Asn Pro Ile Asp Phe  Leu Glu Ala Lys Gly  Tyr Lys Glu
    1175             1180             1185

Val Lys  Lys Asp Leu Ile Ile  Lys Leu Pro Lys Tyr  Ser Leu Phe
    1190             1195             1200

Glu Leu  Glu Asn Gly Arg Lys  Arg Met Leu Ala Ser  Ala Gly Glu
    1205             1210             1215

Leu Gln  Lys Gly Asn Glu Leu  Ala Leu Pro Ser Lys  Tyr Val Asn
    1220             1225             1230

Phe Leu  Tyr Leu Ala Ser His  Tyr Glu Lys Leu Lys  Gly Ser Pro
    1235             1240             1245

Glu Asp  Asn Glu Gln Lys Gln  Leu Phe Val Glu Gln  His Lys His
    1250             1255             1260
```

| Tyr | Leu | Asp | Glu | Ile | Ile | Glu | Gln | Ile | Ser | Glu | Phe | Ser | Lys | Arg |
|---|---|---|---|---|---|---|---|---|---|---|---|---|---|---|
| | 1265 | | | | 1270 | | | | 1275 | | | | | |

| Val | Ile | Leu | Ala | Asp | Ala | Asn | Leu | Asp | Lys | Val | Leu | Ser | Ala | Tyr |
|---|---|---|---|---|---|---|---|---|---|---|---|---|---|---|
| 1280 | | | | | 1285 | | | | | 1290 | | | | |

| Asn | Lys | His | Arg | Asp | Lys | Pro | Ile | Arg | Glu | Gln | Ala | Glu | Asn | Ile |
|---|---|---|---|---|---|---|---|---|---|---|---|---|---|---|
| 1295 | | | | | 1300 | | | | | 1305 | | | | |

| Ile | His | Leu | Phe | Thr | Leu | Thr | Asn | Leu | Gly | Ala | Pro | Ala | Ala | Phe |
|---|---|---|---|---|---|---|---|---|---|---|---|---|---|---|
| 1310 | | | | | 1315 | | | | | 1320 | | | | |

| Lys | Tyr | Phe | Asp | Thr | Thr | Ile | Asp | Arg | Lys | Arg | Tyr | Thr | Ser | Thr |
|---|---|---|---|---|---|---|---|---|---|---|---|---|---|---|
| 1325 | | | | | 1330 | | | | | 1335 | | | | |

| Lys | Glu | Val | Leu | Asp | Ala | Thr | Leu | Ile | His | Gln | Ser | Ile | Thr | Gly |
|---|---|---|---|---|---|---|---|---|---|---|---|---|---|---|
| 1340 | | | | | 1345 | | | | | 1350 | | | | |

| Leu | Tyr | Glu | Thr | Arg | Ile | Asp | Leu | Ser | Gln | Leu | Gly | Gly | Asp |
|---|---|---|---|---|---|---|---|---|---|---|---|---|---|
| 1355 | | | | | 1360 | | | | | 1365 | | | |

<210> SEQ ID NO 3
<211> LENGTH: 4212
<212> TYPE: DNA
<213> ORGANISM: Artificial Sequence
<220> FEATURE:
<223> OTHER INFORMATION: Synthetic

<400> SEQUENCE: 3

| | | | | | |
|---|---|---|---|---|---|
| atggataaaa | agtattctat | tggtttagac | atcggcacta | attccgttgg | atgggctgtc | 60 |
| ataaccgatg | aatacaaagt | accttcaaag | aaatttaagg | tgttggggaa | cacagaccgt | 120 |
| cattcgatta | aaaagaatct | tatcggtgcc | ctcctattcg | atagtggcga | aacggcagag | 180 |
| gcgactcgcc | tgaaacgaac | cgctcggaga | aggtatacac | gtcgcaagaa | ccgaatatgt | 240 |
| tacttacaag | aaattttag | caatgagatg | gccaaagttg | acgattcttt | ctttcaccgt | 300 |
| ttggaagagt | ccttccttgt | cgaagaggac | aagaaacatg | aacggcaccc | catctttgga | 360 |
| aacatagtag | atgaggtggc | atatcatgaa | agtacccaa | cgatttatca | cctcagaaaa | 420 |
| aagctagttg | actcaactga | taaagcggac | ctgaggttaa | tctacttggc | tcttgcccat | 480 |
| atgataaagt | tccgtgggca | ctttctcatt | gagggtgatc | taaatccgga | caactcggat | 540 |
| gtcgacaaac | tgttcatcca | gttagtacaa | acctataatc | agttgtttga | agagaaccct | 600 |
| ataaatgcaa | gtggcgtgga | tgcgaaggct | attcttagcg | cccgcctctc | taatcccga | 660 |
| cggctagaaa | acctgatcgc | acaattaccc | ggagagaaga | aaaatgggtt | gttcggtaac | 720 |
| cttatagcgc | tctcactagg | cctgacacca | aattttaagt | cgaacttcga | cttagctgaa | 780 |
| gatgccaaat | tgcagcttag | taaggacacg | tacgatgacg | atctcgacaa | tctactggca | 840 |
| caaattggag | atcagtatgc | ggacttattt | ttggctgcca | aaaaccttag | cgatgcaatc | 900 |
| ctcctatctg | acatactgag | agttaatact | gagattacca | aggcgccgtt | atccgcttca | 960 |
| atgatcaaaa | ggtacgatga | acatcaccaa | gacttgacac | ttctcaaggc | cctagtccgt | 1020 |
| cagcaactgc | ctgagaaata | taaggaaata | ttctttgatc | agtcgaaaaa | cgggtacgca | 1080 |
| ggttatattg | acggcggagc | gagtcaagag | gaattctaca | agtttatcaa | acccatatta | 1140 |
| gagaagatgg | atgggacgga | agagttgctt | gtaaaactca | atcgcgaaga | tctactgcga | 1200 |
| aagcagcgga | ctttcgacaa | cggtagcatt | ccacatcaaa | tccacttagg | cgaattgcat | 1260 |
| gctatactta | gaaggcagga | ggattttat | ccgttcctca | agacaatcg | tgaaaagatt | 1320 |
| gagaaaatcc | taacctttcg | catacctac | tatgtgggac | ccctggcccg | agggaactct | 1380 |
| cggttcgcat | ggatgacaag | aaagtccgaa | gaaacgatta | ctccatggaa | ttttgaggaa | 1440 |

```
gttgtcgata aaggtgcgtc agctcaatcg ttcatcgaga ggatgaccaa ctttgacaag    1500
aatttaccga acgaaaaagt attgcctaag cacagtttac tttacgagta tttcacagtg    1560
tacaatgaac tcacgaaagt taagtatgtc actgagggca tgcgtaaacc cgcctttcta    1620
agcggagaac agaagaaagc aatagtagat ctgttattca agaccaaccg caaagtgaca    1680
gttaagcaat tgaaagagga ctactttaag aaaattgaat gcttcgattc tgtcgagatc    1740
tccggggtag aagatcgatt taatgcgtca cttggtacgt atcatgacct cctaaagata    1800
attaaagata aggacttcct ggataacgaa gagaatgaag atatcttaga agatatagtg    1860
ttgactctta ccctctttga agatcggaa atgattgagg aaagactaaa acatacgct     1920 cacctgttcg acgataaggt tatgaaacag ttaaagaggc gtcgctatac gggctggga    1980 cgattgtcgc ggaaacttat caacgggata agagacaagc aaagtggtaa aactattctc    2040
gattttctaa agagcgacgg cttcgccaat aggaacttta tgcagctgat ccatgatgac    2100
tctttaacct tcaaagagga tatacaaaag gcacaggttt ccggacaagg ggactcattg    2160
cacgaacata ttgcgaatct tgctggttcg ccagccatca aaagggcat actccagaca     2220 gtcaaagtag tggatgagct agttaaggtc atgggacgtc acaaaccgga aaacattgta    2280
atcgagatgg cacgcgaaaa tcaaacgact cagaaggggc aaaaaaacag tcgagagcgg    2340
atgaagagaa tagaagaggg tattaaagaa ctgggcagcc agatcttaaa ggagcatcct    2400
gtggaaaata cccaattgca gaacgagaaa ctttacctct attacctaca aaatggaagg    2460
gacatgtatg ttgatcagga actggacata aaccgtttat ctgattacga cgtcgatcac    2520
attgtacccc aatccttttt gaaggacgat tcaatcgaca ataaagtgct tacacgctcg    2580
gataagaacc gagggaaaag tgacaatgtt ccaagcgagg aagtcgtaaa gaaaatgaag    2640
aactattggc ggcagctcct aaatgcgaaa ctgataacgc aaagaaagtt cgataactta    2700
actaaagctg agaggggtgg cttgtctgaa cttgacaagg ccggatttat taaacgtcag    2760
ctcgtggaaa cccgccaaat cacaaagcat gttgcacaga tactagattc ccgaatgaat    2820
acgaaatacg acgagaacga taagctgatt cgggaagtca aagtaatcac tttaaagtca    2880
aaattggtgt cggacttcag aaaggatttt caattctata agttaggga gataaataac     2940 taccaccatg cgcacgacgc ttatcttaat gccgtcgtag ggaccgcact cattaagaaa    3000
tacccgaagc tagaaagtga gttgtgtat ggtgattaca aagtttatga cgtccgtaag     3060
atgatcgcga aaagcgaaca ggagataggc aaggctacag ccaaatactt cttttattct    3120
aacattatga atttctttaa gacgaaatc actctggcaa acggagagat acgcaaacga     3180
cctttaattg aaaccaatgg ggagacaggt gaaatcgtat gggataaggg ccgggacttc    3240
gcgacggtga gaaaagtttt gtccatgccc caagtcaaca tagtaaagaa aactgaggtg    3300
cagaccggag ggttttcaaa ggaatcgatt cttccaaaaa ggaatagtga taagctcatc    3360
gctcgtaaaa aggactggga cccgaaaaag tacggtggct tcgatagccc tacagttgcc    3420
tattctgtcc tagtagtggc aaaagttgag aagggaaaat ccaagaaact gaagtcagtc    3480
aaagaattat tggggataac gattatggag cgctcgtctt ttgaaaagaa ccccatcgac    3540
ttccttgagg cgaaaggtta caaggaagta aaaaaggatc tcataattaa actaccaaag    3600
tatagtctgt ttgagttaga aaatggccga aaacggatgt ggctagcgc cggagagctt     3660 caaaagggga cgaactcgc actaccgtct aaatacgtga atttcctgta tttagcgtcc    3720
cattacgaga agttgaaagg ttcacctgaa gataacgaac agaagcaact ttttgttgag    3780
```

```
cagcacaaac attatctcga cgaaatcata gagcaaattt cggaattcag taagagagtc   3840
atcctagctg atgccaatct ggacaaagta ttaagcgcat acaacaagca cagggataaa   3900
cccatacgtg agcaggcgga aaatattatc catttgttta ctcttaccaa cctcggcgct   3960
ccagccgcat tcaagtattt tgacacaacg atagatcgca aacgatacac ttctaccaag   4020
gaggtgctag acgcgacact gattcaccaa tccatcacgg gattatatga aactcggata   4080
gatttgtcac agcttggggg tgacggatcc cccaagaaga agaggaaagt ctcgagcgac   4140
tacaaagacc atgacggtga ttataaagat catgacatcg attacaagga tgacgatgac   4200
aaggctgcag ga                                                      4212
```

<210> SEQ ID NO 4
<211> LENGTH: 1368
<212> TYPE: PRT
<213> ORGANISM: Artificial Sequence
<220> FEATURE:
<223> OTHER INFORMATION: Synthetic

<400> SEQUENCE: 4

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285
```

```
Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700
```

```
Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
```

```
                    1115                1120                1125

Lys Lys Tyr Gly Gly Phe Asp Ser Pro Thr Val Ala Tyr Ser Val
            1130                1135                1140

Leu Val Val Ala Lys Val Glu Lys Gly Lys Ser Lys Lys Leu Lys
            1145                1150                1155

Ser Val Lys Glu Leu Leu Gly Ile Thr Ile Met Glu Arg Ser Ser
            1160                1165                1170

Phe Glu Lys Asn Pro Ile Asp Phe Leu Glu Ala Lys Gly Tyr Lys
            1175                1180                1185

Glu Val Lys Lys Asp Leu Ile Ile Lys Leu Pro Lys Tyr Ser Leu
            1190                1195                1200

Phe Glu Leu Glu Asn Gly Arg Lys Arg Met Leu Ala Ser Ala Gly
            1205                1210                1215

Glu Leu Gln Lys Gly Asn Glu Leu Ala Leu Pro Ser Lys Tyr Val
            1220                1225                1230

Asn Phe Leu Tyr Leu Ala Ser His Tyr Glu Lys Leu Lys Gly Ser
            1235                1240                1245

Pro Glu Asp Asn Glu Gln Lys Gln Leu Phe Val Glu Gln His Lys
            1250                1255                1260

His Tyr Leu Asp Glu Ile Ile Glu Gln Ile Ser Glu Phe Ser Lys
            1265                1270                1275

Arg Val Ile Leu Ala Asp Ala Asn Leu Asp Lys Val Leu Ser Ala
            1280                1285                1290

Tyr Asn Lys His Arg Asp Lys Pro Ile Arg Glu Gln Ala Glu Asn
            1295                1300                1305

Ile Ile His Leu Phe Thr Leu Thr Asn Leu Gly Ala Pro Ala Ala
            1310                1315                1320

Phe Lys Tyr Phe Asp Thr Thr Ile Asp Arg Lys Arg Tyr Thr Ser
            1325                1330                1335

Thr Lys Glu Val Leu Asp Ala Thr Leu Ile His Gln Ser Ile Thr
            1340                1345                1350

Gly Leu Tyr Glu Thr Arg Ile Asp Leu Ser Gln Leu Gly Gly Asp
            1355                1360                1365

<210> SEQ ID NO 5
<211> LENGTH: 1368
<212> TYPE: PRT
<213> ORGANISM: Artificial Sequence
<220> FEATURE:
<223> OTHER INFORMATION: Synthetic

<400> SEQUENCE: 5

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
```

```
                100             105             110
His Glu Arg His Pro Ile Phe Gly Asn Ile Val Asp Glu Val Ala Tyr
            115                 120             125
His Glu Lys Tyr Pro Thr Ile Tyr His Leu Arg Lys Lys Leu Val Asp
            130                 135             140
Ser Thr Asp Lys Ala Asp Leu Arg Leu Ile Tyr Leu Ala Leu Ala His
145                 150             155                         160
Met Ile Lys Phe Arg Gly His Phe Leu Ile Glu Gly Asp Leu Asn Pro
                165             170             175
Asp Asn Ser Asp Val Asp Lys Leu Phe Ile Gln Leu Val Gln Thr Tyr
            180                 185             190
Asn Gln Leu Phe Glu Glu Asn Pro Ile Asn Ala Ser Gly Val Asp Ala
            195                 200             205
Lys Ala Ile Leu Ser Ala Arg Leu Ser Lys Ser Arg Arg Leu Glu Asn
            210                 215             220
Leu Ile Ala Gln Leu Pro Gly Glu Lys Lys Asn Gly Leu Phe Gly Asn
225                 230             235                         240
Leu Ile Ala Leu Ser Leu Gly Leu Thr Pro Asn Phe Lys Ser Asn Phe
                245             250             255
Asp Leu Ala Glu Asp Ala Lys Leu Gln Leu Ser Lys Asp Thr Tyr Asp
            260                 265             270
Asp Asp Leu Asp Asn Leu Leu Ala Gln Ile Gly Asp Gln Tyr Ala Asp
            275                 280             285
Leu Phe Leu Ala Ala Lys Asn Leu Ser Asp Ala Ile Leu Leu Ser Asp
            290                 295             300
Ile Leu Arg Val Asn Thr Glu Ile Thr Lys Ala Pro Leu Ser Ala Ser
305                 310             315                         320
Met Ile Lys Arg Tyr Asp Glu His His Gln Asp Leu Thr Leu Leu Lys
                325             330             335
Ala Leu Val Arg Gln Gln Leu Pro Glu Lys Tyr Lys Glu Ile Phe Phe
            340                 345             350
Asp Gln Ser Lys Asn Gly Tyr Ala Gly Tyr Ile Asp Gly Gly Ala Ser
            355                 360             365
Gln Glu Glu Phe Tyr Lys Phe Ile Lys Pro Ile Leu Glu Lys Met Asp
            370                 375             380
Gly Thr Glu Glu Leu Leu Val Lys Leu Asn Arg Glu Asp Leu Leu Arg
385                 390             395                         400
Lys Gln Arg Thr Phe Asp Asn Gly Ser Ile Pro His Gln Ile His Leu
                405             410             415
Gly Glu Leu His Ala Ile Leu Arg Arg Gln Glu Asp Phe Tyr Pro Phe
            420                 425             430
Leu Lys Asp Asn Arg Glu Lys Ile Glu Lys Ile Leu Thr Phe Arg Ile
            435                 440             445
Pro Tyr Tyr Val Gly Pro Leu Ala Arg Gly Asn Ser Arg Phe Ala Trp
            450                 455             460
Met Thr Arg Lys Ser Glu Glu Thr Ile Thr Pro Trp Asn Phe Glu Glu
465                 470             475                         480
Val Val Asp Lys Gly Ala Ser Ala Gln Ser Phe Ile Glu Arg Met Thr
                485             490             495
Asn Phe Asp Lys Asn Leu Pro Asn Glu Lys Val Leu Pro Lys His Ser
            500                 505             510
Leu Leu Tyr Glu Tyr Phe Thr Val Tyr Asn Glu Leu Thr Lys Val Lys
            515                 520             525
```

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

```
Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
```

<210> SEQ ID NO 6
<211> LENGTH: 922
<212> TYPE: PRT
<213> ORGANISM: Homo sapiens

<400> SEQUENCE: 6

```
Met Ala Thr Ala Ser Pro Arg Ser Asp Thr Ser Asn Asn His Ser Gly
 1               5                  10                  15
Arg Leu Gln Leu Gln Val Thr Val Ser Ser Ala Lys Leu Lys Arg Lys
            20                  25                  30
Lys Asn Trp Phe Gly Thr Ala Ile Tyr Thr Glu Val Val Val Asp Gly
        35                  40                  45
Glu Ile Thr Lys Thr Ala Lys Ser Ser Ser Ser Asn Pro Lys Trp
    50                  55                  60
Asp Glu Gln Leu Thr Val Asn Val Thr Pro Gln Thr Thr Leu Glu Phe
65                  70                  75                  80
Gln Val Trp Ser His Arg Thr Leu Lys Ala Asp Ala Leu Leu Gly Lys
                85                  90                  95
Ala Thr Ile Asp Leu Lys Gln Ala Leu Leu Ile His Asn Arg Lys Leu
            100                 105                 110
Glu Arg Val Lys Glu Gln Leu Lys Leu Ser Leu Glu Asn Lys Asn Gly
        115                 120                 125
Ile Ala Gln Thr Gly Glu Leu Thr Val Val Leu Asp Gly Leu Val Ile
    130                 135                 140
Glu Gln Glu Asn Ile Thr Asn Cys Ser Ser Pro Thr Ile Glu Ile
145                 150                 155                 160
Gln Glu Asn Gly Asp Ala Leu His Glu Asn Gly Glu Pro Ser Ala Arg
                165                 170                 175
Thr Thr Ala Arg Leu Ala Val Glu Gly Thr Asn Gly Ile Asp Asn His
            180                 185                 190
Val Pro Thr Ser Thr Leu Val Gln Asn Ser Cys Cys Ser Tyr Val Val
        195                 200                 205
Asn Gly Asp Asn Thr Pro Ser Ser Pro Ser Gln Val Ala Ala Arg Pro
    210                 215                 220
Lys Asn Thr Pro Ala Pro Lys Pro Leu Ala Ser Glu Pro Ala Asp Asp
225                 230                 235                 240
Thr Val Asn Gly Glu Ser Ser Phe Ala Pro Thr Asn Ala Ser
                245                 250                 255
Val Thr Gly Thr Pro Val Val Ser Glu Glu Asn Ala Leu Ser Pro Asn
            260                 265                 270
Cys Thr Ser Thr Thr Val Glu Asp Pro Pro Val Gln Glu Ile Leu Thr
        275                 280                 285
Ser Ser Glu Asn Asn Glu Cys Ile Pro Ser Thr Ser Ala Glu Leu Glu
    290                 295                 300
Ser Glu Ala Arg Ser Ile Leu Glu Pro Asp Thr Ser Asn Ser Arg Ser
305                 310                 315                 320
Ser Ser Ala Phe Glu Ala Ala Lys Ser Arg Gln Pro Asp Gly Cys Met
                325                 330                 335
Asp Pro Val Arg Gln Gln Ser Gly Asn Ala Asn Thr Glu Thr Leu Pro
            340                 345                 350
```

-continued

```
Ser Gly Trp Glu Gln Arg Lys Asp Pro His Gly Arg Thr Tyr Tyr Val
        355                 360                 365

Asp His Asn Thr Arg Thr Thr Thr Trp Glu Arg Pro Gln Pro Leu Pro
370                 375                 380

Pro Gly Trp Glu Arg Arg Val Asp Asp Arg Arg Arg Val Tyr Tyr Val
385                 390                 395                 400

Asp His Asn Thr Arg Thr Thr Thr Trp Gln Arg Pro Thr Met Glu Ser
                405                 410                 415

Val Arg Asn Phe Glu Gln Trp Gln Ser Gln Arg Asn Gln Leu Gln Gly
                420                 425                 430

Ala Met Gln Gln Phe Asn Gln Arg Tyr Leu Tyr Ser Ala Ser Met Leu
        435                 440                 445

Ala Ala Glu Asn Asp Pro Tyr Gly Pro Leu Pro Pro Gly Trp Glu Lys
    450                 455                 460

Arg Val Asp Ser Thr Asp Arg Val Tyr Phe Val Asn His Asn Thr Lys
465                 470                 475                 480

Thr Thr Gln Trp Glu Asp Pro Arg Thr Gln Gly Leu Gln Asn Glu Glu
                485                 490                 495

Pro Leu Pro Glu Gly Trp Glu Ile Arg Tyr Thr Arg Glu Gly Val Arg
                500                 505                 510

Tyr Phe Val Asp His Asn Thr Arg Thr Thr Thr Phe Lys Asp Pro Arg
        515                 520                 525

Asn Gly Lys Ser Ser Val Thr Lys Gly Gly Pro Gln Ile Ala Tyr Glu
    530                 535                 540

Arg Gly Phe Arg Trp Lys Leu Ala His Phe Arg Tyr Leu Cys Gln Ser
545                 550                 555                 560

Asn Ala Leu Pro Ser His Val Lys Ile Asn Val Ser Arg Gln Thr Leu
                565                 570                 575

Phe Glu Asp Ser Phe Gln Gln Ile Met Ala Leu Lys Pro Tyr Asp Leu
                580                 585                 590

Arg Arg Arg Leu Tyr Val Ile Phe Arg Gly Glu Glu Gly Leu Asp Tyr
        595                 600                 605

Gly Gly Leu Ala Arg Glu Trp Phe Phe Leu Leu Ser His Glu Val Leu
610                 615                 620

Asn Pro Met Tyr Cys Leu Phe Glu Tyr Ala Gly Lys Asn Asn Tyr Cys
625                 630                 635                 640

Leu Gln Ile Asn Pro Ala Ser Thr Ile Asn Pro Asp His Leu Ser Tyr
                645                 650                 655

Phe Cys Phe Ile Gly Arg Phe Ile Ala Met Ala Leu Phe His Gly Lys
        660                 665                 670

Phe Ile Asp Thr Gly Phe Ser Leu Pro Phe Tyr Lys Arg Met Leu Ser
        675                 680                 685

Lys Lys Leu Thr Ile Lys Asp Leu Glu Ser Ile Asp Thr Glu Phe Tyr
690                 695                 700

Asn Ser Leu Ile Trp Ile Arg Asp Asn Ile Glu Glu Cys Gly Leu
705                 710                 715                 720

Glu Met Tyr Phe Ser Val Asp Met Glu Ile Leu Gly Lys Val Thr Ser
                725                 730                 735

His Asp Leu Lys Leu Gly Gly Ser Asn Ile Leu Val Thr Glu Glu Asn
                740                 745                 750

Lys Asp Glu Tyr Ile Gly Leu Met Thr Glu Trp Arg Phe Ser Arg Gly
        755                 760                 765

Val Gln Glu Gln Thr Lys Ala Phe Leu Asp Gly Phe Asn Glu Val Val
```

```
                    770                 775                 780
Pro Leu Gln Trp Leu Gln Tyr Phe Asp Glu Lys Glu Leu Glu Val Met
785                 790                 795                 800

Leu Cys Gly Met Gln Glu Val Asp Leu Ala Asp Trp Gln Arg Asn Thr
                    805                 810                 815

Val Tyr Arg His Tyr Thr Arg Asn Ser Lys Gln Ile Ile Trp Phe Trp
                    820                 825                 830

Gln Phe Val Lys Glu Thr Asp Asn Glu Val Arg Met Arg Leu Leu Gln
                    835                 840                 845

Phe Val Thr Gly Thr Cys Arg Leu Pro Leu Gly Gly Phe Ala Glu Leu
                    850                 855                 860

Met Gly Ser Asn Gly Pro Gln Lys Phe Cys Ile Glu Lys Val Gly Lys
865                 870                 875                 880

Asp Thr Trp Leu Pro Arg Ser His Thr Cys Phe Asn Arg Leu Asp Leu
                    885                 890                 895

Pro Pro Tyr Lys Ser Tyr Glu Gln Leu Lys Glu Lys Leu Leu Phe Ala
                    900                 905                 910

Ile Glu Glu Thr Glu Gly Phe Gly Gln Glu
                    915                 920

<210> SEQ ID NO 7
<211> LENGTH: 870
<212> TYPE: PRT
<213> ORGANISM: Homo sapiens

<400> SEQUENCE: 7

Met Ala Ser Ala Ser Ser Arg Ala Gly Val Ala Leu Pro Phe Glu
1               5                   10                  15

Lys Ser Gln Leu Thr Leu Lys Val Val Ser Ala Lys Pro Lys Val His
                    20                  25                  30

Asn Arg Gln Pro Arg Ile Asn Ser Tyr Val Glu Val Ala Val Asp Gly
                    35                  40                  45

Leu Pro Ser Glu Thr Lys Lys Thr Gly Lys Arg Ile Gly Ser Ser Glu
50                  55                  60

Leu Leu Trp Asn Glu Ile Ile Ile Leu Asn Val Thr Ala Gln Ser His
65                  70                  75                  80

Leu Asp Leu Lys Val Trp Ser Cys His Thr Leu Arg Asn Glu Leu Leu
                    85                  90                  95

Gly Thr Ala Ser Val Asn Leu Ser Asn Val Leu Lys Asn Asn Gly Gly
                    100                 105                 110

Lys Met Glu Asn Met Gln Leu Thr Leu Asn Leu Gln Thr Glu Asn Lys
                    115                 120                 125

Gly Ser Val Val Ser Gly Gly Glu Leu Thr Ile Phe Leu Asp Gly Pro
                    130                 135                 140

Thr Val Asp Leu Gly Asn Val Pro Asn Gly Ser Ala Leu Thr Asp Gly
145                 150                 155                 160

Ser Gln Leu Pro Ser Arg Asp Ser Ser Gly Thr Ala Val Ala Pro Glu
                    165                 170                 175

Asn Arg His Gln Pro Pro Ser Thr Asn Cys Phe Gly Gly Arg Ser Arg
                    180                 185                 190

Thr His Arg His Ser Gly Ala Ser Ala Arg Thr Thr Pro Ala Thr Gly
                    195                 200                 205

Glu Gln Ser Pro Gly Ala Arg Ser Arg His Arg Gln Pro Val Lys Asn
                    210                 215                 220
```

```
Ser Gly His Ser Gly Leu Ala Asn Gly Thr Val Asn Asp Glu Pro Thr
225                 230                 235                 240

Thr Ala Thr Asp Pro Glu Glu Pro Ser Val Val Gly Val Thr Ser Pro
            245                 250                 255

Pro Ala Ala Pro Leu Ser Val Thr Pro Asn Pro Asn Thr Thr Ser Leu
        260                 265                 270

Pro Ala Pro Ala Thr Pro Ala Glu Gly Glu Pro Ser Thr Ser Gly
    275                 280                 285

Thr Gln Gln Leu Pro Ala Ala Gln Ala Pro Asp Ala Leu Pro Ala
290                 295                 300

Gly Trp Glu Gln Arg Glu Leu Pro Asn Gly Arg Val Tyr Tyr Val Asp
305                 310                 315                 320

His Asn Thr Lys Thr Thr Thr Trp Glu Arg Pro Leu Pro Pro Gly Trp
            325                 330                 335

Glu Lys Arg Thr Asp Pro Arg Gly Arg Phe Tyr Tyr Val Asp His Asn
        340                 345                 350

Thr Arg Thr Thr Thr Trp Gln Arg Pro Thr Ala Glu Tyr Val Arg Asn
    355                 360                 365

Tyr Glu Gln Trp Gln Ser Gln Arg Asn Gln Leu Gln Gly Ala Met Gln
370                 375                 380

His Phe Ser Gln Arg Phe Leu Tyr Gln Ser Ser Ala Ser Thr Asp
385                 390                 395                 400

His Asp Pro Leu Gly Pro Leu Pro Pro Gly Trp Glu Lys Arg Gln Asp
                405                 410                 415

Asn Gly Arg Val Tyr Tyr Val Asn His Asn Thr Arg Thr Thr Gln Trp
            420                 425                 430

Glu Asp Pro Arg Thr Gln Gly Met Ile Gln Glu Pro Ala Leu Pro Pro
        435                 440                 445

Gly Trp Glu Met Lys Tyr Thr Ser Glu Gly Val Arg Tyr Phe Val Asp
    450                 455                 460

His Asn Thr Arg Thr Thr Thr Phe Lys Asp Pro Arg Pro Gly Phe Glu
465                 470                 475                 480

Ser Gly Thr Lys Gln Gly Ser Pro Gly Ala Tyr Asp Arg Ser Phe Arg
                485                 490                 495

Trp Lys Tyr His Gln Phe Arg Phe Leu Cys His Ser Asn Ala Leu Pro
            500                 505                 510

Ser His Val Lys Ile Ser Val Ser Arg Gln Thr Leu Phe Glu Asp Ser
        515                 520                 525

Phe Gln Gln Ile Met Asn Met Lys Pro Tyr Asp Leu Arg Arg Arg Leu
    530                 535                 540

Tyr Ile Ile Met Arg Gly Glu Glu Gly Leu Asp Tyr Gly Gly Ile Ala
545                 550                 555                 560

Arg Glu Trp Phe Phe Leu Leu Ser His Glu Val Leu Asn Pro Met Tyr
                565                 570                 575

Cys Leu Phe Glu Tyr Ala Gly Lys Asn Asn Tyr Cys Leu Gln Ile Asn
            580                 585                 590

Pro Ala Ser Ser Ile Asn Pro Asp His Leu Thr Tyr Phe Arg Phe Ile
        595                 600                 605

Gly Arg Phe Ile Ala Met Ala Leu Tyr His Gly Lys Phe Ile Asp Thr
    610                 615                 620

Gly Phe Thr Leu Pro Phe Tyr Lys Arg Met Leu Asn Lys Arg Pro Thr
625                 630                 635                 640

Leu Lys Asp Leu Glu Ser Ile Asp Pro Glu Phe Tyr Asn Ser Ile Val
```

```
                    645                 650                 655
Trp Ile Lys Glu Asn Asn Leu Glu Glu Cys Gly Leu Glu Leu Tyr Phe
                660                 665                 670

Ile Gln Asp Met Glu Ile Leu Gly Lys Val Thr Thr His Glu Leu Lys
            675                 680                 685

Glu Gly Gly Glu Ser Ile Arg Val Thr Glu Glu Asn Lys Glu Glu Tyr
        690                 695                 700

Ile Met Leu Leu Thr Asp Trp Arg Phe Thr Arg Gly Val Glu Glu Gln
705                 710                 715                 720

Thr Lys Ala Phe Leu Asp Gly Phe Asn Glu Val Ala Pro Leu Glu Trp
                725                 730                 735

Leu Arg Tyr Phe Asp Glu Lys Glu Leu Glu Leu Met Leu Cys Gly Met
            740                 745                 750

Gln Glu Ile Asp Met Ser Asp Trp Gln Lys Ser Thr Ile Tyr Arg His
        755                 760                 765

Tyr Thr Lys Asn Ser Lys Gln Ile Gln Trp Phe Trp Gln Val Val Lys
    770                 775                 780

Glu Met Asp Asn Glu Lys Arg Ile Arg Leu Leu Gln Phe Val Thr Gly
785                 790                 795                 800

Thr Cys Arg Leu Pro Val Gly Gly Phe Ala Glu Leu Ile Gly Ser Asn
                805                 810                 815

Gly Pro Gln Lys Phe Cys Ile Asp Lys Val Gly Lys Glu Thr Trp Leu
            820                 825                 830

Pro Arg Ser His Thr Cys Phe Asn Arg Leu Asp Leu Pro Pro Tyr Lys
        835                 840                 845

Ser Tyr Glu Gln Leu Arg Glu Lys Leu Leu Tyr Ala Ile Glu Glu Thr
    850                 855                 860

Glu Gly Phe Gly Gln Glu
865                 870

<210> SEQ ID NO 8
<211> LENGTH: 1319
<212> TYPE: PRT
<213> ORGANISM: Homo sapiens

<400> SEQUENCE: 8

Met Ala Gln Ser Leu Arg Leu His Phe Ala Ala Arg Arg Ser Asn Thr
1               5                   10                  15

Tyr Pro Leu Ser Glu Thr Ser Gly Asp Asp Leu Asp Ser His Val His
            20                  25                  30

Met Cys Phe Lys Arg Pro Thr Arg Ile Ser Thr Ser Asn Val Val Gln
        35                  40                  45

Met Lys Leu Thr Pro Arg Gln Thr Ala Leu Ala Pro Leu Ile Lys Glu
    50                  55                  60

Asn Val Gln Ser Gln Glu Arg Ser Ser Val Pro Ser Ser Glu Asn Val
65                  70                  75                  80

Asn Lys Lys Ser Ser Cys Leu Gln Ile Ser Leu Gln Pro Thr Arg Tyr
                85                  90                  95

Ser Gly Tyr Leu Gln Ser Ser Asn Val Leu Ala Asp Ser Asp Asp Ala
            100                 105                 110

Ser Phe Thr Cys Ile Leu Lys Asp Gly Ile Tyr Ser Ser Ala Val Val
        115                 120                 125

Asp Asn Glu Leu Asn Ala Val Asn Asp Gly His Leu Val Ser Ser Pro
    130                 135                 140
```

```
Ala Ile Cys Ser Gly Ser Leu Ser Asn Phe Ser Thr Ser Asp Asn Gly
145                 150                 155                 160

Ser Tyr Ser Ser Asn Gly Ser Asp Phe Gly Ser Cys Ala Ser Ile Thr
            165                 170                 175

Ser Gly Gly Ser Tyr Thr Asn Ser Val Ile Ser Asp Ser Ser Ser Tyr
        180                 185                 190

Thr Phe Pro Pro Ser Asp Asp Thr Phe Leu Gly Gly Asn Leu Pro Ser
    195                 200                 205

Asp Ser Thr Ser Asn Arg Ser Val Pro Asn Arg Asn Thr Thr Pro Cys
    210                 215                 220

Glu Ile Phe Ser Arg Ser Thr Ser Thr Asp Pro Phe Val Gln Asp Asp
225                 230                 235                 240

Leu Glu His Gly Leu Glu Ile Met Lys Leu Pro Val Ser Arg Asn Thr
                245                 250                 255

Lys Ile Pro Leu Lys Arg Tyr Ser Ser Leu Val Ile Phe Pro Arg Ser
                260                 265                 270

Pro Ser Thr Thr Arg Pro Thr Ser Pro Thr Ser Leu Cys Thr Leu Leu
        275                 280                 285

Ser Lys Gly Ser Tyr Gln Thr Ser His Gln Phe Ile Ile Ser Pro Ser
290                 295                 300

Glu Ile Ala His Asn Glu Asp Gly Thr Ser Ala Lys Gly Phe Leu Ser
305                 310                 315                 320

Thr Ala Val Asn Gly Leu Arg Leu Ser Lys Thr Ile Cys Thr Pro Gly
                325                 330                 335

Glu Val Arg Asp Ile Arg Pro Leu His Arg Lys Gly Ser Leu Gln Lys
                340                 345                 350

Lys Ile Val Leu Ser Asn Asn Thr Pro Arg Gln Thr Val Cys Glu Lys
                355                 360                 365

Ser Ser Glu Gly Tyr Ser Cys Val Ser Val His Phe Thr Gln Arg Lys
        370                 375                 380

Ala Ala Thr Leu Asp Cys Glu Thr Thr Asn Gly Asp Cys Lys Pro Glu
385                 390                 395                 400

Met Ser Glu Ile Lys Leu Asn Ser Asp Ser Glu Tyr Ile Lys Leu Met
                405                 410                 415

His Arg Thr Ser Ala Cys Leu Pro Ser Ser Gln Asn Val Asp Cys Gln
            420                 425                 430

Ile Asn Ile Asn Gly Glu Leu Glu Arg Pro His Ser Gln Met Asn Lys
        435                 440                 445

Asn His Gly Ile Leu Arg Arg Ser Ile Ser Leu Gly Gly Ala Tyr Pro
    450                 455                 460

Asn Ile Ser Cys Leu Ser Ser Leu Lys His Asn Cys Ser Lys Gly Gly
465                 470                 475                 480

Pro Ser Gln Leu Leu Ile Lys Phe Ala Ser Gly Asn Glu Gly Lys Val
                485                 490                 495

Asp Asn Leu Ser Arg Asp Ser Asn Arg Asp Cys Thr Asn Glu Leu Ser
            500                 505                 510

Asn Ser Cys Lys Thr Arg Asp Asp Phe Leu Gly Gln Val Asp Val Pro
        515                 520                 525

Leu Tyr Pro Leu Pro Thr Glu Asn Pro Arg Leu Glu Arg Pro Tyr Thr
    530                 535                 540

Phe Lys Asp Phe Val Leu His Pro Arg Ser His Lys Ser Arg Val Lys
545                 550                 555                 560

Gly Tyr Leu Arg Leu Lys Met Thr Tyr Leu Pro Lys Thr Ser Gly Ser
```

```
              565                 570                 575
Glu Asp Asn Ala Glu Gln Ala Glu Glu Leu Glu Pro Gly Trp Val
            580                 585                 590

Val Leu Asp Gln Pro Asp Ala Ala Cys His Leu Gln Gln Gln Gln
            595                 600                 605

Pro Ser Pro Leu Pro Pro Gly Trp Glu Glu Arg Gln Asp Ile Leu Gly
610                 615                 620

Arg Thr Tyr Tyr Val Asn His Glu Ser Arg Arg Thr Gln Trp Lys Arg
625                 630                 635                 640

Pro Thr Pro Gln Asp Asn Leu Thr Asp Ala Glu Asn Gly Asn Ile Gln
                645                 650                 655

Leu Gln Ala Gln Arg Ala Phe Thr Thr Arg Arg Gln Ile Ser Glu Glu
            660                 665                 670

Thr Glu Ser Val Asp Asn Arg Glu Ser Ser Glu Asn Trp Glu Ile Ile
            675                 680                 685

Arg Glu Asp Glu Ala Thr Met Tyr Ser Asn Gln Ala Phe Pro Ser Pro
            690                 695                 700

Pro Pro Ser Ser Asn Leu Asp Val Pro Thr His Leu Ala Glu Glu Leu
705                 710                 715                 720

Asn Ala Arg Leu Thr Ile Phe Gly Asn Ser Ala Val Ser Gln Pro Ala
                725                 730                 735

Ser Ser Ser Asn His Ser Ser Arg Arg Gly Ser Leu Gln Ala Tyr Thr
            740                 745                 750

Phe Glu Glu Gln Pro Thr Leu Pro Val Leu Leu Pro Thr Ser Ser Gly
            755                 760                 765

Leu Pro Pro Gly Trp Glu Glu Lys Gln Asp Glu Arg Gly Arg Ser Tyr
770                 775                 780

Tyr Val Asp His Asn Ser Arg Thr Thr Thr Trp Thr Lys Pro Thr Val
785                 790                 795                 800

Gln Ala Thr Val Glu Thr Ser Gln Leu Thr Ser Ser Gln Ser Ser Ala
                805                 810                 815

Gly Pro Gln Ser Gln Ala Ser Thr Ser Asp Ser Gly Gln Gln Val Thr
            820                 825                 830

Gln Pro Ser Glu Ile Glu Gln Gly Phe Leu Pro Lys Gly Trp Glu Val
            835                 840                 845

Arg His Ala Pro Asn Gly Arg Pro Phe Phe Ile Asp His Asn Thr Lys
850                 855                 860

Thr Thr Thr Trp Glu Asp Pro Arg Leu Lys Ile Pro Ala His Leu Arg
865                 870                 875                 880

Gly Lys Thr Ser Leu Asp Thr Ser Asn Asp Leu Gly Pro Leu Pro Pro
                885                 890                 895

Gly Trp Glu Glu Arg Thr His Thr Asp Gly Arg Ile Phe Tyr Ile Asn
            900                 905                 910

His Asn Ile Lys Arg Thr Gln Trp Glu Asp Pro Arg Leu Glu Asn Val
            915                 920                 925

Ala Ile Thr Gly Pro Ala Val Pro Tyr Ser Arg Asp Tyr Lys Arg Lys
930                 935                 940

Tyr Glu Phe Phe Arg Arg Lys Leu Lys Lys Gln Asn Asp Ile Pro Asn
945                 950                 955                 960

Lys Phe Glu Met Lys Leu Arg Arg Ala Thr Val Leu Glu Asp Ser Tyr
                965                 970                 975

Arg Arg Ile Met Gly Val Lys Arg Ala Asp Phe Leu Lys Ala Arg Leu
            980                 985                 990
```

Trp Ile Glu Phe Asp Gly Glu Lys Gly Leu Asp Tyr Gly Gly Val Ala
        995                 1000                1005

Arg Glu Trp Phe Phe Leu Ile Ser Lys Glu Met Phe Asn Pro Tyr
    1010                1015                1020

Tyr Gly Leu Phe Glu Tyr Ser Ala Thr Asp Asn Tyr Thr Leu Gln
    1025                1030                1035

Ile Asn Pro Asn Ser Gly Leu Cys Asn Glu Asp His Leu Ser Tyr
    1040                1045                1050

Phe Lys Phe Ile Gly Arg Val Ala Gly Met Ala Val Tyr His Gly
    1055                1060                1065

Lys Leu Leu Asp Gly Phe Phe Ile Arg Pro Phe Tyr Lys Met Met
    1070                1075                1080

Leu His Lys Pro Ile Thr Leu His Asp Met Glu Ser Val Asp Ser
    1085                1090                1095

Glu Tyr Tyr Asn Ser Leu Arg Trp Ile Leu Glu Asn Asp Pro Thr
    1100                1105                1110

Glu Leu Asp Leu Arg Phe Ile Ile Asp Glu Glu Leu Phe Gly Gln
    1115                1120                1125

Thr His Gln His Glu Leu Lys Asn Gly Gly Ser Glu Ile Val Val
    1130                1135                1140

Thr Asn Lys Asn Lys Lys Glu Tyr Ile Tyr Leu Val Ile Gln Trp
    1145                1150                1155

Arg Phe Val Asn Arg Ile Gln Lys Gln Met Ala Ala Phe Lys Glu
    1160                1165                1170

Gly Phe Phe Glu Leu Ile Pro Gln Asp Leu Ile Lys Ile Phe Asp
    1175                1180                1185

Glu Asn Glu Leu Glu Leu Leu Met Cys Gly Leu Gly Asp Val Asp
    1190                1195                1200

Val Asn Asp Trp Arg Glu His Thr Lys Tyr Lys Asn Gly Tyr Ser
    1205                1210                1215

Ala Asn His Gln Val Ile Gln Trp Phe Trp Lys Ala Val Leu Met
    1220                1225                1230

Met Asp Ser Glu Lys Arg Ile Arg Leu Leu Gln Phe Val Thr Gly
    1235                1240                1245

Thr Ser Arg Val Pro Met Asn Gly Phe Ala Glu Leu Tyr Gly Ser
    1250                1255                1260

Asn Gly Pro Gln Ser Phe Thr Val Glu Gln Trp Gly Thr Pro Glu
    1265                1270                1275

Lys Leu Pro Arg Ala His Thr Cys Phe Asn Arg Leu Asp Leu Pro
    1280                1285                1290

Pro Tyr Glu Ser Phe Glu Glu Leu Trp Asp Lys Leu Gln Met Ala
    1295                1300                1305

Ile Glu Asn Thr Gln Gly Phe Asp Gly Val Asp
    1310                1315

<210> SEQ ID NO 9
<211> LENGTH: 955
<212> TYPE: PRT
<213> ORGANISM: Homo sapiens

<400> SEQUENCE: 9

Met Ala Thr Gly Leu Gly Glu Pro Val Tyr Gly Leu Ser Glu Asp Glu
1               5                   10                  15

Gly Glu Ser Arg Ile Leu Arg Val Lys Val Val Ser Gly Ile Asp Leu

-continued

```
                20                  25                  30
Ala Lys Lys Asp Ile Phe Gly Ala Ser Asp Pro Tyr Val Lys Leu Ser
            35                  40                  45

Leu Tyr Val Ala Asp Glu Asn Arg Glu Leu Ala Leu Val Gln Thr Lys
        50                  55                  60

Thr Ile Lys Lys Thr Leu Asn Pro Lys Trp Asn Glu Glu Phe Tyr Phe
65                  70                  75                  80

Arg Val Asn Pro Ser Asn His Arg Leu Leu Phe Glu Val Phe Asp Glu
                85                  90                  95

Asn Arg Leu Thr Arg Asp Asp Phe Leu Gly Gln Val Asp Val Pro Leu
            100                 105                 110

Ser His Leu Pro Thr Glu Asp Pro Thr Met Glu Arg Pro Tyr Thr Phe
        115                 120                 125

Lys Asp Phe Leu Leu Arg Pro Arg Ser His Lys Ser Arg Val Lys Gly
    130                 135                 140

Phe Leu Arg Leu Lys Met Ala Tyr Met Pro Lys Asn Gly Gly Gln Asp
145                 150                 155                 160

Glu Glu Asn Ser Asp Gln Arg Asp Asp Met Glu His Gly Trp Glu Val
                165                 170                 175

Val Asp Ser Asn Asp Ser Ala Ser Gln His Gln Glu Glu Leu Pro Pro
            180                 185                 190

Pro Pro Leu Pro Pro Gly Trp Glu Glu Lys Val Asp Asn Leu Gly Arg
        195                 200                 205

Thr Tyr Tyr Val Asn His Asn Asn Arg Thr Thr Gln Trp His Arg Pro
    210                 215                 220

Ser Leu Met Asp Val Ser Ser Glu Ser Asp Asn Asn Ile Arg Gln Ile
225                 230                 235                 240

Asn Gln Glu Ala Ala His Arg Arg Phe Arg Ser Arg Arg His Ile Ser
                245                 250                 255

Glu Asp Leu Glu Pro Glu Pro Ser Glu Gly Gly Asp Val Pro Glu Pro
            260                 265                 270

Trp Glu Thr Ile Ser Glu Glu Val Asn Ile Ala Gly Asp Ser Leu Gly
        275                 280                 285

Leu Ala Leu Pro Pro Pro Pro Ala Ser Pro Gly Ser Arg Thr Ser Pro
    290                 295                 300

Gln Glu Leu Ser Glu Glu Leu Ser Arg Arg Leu Gln Ile Thr Pro Asp
305                 310                 315                 320

Ser Asn Gly Glu Gln Phe Ser Ser Leu Ile Gln Arg Glu Pro Ser Ser
                325                 330                 335

Arg Leu Arg Ser Cys Ser Val Thr Asp Ala Val Ala Glu Gln Gly His
            340                 345                 350

Leu Pro Pro Pro Ser Val Ala Tyr Val His Thr Thr Pro Gly Leu Pro
        355                 360                 365

Ser Gly Trp Glu Glu Arg Lys Asp Ala Lys Gly Arg Thr Tyr Tyr Val
    370                 375                 380

Asn His Asn Asn Arg Thr Thr Thr Trp Thr Arg Pro Ile Met Gln Leu
385                 390                 395                 400

Ala Glu Asp Gly Ala Ser Gly Ser Ala Thr Asn Ser Asn Asn His Leu
                405                 410                 415

Ile Glu Pro Gln Ile Arg Arg Pro Arg Ser Leu Ser Ser Pro Thr Val
            420                 425                 430

Thr Leu Ser Ala Pro Leu Glu Gly Ala Lys Asp Ser Pro Val Arg Arg
        435                 440                 445
```

```
Ala Val Lys Asp Thr Leu Ser Asn Pro Gln Ser Pro Gln Pro Ser Pro
            450                 455                 460
Tyr Asn Ser Pro Lys Pro Gln His Lys Val Thr Gln Ser Phe Leu Pro
465                 470                 475                 480
Pro Gly Trp Glu Met Arg Ile Ala Pro Asn Gly Arg Pro Phe Phe Ile
                485                 490                 495
Asp His Asn Thr Lys Thr Thr Thr Trp Glu Asp Pro Arg Leu Lys Phe
                500                 505                 510
Pro Val His Met Arg Ser Lys Thr Ser Leu Asn Pro Asn Asp Leu Gly
                515                 520                 525
Pro Leu Pro Pro Gly Trp Glu Glu Arg Ile His Leu Asp Gly Arg Thr
        530                 535                 540
Phe Tyr Ile Asp His Asn Ser Lys Ile Thr Gln Trp Glu Asp Pro Arg
545                 550                 555                 560
Leu Gln Asn Pro Ala Ile Thr Gly Pro Ala Val Pro Tyr Ser Arg Glu
                565                 570                 575
Phe Lys Gln Lys Tyr Asp Tyr Phe Arg Lys Lys Leu Lys Lys Pro Ala
                580                 585                 590
Asp Ile Pro Asn Arg Phe Glu Met Lys Leu His Arg Asn Asn Ile Phe
            595                 600                 605
Glu Glu Ser Tyr Arg Arg Ile Met Ser Val Lys Arg Pro Asp Val Leu
            610                 615                 620
Lys Ala Arg Leu Trp Ile Glu Phe Glu Ser Glu Lys Gly Leu Asp Tyr
625                 630                 635                 640
Gly Gly Val Ala Arg Glu Trp Phe Phe Leu Leu Ser Lys Glu Met Phe
                645                 650                 655
Asn Pro Tyr Tyr Gly Leu Phe Glu Tyr Ser Ala Thr Asp Asn Tyr Thr
            660                 665                 670
Leu Gln Ile Asn Pro Asn Ser Gly Leu Cys Asn Glu Asp His Leu Ser
            675                 680                 685
Tyr Phe Thr Phe Ile Gly Arg Val Ala Gly Leu Ala Val Phe His Gly
        690                 695                 700
Lys Leu Leu Asp Gly Phe Phe Ile Arg Pro Phe Tyr Lys Met Met Leu
705                 710                 715                 720
Gly Lys Gln Ile Thr Leu Asn Asp Met Glu Ser Val Asp Ser Glu Tyr
                725                 730                 735
Tyr Asn Ser Leu Lys Trp Ile Leu Glu Asn Asp Pro Thr Glu Leu Asp
                740                 745                 750
Leu Met Phe Cys Ile Asp Glu Glu Asn Phe Gly Gln Thr Tyr Gln Val
            755                 760                 765
Asp Leu Lys Pro Asn Gly Ser Glu Ile Met Val Thr Asn Glu Asn Lys
            770                 775                 780
Arg Glu Tyr Ile Asp Leu Val Ile Gln Trp Arg Phe Val Asn Arg Val
785                 790                 795                 800
Gln Lys Gln Met Asn Ala Phe Leu Glu Gly Phe Thr Glu Leu Leu Pro
                805                 810                 815
Ile Asp Leu Ile Lys Ile Phe Asp Glu Asn Glu Leu Glu Leu Leu Met
            820                 825                 830
Cys Gly Leu Gly Asp Val Asp Val Asn Asp Trp Arg Gln His Ser Ile
        835                 840                 845
Tyr Lys Asn Gly Tyr Cys Pro Asn His Pro Val Ile Gln Trp Phe Trp
850                 855                 860
```

```
Lys Ala Val Leu Leu Met Asp Ala Glu Lys Arg Ile Arg Leu Leu Gln
865                 870                 875                 880

Phe Val Thr Gly Thr Ser Arg Val Pro Met Asn Gly Phe Ala Glu Leu
                885                 890                 895

Tyr Gly Ser Asn Gly Pro Gln Leu Phe Thr Ile Glu Gln Trp Gly Ser
            900                 905                 910

Pro Glu Lys Leu Pro Arg Ala His Thr Cys Phe Asn Arg Leu Asp Leu
            915                 920                 925

Pro Pro Tyr Glu Thr Phe Glu Asp Leu Arg Glu Lys Leu Leu Met Ala
            930                 935                 940

Val Glu Asn Ala Gln Gly Phe Glu Gly Val Asp
945                 950                 955

<210> SEQ ID NO 10
<211> LENGTH: 757
<212> TYPE: PRT
<213> ORGANISM: Homo sapiens

<400> SEQUENCE: 10

Met Ser Asn Pro Gly Thr Arg Arg Asn Gly Ser Ser Ile Lys Ile Arg
1               5                   10                  15

Leu Thr Val Leu Cys Ala Lys Asn Leu Ala Lys Lys Asp Phe Phe Arg
                20                  25                  30

Leu Pro Asp Pro Phe Ala Lys Ile Val Val Asp Gly Ser Gly Gln Cys
            35                  40                  45

His Ser Thr Asp Thr Val Lys Asn Thr Leu Asp Pro Lys Trp Asn Gln
        50                  55                  60

His Tyr Asp Leu Tyr Val Gly Lys Thr Asp Ser Ile Thr Ile Ser Val
65                  70                  75                  80

Trp Asn His Lys Lys Ile His Lys Lys Gln Gly Ala Gly Phe Leu Gly
                85                  90                  95

Cys Val Arg Leu Leu Ser Asn Ala Ile Ser Arg Leu Lys Asp Thr Gly
                100                 105                 110

Tyr Gln Arg Leu Asp Leu Cys Lys Leu Asn Pro Ser Asp Thr Asp Ala
            115                 120                 125

Val Arg Gly Gln Ile Val Val Ser Leu Gln Thr Arg Asp Arg Ile Gly
130                 135                 140

Thr Gly Gly Ser Val Val Asp Cys Arg Gly Leu Leu Glu Asn Glu Gly
145                 150                 155                 160

Thr Val Tyr Glu Asp Ser Gly Pro Gly Arg Pro Leu Ser Cys Phe Met
                165                 170                 175

Glu Glu Pro Ala Pro Tyr Thr Asp Ser Thr Gly Ala Ala Ala Gly Gly
            180                 185                 190

Gly Asn Cys Arg Phe Val Glu Ser Pro Ser Gln Asp Gln Arg Leu Gln
            195                 200                 205

Ala Gln Arg Leu Arg Asn Pro Asp Val Arg Gly Ser Leu Gln Thr Pro
        210                 215                 220

Gln Asn Arg Pro His Gly His Gln Ser Pro Glu Leu Pro Glu Gly Tyr
225                 230                 235                 240

Glu Gln Arg Thr Thr Val Gln Gly Gln Val Tyr Phe Leu His Thr Gln
                245                 250                 255

Thr Gly Val Ser Thr Trp His Asp Pro Arg Ile Pro Ser Pro Ser Gly
            260                 265                 270

Thr Ile Pro Gly Gly Asp Ala Ala Phe Leu Tyr Glu Phe Leu Leu Gln
            275                 280                 285
```

```
Gly His Thr Ser Glu Pro Arg Asp Leu Asn Ser Val Asn Cys Asp Glu
    290                 295                 300

Leu Gly Pro Leu Pro Pro Gly Trp Glu Val Arg Ser Thr Val Ser Gly
305                 310                 315                 320

Arg Ile Tyr Phe Val Asp His Asn Asn Arg Thr Thr Gln Phe Thr Asp
                325                 330                 335

Pro Arg Leu His His Ile Met Asn His Gln Cys Gln Leu Lys Glu Pro
                340                 345                 350

Ser Gln Pro Leu Pro Leu Pro Ser Glu Gly Ser Leu Glu Asp Glu Glu
            355                 360                 365

Leu Pro Ala Gln Arg Tyr Glu Arg Asp Leu Val Gln Lys Leu Lys Val
370                 375                 380

Leu Arg His Glu Leu Ser Leu Gln Gln Pro Gln Ala Gly His Cys Arg
385                 390                 395                 400

Ile Glu Val Ser Arg Glu Glu Ile Phe Glu Glu Ser Tyr Arg Gln Ile
                405                 410                 415

Met Lys Met Arg Pro Lys Asp Leu Lys Lys Arg Leu Met Val Lys Phe
                420                 425                 430

Arg Gly Glu Glu Gly Leu Asp Tyr Gly Gly Val Ala Arg Glu Trp Leu
                435                 440                 445

Tyr Leu Leu Cys His Glu Met Leu Asn Pro Tyr Tyr Gly Leu Phe Gln
450                 455                 460

Tyr Ser Thr Asp Asn Ile Tyr Met Leu Gln Ile Asn Pro Asp Ser Ser
465                 470                 475                 480

Ile Asn Pro Asp His Leu Ser Tyr Phe His Phe Val Gly Arg Ile Met
                485                 490                 495

Gly Leu Ala Val Phe His Gly His Tyr Ile Asn Gly Gly Phe Thr Val
                500                 505                 510

Pro Phe Tyr Lys Gln Leu Leu Gly Lys Pro Ile Gln Leu Ser Asp Leu
                515                 520                 525

Glu Ser Val Asp Pro Glu Leu His Lys Ser Leu Val Trp Ile Leu Glu
            530                 535                 540

Asn Asp Ile Thr Pro Val Leu Asp His Thr Phe Cys Val Glu His Asn
545                 550                 555                 560

Ala Phe Gly Arg Ile Leu Gln His Glu Leu Lys Pro Asn Gly Arg Asn
                565                 570                 575

Val Pro Val Thr Glu Glu Asn Lys Lys Glu Tyr Val Arg Leu Tyr Val
                580                 585                 590

Asn Trp Arg Phe Met Arg Gly Ile Glu Ala Gln Phe Leu Ala Leu Gln
            595                 600                 605

Lys Gly Phe Asn Glu Leu Ile Pro Gln His Leu Leu Lys Pro Phe Asp
610                 615                 620

Gln Lys Glu Leu Glu Leu Ile Ile Gly Gly Leu Asp Lys Ile Asp Leu
625                 630                 635                 640

Asn Asp Trp Lys Ser Asn Thr Arg Leu Lys His Cys Val Ala Asp Ser
                645                 650                 655

Asn Ile Val Arg Trp Phe Trp Gln Ala Val Glu Thr Phe Asp Glu Glu
                660                 665                 670

Arg Arg Ala Arg Leu Leu Gln Phe Val Thr Gly Ser Thr Arg Val Pro
                675                 680                 685

Leu Gln Gly Phe Lys Ala Leu Gln Gly Ser Thr Gly Ala Ala Gly Pro
            690                 695                 700
```

```
Arg Leu Phe Thr Ile His Leu Ile Asp Ala Asn Thr Asp Asn Leu Pro
705                 710                 715                 720

Lys Ala His Thr Cys Phe Asn Arg Ile Asp Ile Pro Pro Tyr Glu Ser
            725                 730                 735

Tyr Glu Lys Leu Tyr Glu Lys Leu Leu Thr Ala Val Glu Glu Thr Cys
        740                 745                 750

Gly Phe Ala Val Glu
        755

<210> SEQ ID NO 11
<211> LENGTH: 748
<212> TYPE: PRT
<213> ORGANISM: Homo sapiens

<400> SEQUENCE: 11

Met Ser Asn Pro Gly Gly Arg Arg Asn Gly Pro Val Lys Leu Arg Leu
1               5                   10                  15

Thr Val Leu Cys Ala Lys Asn Leu Val Lys Lys Asp Phe Phe Arg Leu
                20                  25                  30

Pro Asp Pro Phe Ala Lys Val Val Val Asp Gly Ser Gly Gln Cys His
            35                  40                  45

Ser Thr Asp Thr Val Lys Asn Thr Leu Asp Pro Lys Trp Asn Gln His
    50                  55                  60

Tyr Asp Leu Tyr Ile Gly Lys Ser Asp Ser Val Thr Ile Ser Val Trp
65                  70                  75                  80

Asn His Lys Lys Ile His Lys Lys Gln Gly Ala Gly Phe Leu Gly Cys
                85                  90                  95

Val Arg Leu Leu Ser Asn Ala Ile Asn Arg Leu Lys Asp Thr Gly Tyr
                100                 105                 110

Gln Arg Leu Asp Leu Cys Lys Leu Gly Pro Asn Asp Asn Asp Thr Val
            115                 120                 125

Arg Gly Gln Ile Val Val Ser Leu Gln Ser Arg Asp Arg Ile Gly Thr
130                 135                 140

Gly Gly Gln Val Val Asp Cys Ser Arg Leu Phe Asp Asn Asp Leu Pro
145                 150                 155                 160

Asp Gly Trp Glu Glu Arg Arg Thr Ala Ser Gly Arg Ile Gln Tyr Leu
                165                 170                 175

Asn His Ile Thr Arg Thr Thr Gln Trp Glu Arg Pro Thr Arg Pro Ala
            180                 185                 190

Ser Glu Tyr Ser Ser Pro Gly Arg Pro Leu Ser Cys Phe Val Asp Glu
        195                 200                 205

Asn Thr Pro Ile Ser Gly Thr Asn Gly Ala Thr Cys Gly Gln Ser Ser
    210                 215                 220

Asp Pro Arg Leu Ala Glu Arg Arg Val Arg Ser Gln Arg His Arg Asn
225                 230                 235                 240

Tyr Met Ser Arg Thr His Leu His Thr Pro Asp Leu Pro Glu Gly
                245                 250                 255

Tyr Glu Gln Arg Thr Gln Gln Gly Gln Val Tyr Phe Leu His Thr
            260                 265                 270

Gln Thr Gly Val Ser Thr Trp His Asp Pro Arg Val Pro Arg Asp Leu
        275                 280                 285

Ser Asn Ile Asn Cys Glu Glu Leu Gly Pro Leu Pro Pro Gly Trp Glu
    290                 295                 300

Ile Arg Asn Thr Ala Thr Gly Arg Val Tyr Phe Val Asp His Asn Asn
305                 310                 315                 320
```

```
Arg Thr Thr Gln Phe Thr Asp Pro Arg Leu Ser Ala Asn Leu His Leu
            325                 330                 335

Val Leu Asn Arg Gln Asn Gln Leu Lys Asp Gln Gln Gln Gln Gln Val
            340                 345                 350

Val Ser Leu Cys Pro Asp Asp Thr Glu Cys Leu Thr Val Pro Arg Tyr
            355                 360                 365

Lys Arg Asp Leu Val Gln Lys Leu Lys Ile Leu Arg Gln Glu Leu Ser
            370                 375                 380

Gln Gln Gln Pro Gln Ala Gly His Cys Arg Ile Glu Val Ser Arg Glu
385                 390                 395                 400

Glu Ile Phe Glu Glu Ser Tyr Arg Gln Val Met Lys Met Arg Pro Lys
                405                 410                 415

Asp Leu Trp Lys Arg Leu Met Ile Lys Phe Arg Gly Glu Gly Leu
                420                 425                 430

Asp Tyr Gly Gly Val Ala Arg Glu Trp Leu Tyr Leu Leu Ser His Glu
                435                 440                 445

Met Leu Asn Pro Tyr Tyr Gly Leu Phe Gln Tyr Ser Arg Asp Asp Ile
    450                 455                 460

Tyr Thr Leu Gln Ile Asn Pro Asp Ser Ala Val Asn Pro Glu His Leu
465                 470                 475                 480

Ser Tyr Phe His Phe Val Gly Arg Ile Met Gly Met Ala Val Phe His
                485                 490                 495

Gly His Tyr Ile Asp Gly Gly Phe Thr Leu Pro Phe Tyr Lys Gln Leu
                500                 505                 510

Leu Gly Lys Ser Ile Thr Leu Asp Asp Met Glu Leu Val Asp Pro Asp
            515                 520                 525

Leu His Asn Ser Leu Val Trp Ile Leu Glu Asn Asp Ile Thr Gly Val
    530                 535                 540

Leu Asp His Thr Phe Cys Val Glu His Asn Ala Tyr Gly Glu Ile Ile
545                 550                 555                 560

Gln His Glu Leu Lys Pro Asn Gly Lys Ser Ile Pro Val Asn Glu Glu
            565                 570                 575

Asn Lys Lys Glu Tyr Val Arg Leu Tyr Val Asn Trp Arg Phe Leu Arg
            580                 585                 590

Gly Ile Glu Ala Gln Phe Leu Ala Leu Gln Lys Gly Phe Asn Glu Val
    595                 600                 605

Ile Pro Gln His Leu Leu Lys Thr Phe Asp Glu Lys Glu Leu Glu Leu
    610                 615                 620

Ile Ile Cys Gly Leu Gly Lys Ile Asp Val Asn Asp Trp Lys Val Asn
625                 630                 635                 640

Thr Arg Leu Lys His Cys Thr Pro Asp Ser Asn Ile Val Lys Trp Phe
                645                 650                 655

Trp Lys Ala Val Glu Phe Phe Asp Glu Glu Arg Arg Ala Arg Leu Leu
            660                 665                 670

Gln Phe Val Thr Gly Ser Ser Arg Val Pro Leu Gln Gly Phe Lys Ala
        675                 680                 685

Leu Gln Gly Ala Ala Gly Pro Arg Leu Phe Thr Ile His Gln Ile Asp
    690                 695                 700

Ala Cys Thr Asn Asn Leu Pro Lys Ala His Thr Cys Phe Asn Arg Ile
705                 710                 715                 720

Asp Ile Pro Pro Tyr Glu Ser Tyr Glu Lys Leu Tyr Glu Lys Leu Leu
                725                 730                 735
```

```
Thr Ala Ile Glu Glu Thr Cys Gly Phe Ala Val Glu
            740                 745

<210> SEQ ID NO 12
<211> LENGTH: 903
<212> TYPE: PRT
<213> ORGANISM: Homo sapiens

<400> SEQUENCE: 12

Met Ser Asp Ser Gly Ser Gln Leu Gly Ser Met Gly Ser Leu Thr Met
1               5                   10                  15

Lys Ser Gln Leu Gln Ile Thr Val Ile Ser Ala Lys Leu Lys Glu Asn
                20                  25                  30

Lys Lys Asn Trp Phe Gly Pro Ser Pro Tyr Val Glu Val Thr Val Asp
            35                  40                  45

Gly Gln Ser Lys Lys Thr Glu Lys Cys Asn Asn Thr Asn Ser Pro Lys
        50                  55                  60

Trp Lys Gln Pro Leu Thr Val Ile Val Thr Pro Val Ser Lys Leu His
65                  70                  75                  80

Phe Arg Val Trp Ser His Gln Thr Leu Lys Ser Asp Val Leu Leu Gly
                85                  90                  95

Thr Ala Ala Leu Asp Ile Tyr Glu Thr Leu Lys Ser Asn Asn Met Lys
                100                 105                 110

Leu Glu Glu Val Val Val Thr Leu Gln Leu Gly Gly Asp Lys Glu Pro
            115                 120                 125

Thr Glu Thr Ile Gly Asp Leu Ser Ile Cys Leu Asp Gly Leu Gln Leu
        130                 135                 140

Glu Ser Glu Val Val Thr Asn Gly Glu Thr Thr Cys Ser Glu Asn Gly
145                 150                 155                 160

Val Ser Leu Cys Leu Pro Arg Leu Glu Cys Asn Ser Ala Ile Ser Ala
                165                 170                 175

His Cys Asn Leu Cys Leu Pro Gly Leu Ser Asp Ser Pro Ile Ser Ala
                180                 185                 190

Ser Arg Val Ala Gly Phe Thr Gly Ala Ser Gln Asn Asp Asp Gly Ser
            195                 200                 205

Arg Ser Lys Asp Glu Thr Arg Val Ser Thr Asn Gly Ser Asp Asp Pro
        210                 215                 220

Glu Asp Ala Gly Ala Gly Glu Asn Arg Arg Val Ser Gly Asn Asn Ser
225                 230                 235                 240

Pro Ser Leu Ser Asn Gly Gly Phe Lys Pro Ser Arg Pro Pro Arg Pro
                245                 250                 255

Ser Arg Pro Pro Pro Thr Pro Arg Arg Pro Ala Ser Val Asn Gly
                260                 265                 270

Ser Pro Ser Ala Thr Ser Glu Ser Asp Gly Ser Ser Thr Gly Ser Leu
            275                 280                 285

Pro Pro Thr Asn Thr Asn Thr Asn Thr Ser Glu Gly Ala Thr Ser Gly
        290                 295                 300

Leu Ile Ile Pro Leu Thr Ile Ser Gly Gly Ser Gly Pro Arg Pro Leu
305                 310                 315                 320

Asn Pro Val Thr Gln Ala Pro Leu Pro Pro Gly Trp Glu Gln Arg Val
                325                 330                 335

Asp Gln His Gly Arg Val Tyr Tyr Val Asp His Val Glu Lys Arg Thr
                340                 345                 350

Thr Trp Asp Arg Pro Glu Pro Leu Pro Pro Gly Trp Glu Arg Arg Val
            355                 360                 365
```

```
Asp Asn Met Gly Arg Ile Tyr Tyr Val Asp His Phe Thr Arg Thr
    370                 375                 380

Thr Trp Gln Arg Pro Thr Leu Glu Ser Val Arg Asn Tyr Glu Gln Trp
385                 390                 395                 400

Gln Leu Gln Arg Ser Gln Leu Gln Gly Ala Met Gln Gln Phe Asn Gln
                405                 410                 415

Arg Phe Ile Tyr Gly Asn Gln Asp Leu Phe Ala Thr Ser Gln Ser Lys
            420                 425                 430

Glu Phe Asp Pro Leu Gly Pro Leu Pro Pro Gly Trp Glu Lys Arg Thr
        435                 440                 445

Asp Ser Asn Gly Arg Val Tyr Phe Val Asn His Asn Thr Arg Ile Thr
    450                 455                 460

Gln Trp Glu Asp Pro Arg Ser Gln Gly Gln Leu Asn Glu Lys Pro Leu
465                 470                 475                 480

Pro Glu Gly Trp Glu Met Arg Phe Thr Val Asp Gly Ile Pro Tyr Phe
                485                 490                 495

Val Asp His Asn Arg Arg Thr Thr Thr Tyr Ile Asp Pro Arg Thr Gly
            500                 505                 510

Lys Ser Ala Leu Asp Asn Gly Pro Gln Ile Ala Tyr Val Arg Asp Phe
        515                 520                 525

Lys Ala Lys Val Gln Tyr Phe Arg Phe Trp Cys Gln Gln Leu Ala Met
    530                 535                 540

Pro Gln His Ile Lys Ile Thr Val Thr Arg Lys Thr Leu Phe Glu Asp
545                 550                 555                 560

Ser Phe Gln Gln Ile Met Ser Phe Ser Pro Gln Asp Leu Arg Arg Arg
                565                 570                 575

Leu Trp Val Ile Phe Pro Gly Glu Gly Leu Asp Tyr Gly Gly Val
            580                 585                 590

Ala Arg Glu Trp Phe Phe Leu Leu Ser His Glu Val Leu Asn Pro Met
        595                 600                 605

Tyr Cys Leu Phe Glu Tyr Ala Gly Lys Asp Asn Tyr Cys Leu Gln Ile
    610                 615                 620

Asn Pro Ala Ser Tyr Ile Asn Pro Asp His Leu Lys Tyr Phe Arg Phe
625                 630                 635                 640

Ile Gly Arg Phe Ile Ala Met Ala Leu Phe His Gly Lys Phe Ile Asp
                645                 650                 655

Thr Gly Phe Ser Leu Pro Phe Tyr Lys Arg Ile Leu Asn Lys Pro Val
            660                 665                 670

Gly Leu Lys Asp Leu Glu Ser Ile Asp Pro Glu Phe Tyr Asn Ser Leu
        675                 680                 685

Ile Trp Val Lys Glu Asn Asn Ile Glu Glu Cys Asp Leu Glu Met Tyr
    690                 695                 700

Phe Ser Val Asp Lys Glu Ile Leu Gly Glu Ile Lys Ser His Asp Leu
705                 710                 715                 720

Lys Pro Asn Gly Gly Asn Ile Leu Val Thr Glu Asn Lys Glu Glu
                725                 730                 735

Tyr Ile Arg Met Val Ala Glu Trp Arg Leu Ser Arg Gly Val Glu Glu
            740                 745                 750

Gln Thr Gln Ala Phe Phe Glu Gly Phe Asn Glu Ile Leu Pro Gln Gln
        755                 760                 765

Tyr Leu Gln Tyr Phe Asp Ala Lys Glu Leu Glu Val Leu Leu Cys Gly
    770                 775                 780
```

```
Met Gln Glu Ile Asp Leu Asn Asp Trp Gln Arg His Ala Ile Tyr Arg
785                 790                 795                 800

His Tyr Ala Arg Thr Ser Lys Gln Ile Met Trp Phe Trp Gln Phe Val
            805                 810                 815

Lys Glu Ile Asp Asn Glu Lys Arg Met Arg Leu Leu Gln Phe Val Thr
        820                 825                 830

Gly Thr Cys Arg Leu Pro Val Gly Phe Ala Asp Leu Met Gly Ser
        835                 840                 845

Asn Gly Pro Gln Lys Phe Cys Ile Glu Lys Val Gly Lys Glu Asn Trp
    850                 855                 860

Leu Pro Arg Ser His Thr Cys Phe Asn Arg Leu Asp Leu Pro Pro Tyr
865                 870                 875                 880

Lys Ser Tyr Glu Gln Leu Lys Glu Lys Leu Leu Phe Ala Ile Glu Glu
                885                 890                 895

Thr Glu Gly Phe Gly Gln Glu
                900

<210> SEQ ID NO 13
<211> LENGTH: 1606
<212> TYPE: PRT
<213> ORGANISM: Homo sapiens

<400> SEQUENCE: 13

Met Leu Leu His Leu Cys Ser Val Lys Asn Leu Tyr Gln Asn Arg Phe
1               5                   10                  15

Leu Gly Leu Ala Ala Met Ala Ser Pro Ser Arg Asn Ser Gln Ser Arg
            20                  25                  30

Arg Arg Cys Lys Glu Pro Leu Arg Tyr Ser Tyr Asn Pro Asp Gln Phe
        35                  40                  45

His Asn Met Asp Leu Arg Gly Gly Pro His Asp Gly Val Thr Ile Pro
    50                  55                  60

Arg Ser Thr Ser Asp Thr Asp Leu Val Thr Ser Asp Ser Arg Ser Thr
65                  70                  75                  80

Leu Met Val Ser Ser Tyr Tyr Ser Ile Gly His Ser Gln Asp Leu
                85                  90                  95

Val Ile His Trp Asp Ile Lys Glu Glu Val Asp Ala Gly Asp Trp Ile
            100                 105                 110

Gly Met Tyr Leu Ile Asp Glu Val Leu Ser Glu Asn Phe Leu Asp Tyr
        115                 120                 125

Lys Asn Arg Gly Val Asn Gly Ser His Arg Gly Gln Ile Ile Trp Lys
    130                 135                 140

Ile Asp Ala Ser Ser Tyr Phe Val Glu Pro Glu Thr Lys Ile Cys Phe
145                 150                 155                 160

Lys Tyr Tyr His Gly Val Ser Gly Ala Leu Arg Ala Thr Thr Pro Ser
                165                 170                 175

Val Thr Val Lys Asn Ser Ala Ala Pro Ile Phe Lys Ser Ile Gly Ala
            180                 185                 190

Asp Glu Thr Val Gln Gly Gln Gly Ser Arg Arg Leu Ile Ser Phe Ser
        195                 200                 205

Leu Ser Asp Phe Gln Ala Met Gly Leu Lys Lys Gly Met Phe Phe Asn
    210                 215                 220

Pro Asp Pro Tyr Leu Lys Ile Ser Ile Gln Pro Gly Lys His Ser Ile
225                 230                 235                 240

Phe Pro Ala Leu Pro His His Gly Gln Glu Arg Arg Ser Lys Ile Ile
                245                 250                 255
```

```
Gly Asn Thr Val Asn Pro Ile Trp Gln Ala Glu Gln Phe Ser Phe Val
            260                 265                 270

Ser Leu Pro Thr Asp Val Leu Glu Ile Glu Val Lys Asp Lys Phe Ala
        275                 280                 285

Lys Ser Arg Pro Ile Ile Lys Arg Phe Leu Gly Lys Leu Ser Met Pro
    290                 295                 300

Val Gln Arg Leu Leu Glu Arg His Ala Ile Gly Asp Arg Val Val Ser
305                 310                 315                 320

Tyr Thr Leu Gly Arg Arg Leu Pro Thr Asp His Val Ser Gly Gln Leu
                325                 330                 335

Gln Phe Arg Phe Glu Ile Thr Ser Ser Ile His Pro Asp Asp Glu Glu
            340                 345                 350

Ile Ser Leu Ser Thr Glu Pro Glu Ser Ala Gln Ile Gln Asp Ser Pro
        355                 360                 365

Met Asn Asn Leu Met Glu Ser Gly Ser Gly Glu Pro Arg Ser Glu Ala
    370                 375                 380

Pro Glu Ser Ser Glu Ser Trp Lys Pro Glu Gln Leu Gly Glu Gly Ser
385                 390                 395                 400

Val Pro Asp Gly Pro Gly Asn Gln Ser Ile Glu Leu Ser Arg Pro Ala
                405                 410                 415

Glu Glu Ala Ala Val Ile Thr Glu Ala Gly Asp Gln Gly Met Val Ser
            420                 425                 430

Val Gly Pro Glu Gly Ala Gly Glu Leu Leu Ala Gln Val Gln Lys Asp
        435                 440                 445

Ile Gln Pro Ala Pro Ser Ala Glu Glu Leu Ala Glu Gln Leu Asp Leu
    450                 455                 460

Gly Glu Glu Ala Ser Ala Leu Leu Leu Glu Asp Gly Glu Ala Pro Ala
465                 470                 475                 480

Ser Thr Lys Glu Glu Pro Leu Glu Glu Glu Ala Thr Thr Gln Ser Arg
                485                 490                 495

Ala Gly Arg Glu Glu Glu Lys Glu Gln Glu Glu Glu Gly Asp Val
            500                 505                 510

Ser Thr Leu Glu Gln Gly Glu Gly Arg Leu Gln Leu Arg Ala Ser Val
        515                 520                 525

Lys Arg Lys Ser Arg Pro Cys Ser Leu Pro Val Ser Glu Leu Glu Thr
    530                 535                 540

Val Ile Ala Ser Ala Cys Gly Asp Pro Glu Thr Pro Arg Thr His Tyr
545                 550                 555                 560

Ile Arg Ile His Thr Leu Leu His Ser Met Pro Ser Ala Gln Gly Gly
                565                 570                 575

Ser Ala Ala Glu Glu Glu Asp Gly Ala Glu Glu Glu Ser Thr Leu Lys
            580                 585                 590

Asp Ser Ser Glu Lys Asp Gly Leu Ser Glu Val Asp Thr Val Ala Ala
        595                 600                 605

Asp Pro Ser Ala Leu Glu Glu Asp Arg Glu Glu Pro Glu Gly Ala Thr
    610                 615                 620

Pro Gly Thr Ala His Pro Gly His Ser Gly Gly His Phe Pro Ser Leu
625                 630                 635                 640

Ala Asn Gly Ala Ala Gln Asp Gly Asp Thr His Pro Ser Thr Gly Ser
                645                 650                 655

Glu Ser Asp Ser Ser Pro Arg Gln Gly Gly Asp His Ser Cys Glu Gly
            660                 665                 670
```

```
Cys Asp Ala Ser Cys Cys Ser Pro Ser Cys Tyr Ser Ser Cys Tyr
            675                 680                 685
Ser Thr Ser Cys Tyr Ser Ser Cys Tyr Ser Ala Ser Cys Tyr Ser
        690                 695                 700
Pro Ser Cys Tyr Asn Gly Asn Arg Phe Ala Ser His Thr Arg Phe Ser
705                 710                 715                 720
Ser Val Asp Ser Ala Lys Ile Ser Glu Ser Thr Val Phe Ser Gln
                725                 730                 735
Asp Asp Glu Glu Glu Asn Ser Ala Phe Glu Ser Val Pro Asp Ser
            740                 745                 750
Met Gln Ser Pro Glu Leu Asp Pro Glu Ser Thr Asn Gly Ala Gly Pro
        755                 760                 765
Trp Gln Asp Glu Leu Ala Ala Pro Ser Gly His Val Glu Arg Ser Pro
        770                 775                 780
Glu Gly Leu Glu Ser Pro Val Ala Gly Pro Ser Asn Arg Arg Glu Gly
785                 790                 795                 800
Glu Cys Pro Ile Leu His Asn Ser Gln Pro Val Ser Gln Leu Pro Ser
                805                 810                 815
Leu Arg Pro Glu His His His Tyr Pro Thr Ile Asp Glu Pro Leu Pro
            820                 825                 830
Pro Asn Trp Glu Ala Arg Ile Asp Ser His Gly Arg Val Phe Tyr Val
        835                 840                 845
Asp His Val Asn Arg Thr Thr Thr Trp Gln Arg Pro Thr Ala Ala Ala
        850                 855                 860
Thr Pro Asp Gly Met Arg Arg Ser Gly Ser Ile Gln Gln Met Glu Gln
865                 870                 875                 880
Leu Asn Arg Arg Tyr Gln Asn Ile Gln Arg Thr Ile Ala Thr Glu Arg
                885                 890                 895
Ser Glu Glu Asp Ser Gly Ser Gln Ser Cys Glu Gln Ala Pro Ala Gly
            900                 905                 910
Gly Gly Gly Gly Gly Ser Asp Ser Glu Ala Glu Ser Ser Gln Ser
        915                 920                 925
Ser Leu Asp Leu Arg Arg Glu Gly Ser Leu Ser Pro Val Asn Ser Gln
930                 935                 940
Lys Ile Thr Leu Leu Leu Gln Ser Pro Ala Val Lys Phe Ile Thr Asn
945                 950                 955                 960
Pro Glu Phe Phe Thr Val Leu His Ala Asn Tyr Ser Ala Tyr Arg Val
                965                 970                 975
Phe Thr Ser Ser Thr Cys Leu Lys His Met Ile Leu Lys Val Arg Arg
            980                 985                 990
Asp Ala Arg Asn Phe Glu Arg Tyr  Gln His Asn Arg  Asp Leu Val Asn
        995                 1000                1005
Phe Ile Asn Met Phe Ala Asp  Thr Arg Leu Glu Leu  Pro Arg Gly
        1010                1015                1020
Trp Glu Ile Lys Thr Asp Gln  Gln Gly Lys Ser Phe  Phe Val Asp
        1025                1030                1035
His Asn Ser Arg Ala Thr Thr  Phe Ile Asp Pro Arg  Ile Pro Leu
        1040                1045                1050
Gln Asn Gly Arg Leu Pro Asn  His Leu Thr His Arg  Gln His Leu
        1055                1060                1065
Gln Arg Leu Arg Ser Tyr Ser  Ala Gly Glu Ala Ser  Glu Val Ser
        1070                1075                1080
Arg Asn Arg Gly Ala Ser Leu  Leu Ala Arg Pro Gly  His Ser Leu
```

```
            1085                1090                1095

Val Ala Ala Ile Arg Ser Gln His Gln His Glu Ser Leu Pro Leu
            1100                1105                1110

Ala Tyr Asn Asp Lys Ile Val Ala Phe Leu Arg Gln Pro Asn Ile
            1115                1120                1125

Phe Glu Met Leu Gln Glu Arg Gln Pro Ser Leu Ala Arg Asn His
            1130                1135                1140

Thr Leu Arg Glu Lys Ile His Tyr Ile Arg Thr Glu Gly Asn His
            1145                1150                1155

Gly Leu Glu Lys Leu Ser Cys Asp Ala Asp Leu Val Ile Leu Leu
            1160                1165                1170

Ser Leu Phe Glu Glu Glu Ile Met Ser Tyr Val Pro Leu Gln Ala
            1175                1180                1185

Ala Phe His Pro Gly Tyr Ser Phe Ser Pro Arg Cys Ser Pro Cys
            1190                1195                1200

Ser Ser Pro Gln Asn Ser Pro Gly Leu Gln Arg Ala Ser Ala Arg
            1205                1210                1215

Ala Pro Ser Pro Tyr Arg Arg Asp Phe Glu Ala Lys Leu Arg Asn
            1220                1225                1230

Phe Tyr Arg Lys Leu Glu Ala Lys Gly Phe Gly Gln Gly Pro Gly
            1235                1240                1245

Lys Ile Lys Leu Ile Ile Arg Arg Asp His Leu Leu Glu Gly Thr
            1250                1255                1260

Phe Asn Gln Val Met Ala Tyr Ser Arg Lys Glu Leu Gln Arg Asn
            1265                1270                1275

Lys Leu Tyr Val Thr Phe Val Gly Glu Gly Leu Asp Tyr Ser
            1280                1285                1290

Gly Pro Ser Arg Glu Phe Phe Phe Leu Leu Ser Gln Glu Leu Phe
            1295                1300                1305

Asn Pro Tyr Tyr Gly Leu Phe Glu Tyr Ser Ala Asn Asp Thr Tyr
            1310                1315                1320

Thr Val Gln Ile Ser Pro Met Ser Ala Phe Val Glu Asn His Leu
            1325                1330                1335

Glu Trp Phe Arg Phe Ser Gly Arg Ile Leu Gly Leu Ala Leu Ile
            1340                1345                1350

His Gln Tyr Leu Leu Asp Ala Phe Phe Thr Arg Pro Phe Tyr Lys
            1355                1360                1365

Ala Leu Leu Arg Leu Pro Cys Asp Leu Ser Asp Leu Glu Tyr Leu
            1370                1375                1380

Asp Glu Glu Phe His Gln Ser Leu Gln Trp Met Lys Asp Asn Asn
            1385                1390                1395

Ile Thr Asp Ile Leu Asp Leu Thr Phe Thr Val Asn Glu Glu Val
            1400                1405                1410

Phe Gly Gln Val Thr Glu Arg Glu Leu Lys Ser Gly Gly Ala Asn
            1415                1420                1425

Thr Gln Val Thr Glu Lys Asn Lys Lys Glu Tyr Ile Glu Arg Met
            1430                1435                1440

Val Lys Trp Arg Val Glu Arg Gly Val Val Gln Gln Thr Glu Ala
            1445                1450                1455

Leu Val Arg Gly Phe Tyr Glu Val Val Asp Ser Arg Leu Val Ser
            1460                1465                1470

Val Phe Asp Ala Arg Glu Leu Glu Leu Val Ile Ala Gly Thr Ala
            1475                1480                1485
```

```
Glu Ile Asp Leu Asn Asp Trp Arg Asn Thr Glu Tyr Arg Gly
    1490                1495                1500

Gly Tyr His Asp Gly His Leu Val Ile Arg Trp Phe Trp Ala Ala
1505                1510                1515

Val Glu Arg Phe Asn Asn Glu Gln Arg Leu Arg Leu Leu Gln Phe
    1520                1525                1530

Val Thr Gly Thr Ser Ser Val Pro Tyr Glu Gly Phe Ala Ala Leu
    1535                1540                1545

Arg Gly Ser Asn Gly Leu Arg Arg Phe Cys Ile Glu Lys Trp Gly
    1550                1555                1560

Lys Ile Thr Ser Leu Pro Arg Ala His Thr Cys Phe Asn Arg Leu
    1565                1570                1575

Asp Leu Pro Pro Tyr Pro Ser Tyr Ser Met Leu Tyr Glu Lys Leu
    1580                1585                1590

Leu Thr Ala Val Glu Glu Thr Ser Thr Phe Gly Leu Glu
    1595                1600                1605

<210> SEQ ID NO 14
<211> LENGTH: 1572
<212> TYPE: PRT
<213> ORGANISM: Homo sapiens

<400> SEQUENCE: 14

Met Ala Ser Ser Ala Arg Glu His Leu Leu Phe Val Arg Arg Arg Asn
1               5                   10                  15

Pro Gln Met Arg Tyr Thr Leu Ser Pro Glu Asn Leu Gln Ser Leu Ala
            20                  25                  30

Ala Gln Ser Ser Met Pro Glu Asn Met Thr Leu Gln Arg Ala Asn Ser
        35                  40                  45

Asp Thr Asp Leu Val Thr Ser Glu Ser Arg Ser Ser Leu Thr Ala Ser
    50                  55                  60

Met Tyr Glu Tyr Thr Leu Gly Gln Ala Gln Asn Leu Ile Ile Phe Trp
65                  70                  75                  80

Asp Ile Lys Glu Glu Val Asp Pro Ser Asp Trp Ile Gly Leu Tyr His
                85                  90                  95

Ile Asp Glu Asn Ser Pro Ala Asn Phe Trp Asp Ser Lys Asn Arg Gly
            100                 105                 110

Val Thr Gly Thr Gln Lys Gly Gln Ile Val Trp Arg Ile Glu Pro Gly
        115                 120                 125

Pro Tyr Phe Met Glu Pro Glu Ile Lys Ile Cys Phe Lys Tyr Tyr His
    130                 135                 140

Gly Ile Ser Gly Ala Leu Arg Ala Thr Thr Pro Cys Ile Thr Val Lys
145                 150                 155                 160

Asn Pro Ala Val Met Met Gly Ala Glu Gly Met Glu Gly Gly Ala Ser
                165                 170                 175

Gly Asn Leu His Ser Arg Lys Leu Val Ser Phe Thr Leu Ser Asp Leu
            180                 185                 190

Arg Ala Val Gly Leu Lys Lys Gly Met Phe Phe Asn Pro Asp Pro Tyr
        195                 200                 205

Leu Lys Met Ser Ile Gln Pro Gly Lys Lys Ser Ser Phe Pro Thr Cys
    210                 215                 220

Ala His His Gly Gln Glu Arg Arg Ser Thr Ile Ile Ser Asn Thr Thr
225                 230                 235                 240

Asn Pro Ile Trp His Arg Glu Lys Tyr Ser Phe Phe Ala Leu Leu Thr
```

-continued

```
                245                 250                 255
Asp Val Leu Glu Ile Glu Ile Lys Asp Lys Phe Ala Lys Ser Arg Pro
                260                 265                 270
Ile Ile Lys Arg Phe Leu Gly Lys Leu Thr Ile Pro Val Gln Arg Leu
                275                 280                 285
Leu Glu Arg Gln Ala Ile Gly Asp Gln Met Leu Ser Tyr Asn Leu Gly
                290                 295                 300
Arg Arg Leu Pro Ala Asp His Val Ser Gly Tyr Leu Gln Phe Lys Val
305                 310                 315                 320
Glu Val Thr Ser Ser Val His Glu Asp Ala Ser Pro Glu Ala Val Gly
                325                 330                 335
Thr Ile Leu Gly Val Asn Ser Val Asn Gly Asp Leu Gly Ser Pro Ser
                340                 345                 350
Asp Asp Glu Asp Met Pro Gly Ser His His Asp Ser Gln Val Cys Ser
                355                 360                 365
Asn Gly Pro Val Ser Glu Asp Ser Ala Ala Asp Gly Thr Pro Lys His
                370                 375                 380
Ser Phe Arg Thr Ser Ser Thr Leu Glu Ile Asp Thr Glu Glu Leu Thr
385                 390                 395                 400
Ser Thr Ser Ser Arg Thr Ser Pro Pro Arg Gly Arg Gln Asp Ser Leu
                405                 410                 415
Asn Asp Tyr Leu Asp Ala Ile Glu His Asn Gly His Ser Arg Pro Gly
                420                 425                 430
Thr Ala Thr Cys Ser Glu Arg Ser Met Gly Ala Ser Pro Lys Leu Arg
                435                 440                 445
Ser Ser Phe Pro Thr Asp Thr Arg Leu Asn Ala Met Leu His Ile Asp
450                 455                 460
Ser Asp Glu Glu Asp His Glu Phe Gln Gln Asp Leu Gly Tyr Pro Ser
465                 470                 475                 480
Ser Leu Glu Glu Glu Gly Gly Leu Ile Met Phe Ser Arg Ala Ser Arg
                485                 490                 495
Ala Asp Asp Gly Ser Leu Thr Ser Gln Thr Lys Leu Glu Asp Asn Pro
                500                 505                 510
Val Glu Asn Glu Glu Ala Ser Thr His Glu Ala Ala Ser Phe Glu Asp
                515                 520                 525
Lys Pro Glu Asn Leu Pro Glu Leu Ala Glu Ser Ser Leu Pro Ala Gly
                530                 535                 540
Pro Ala Pro Glu Glu Gly Glu Gly Pro Glu Pro Gln Pro Ser Ala
545                 550                 555                 560
Asp Gln Gly Ser Ala Glu Leu Cys Gly Ser Gln Glu Val Asp Gln Pro
                565                 570                 575
Thr Ser Gly Ala Asp Thr Gly Thr Ser Asp Ala Ser Gly Gly Ser Arg
                580                 585                 590
Arg Ala Val Ser Glu Thr Glu Ser Leu Asp Gln Gly Ser Glu Pro Ser
                595                 600                 605
Gln Val Ser Ser Glu Thr Glu Pro Ser Asp Pro Ala Arg Thr Glu Ser
                610                 615                 620
Val Ser Glu Ala Ser Thr Arg Pro Glu Gly Glu Ser Asp Leu Glu Cys
625                 630                 635                 640
Ala Asp Ser Ser Cys Asn Glu Ser Val Thr Thr Gln Leu Ser Ser Val
                645                 650                 655
Asp Thr Arg Cys Ser Ser Leu Glu Ser Ala Arg Phe Pro Glu Thr Pro
                660                 665                 670
```

```
Ala Phe Ser Ser Gln Glu Glu Asp Gly Ala Cys Ala Ala Glu Pro
            675                 680                 685

Thr Ser Ser Gly Pro Ala Glu Gly Ser Gln Glu Ser Val Cys Thr Ala
690             695                 700

Gly Ser Leu Pro Val Val Gln Val Pro Ser Gly Glu Asp Glu Gly Pro
705                 710                 715                 720

Gly Ala Glu Ser Ala Thr Val Pro Asp Gln Glu Glu Leu Gly Glu Val
                725                 730                 735

Trp Gln Arg Arg Gly Ser Leu Glu Gly Ala Ala Ala Ala Glu Ser
            740                 745                 750

Pro Pro Gln Glu Glu Gly Ser Ala Gly Glu Ala Gln Gly Thr Cys Glu
            755                 760                 765

Gly Ala Thr Ala Gln Glu Glu Gly Ala Thr Gly Gly Ser Gln Ala Asn
770                 775                 780

Gly His Gln Pro Leu Arg Ser Leu Pro Ser Val Arg Gln Asp Val Ser
785                 790                 795                 800

Arg Tyr Gln Arg Val Asp Glu Ala Leu Pro Pro Asn Trp Glu Ala Arg
                805                 810                 815

Ile Asp Ser His Gly Arg Ile Phe Tyr Val Asp His Val Asn Arg Thr
            820                 825                 830

Thr Thr Trp Gln Arg Pro Thr Ala Pro Pro Ala Pro Gln Val Leu Gln
        835                 840                 845

Arg Ser Asn Ser Ile Gln Gln Met Glu Gln Leu Asn Arg Arg Tyr Gln
850                 855                 860

Ser Ile Arg Arg Thr Met Thr Asn Glu Arg Pro Glu Glu Asn Thr Asn
865                 870                 875                 880

Ala Ile Asp Gly Ala Gly Glu Glu Ala Asp Phe His Gln Ala Ser Ala
                885                 890                 895

Asp Phe Arg Arg Glu Asn Ile Leu Pro His Ser Thr Arg Ser Arg
            900                 905                 910

Ile Thr Leu Leu Leu Gln Ser Pro Pro Val Lys Phe Leu Ile Ser Pro
            915                 920                 925

Glu Phe Phe Thr Val Leu His Ser Asn Pro Ser Ala Tyr Arg Met Phe
            930                 935                 940

Thr Asn Asn Thr Cys Leu Lys His Met Ile Thr Lys Val Arg Arg Asp
945                 950                 955                 960

Thr His His Phe Glu Arg Tyr Gln His Asn Arg Asp Leu Val Gly Phe
                965                 970                 975

Leu Asn Met Phe Ala Asn Lys Gln Leu Glu Leu Pro Arg Gly Trp Glu
            980                 985                 990

Met Lys His Asp His Gln Gly Lys Ala Phe Phe Val Asp His Asn Ser
            995                 1000                1005

Arg Thr Thr Thr Phe Ile Asp Pro Arg Leu Pro Leu Gln Ser Ser
      1010                1015                1020

Arg Pro Thr Ser Ala Leu Val His Arg Gln His Leu Thr Arg Gln
      1025                1030                1035

Arg Ser His Ser Ala Gly Glu Val Gly Glu Asp Ser Arg His Ala
      1040                1045                1050

Gly Pro Pro Val Leu Pro Arg Pro Ser Ser Thr Phe Asn Thr Val
      1055                1060                1065

Ser Arg Pro Gln Tyr Gln Asp Met Val Pro Val Ala Tyr Asn Asp
      1070                1075                1080
```

-continued

```
Lys Ile Val Ala Phe Leu Arg Gln Pro Asn Ile Phe Glu Ile Leu
    1085                1090                1095

Gln Glu Arg Gln Pro Asp Leu Thr Arg Asn His Ser Leu Arg Glu
    1100                1105                1110

Lys Ile Gln Phe Ile Arg Thr Glu Gly Thr Pro Gly Leu Val Arg
    1115                1120                1125

Leu Ser Ser Asp Ala Asp Leu Val Met Leu Leu Ser Leu Phe Glu
    1130                1135                1140

Glu Glu Ile Met Ser Tyr Val Pro Pro His Ala Leu Leu His Pro
    1145                1150                1155

Ser Tyr Cys Gln Ser Pro Arg Gly Ser Pro Val Ser Ser Pro Gln
    1160                1165                1170

Asn Ser Pro Gly Thr Gln Arg Ala Asn Ala Arg Ala Pro Ala Pro
    1175                1180                1185

Tyr Lys Arg Asp Phe Glu Ala Lys Leu Arg Asn Phe Tyr Arg Lys
    1190                1195                1200

Leu Glu Thr Lys Gly Tyr Gly Gln Gly Pro Gly Lys Leu Lys Leu
    1205                1210                1215

Ile Ile Arg Arg Asp His Leu Leu Glu Asp Ala Phe Asn Gln Ile
    1220                1225                1230

Met Gly Tyr Ser Arg Lys Asp Leu Gln Arg Asn Lys Leu Tyr Val
    1235                1240                1245

Thr Phe Val Gly Glu Glu Gly Leu Asp Tyr Ser Gly Pro Ser Arg
    1250                1255                1260

Glu Phe Phe Phe Leu Val Ser Arg Glu Leu Phe Asn Pro Tyr Tyr
    1265                1270                1275

Gly Leu Phe Glu Tyr Ser Ala Asn Asp Thr Tyr Thr Val Gln Ile
    1280                1285                1290

Ser Pro Met Ser Ala Phe Val Asp Asn His His Glu Trp Phe Arg
    1295                1300                1305

Phe Ser Gly Arg Ile Leu Gly Leu Ala Leu Ile His Gln Tyr Leu
    1310                1315                1320

Leu Asp Ala Phe Phe Thr Arg Pro Phe Tyr Lys Ala Leu Leu Arg
    1325                1330                1335

Ile Leu Cys Asp Leu Ser Asp Leu Glu Tyr Leu Asp Glu Glu Phe
    1340                1345                1350

His Gln Ser Leu Gln Trp Met Lys Asp Asn Asp Ile His Asp Ile
    1355                1360                1365

Leu Asp Leu Thr Phe Thr Val Asn Glu Glu Val Phe Gly Gln Ile
    1370                1375                1380

Thr Glu Arg Glu Leu Lys Pro Gly Gly Ala Asn Ile Pro Val Thr
    1385                1390                1395

Glu Lys Asn Lys Lys Glu Tyr Ile Glu Arg Met Val Lys Trp Arg
    1400                1405                1410

Ile Glu Arg Gly Val Val Gln Gln Thr Glu Ser Leu Val Arg Gly
    1415                1420                1425

Phe Tyr Glu Val Val Asp Ala Arg Leu Val Ser Val Phe Asp Ala
    1430                1435                1440

Arg Glu Leu Glu Leu Val Ile Ala Gly Thr Ala Glu Ile Asp Leu
    1445                1450                1455

Ser Asp Trp Arg Asn Asn Thr Glu Tyr Arg Gly Gly Tyr His Asp
    1460                1465                1470

Asn His Ile Val Ile Arg Trp Phe Trp Ala Ala Val Glu Arg Phe
```

```
                            1475                1480                1485

Asn Asn Glu Gln Arg Leu Arg Leu Leu Gln Phe Val Thr Gly Thr
        1490                1495                1500

Ser Ser Ile Pro Tyr Glu Gly Phe Ala Ser Leu Arg Gly Ser Asn
    1505                1510                1515

Gly Pro Arg Arg Phe Cys Val Glu Lys Trp Gly Lys Ile Thr Ala
    1520                1525                1530

Leu Pro Arg Ala His Thr Cys Phe Asn Arg Leu Asp Leu Pro Pro
    1535                1540                1545

Tyr Pro Ser Phe Ser Met Leu Tyr Glu Lys Leu Leu Thr Ala Val
    1550                1555                1560

Glu Glu Thr Ser Thr Phe Gly Leu Glu
    1565                1570

<210> SEQ ID NO 15
<211> LENGTH: 433
<212> TYPE: PRT
<213> ORGANISM: Homo sapiens

<400> SEQUENCE: 15

Met Gly Arg Val Gln Leu Phe Glu Ile Ser Leu Ser His Gly Arg Val
1               5                   10                  15

Val Tyr Ser Pro Gly Glu Pro Leu Ala Gly Thr Val Arg Val Arg Leu
            20                  25                  30

Gly Ala Pro Leu Pro Phe Arg Ala Ile Arg Val Thr Cys Ile Gly Ser
        35                  40                  45

Cys Gly Val Ser Asn Lys Ala Asn Asp Thr Ala Trp Val Val Glu Glu
    50                  55                  60

Gly Tyr Phe Asn Ser Ser Leu Ser Leu Ala Asp Lys Gly Ser Leu Pro
65                  70                  75                  80

Ala Gly Glu His Ser Phe Pro Phe Gln Phe Leu Leu Pro Ala Thr Ala
                85                  90                  95

Pro Thr Ser Phe Glu Gly Pro Phe Gly Lys Ile Val His Gln Val Arg
            100                 105                 110

Ala Ala Ile His Thr Pro Arg Phe Ser Lys Asp His Lys Cys Ser Leu
        115                 120                 125

Val Phe Tyr Ile Leu Ser Pro Leu Asn Leu Asn Ser Ile Pro Asp Ile
    130                 135                 140

Glu Gln Pro Asn Val Ala Ser Ala Thr Lys Lys Phe Ser Tyr Lys Leu
145                 150                 155                 160

Val Lys Thr Gly Ser Val Val Leu Thr Ala Ser Thr Asp Leu Arg Gly
                165                 170                 175

Tyr Val Val Gly Gln Ala Leu Gln Leu His Ala Asp Val Glu Asn Gln
            180                 185                 190

Ser Gly Lys Asp Thr Ser Pro Val Val Ala Ser Leu Leu Gln Lys Val
        195                 200                 205

Ser Tyr Lys Ala Lys Arg Trp Ile His Asp Val Arg Thr Ile Ala Glu
    210                 215                 220

Val Glu Gly Ala Gly Val Lys Ala Trp Arg Arg Ala Gln Trp His Glu
225                 230                 235                 240

Gln Ile Leu Val Pro Ala Leu Pro Gln Ser Ala Leu Pro Gly Cys Ser
                245                 250                 255

Leu Ile His Ile Asp Tyr Tyr Leu Gln Val Ser Leu Lys Ala Pro Glu
            260                 265                 270
```

Ala Thr Val Thr Leu Pro Val Phe Ile Gly Asn Ile Ala Val Asn His
            275                 280                 285

Ala Pro Val Ser Pro Arg Pro Gly Leu Gly Leu Pro Pro Gly Ala Pro
290                 295                 300

Pro Leu Val Val Pro Ser Ala Pro Pro Gln Glu Glu Ala Glu Ala Glu
305                 310                 315                 320

Ala Ala Ala Gly Gly Pro His Phe Leu Asp Pro Val Phe Leu Ser Thr
            325                 330                 335

Lys Ser His Ser Gln Arg Gln Pro Leu Leu Ala Thr Leu Ser Ser Val
            340                 345                 350

Pro Gly Ala Pro Glu Pro Cys Pro Gln Asp Gly Ser Pro Ala Ser His
            355                 360                 365

Pro Leu His Pro Pro Leu Cys Ile Ser Thr Gly Ala Thr Val Pro Tyr
            370                 375                 380

Phe Ala Glu Gly Ser Gly Gly Pro Val Pro Thr Thr Ser Thr Leu Ile
385                 390                 395                 400

Leu Pro Pro Glu Tyr Ser Ser Trp Gly Tyr Pro Tyr Glu Ala Pro Pro
            405                 410                 415

Ser Tyr Glu Gln Ser Cys Gly Gly Val Glu Pro Ser Leu Thr Pro Glu
            420                 425                 430

Ser

<210> SEQ ID NO 16
<211> LENGTH: 434
<212> TYPE: PRT
<213> ORGANISM: Mus musculus

<400> SEQUENCE: 16

Met Gly Arg Val Gln Leu Phe Glu Ile Arg Leu Ser Gln Gly Arg Val
1               5                   10                  15

Val Tyr Gly Pro Gly Glu Pro Leu Ala Gly Thr Val His Leu Arg Leu
            20                  25                  30

Gly Ala Pro Leu Pro Phe Arg Ala Ile Arg Val Thr Cys Met Gly Ser
            35                  40                  45

Cys Gly Val Ser Thr Lys Ala Asn Asp Gly Ala Trp Val Val Glu Glu
        50                  55                  60

Ser Tyr Phe Asn Ser Ser Leu Ser Leu Ala Asp Lys Gly Ser Leu Pro
65                  70                  75                  80

Ala Gly Glu His Asn Phe Pro Phe Gln Phe Leu Leu Pro Ala Thr Ala
                85                  90                  95

Pro Thr Ser Phe Glu Gly Pro Phe Gly Lys Ile Val His Gln Val Arg
            100                 105                 110

Ala Ser Ile Asp Thr Pro Arg Phe Ser Lys Asp His Lys Cys Ser Leu
            115                 120                 125

Val Phe Tyr Ile Leu Ser Pro Leu Asn Leu Asn Ser Ile Pro Asp Ile
        130                 135                 140

Glu Gln Pro Asn Val Ala Ser Thr Thr Lys Lys Phe Ser Tyr Lys Leu
145                 150                 155                 160

Val Lys Thr Gly Asn Val Val Leu Thr Ala Ser Thr Asp Leu Arg Gly
                165                 170                 175

Tyr Val Val Gly Gln Val Leu Arg Leu Gln Ala Asp Ile Glu Asn Gln
            180                 185                 190

Ser Gly Lys Asp Thr Ser Pro Val Val Ala Ser Leu Leu Gln Lys Val
            195                 200                 205

```
Ser Tyr Lys Ala Lys Arg Trp Ile Tyr Asp Val Arg Thr Ile Ala Glu
    210             215                 220
Val Glu Gly Thr Gly Val Lys Ala Trp Arg Arg Ala Gln Trp Gln Glu
225             230                 235                 240
Gln Ile Leu Val Pro Ala Leu Pro Gln Ser Ala Leu Pro Gly Cys Ser
                245                 250                 255
Leu Ile His Ile Asp Tyr Tyr Leu Gln Val Ser Met Lys Ala Pro Glu
                260                 265                 270
Ala Thr Val Thr Leu Pro Leu Phe Val Gly Asn Ile Ala Val Asn Gln
            275                 280                 285
Thr Pro Leu Ser Pro Cys Pro Gly Arg Glu Ser Ser Pro Gly Thr Leu
    290                 295                 300
Ser Leu Val Val Pro Ser Ala Pro Pro Gln Glu Ala Glu Ala Val
305             310                 315                 320
Ala Ser Gly Pro His Phe Ser Asp Pro Val Ser Leu Ser Thr Lys Ser
                325                 330                 335
His Ser Gln Gln Gln Pro Leu Ser Ala Pro Leu Gly Ser Val Ser Val
            340                 345                 350
Thr Thr Thr Glu Pro Trp Val Gln Val Gly Ser Pro Ala Arg His Ser
    355                 360                 365
Leu His Pro Pro Leu Cys Ile Ser Ile Gly Ala Thr Val Pro Tyr Phe
    370                 375                 380
Ala Glu Gly Ser Ala Gly Pro Val Pro Thr Thr Ser Ala Leu Ile Leu
385             390                 395                 400
Pro Pro Glu Tyr Ser Ser Trp Gly Tyr Pro Tyr Glu Ala Pro Pro Ser
                405                 410                 415
Tyr Glu Gln Ser Cys Gly Ala Ala Gly Thr Asp Leu Gly Leu Ile Pro
            420                 425                 430
Gly Ser

<210> SEQ ID NO 17
<211> LENGTH: 433
<212> TYPE: PRT
<213> ORGANISM: Mus musculus

<400> SEQUENCE: 17

Met Gly Arg Val Gln Leu Phe Glu Ile Arg Leu Ser Gln Gly Arg Val
1               5                   10                  15
Val Tyr Gly Pro Gly Glu Pro Leu Ala Gly Thr Val His Leu Arg Leu
            20                  25                  30
Gly Ala Pro Leu Pro Phe Arg Ala Ile Arg Val Thr Cys Met Gly Ser
        35                  40                  45
Cys Gly Val Ser Thr Lys Ala Asn Asp Gly Ala Trp Val Val Glu Glu
    50                  55                  60
Ser Tyr Phe Asn Ser Ser Leu Ser Leu Ala Asp Lys Gly Ser Leu Pro
65              70                  75                  80
Ala Gly Glu His Asn Phe Pro Phe Gln Phe Leu Leu Pro Ala Thr Ala
                85                  90                  95
Pro Thr Ser Phe Glu Gly Pro Phe Gly Lys Ile Val His Gln Val Arg
            100                 105                 110
Ala Ser Ile Asp Thr Pro Arg Phe Ser Lys Asp His Lys Cys Ser Leu
        115                 120                 125
Val Phe Tyr Ile Leu Ser Pro Leu Asn Leu Asn Ser Ile Pro Asp Ile
    130                 135                 140
```

-continued

```
Glu Gln Pro Asn Val Ala Ser Thr Lys Lys Phe Ser Tyr Lys Leu
145                 150                 155                 160

Val Lys Thr Gly Asn Val Val Leu Thr Ala Ser Thr Asp Leu Arg Gly
            165                 170                 175

Tyr Val Gly Gln Val Leu Arg Leu Gln Ala Asp Ile Glu Asn Gln
        180                 185                 190

Ser Gly Lys Asp Thr Ser Pro Val Ala Ser Leu Leu Gln Val Ser
        195                 200                 205

Tyr Lys Ala Lys Arg Trp Ile Tyr Asp Val Arg Thr Ile Ala Glu Val
        210                 215                 220

Glu Gly Thr Gly Val Lys Ala Trp Arg Ala Gln Trp Gln Glu Gln
225                 230                 235                 240

Ile Leu Val Pro Ala Leu Pro Gln Ser Ala Leu Pro Gly Cys Ser Leu
                245                 250                 255

Ile His Ile Asp Tyr Tyr Leu Gln Val Ser Met Lys Ala Pro Glu Ala
            260                 265                 270

Thr Val Thr Leu Pro Leu Phe Val Gly Asn Ile Ala Val Asn Gln Thr
                275                 280                 285

Pro Leu Ser Pro Cys Pro Gly Arg Glu Ser Ser Pro Gly Thr Leu Ser
        290                 295                 300

Leu Val Val Pro Ser Ala Pro Pro Gln Glu Glu Ala Glu Ala Val Ala
305                 310                 315                 320

Ser Gly Pro His Phe Ser Asp Pro Val Ser Leu Ser Thr Lys Ser His
                325                 330                 335

Ser Gln Gln Gln Pro Leu Ser Ala Pro Leu Gly Ser Val Ser Val Thr
            340                 345                 350

Thr Thr Glu Pro Trp Val Gln Val Gly Ser Pro Ala Arg His Ser Leu
                355                 360                 365

His Pro Pro Leu Cys Ile Ser Ile Gly Ala Thr Val Pro Tyr Phe Ala
    370                 375                 380

Glu Gly Ser Ala Gly Pro Val Pro Thr Thr Ser Ala Leu Ile Leu Pro
385                 390                 395                 400

Pro Glu Tyr Ser Ser Trp Gly Tyr Pro Tyr Glu Ala Pro Pro Ser Tyr
                405                 410                 415

Glu Gln Ser Cys Gly Ala Ala Gly Thr Asp Leu Gly Leu Ile Pro Gly
            420                 425                 430

Ser

<210> SEQ ID NO 18
<211> LENGTH: 65
<212> TYPE: PRT
<213> ORGANISM: Homo sapiens

<400> SEQUENCE: 18

Pro Leu Pro Pro Gly Trp Glu Gln Arg Val Asp Gln His Gly Arg Val
1               5                   10                  15

Tyr Tyr Val Asp His Val Glu Lys Arg Thr Thr Trp Asp Arg Pro Glu
            20                  25                  30

Pro Leu Pro Pro Gly Trp Glu Arg Arg Val Asp Asn Met Gly Arg Ile
        35                  40                  45

Tyr Tyr Val Asp His Phe Thr Arg Thr Thr Trp Gln Arg Pro Thr
    50                  55                  60

Leu
65
```

<210> SEQ ID NO 19
<211> LENGTH: 185
<212> TYPE: PRT
<213> ORGANISM: Homo sapiens

<400> SEQUENCE: 19

```
Pro Leu Pro Pro Gly Trp Glu Gln Arg Val Asp Gln His Gly Arg Val
1               5                   10                  15

Tyr Tyr Val Asp His Val Glu Lys Arg Thr Thr Trp Asp Arg Pro Glu
            20                  25                  30

Pro Leu Pro Pro Gly Trp Glu Arg Arg Val Asp Asn Met Gly Arg Ile
        35                  40                  45

Tyr Tyr Val Asp His Phe Thr Arg Thr Thr Trp Gln Arg Pro Thr
    50                  55                  60

Leu Glu Ser Val Arg Asn Tyr Glu Gln Trp Gln Leu Gln Arg Ser Gln
65                  70                  75                  80

Leu Gln Gly Ala Met Gln Gln Phe Asn Gln Arg Phe Ile Tyr Gly Asn
                85                  90                  95

Gln Asp Leu Phe Ala Thr Ser Gln Ser Lys Glu Phe Asp Pro Leu Gly
            100                 105                 110

Pro Leu Pro Pro Gly Trp Glu Lys Arg Thr Asp Ser Asn Gly Arg Val
        115                 120                 125

Tyr Phe Val Asn His Asn Thr Arg Ile Thr Gln Trp Glu Asp Pro Arg
    130                 135                 140

Ser Gln Gly Gln Leu Asn Glu Lys Pro Leu Pro Glu Gly Trp Glu Met
145                 150                 155                 160

Arg Phe Thr Val Asp Gly Ile Pro Tyr Phe Val Asp His Asn Arg Arg
                165                 170                 175

Thr Thr Thr Tyr Ile Asp Pro Arg Thr
            180                 185
```

<210> SEQ ID NO 20
<211> LENGTH: 390
<212> TYPE: PRT
<213> ORGANISM: Homo sapiens

<400> SEQUENCE: 20

```
Met Ala Val Ser Glu Ser Gln Leu Lys Lys Met Val Ser Lys Tyr Lys
1               5                   10                  15

Tyr Arg Asp Leu Thr Val Arg Glu Thr Val Asn Val Ile Thr Leu Tyr
            20                  25                  30

Lys Asp Leu Lys Pro Val Leu Asp Ser Tyr Val Phe Asn Asp Gly Ser
        35                  40                  45

Ser Arg Glu Leu Met Asn Leu Thr Gly Thr Ile Pro Val Pro Tyr Arg
    50                  55                  60

Gly Asn Thr Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
                85                  90                  95

Ile Lys Thr Gly Lys His Val Asp Ala Asn Gly Lys Ile Tyr Leu Pro
            100                 105                 110

Tyr Leu His Glu Trp Lys His Pro Gln Ser Asp Leu Leu Gly Leu Ile
        115                 120                 125

Gln Val Met Ile Val Val Phe Gly Asp Glu Pro Pro Val Phe Ser Arg
    130                 135                 140
```

```
Pro Ile Ser Ala Ser Tyr Pro Pro Tyr Gln Ala Thr Gly Pro Pro Asn
145                 150                 155                 160

Thr Ser Tyr Met Pro Gly Met Pro Gly Gly Ile Ser Pro Tyr Pro Ser
                165                 170                 175

Gly Tyr Pro Pro Asn Pro Ser Gly Tyr Pro Gly Cys Pro Tyr Pro Pro
            180                 185                 190

Gly Gly Pro Tyr Pro Ala Thr Thr Ser Ser Gln Tyr Pro Ser Gln Pro
        195                 200                 205

Pro Val Thr Thr Val Gly Pro Ser Arg Asp Gly Thr Ile Ser Glu Asp
    210                 215                 220

Thr Ile Arg Ala Ser Leu Ile Ser Ala Val Ser Asp Lys Leu Arg Trp
225                 230                 235                 240

Arg Met Lys Glu Glu Met Asp Arg Ala Gln Ala Glu Leu Asn Ala Leu
                245                 250                 255

Lys Arg Thr Glu Glu Asp Leu Lys Lys Gly His Gln Lys Leu Glu Glu
            260                 265                 270

Met Val Thr Arg Leu Asp Gln Glu Val Ala Glu Val Asp Lys Asn Ile
        275                 280                 285

Glu Leu Leu Lys Lys Lys Asp Glu Glu Leu Ser Ser Ala Leu Glu Lys
    290                 295                 300

Met Glu Asn Gln Ser Glu Asn Asn Asp Ile Asp Glu Val Ile Ile Pro
305                 310                 315                 320

Thr Ala Pro Leu Tyr Lys Gln Ile Leu Asn Leu Tyr Ala Glu Glu Asn
                325                 330                 335

Ala Ile Glu Asp Thr Ile Phe Tyr Leu Gly Glu Ala Leu Arg Arg Gly
            340                 345                 350

Val Ile Asp Leu Asp Val Phe Leu Lys His Val Arg Leu Leu Ser Arg
        355                 360                 365

Lys Gln Phe Gln Leu Arg Ala Leu Met Gln Lys Ala Arg Lys Thr Ala
    370                 375                 380

Gly Leu Ser Asp Leu Tyr
385                 390

<210> SEQ ID NO 21
<211> LENGTH: 391
<212> TYPE: PRT
<213> ORGANISM: Mus musculus

<400> SEQUENCE: 21

Met Ala Val Ser Glu Ser Gln Leu Lys Lys Met Met Ser Lys Tyr Lys
1               5                   10                  15

Tyr Arg Asp Leu Thr Val Arg Gln Thr Val Asn Val Ile Ala Met Tyr
                20                  25                  30

Lys Asp Leu Lys Pro Val Leu Asp Ser Tyr Val Phe Asn Asp Gly Ser
            35                  40                  45

Ser Arg Glu Leu Val Asn Leu Thr Gly Thr Ile Pro Val Arg Tyr Arg
        50                  55                  60

Gly Asn Ile Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
                85                  90                  95

Ile Lys Thr Gly Lys His Val Asp Ala Asn Gly Lys Ile Tyr Leu Pro
            100                 105                 110

Tyr Leu His Asp Trp Lys His Pro Arg Ser Glu Leu Leu Glu Leu Ile
        115                 120                 125
```

Gln Ile Met Ile Val Ile Phe Gly Glu Glu Pro Val Phe Ser Arg
            130                 135                 140

Pro Thr Val Ser Ala Ser Tyr Pro Pro Tyr Thr Ala Thr Gly Pro Pro
145                 150                 155                 160

Asn Thr Ser Tyr Met Pro Gly Met Pro Ser Gly Ile Ser Ala Tyr Pro
                165                 170                 175

Ser Gly Tyr Pro Pro Asn Pro Ser Gly Tyr Pro Gly Cys Pro Tyr Pro
            180                 185                 190

Pro Ala Gly Pro Tyr Pro Ala Thr Thr Ser Ser Gln Tyr Pro Ser Gln
            195                 200                 205

Pro Pro Val Thr Thr Val Gly Pro Ser Arg Asp Gly Thr Ile Ser Glu
210                 215                 220

Asp Thr Ile Arg Ala Ser Leu Ile Ser Ala Val Ser Asp Lys Leu Arg
225                 230                 235                 240

Trp Arg Met Lys Glu Glu Met Asp Gly Ala Gln Ala Glu Leu Asn Ala
                245                 250                 255

Leu Lys Arg Thr Glu Glu Asp Leu Lys Lys Gly His Gln Lys Leu Glu
                260                 265                 270

Glu Met Val Thr Arg Leu Asp Gln Glu Val Ala Glu Val Asp Lys Asn
            275                 280                 285

Ile Glu Leu Leu Lys Lys Lys Asp Glu Glu Leu Ser Ser Ala Leu Glu
290                 295                 300

Lys Met Glu Asn Gln Ser Glu Asn Asn Asp Ile Asp Glu Val Ile Ile
305                 310                 315                 320

Pro Thr Ala Pro Leu Tyr Lys Gln Ile Leu Asn Leu Tyr Ala Glu Glu
                325                 330                 335

Asn Ala Ile Glu Asp Thr Ile Phe Tyr Leu Gly Glu Ala Leu Arg Arg
            340                 345                 350

Gly Val Ile Asp Leu Asp Val Phe Leu Lys His Val Arg Leu Leu Ser
            355                 360                 365

Arg Lys Gln Phe Gln Leu Arg Ala Leu Met Gln Lys Ala Arg Lys Thr
370                 375                 380

Ala Gly Leu Ser Asp Leu Tyr
385                 390

<210> SEQ ID NO 22
<211> LENGTH: 391
<212> TYPE: PRT
<213> ORGANISM: Rattus norvegicus

<400> SEQUENCE: 22

Met Ala Val Ser Glu Ser Gln Leu Lys Lys Met Met Ser Lys Tyr Lys
1               5                   10                  15

Tyr Arg Asp Leu Thr Val Arg Gln Thr Val Asn Val Ile Ala Met Tyr
            20                  25                  30

Lys Asp Leu Lys Pro Val Leu Asp Ser Tyr Val Phe Asn Asp Gly Ser
        35                  40                  45

Ser Arg Glu Leu Val Asn Leu Thr Gly Thr Ile Pro Val Arg Tyr Arg
    50                  55                  60

Gly Asn Ile Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
                85                  90                  95

Ile Lys Thr Gly Lys His Val Asp Ala Asn Gly Lys Ile Tyr Leu Pro

```
            100                 105                 110
Tyr Leu His Asp Trp Lys His Pro Arg Ser Glu Leu Leu Glu Leu Ile
        115                 120                 125

Gln Ile Met Ile Val Ile Phe Gly Glu Glu Pro Pro Val Phe Ser Arg
    130                 135                 140

Pro Thr Val Ser Ala Ser Tyr Pro Pro Tyr Thr Ala Ala Gly Pro Pro
145                 150                 155                 160

Asn Thr Ser Tyr Leu Pro Ser Met Pro Ser Gly Ile Ser Ala Tyr Pro
                165                 170                 175

Ser Gly Tyr Pro Pro Asn Pro Ser Gly Tyr Pro Gly Cys Pro Tyr Pro
            180                 185                 190

Pro Ala Gly Pro Tyr Pro Ala Thr Thr Ser Ser Gln Tyr Pro Ser Gln
        195                 200                 205

Pro Pro Val Thr Thr Ala Gly Pro Ser Arg Asp Gly Thr Ile Ser Glu
    210                 215                 220

Asp Thr Ile Arg Ala Ser Leu Ile Ser Ala Val Ser Asp Lys Leu Arg
225                 230                 235                 240

Trp Arg Met Lys Glu Glu Met Asp Gly Ala Gln Ala Glu Leu Asn Ala
                245                 250                 255

Leu Lys Arg Thr Glu Glu Asp Leu Lys Lys Gly His Gln Lys Leu Glu
            260                 265                 270

Glu Met Val Thr Arg Leu Asp Gln Glu Val Ala Glu Val Asp Lys Asn
        275                 280                 285

Ile Glu Leu Leu Lys Lys Lys Asp Glu Glu Leu Ser Ser Ala Leu Glu
    290                 295                 300

Lys Met Glu Asn Gln Ser Glu Asn Asn Asp Ile Asp Glu Val Ile Ile
305                 310                 315                 320

Pro Thr Ala Pro Leu Tyr Lys Gln Ile Leu Asn Leu Tyr Ala Glu Glu
                325                 330                 335

Asn Ala Ile Glu Asp Thr Ile Phe Tyr Leu Gly Glu Ala Leu Arg Arg
            340                 345                 350

Gly Val Ile Asp Leu Asp Val Phe Leu Lys His Val Arg Leu Leu Ser
        355                 360                 365

Arg Lys Gln Phe Gln Leu Arg Ala Leu Met Gln Lys Ala Arg Lys Thr
    370                 375                 380

Ala Gly Leu Ser Asp Leu Tyr
385                 390

<210> SEQ ID NO 23
<211> LENGTH: 3475
<212> TYPE: DNA
<213> ORGANISM: Homo sapiens

<400> SEQUENCE: 23
gaattcgcgg ccgcgtcgac cgcttctgtg gccacggcag atgaaacaga aaggctaaag      60
agggctggag tcaggggact tctcttccac cagcttcacg gtgatgatat ggcatctgcc     120
agctctagcc gggcaggagt ggccctgcct tttgagaagt ctcagctcac tttgaaagtg     180
gtgtccgcaa agcccaaggt gcataatcgt caacctcgaa ttaactccta cgtggaggtg     240
gcggtggatg gactccccag tgagaccaag aagactggga agcgcattgg gagctctgag     300
cttctctgga atgagatcat cattttgaat gtcacggcac agagtcattt agatttaaag     360
gtctggagct gccataccct gagaaatgaa ctgctaggca ccgcatctgt caacctctcc     420
aacgtcttga agaacaatgg gggcaaaatg gagaacatgc agctgaccct gaacctgcag     480
```

```
acggagaaca aaggcagcgt tgtctcaggc ggaaaactga caattttcct ggacgggcca    540
actgttgatc tgggaaatgt gcctaatggc agtgccctga cagatggatc acagctgcct    600
tcgagagact ccagtggaac agcagtagct ccagagaacc ggcaccagcc ccccagcaca    660
aactgctttg gtggaagatc ccggacgcac agacattcgg gtgcttcagc cagaacaacc    720
ccagcaaccg gcgagcaaag ccccggtgct cggagccggc accgccagcc cgtcaagaac    780
tcaggccaca gtggcttggc caatggcaca gtgaatgatg aacccacaac agccactgat    840
cccgaagaac cttccgttgt tggtgtgacg tccccacctg ctgcacccct gagtgtgacc    900
ccgaatccca acacgacttc tctccctgcc cagccacac cggctgaagg agaggaaccc    960
agcacttcgg gtacacagca gctcccagcg gctgcccagg ccccgacgc tctgcctgct   1020
ggatgggaac agcgagagct gcccaacgga cgtgtctatt atgttgacca caataccaag   1080
accaccacct gggagcggcc ccttcctcca ggctgggaaa aacgcacaga tccccgaggc   1140
aggttttact atgtggatca caatactcgg accaccacct ggcagcgtcc gaccgcggag   1200
tacgtgcgca actatgagca gtggcagtcg cagcggaatc agctccaggg ggccatgcag   1260
cacttcagcc aaagattcct ataccagttt tggagtgctt cgactgacca tgatcccctg   1320
ggccccctcc ctcctggttg ggagaaaaga caggacaatg gacgggtgta ttacgtgaac   1380
cataacactc gcacgaccca gtgggaggat ccccggaccc aggggatgat ccaggaacca   1440
gctttgcccc caggatggga gatgaaatac accagcgagg gggtgcgata ctttgtggac   1500
cacaataccc gcaccaccac ctttaaggat cctcgcccgg ggtttgagtc ggggacgaag   1560
caaggttccc ctggtgctta tgaccgcagt tttcggtgga agtatcacca gttccgtttc   1620
ctctgccatt caaatgccct acctagccac gtgaagatca gcgtttccag gcagacgctt   1680
ttcgaagatt ccttccaaca gatcatgaac atgaaccct atgacctgcg ccgccggctt   1740
tacatcatca tgcgtggcga ggagggcctg gactatgggg gcatcgccag agagtggttt   1800
ttcctcctgt ctcacgaggt gctcaaccct atgtattgtt tatttgaata tgccggaaag   1860
aacaattact gcctgcagat caaccccgcc tcctccatca acccggacca cctcacctac   1920
tttcgcttta taggcagatt catcgccatg gcgctgtacc atggaaagtt catcgacacg   1980
ggcttcaccc tccctttcta caagcggatg ctcaataaga gaccaaccct gaaagacctg   2040
gagtccattg accctgagtt ctacaactcc attgtctgga tcaaagagaa caacctggaa   2100
gaatgtggcc tggagctgta cttcatccag gacatggaga tactgggcaa ggtgacgacc   2160
cacgagctga aggagggcgg cgagagcatc cgggtcacgg aggagaacaa ggaagagtac   2220
atcatgctgc tgactgactg gcgtttcacc cgaggcgtgg aagagcagac caaagccttc   2280
ctggatggct tcaacgaggt ggccccgctg gagtggctgc gctactttga cgagaaagag   2340
ctggagctga tgctgtgcgg catgcaggag atagacatga gcgactggca gaagagcacc   2400
atctaccggc actacaccaa gaacagcaag cagatccagt ggttctggca ggtggtgaag   2460
gagatggaca acgagaagag gatccggctg ctgcagtttg tcaccggtac ctgccgcctg   2520
cccgtcgggg gatttgccga actcatcggt agcaacggac cacagaagtt ttgcattgac   2580
aaagttggca aggaaacctg gctgcccaga gccacacct gcttcaaccg tctggatctt   2640
ccaccctaca gagctacga acagctgaga gagaagctgc tgtatgccat tgaggagacc   2700
gagggctttg gacaggagta accgaggccg ccctcccac gccccccagc gcacatgtag   2760
tcctgagtcc tccctgcctg agaggccact ggccccgcag cccttgggag gccccgtgg   2820
```

```
atgtggccct gtgtgggacc acactgtcat ctcgctgctg gcagaaaagc ctgatcccag    2880
gaggccctgc agttccccg  acccgcggat ggcagtctgg aataaagccc cctagttgcc    2940
tttggcccca ccttttgcaaa gttccagagg gctgaccctc tctgcaaaac tctcccctgt   3000
cctctagacc ccaccctggg tgtatgtgag tgtgcaaggg aaggtgttgc atccccaggg    3060
gctgccgcag aggccggaga cctcctggac tagttcggcg aggagactgg ccactggggg    3120
tggctgttcg ggactgagag cgccaagggt ctttgccagc aaaggaggtt ctgcctgtaa    3180
ttgagcctct ctgatgatgg agatgaagtg aaggtctgag ggacgggccc tggggctagg    3240
ccatctctgc ctgcctccct agcaggcgcc agcggtggag gctgagtcgc aggacacatg    3300
ccggccagtt aattcattct cagcaaatga aggtttgtct aagctgcctg ggtatccacg    3360
ggacaaaaac agcaaactcc ctccagactt tgtccatgtt ataaacttga aagttggttg    3420
ttgtttgtta ggtttgccag ttttttttgt ttacgcctgc tgtcactttc ctgtc         3475
```

<210> SEQ ID NO 24
<211> LENGTH: 3475
<212> TYPE: DNA
<213> ORGANISM: Homo sapiens

<400> SEQUENCE: 24

```
gaattcgcgg ccgcgtcgac cgcttctgtg gccacggcag atgaaacaga aaggctaaag      60
agggctggag tcaggggact tctcttccac cagcttcacg gtgatgatat ggcatctgcc     120
agctctagcc gggcaggagt ggccctgcct tttgagaagt ctcagctcac tttgaaagtg     180
gtgtccgcaa agcccaaggt gcataatcgt caacctcgaa ttaactccta cgtggaggtg     240
gcggtggatg gactccccag tgagaccaag aagactggga agcgcattgg gagctctgag     300
cttctctgga tgagatcat  cattttgaat gtcacggcac agagtcattt agatttaaag     360
gtctggagct gccataccttt gagaaatgaa ctgctaggca ccgcatctgt caacctctcc    420
aacgtcttga agaacaatgg gggcaaaatg gagaacatgc agctgaccct gaacctgcag    480
acggagaaca aaggcagcgt tgtctcaggc ggaaaactga caattttcct ggacgggcca   540
actgttgatc tggaaatgt  gcctaatggc agtgccctga cagatggatc acagctgcct    600
tcgagagact ccagtggaac agcagtagct ccagagaacc ggcaccagcc cccagcaca    660 aactgctttg gtgaagatc ccggacgcac agacattcgg gtgcttcagc cagaacaacc    720
ccagcaaccg gcgagcaaag ccccggtgct cggagccggc accgccagcc cgtcaagaac    780
tcaggccaca gtggcttggc caatggcaca gtgaatgatg aacccacaac agccactgat    840
cccgaagaac cttccgttgt tggtgtgacg tccccacctg ctgcacccTT gagtgtgacc     900
ccgaatccca acacgacttc tctccctgcc ccagccacac cggctgaagg agaggaaccc    960
agcacttcgg gtacacagca gctcccagcg gctgcccagg cccccgacgc tctgcctgct   1020
ggatgggaac agcgagagct gcccaacgga cgtgtctatt atgttgacca caataccaag   1080
accaccacct gggagcggcc ccttcctcca ggctgggaaa acgcacaga  tccccgaggc   1140 aggttttact atgtggatca caatactcgg accaccacct ggcagcgtcc gaccgcggag   1200
tacgtgcgca actatgagca gtggcagtcg cagcggaatc agctccaggg ggccatgcag   1260
cacttcagcc aaagattcct ataccagttt tggagtgctt cgactgacca tgatcccctg   1320
ggccccctcc ctcctggttg ggagaaaaga caggacaatg gacgggtgta ttacgtgaac   1380
cataacactc gcacgaccca gtgggaggat ccccggaccc aggggatgat ccaggaacca    1440
gctttgcccc caggatggga gatgaaatac accagcgagg gggtgcgata ctttgtggac    1500
```

```
cacaatacccc gcaccaccac ctttaaggat cctcgcccgg ggtttgagtc ggggacgaag    1560
caaggttccc ctggtgctta tgaccgcagt tttcggtgga agtatcacca gttccgtttc    1620
ctctgccatt caaatgccct acctagccac gtgaagatca gcgtttccag gcagacgctt    1680
ttcgaagatt ccttccaaca gatcatgaac atgaaaccct atgacctgcg ccgccggctt    1740
tacatcatca tgcgtggcga ggagggcctg gactatgggg gcatcgccag agagtggttt    1800
ttcctcctgt ctcacgaggt gctcaaccct atgtattgtt tatttgaata tgccggaaag    1860
aacaattact gcctgcagat caaccccgcc tcctccatca acccggacca cctcacctac    1920
tttcgcttta taggcagatt catcgccatg gcgctgtacc atggaaagtt catcgacacg    1980
ggcttcaccc tccctttcta caagcggatg ctcaataaga gaccaaccct gaaagacctg    2040
gagtccattg accctgagtt ctacaactcc attgtctgga tcaaagagaa caacctggaa    2100
gaatgtggcc tggagctgta cttcatccag gacatggaga tactgggcaa ggtgacgacc    2160
cacgagctga aggagggcgg cgagagcatc cgggtcacgg aggagaacaa ggaagagtac    2220
atcatgctgc tgactgactg gcgtttcacc cgaggcgtgg aagagcagac caaagccttc    2280
ctggatggct tcaacgaggt ggccccgctg gagtggctgc gctactttga cgagaaagag    2340
ctggagctga tgctgtgcgg catgcaggag atagacatga gcgactggca aaagagcacc    2400
atctaccggc actacaccaa gaacagcaag cagatccagt ggttctggca ggtggtgaag    2460
gagatggaca acgagaagag gatccggctg ctgcagtttg tcaccggtac ctgccgcctg    2520
cccgtcgggg gatttgccga actcatcggt agcaacggac cacagaagtt ttgcattgac    2580
aaagttggca aggaaacctg gctgcccaga agccacacct gcttcaaccg tctggatctt    2640
ccaccctaca gagctacgac acagctgaga gagaagctgc tgtatgccat tgaggagacc    2700
gagggctttg acaggagta accgaggccg cccctcccac gcccccccagc gcacatgtag    2760 tcctgagtcc tccctgcctg agaggccact ggccccgcag ccctttgggag gccccgtgg    2820 atgtggccct gtgtgggacc acactgtcat ctcgctgctg gcagaaaagc ctgatcccag    2880
gaggccctgc agttcccccg acccgcggat ggcagtctgg aataaagccc ctagttgcc    2940 tttggcccca cctttgcaaa gttccagagg gctgaccctc tctgcaaaac tctcccctgt    3000
cctctagacc ccaccctggg tgtatgtgag tgtgcaaggg aaggtgttgc atccccaggg    3060
gctgccgcag aggccggaga cctcctggac tagttcggcg aggagactgg ccactggggg    3120
tggctgttcg ggactgagag cgccaagggt cttttgccagc aaaggaggtt ctgcctgtaa    3180
ttgagcctct ctgatgatgg agatgaagtg aaggtctgag ggacgggccc tggggctagg    3240
ccatctctgc ctgcctccct agcaggcgcc agcggtggag gctgagtcgc aggacacatg    3300
ccggccagtt aattcattct cagcaaatga aggtttgtct aagctgcctg ggtatccacg    3360
ggacaaaaac agcaaactcc ctccagactt tgtccatgtt ataaacttga aagttggttg    3420
ttgtttgtta ggtttgccag gttttttttgt ttacgcctgc tgtcactttc ctgtc        3475
```

<210> SEQ ID NO 25
<211> LENGTH: 2914
<212> TYPE: DNA
<213> ORGANISM: Homo sapiens

<400> SEQUENCE: 25

```
acagttgcct gccctgggcg ggggcgagcg cgtccggttt gctggaagcg ttcggaaatg      60
gcaacttgcg cggtggaggt gttcgggctc ctggaggacg aggaaaattc acgaattgtg     120
```

```
agagtaagag ttatagccgg aataggcctt gccaagaagg atatattggg agctagtgat    180
ccttacgtga gagtgacgtt atatgaccca atgaatggag ttcttacaag tgtgcaaaca    240
aaaaccatta aaaagagttt gaatccaaag tggaatgaag aaatattatt cagagttcat    300
cctcagcagc accggcttct ttttgaagtg tttgacgaaa accgattgac aagagatgat    360
ttcctaggtc aagtggatgt tccactttat ccattaccga cagaaaatcc aagattggag    420
agaccatata catttaagga ttttgttctt catccaagaa gtcacaaatc aagagttaaa    480
ggttatctga gactaaaaat gacttattta cctaaaacca gtggctcaga agatgataat    540
gcagaacagg ctgaggaatt agagcctggc tgggttgttt tggaccaacc agatgctgct    600
tgccatttgc agcaacaaca agaaccttct cctctacctc agggtggga agagaggcag    660
gatatccttg gaaggaccta ttatgtaaac catgaatcta agaacacaa gtggaaaaga    720
ccaaccccctc aggacaacct aacagatgct gagaatggca acattcaact gcaagcacaa    780
cgtgcattta ccaccaggcg gcagatatcc gaggaaacag aaagtgttga caaccaagag    840
tcttccgaga actgggaaat tataagagaa gatgaagcca ccatgtatag cagccaggcc    900
ttcccatcac ctccaccgtc aagtaacttg gatgttccaa ctcatcttgc agaagaattg    960
aatgccgac tcaccatttt tggaaaattca gccgtgagcc agccagcatc gagctcaaat    1020
cattccagca agaggcag cttacaagcc tatactttg aggaacaacc tacacttcct    1080
gtgcttttgc ctacttcatc tggattacca ccaggtggg aagaaaaaca agatgaaaga    1140
ggaagatcat attatgtaga tcacaattcc agaacgacta cttggacaaa gcccactgta    1200
caggccacag tggagaccag tcagctgacc tcaagccaga gttctgcagg ccctcaatca    1260
caagcctcca ccagtgattc aggccagcag gtgacccagc catctgaaat tgagcaagga    1320
ttccttccta aaggctggga agtccggcat gcaccaaatg ggaggccttt ctttattgac    1380
cacaacacta aaaccaccac ctgggaagat ccaagattga aaattccagc ccatctgaga    1440
ggaaagacat cacttgatac ttccaatgat ctagggcctt acctccagg atgggaagag    1500
agaactcaca cagatggaag aatcttctac ataaatcaca atataaaag aacacaatgg    1560
gaagatcctc ggttggagaa tgtagcaata actggaccag cagtgcccta ctccagggat    1620
tacaaaagaa agtatgagtt cttccgaaga aagttgaaga agcagaatga cattccaaac    1680
aaatttgaaa tgaaacttcg ccgagcaact gttcttgaag actcttaccg gagaattatg    1740
ggtgtcaaga gagcagactt cctgaaggct cgactgtgga ttgagtttga tggtgaaaag    1800
ggattggatt atgaggagt tgccagagaa tggttcttcc tgatctcaaa ggaaatgttt    1860
aaccccttatt atgggttgtt tgaatattct gctacggaca attatccct acagataaat    1920
ccaaactctg gattgtgtaa cgaagatcac ctctcttact tcaagtttat tggtcgggta    1980
gctggaatgg cagtttatca tggcaaactg ttggatggtt ttttcatccg cccatttttac    2040
aagatgatgc ttcacaaacc aataacccctt catgatatgg aatctgtgga tagtgaatat    2100
tacaattccc taagatggat tcttgaaaat gacccaacag aattggacct caggtttatc    2160
atagatgaag aacttttggg acagacacat caacatgagc tgaaaaatgg tggatcagaa    2220
atagttgtca ccaataagaa caaaaaggaa tatatttatc ttgtaataca atggcgattt    2280
gtaaaccgaa tccagaagca aatggctgct tttaagagg gattctttga actaatacca    2340
caggatctca tcaaaatttt tgatgaaaat gaactagagc ttcttatgtg tggaccggga    2400
gatgttgatg tgaatgactg gagggaacat acaaagtata aaaatggcta cagtgcaaat    2460
catcaggtta tacagtggtt ttggaaggct gttttaatga tggattcaga aaaaagaata    2520
```

| | |
|---|---|
| agattacttc agtttgtcac tggcacatct cgggtgccta tgaatggatt tgctgaacta | 2580 |
| tacggttcaa atggaccaca gtcatttaca gttgaacagt ggggtactcc tgaaaagctg | 2640 |
| ccaagagctc atacctgttt taatcgcctg gacttgccac cttatgaatc atttgaagaa | 2700 |
| ttatgggata aacttcagat ggcaattgaa aacacccagg gctttgatgg agttgattag | 2760 |
| attacaaata acaatctgta gtgtttttac tgccatagtt ttataaccaa aatcttgact | 2820 |
| taaaattttc cggggaacta ctaaaatgtg gccactgagt cttcccagat cttgaagaaa | 2880 |
| atcatataaa aagcatttga agaaatagta cgac | 2914 |

<210> SEQ ID NO 26
<211> LENGTH: 2868
<212> TYPE: DNA
<213> ORGANISM: Homo sapiens

<400> SEQUENCE: 26

| | |
|---|---|
| atggcgaccg ggctcgggga gccggtctat ggactttccg aagacgaggg agagtcccgt | 60 |
| attctcagag taaaagttgt ttctggaatt gatctcgcca aaaaggacat ctttggagcc | 120 |
| agtgatccgt atgtgaaact ttcattgtac gtagcggatg agaatagaga acttgctttg | 180 |
| gtccagacaa aaacaattaa aaagacactg aacccaaaat ggaatgaaga atttttatttc | 240 |
| agggtaaacc catctaatca cagactccta tttgaagtat ttgacgaaaa tagactgaca | 300 |
| cgagacgact tcctgggcca ggtggacgtg cccttagtc accttccgac agaagatcca | 360 |
| accatggagc gaccctatac atttaaggac tttctcctca gaccaagaag tcataagtct | 420 |
| cgagttaagg gattttttgcg attgaaaatg gcctatatgc caaaaaatgg aggtcaagat | 480 |
| gaagaaaaca gtgaccagag ggatgacatg gagcatggat gggaagttgt tgactcaaat | 540 |
| gactcggctt ctcagcacca agaggaactt cctcctcctc ctctgcctcc cgggtgggaa | 600 |
| gaaaaagtgg acaatttagg ccgaacttac tatgtcaacc acaacaaccg gaccactcag | 660 |
| tggcacagac caagcctgat ggacgtgtcc tcggagtcgg acaataacat cagacagatc | 720 |
| aaccaggagg cagcacaccg cgcttccgc tcccgcaggc acatcagcga agacttggag | 780 |
| cccgagccct cggagggcgg ggatgtcccc gagccttggg agaccatttc agaggaagtg | 840 |
| aatatcgctg gagactctct cggtctggct ctgcccccac caccggcctc cccaggatct | 900 |
| cggaccagcc ctcaggagct gtcagaggaa ctaagcagaa ggcttcagat cactccagac | 960 |
| tccaatgggg aacagttcag ctctttgatt caaagagaac cctcctcaag gttgaggtca | 1020 |
| tgcagtgtca ccgacgcagt tgcagaacag ggccatctac caccgccatc agtggcctat | 1080 |
| gtacatacca cgccgggtct gccttcaggc tgggaagaaa gaaagatgc taagggcgc | 1140 |
| acatactatg tcaatcataa caatcgaacc acaacttgga ctcgacctat catgcagctt | 1200 |
| gcagaagatg gtgcgtccgg atcagccaca aacagtaaca accatctaat cgagcctcag | 1260 |
| atccgccggc ctcgtagcct cagctcgcca acagtaactt tatctgcccc gctggagggt | 1320 |
| gccaaggact cacccgtacg tcgggctgtg aaagacaccc tttccaaccc acagtcccca | 1380 |
| cagccatcac cttacaactc ccccaaacca caacacaaag tcacacagag cttcttgcca | 1440 |
| cccggctggg aaatgaggat agcgccaaac ggccggccct tcttcattga tcataacaca | 1500 |
| aagactacaa cctgggaaga tccacgtttg aaatttccag tacatatgcg gtcaaagaca | 1560 |
| tcttttaaacc ccaatgacct tggccccctt cctcctggct gggaagaaag aattcacttg | 1620 |
| gatggccgaa cgttttatat tgatcataat agcaaaatta ctcagtggga agacccaaga | 1680 |

```
ctgcagaacc cagctattac tggtccggct gtcccttact ccagagaatt taagcagaaa    1740
tatgactact tcaggaagaa attaaagaaa cctgctgata tccccaatag gtttgaaatg    1800
aaacttcaca gaaataacat atttgaagag tcctatcgga gaattatgtc cgtgaaaaga    1860
ccagatgtcc taaaagctag actgtggatt gagtttgaat cagagaaagg tcttgactat    1920
gggggtgtgg ccagagaatg gttcttctta ctgtccaaag agatgttcaa cccctactac    1980
ggcctctttg agtactctgc cacggacaac tacacccttc agatcaaccc taattcaggc    2040
ctctgtaatg aggatcattt gtcctacttc acttttattg gaagagttgc tggtctggcc    2100
gtatttcatg ggaagctctt agatggtttc ttcattagac cattttacaa gatgatgttg    2160
ggaaagcaga taaccctgaa tgacatggaa tctgtggata gtgaatatta caactctttg    2220
aaatggatcc tggagaatga ccctactgag ctggacctca tgttctgcat agacgaagaa    2280
aactttggac agacatatca agtggatttg aagcccaatg ggtcagaaat aatggtcaca    2340
aatgaaaaca aaagggaata tatcgactta gtcatccagt ggagatttgt gaacagggtc    2400
cagaagcaga tgaacgcctt cttggaggga ttcacagaac tacttcctat tgatttgatt    2460
aaaatttttg atgaaaatga gctggagttg ctcatgtgcg gcctcggtga tgtggatgtg    2520
aatgactgga gacagcattc tatttacaag aacggctact gcccaaacca ccccgtcatt    2580
cagtggttct ggaaggctgt gctactcatg gacgccgaaa agcgtatccg gttactgcag    2640
tttgtcacag gacatcgcg agtacctatg aatggatttg ccgaacttta tggttccaat    2700
ggtcctcagc tgtttacaat agagcaatgg ggcagtcctg agaaactgcc cagagctcac    2760
acatgcttta atcgccttga cttacctcca tatgaaacct tgaagatttt acgagagaaa    2820
cttctcatgg ccgtggaaaa tgctcaagga tttgaagggg tggattaa             2868
```

<210> SEQ ID NO 27
<211> LENGTH: 2274
<212> TYPE: DNA
<213> ORGANISM: Homo sapiens

<400> SEQUENCE: 27

```
atgtcgaacc ccgggacacg caggaacggc tccagcatca agatccgtct gacagtgtta     60
tgtgccaaga accttgcaaa gaaagacttc ttcaggctcc ctgacccttt tgcaaagatt    120
gtcgtggatg ggtctgggca gtgccactca accgacactg tgaaaaacac attggaccca    180
aagtggaacc agcactatga tctatatgtt gggaaaacgg attcgataac cattagcgtg    240
tggaaccata agaaaattca caagaaacag ggagctggct tcctgggctg tgtgcggctg    300
ctctccaatg ccatcagcag attaaaagat accggatacc agcgtttgga tctatgcaaa    360
ctaaacccct cagatactga tgcagttcgt ggccagatag tggtcagttt acagacacga    420
gacagaatag gaaccggcgg ctcggtggtg gactgcagag gactgttaga aaatgaagga    480
acggtgtatg aagactccgg gcctggggag ccgctcagct gcttcatgga ggaaccagcc    540
ccttacacag atagcaccgg tgctgctgct ggaggaggga attgcaggtt cgtggagtcc    600
ccaagtcaag atcaaagact tcaggcacag cggcttcgaa accctgatgt gcgaggttca    660
ctacagacgc cccagaaccg accacacggc caccagtccc cggaactgcc cgaaggctac    720
gaacaaagaa caacagtcca gggccaagtt tacttttttgc atacacagac tggagttagc    780
acgtggcacg accccaggat accaagtccc tcggggacca ttcctggggg agatgcagct    840
tttctatacg aattccttct acaaggccat acatctgagc ccagagacct taacagtgtg    900
aactgtgatg aacttggacc actgccgcca ggctgggaag tcagaagtac agtttctggg    960
```

```
aggatatatt tgtagatca taataaccga acaacccagt ttacagaccc aaggttacac    1020
cacatcatga atcaccagtg ccaactcaag gagcccagcc agccgctgcc actgcccagt    1080
gagggctctc tggaggacga ggagcttcct gcccagagat acgaaagaga tctagtccag    1140
aagctgaaag tcctcagaca cgaactgtcg cttcagcagc cccaagctgg tcattgccgc    1200
atcgaagtgt ccagagaaga aatctttgag gagtcttacc gccagataat gaagatgcga    1260
ccgaaagact tgaaaaaacg gctgatggtg aaattccgtg gggaagaagg tttggattac    1320
ggtggtgtgg ccagggagtg gctttacttg ctgtgccatg aaatgctgaa tccttattac    1380
gggctcttcc agtattctac ggacaatatt tacatgttgc aaataaatcc ggattcttca    1440
atcaaccccg accacttgtc ttatttccac tttgtggggc ggatcatggg gctggctgtg    1500
ttccatggac actacatcaa cgggggcttc acagtgccct tctacaagca gctgctgggg    1560
aagcccatcc agctctcaga tctggaatct gtggacccag agctgcataa gagcttggtg    1620
tggatcctag agaacgacat cacgcctgta ctggaccaca ccttctgcgt ggaacacaac    1680
gccttcgggc ggatcctgca gcatgaactg aaacccaatg gcagaaatgt gccagtcaca    1740
gaggagaata agaaagaata cgtccggttg tatgtaaact ggaggtttat gagaggaatc    1800
gaagcccagt tcttagctct gcagaagggg ttcaatgagc tcatccctca acatctgctg    1860
aagccttttg accagaagga actggagctg atcataggcg gcctggataa aatagacttg    1920
aacgactgga agtcgaacac gcggctgaag cactgtgtgg ccgacagcaa catcgtgcgg    1980
tggttctggc aagcggtgga gacgttcgat gaagaaagga gggccaggct cctgcagttt    2040
gtgactgggt ccacgcgagt cccgctccaa ggcttcaagg ctttgcaagg ttctacaggc    2100
gcggcagggc cccggctgtt caccatccac ctgatagacg cgaacacaga caaccttccg    2160
aaggcccata cctgctttaa ccggatcgac attccaccat atgagtccta tgagaagctc    2220
tacgagaagc tgctgacagc cgtggaggag acctgcgggt ttgctgtgga gtga          2274
```

<210> SEQ ID NO 28
<211> LENGTH: 2247
<212> TYPE: DNA
<213> ORGANISM: Homo sapiens

<400> SEQUENCE: 28

```
atgtctaacc ccggacgccg gaggaacggg cccgtcaagc tgcgcctgac agtactctgt     60
gcaaaaaacc tggtgaaaaa ggatttttc cgacttcctg atccatttgc taaggtggtg    120
gttgatggat ctgggcaatg ccattctaca gatactgtga agaatacgct tgatccaaag    180
tggaatcagc attatgacct gtatattgga aagtctgatt cagttacgat cagtgtatgg    240
aatcacaaga agatccataa gaaacaaggt gctggatttc tcggttgtgt tcgtcttctt    300
tccaatgcca tcaaccgcct caaagacact ggttatcaga ggttggattt atgcaaactc    360
gggccaaatg acaatgatac agttagagga cagatagtag taagtcttca gtccagagac    420
cgaataggca caggaggaca agttgtggac tgcagtcgtt tatttgataa cgatttacca    480
gacggctggg aagaaaggag aaccgcctct ggaagaatcc agtatctaaa ccatataaca    540
agaactacgc aatgggagcg cccaacacga ccggcatccg aatattctag ccctggcaga    600
cctcttagct gctttgttga tgagaacact ccaattagtg aacaaatgg tgcaacatgt    660 ggacagtctt cagatcccag gctggcagag aggagagtca ggtcacaacg acatagaaat    720
tacatgagca gaacacattt acatactcct ccagacctac cagaaggcta tgaacagagg    780
```

| | |
|---|---:|
| acaacgcaac aaggccaggt gtatttctta catacacaga ctggtgtgag cacatggcat | 840 |
| gatccaagag tgcccaggga tcttagcaac atcaattgtg aagagcttgg tccattgcct | 900 |
| cctggatggg agatccgtaa tacggcaaca ggcagagttt atttcgttga ccataacaac | 960 |
| agaacaacac aatttacaga tcctcggctg tctgctaact tgcatttagt tttaaatcgg | 1020 |
| cagaaccaat tgaaagacca acagcaacag caagtggtat cgttatgtcc tgatgacaca | 1080 |
| gaatgcctga cagtcccaag gtacaagcga gacctggttc agaaactaaa aattttgcgg | 1140 |
| caagaacttt cccaacaaca gcctcaggca ggtcattgcc gcattgaggt ttccagggaa | 1200 |
| gagattttg aggaatcata tcgacaggtc atgaaaatga gaccaaaaga tctctggaag | 1260 |
| cgattaatga taaaatttcg tggagaagaa ggccttgact atggaggcgt tgccagggaa | 1320 |
| tggttgtatc tcttgtcaca tgaaatgttg aatccatact atggcctctt ccagtattca | 1380 |
| agagatgata tttatacatt gcagatcaat cctgattctg cagttaatcc ggaacattta | 1440 |
| tcctatttcc actttgttgg acgaataatg ggaatggctg tgtttcatgg acattatatt | 1500 |
| gatggtggtt tcacattgcc tttttataag caattgcttg ggaagtcaat taccttggat | 1560 |
| gacatggagt tagtagatcc ggatcttcac aacagtttag tgtggatact tgagaatgat | 1620 |
| attacaggtg ttttggacca taccttctgt gttgaacata tgcatatgg tgaaattatt | 1680 |
| cagcatgaac ttaaaccaaa tggcaaaagt atccctgtta atgaagaaaa taaaaaagaa | 1740 |
| tatgtcaggc tctatgtgaa ctggagattt ttacgaggca ttgaggctca attcttggct | 1800 |
| ctgcagaaag gatttaatga agtaattcca caacatctgc tgaagacatt tgatgagaag | 1860 |
| gagttagagc tcattatttg tggacttgga agatagatg ttaatgactg aaggtaaac | 1920 |
| acccggttaa acactgtac accagacagc aacattgtca aatggttctg gaaagctgtg | 1980 |
| gagttttttg atgaagagcg acgagcaaga ttgcttcagt ttgtgacagg atcctctcga | 2040 |
| gtgcctctgc agggcttcaa agcattgcaa ggtgctgcag gcccgagact ctttaccata | 2100 |
| caccagattg atgcctgcac taacaacctg ccgaaagccc acacttgctt caatcgaata | 2160 |
| gacattccac cctatgaaag ctatgaaaag ctatatgaaa agctgctaac agccattgaa | 2220 |
| gaaacatgtg gatttgctgt ggaatga | 2247 |

<210> SEQ ID NO 29
<211> LENGTH: 2869
<212> TYPE: DNA
<213> ORGANISM: Homo sapiens

<400> SEQUENCE: 29

| | |
|---|---:|
| ggagtcgccg ccgccccgag ttccggtacc atgcatttca cggtggcctt gtggagacaa | 60 |
| cgccttaacc caaggaagtg actcaaactg tgagaactcc aggttttcca acctattggt | 120 |
| ggtatgtctg acagtggatc acaacttggt tcaatgggta gcctcaccat gaaatcacag | 180 |
| cttcagatca ctgtcatctc agcaaaactt aaggaaaata agaagaattg gtttggacca | 240 |
| agtccttacg tagaggtcac agtagatgga cagtcaaaga agacagaaaa atgcaacaac | 300 |
| acaaacagtc ccaagtggaa gcaacccctt acagttatcg ttaccccctgt gagtaaatta | 360 |
| cattttcgtg tgtggagtca ccagacactg aaatctgatg ttttgttggg aactgctgca | 420 |
| ttagatattt atgaaacatt aaagtcaaac aatatgaaac ttgaagaagt agttgtgact | 480 |
| ttgcagcttg gaggtgacaa agagccaaca gagacaatag agacttgtc aatttgtctt | 540 |
| gatgggctac agttagagtc tgaagttgtt accaatggtg aaactacatg ttcagaaagt | 600 |
| gcttctcaga atgatgatgg ctccagatcc aaggatgaaa caagagtgag cacaaatgga | 660 |

```
tcagatgacc ctgaagatgc aggagctggt gaaaatagga gagtcagtgg gaataattct    720
ccatcactct caaatggtgg ttttaaacct tctagacctc caagaccttc acgaccacca    780
ccacccaccc cacgtagacc agcatctgtc aatggttcac catctgccac ttctgaaagt    840
gatgggtcta gtacaggctc tctgccgccg acaaatacaa atacaaatac atctgaagga    900
gcaacatctg gattaataat tcctcttact atatctggag gctcaggccc taggccatta    960
aatcctgtaa ctcaagctcc cttgccacct ggttgggagc agagagtgga ccagcacggg   1020
cgagtttact atgtagatca tgttgagaaa agaacaacat gggatagacc agaacctcta   1080
cctcctggct gggaacggcg ggttgacaac atgggacgta tttattatgt tgaccatttc   1140
acaagaacaa caacgtggca gaggccaaca ctggaatccg tccggaacta tgaacaatgg   1200
cagctacagc gtagtcagct tcaaggagca atgcagcagt ttaaccagag attcatttat   1260
gggaatcaag atttatttgc tacatcacaa agtaaagaat ttgatcctct tggtccattg   1320
ccacctggat gggagaagag aacagacagc aatggcagag tatatttcgt caaccacaac   1380
acacgaatta cacaatggga agacccccaga agtcaaggtc aattaaatga aaagccctta   1440
cctgaaggtt gggaaatgag attcacagtg gatggaattc catattttgt ggaccacaat   1500
agaagaacta ccacctatat agatccccgc acaggaaaat ctgccctaga caatggacct   1560
cagatagcct atgttcggga cttcaaagca aaggttcagt atttccggtt ctggtgtcag   1620
caactggcca tgccacagca cataaagatt acagtgacaa gaaaaacatt gtttgaggat   1680
tcctttcaac agataatgag cttcagtccc caagatctgc gaagacgttt gtgggtgatt   1740
tttccaggag aagaaggttt agattatgga ggtgtagcaa gagaatggtt cttttctttg   1800
tcacatgaag tgttgaaccc aatgtattgc ctgtttgaat atgcagggaa ggataactac   1860
tgcttgcaga taaaccccgc ttcttacatc aatccagatc acctgaaata ttttcgtttt   1920
attggcagat ttattgccat ggctctgttc catgggaaat tcatagacac gggttttttct   1980 ttaccattct ataagcgtat cttgaacaaa ccagttggac tcaaggattt agaatctatt   2040
gatccagaat tttacaattc tctcatctgg gttaaggaaa acaatattga ggaatgtgat   2100
ttggaaatgt acttctccgt tgacaaagaa attctaggtg aaattaagag tcatgatctg   2160
aaacctaatg gtggcaatat tcttgtaaca gaagaaaata agaggaata catcagaatg   2220 gtagctgagt ggaggttgtc tcgaggtgtt gaagaacaga cacaagcttt ctttgaaggc   2280
tttaatgaaa ttcttcccca gcaatatttg caatactttg atgcaaagga attagaggtc   2340
cttttatgtg gaatgcaaga gattgatttg aatgactggc aaagacatgc catctaccgt   2400
cattatgcaa ggaccagcaa acaaatcatg tggttttggc agtttgttaa agaaattgat   2460
aatgagaaga gaatgagact tctgcagttt gttactggaa cctgccgatt gccagtagga   2520
ggatttgctg atctcatggg gagcaatgga ccacagaaat tctgcattga aaaagttggg   2580
aaagaaaatt ggctacccag aagtcatacc tgtttttaatc gcctggacct gccaccatac   2640
aagagctatg agcaactgaa ggaaaagctg ttgtttgcca tagaagaaac agaaggattt   2700
ggacaagagt aacttctgag aacttgcacc atgaatgggc aagaacttat ttgcaatgtt   2760
tgtccttctc tgcctgttgc acatcttgta aaattggaca atggctcttt agagagttat   2820
ctgagtgtaa gtaaattaat gttctcattt aaaaaaaaaa aaaaaaaa              2869

<210> SEQ ID NO 30
<211> LENGTH: 5169
<212> TYPE: DNA
```

<213> ORGANISM: Homo sapiens

<400> SEQUENCE: 30

```
gcgcatcagg cgctgttgtt ggagccggaa caccgtgcga ctctgaccga accggccccc      60
tcctcgcgca cacactcgcc gagccgcgcg cgccctccg ccgtgacagt ggccgtggcc     120
tccgctctct cggggcaccc ggcagccaga gcgcagcgag agcgggcggt cgccagggtc     180
ccctccccag ccagtcccag gcgcccggtg cactatgcgg ggcacgtgcg cccccagct      240
ctaatctgcg cgctgacagg agcatgatct gtgcccaggc cagggctgcc aaggaattga     300
tgcgcgtaca cgtggtgggt cattatgctg ctacacctgt gtagtgtgaa gaatctgtac     360
cagaacaggt ttttaggcct ggccgccatg gcgtctcctt ctagaaactc ccagagccga     420
cgccggtgca aggagccgct ccgatacagc tacaaccccg accagttcca caacatggac     480
ctcaggggcg gcccccacga tggcgtcacc attccccgct ccaccagcga cactgacctg     540
gtcacctcgg acagccgctc cacgctcatg gtcagcagct cctactattc catcgggcac     600
tctcaggacc tggtcatcca ctgggacata aaggaggaag tggacgctgg ggactggatt     660
ggcatgtacc tcattgatga ggtcttgtcc gaaaactttc tggactataa aaaccgtgga     720
gtcaatggtt ctcatcgggg ccagatcatc tggaagatcg atgccagctc gtactttgtg     780
gaacctgaaa ctaagatctg cttcaaatac taccatggag tgagtggggc cctgcgagca     840
accaccccca gtgtcacggt caaaaactcg gcagctccta tttttaaaag cattggtgct     900
gatgagaccg tccaaggaca aggaagtcgg aggctgatca gcttctctct ctcagatttc     960
caagccatgg ggttgaagaa agggatgttt ttcaacccag acccttatct gaagatttcc    1020
attcagcctg ggaaacacag catcttcccc gccctccctc accatggaca ggagaggaga    1080
tccaagatca taggcaacac cgtgaacccc atctggcagg ccgagcaatt cagttttgtg    1140
tccttgccca ctgacgtgct ggaaattgag gtgaaggaca gtttgccaa gagccgcccc    1200
atcatcaagc gcttcttggg aaagctgtcg atgcccgttc aaagactcct ggagagacac    1260
gccatagggg ataggtggt cagctacaca cttggccgca ggcttccaac agatcatgtg    1320
agtggacagc tgcaattccg atttgagatc acttcctcca tccacccaga tgatgaggag    1380
atttccctga gtaccgagcc tgagtcagcc caaattcagg acagccccat gaacaacctg    1440
atggaaagcg gcagtgggga acctcggtct gaggcaccag agtcctctga gagctggaag    1500
ccagagcagc tgggtgaggg cagtgtcccc gatggtccag ggaaccaaag catagagctt    1560
tccagaccag ctgaggaagc agcagtcatc acggaggcag gagaccaggg catggtctct    1620
gtgggacctg aaggggctgg ggagctcctg gcccaggtgc aaaaggacat ccagcctgcc    1680
cccagtgcag aagagctggc cgagcagctg gacctgggtg aggaggcatc agcactgctg    1740
ctggaagacg gtgaagcccc agccagcacc aaggaggagc ccttggagga ggaagcaacg    1800
acccagagcc gggctggaag ggaagaagag gagaaggagc aggaggagga gggagatgtg    1860
tctaccctgg agcaggagag gggcaggctg cagctgcggg cctcggtgaa gagaaaaagc    1920
aggccctgct ccttgcctgt gtccgagctg gagacggtga tcgcgtcagc ctgcggggac    1980
cccgagaccc cgcggacaca ctacatccgc atccacaccc tgctgcacag catgccctcc    2040
gcccagggcg gcagcgcggc agaggaggag gacgcgcgcg gaggagagtc caccctcaag    2100
gactcctcgg agaaggatgg gctcagcgag gtggacacgg tggccgctga cccgtctgcc    2160
ctggaagagc acagagaaga gcccgagggg gctactccag gcacgcgcca ccctggccac    2220
tccgggggcc acttccccag cctggccaat ggcgcggccc aggatggcga cacgcaccccc    2280
```

```
agcaccggga gcgagagcga ctccagcccc aggcaaggcg gggaccacag ttgcgagggc    2340
tgtgacgcgt cctgctgcag cccctcgtgc tacagctcct cgtgctacag cacgtcctgc    2400
tacagcagct cgtgctacag cgcctcgtgc tacagcccct cctgctacaa cggcaacagg    2460
ttcgccagcc acacgcgctt ctcctccgtg gacagcgcca agatctccga gagcacggtc    2520
ttctcctcgc aagacgacga ggaggaggag aacagcgcgt tcgagtcggt acccgactcc    2580
atgcagagcc ctgagctgga cccggagtcc acgaacggcg ctgggccgtg gcaagacgag    2640
ctggccgccc ctagcgggca cgtggaaaga agcccggaag gtctggaatc ccccgtggca    2700
ggtccaagca atcggagaga agactgggaa gctcgaattg acagccacgg gcgggtcttt    2760
tatgtggacc acgtgaaccg cacaaccacc tggcagcgtc cgacggcagc agccaccccg    2820
gatggcatgc ggagatcggg gtccatccag cagatggagc aactcaacag gcggtatcaa    2880
aacattcagc gaaccattgc aacagagagg tccgaagaag attctggcag ccaaagctgc    2940
gagcaagccc cagcaggagg aggcggaggt ggagggagtg actcagaagc cgaatcttcc    3000
cagtccagct tagatctaag gagagagggg tcactttctc cagtgaactc acaaaaaatc    3060
accttgctgt gcagtcccc agcggtcaag ttcatcacca cccccgagtt cttcactgtg    3120
ctacacgcca attatagtgc ctaccgagtc ttcaccagta gcacctgctt aaagcacatg    3180
attctgaaag tccgacggga tgctcgcaat tttgaacgct accagcacaa ccggacttg    3240 gtgaatttca tcaacatgtt cgcagacact cggctggaac tgccccgggg ctgggagatc    3300
aaaacggacc agcagggaaa gtctttttt gtggaccaca cagtcgagc taccactttc    3360 attgaccccc gaatccctct tcagaacggt cgtcttccca atcatctaac tcaccgacag    3420
cacctccaga ggctccgaag ttacagcgcc ggagaggcct cagaagtttc tagaaacaga    3480
ggagcctctt tactggccag gccaggacac agcttagtag ctgctattcg aagccaacat    3540
caacatgagt cattgccact ggcatataat gacaagattg tggcatttct tcgccagcca    3600 aacattttg aaatgctgca agagcgtcag ccaagcttag caagaaacca cacactcagg    3660
gagaaaatcc attacattcg gactgagggt aatcacgggc ttgagaagtt gtcctgtgat    3720
gcggatctgg tcattttgct gagtctcttt gaagaagaga ttatgtccta cgtcccctg    3780 caggctgcct tccaccctgg gtatagcttc tctccccgat gttcaccctg ttcttcacct    3840
cagaactccc caggttttaca gagagccagt gcaagagccc cttcccccta ccgaagagac    3900
tttgaggcca agctccgcaa tttctacaga aaactggaag ccaaaggatt tggtcagggt    3960
ccggggaaaa ttaagctcat tattcgccgg gatcatttgt tggagggaac cttcaatcag    4020
gtgatggcct attcgcggaa agagctccag cgaaacaagc tctacgtcac ctttgttgga    4080
gaggagggcc tggactacag tggccccctcg cgggagttct cttccttct gtctcaggag    4140 ctcttcaacc cttactatgg actctttgag tactcggcaa atgatactta cacggtgcag    4200
atcagcccca tgtccgcatt tgtagaaaac catcttgagt ggttcaggtt tagcggtcgc    4260
atcctgggtc tggctctgat ccatcagtac cttcttgacg cttcttcac gaggcccttc    4320 tacaaggcac tcctgagact gcccttgtgat ttgagtgacc tggaatattt ggatgaggaa    4380
ttccaccaga gtttgcagtg gatgaaggac aacaacatca cagacatctt agacctcact    4440
ttcactgtta atgaagaggt ttttggacag gtcacggaaa gggagttgaa gtctggagga    4500
gccaacacac aggtgacgga gaaaacaag aaggagtaca tcgagcgcat ggtgaagtgg    4560
cgggtggagc gcggcgtggt acagcagacc gaggcgctgg tgcgcggctt ctacgaggtt    4620
```

| | |
|---|---|
| gtagactcga ggctggtgtc cgtgtttgat gccagggagc tggagctggt gatagctggc | 4680 |
| accgcggaaa tcgacctaaa tgactggcgg aataacactg agtaccgggg aggttaccac | 4740 |
| gatgggcatc ttgtgatccg ctggttctgg gctgcggtgg agcgcttcaa taatgagcag | 4800 |
| aggctgagat tactgcagtt tgtcacggga acatccagcg tgccctacga aggcttcgca | 4860 |
| gccctccgtg ggagcaatgg gcttcggcgc ttctgcatag agaaatgggg gaaaattact | 4920 |
| tctctcccca gggcacacac atgcttcaac cgactggatc ttccaccgta tccctcgtac | 4980 |
| tccatgttgt atgaaaagct gttaacagca gtagaggaaa ccagcacctt tggacttgag | 5040 |
| tgaggacatg gaacctcgcc tgacattttc ctggccagtg acatcaccct tcctgggatg | 5100 |
| atccccttttt cccttttccct taatcaactc tcctttgatt ttggtattcc atgatttttta | 5160 |
| ttttcaaac | 5169 |

<210> SEQ ID NO 31
<211> LENGTH: 2715
<212> TYPE: DNA
<213> ORGANISM: Homo sapiens

<400> SEQUENCE: 31

| | |
|---|---|
| agagttccat cagagcctgc agtggatgaa agacaatgat atccatgaca tcctagacct | 60 |
| cacgttcact gtgaacgaag aagtatttgg gcagataact gaacgagaat taaagccagg | 120 |
| gggtgccaat atcccagtta cagagaagaa caagaaggag tacatcgaga ggatggtgaa | 180 |
| gtggaggatt gagaggggtg ttgtacagca acagagagc ttagtgcgtg gcttctatga | 240 |
| ggtggtggat gccaggctgg tatctgtttt tgatgcaaga gaactggaat tggtcatcgc | 300 |
| aggcacagct gaaatagacc taagtgattg gagaaacaac acagaatata gaggaggata | 360 |
| ccatgacaat catattgtaa ttcggtggtt ctgggctgca gtggaaagat caacaatga | 420 |
| acaacgacta aggttgttac agtttgttac aggcacatcc agcattccct atgaaggatt | 480 |
| tgcttcactc cgagggagta acggcccaag aagattctgt gtggagaaat gggggaaaat | 540 |
| cactgctctt cccagagcgc atacatgttt taaccgtctg atctgcctc cctacccatc | 600 |
| cttttccatg cttatgaaa aactgttgac agcagttgaa gaaaccagta cttttggact | 660 |
| tgagtgacct ggaagctgaa tgcccatctc tgtggacagg cagtttcaga agctgccttc | 720 |
| tagaagaatg attgaacatt ggaagtttca agaggatgct tcctttagga taaagctacg | 780 |
| tgctgttgtt ttccaggaac aagtgctctg tcacatttgg ggactggaga tgagtcctct | 840 |
| tggaaggatt tgggtgagct tgatgcccag ggaacaaccc aaccgtcttt caatcaacag | 900 |
| ttcttgactg ccaaactttt tccatttgtt atgttccaag acaaagatga acccatacat | 960 |
| gatcagctcc acggtaattt ttagggactc aggagaatct tgaaacttac ccttgaacgt | 1020 |
| ggttcaagcc aaactggcag catttggccc aatctccaaa ttagagcaag ttaaataata | 1080 |
| taataaaagt aaatatattt cctgaaagta cattcattta agccctaagt tataacagaa | 1140 |
| tattcatttc ttgcttatga gtgcctgcat ggtgtgcacc ataggtttcc gctttcatgg | 1200 |
| gacatgagtg aaaatgaaac caagtcaata tgaggtacct ttacagattt gcaataagat | 1260 |
| ggtctgtgac aatgtatatg caagtggtat gtgtgtaatt atggctaaag acaaaccatt | 1320 |
| attcagtgaa ttactaatga cagatttat gctttataat gcatgaaaac aatttttaaaa | 1380 |
| taactagcaa ttaatcacag catatcagga aaaagtacac agtgagttct gtttattttt | 1440 |
| tgtaggctca ttatgtttat gttctttaag atgtatataa gaacctactt atcatgctgt | 1500 |
| atgtatcact cattccattt tcatgttcca tgcatactcg ggcatcatgc taatatgtat | 1560 |

```
ccttttaagc actctcaagg aaacaaaagg gccttttatt tttataaagg taaaaaaaat    1620
tccccaaata ttttgcactg aatgtaccaa aggtgaaggg acattacaat atgactaaca    1680
gcaactccat cacttgagaa gtaataraga aaatagcttc taaatcaaac ttccttcaca    1740
gtgccgtgtc taccactaca aggactgtgc atctaagtaa taattttta agattcacta    1800 tatgtgatag tatgatatgc atttatttaa aatgcattag actctcttcc atccatcaaa    1860
tactttacag gatggcattt aatacagata tttcgtattt cccccactgc ttttatttg    1920 tacagcatca ttaaacacta agctcagtta aggagccatc agcaacactg aagagatcag    1980
tagtaagaat tccatttcc ctcatcagtg aagacaccac aaattgaaac tcagaactat     2040
atttctaagc ctgcattttc actgatgcat aattttctta ttaatattaa gagacagttt    2100
ttctatggca tctccaaaac tgcatgacat cactagtctt acttctgctt aattttatga    2160
gaaggtattc ttcattttaa ttgcttttgg gattactcca catctttgtt tatttcttga    2220
ctaatcagat tttcaataga gtgaagttaa attgggggtc ataaaagcat tggattgaca    2280
tatggtttgc cagcctatgg gtttacaggc attgcccaaa catttctttg agatctatat    2340
ttataagcag ccatggaatt cctattatgg gatgttggca atcttacatt ttatagaggt    2400
catatgcata gttttcatag gtgttttgta agaactgatt gctctcctgt gagttaagct    2460
atgtttacta ctgggaccct caagaggaat accacttatg ttacactcct gcactaaagg    2520
cacgtactgc agtgtgaaga atgttctga aaaagggtta tagaaatctg gaaataagaa     2580
aggaagagct ctctgtattc tataattgga agagaaaaaa agaaaaactt ttaactggaa    2640
atgttagttt gtacttattg atcatgaata caagtatata tttaattttg caaaaaaaa     2700 aaaaaaaaaa aaaag                                                    2715

<210> SEQ ID NO 32
<211> LENGTH: 195
<212> TYPE: DNA
<213> ORGANISM: Homo sapiens

<400> SEQUENCE: 32
cccttgccac ctggttggga gcagagagtg gaccagcacg ggcgagttta ctatgtagat      60
catgttgaga aagaacaac atgggataga ccagaacctc tacctcctgg ctgggaacgg     120
cgggttgaca acatgggacg tatttattat gttgaccatt tcacaagaac aacaacgtgg    180
cagaggccaa cactg                                                    195

<210> SEQ ID NO 33
<211> LENGTH: 555
<212> TYPE: DNA
<213> ORGANISM: Homo sapiens

<400> SEQUENCE: 33
cccttgccac ctggttggga gcagagagtg gaccagcacg ggcgagttta ctatgtagat      60
catgttgaga aagaacaac atgggataga ccagaacctc tacctcctgg ctgggaacgg     120
cgggttgaca acatgggacg tatttattat gttgaccatt tcacaagaac aacaacgtgg    180
cagaggccaa cactggaatc cgtccggaac tatgaacaat ggcagctaca gcgtagtcag    240
cttcaaggag caatgcagca gtttaaccag agattcattt atgggaatca agatttattt    300
gctacatcac aaagtaaaga atttgatcct cttggtccat tgccacctgg atgggagaag    360
agaacagaca gcaatggcag agtatatttc gtcaaccaca acacacgaat tacacaatgg    420
```

```
gaagacccca gaagtcaagg tcaattaaat gaaaagccct tacctgaagg ttgggaaatg    480
agattcacag tggatggaat tccatatttt gtggaccaca atagaagaac taccacctat    540
atagatcccc gcaca                                                     555
```

<210> SEQ ID NO 34
<211> LENGTH: 8506
<212> TYPE: DNA
<213> ORGANISM: Artificial Sequence
<220> FEATURE:
<223> OTHER INFORMATION: Synthetic

<400> SEQUENCE: 34

```
gagggcctat ttcccatgat tccttcatat ttgcatatac gatacaaggc tgttagagag     60
ataattggaa ttaatttgac tgtaaacaca aagatattag tacaaaatac gtgacgtaga    120
aagtaataat ttcttgggta gtttgcagtt ttaaaattat gttttaaaat ggactatcat    180
atgcttaccg taacttgaaa gtatttcgat tcttggcctt tatatatctt gtggaaagga    240
cgaaacaccg gtcttcgag aagacctgtt ttagagctag aaatagcaag ttaaaataag    300
gctagtccgt tatcaacttg aaaaagtggc accgagtcgg tgctttttg ttttagagct    360 agaaatagca agttaaaata aggctagtcc gttttagcg cgtgcgccaa ttctgcagac    420
aaatggctct agaggtaccc gttacataac ttacggtaaa tggcccgcct ggctgaccgc    480
ccaacgaccc ccgcccattg acgtcaatag taacgccaat agggactttc cattgacgtc    540
aatgggtgga gtatttacgg taaactgccc acttggcagt acatcaagtg tatcatatgc    600
caagtacgcc ccctattgac gtcaatgacg gtaaatggcc cgcctggcat tgtgcccagt    660
acatgacctt atgggacttt cctacttggc agtacatcta cgtattagtc atcgctatta    720
ccatggtcga ggtgagcccc acgttctgct tcactctccc catctccccc cctccccac    780 ccccaatttt gtatttattt attttttaat tattttgtgc agcgatgggg gcgggggggg    840
ggggggggcg cgcgccaggc ggggcggggc gggcgaggg gcgggcggg gcgaggcgga    900 gaggtgcggc ggcagccaat cagagcggcg cgctccgaaa gtttccttt atggcgaggc    960 ggcggcggcg gcgccctat aaaaagcgaa gcgcgcggcg gcgggagtc gctgcgacgc   1020 tgccttcgcc ccgtgccccg ctccgccgcc gcctcgcgcc gcccgccccg gctctgactg   1080
accgcgttac tcccacaggt gagcgggcgg gacggccctt ctcctccggg ctgtaattag   1140
ctgagcaaga ggtaagggtt taagggatgg ttggttggtg gggtattaat gtttaattac   1200
ctggagcacc tgcctgaaat cactttttt caggttggac cggtgccacc atggactata   1260
aggaccacga cggagactac aaggatcatg atattgatta caaagacgat gacgataaga   1320
tggccccaaa gaagaagcgg aaggtcggta tccacggagt cccagcagcc gacaagaagt   1380
acagcatcgg cctggacatc ggcaccaact ctgtgggctg ggccgtgatc accgacgagt   1440
acaaggtgcc cagcaagaaa ttcaaggtgc tgggcaacac cgaccggcac agcatcaaga   1500
agaacctgat cggagccctg ctgttcgaca gcggcgaaac agccgaggcc acccggctga   1560
agagaaccgc cagaagaaga tacaccagac ggaagaaccg gatctgctat ctgcaagaga   1620
tcttcagcaa cgagatggcc aaggtggacg acagcttctt ccacagactg gaagagtcct   1680
tcctggtgga agaggataag aagcacgagc ggcaccccat cttcggcaac atcgtggacg   1740
aggtggccta ccacgagaag taccccacca tctaccacct gagaaagaaa ctggtggaca   1800
gcaccgacaa ggccgacctg cggctgatct atctggccct ggcccacatg atcaagttcc   1860
ggggccactt cctgatcgag ggcgacctga accccgacaa cagcgacgtg gacaagctgt   1920
```

```
tcatccagct ggtgcagacc tacaaccagc tgttcgagga aaacccccatc aacgccagcg   1980
gcgtggacgc caaggccatc ctgtctgcca gactgagcaa gagcagacgg ctggaaaatc   2040
tgatcgccca gctgccggc  gagaagaaga atggcctgtt cggaaacctg attgccctga   2100
gcctgggcct gacccccaac ttcaagagca acttcgacct ggccgaggat gccaaactgc   2160
agctgagcaa ggacacctac gacgacgacc tggacaacct gctggcccag atcggcgacc   2220
agtacgccga cctgtttctg ccgccaagaa cctgtccga  cgccatcctg ctgagcgaca   2280
tcctgagagt gaacaccgag atcaccaagg ccccctgag  cgcctctatg atcaagagat   2340
acgacgagcc ccaccaggac ctgaccctgc tgaaagctct cgtgcggcag cagctgcctg   2400
agaagtacaa agagattttc ttcgaccaga gcaagaacgg ctacgccggc tacattgacg   2460
gcggagccag ccaggaagag ttctacaagt tcatcaagcc catcctggaa agatgggacg   2520
gcaccgagga actgctcgtg aagctgaaca gagaggacct gctgcggaag cagcggacct   2580
tcgacaacgg cagcatcccc caccagatcc acctgggaga gctgcacgcc attctgcggc   2640
ggcaggaaga tttttacccca ttcctgaagg acaaccggga aaagatcgag aagatcctga   2700
ccttccgcat cccctactac gtgggccctc tggccagggg aaacagcaga ttcgcctgga   2760
tgaccagaaa gagcgaggaa accatcaccc cctggaactt cgaggaagtg gtggacaagg   2820
gcgcttccgc ccagagcttc atcgagcgga tgaccaactt cgataagaac ctgcccaacg   2880
agaaggtgct gcccaagcac agcctgctgt acgagtactt caccgtgtat aacgagctga   2940
ccaaagtgaa atacgtgacc gagggaatga gaaagcccgc cttcctgagc ggcgagcaga   3000
aaaaggccat cgtggacctg ctgttcaaga ccaaccggaa agtgaccgtg aagcagctga   3060
aagaggacta cttcaagaaa atcgagtgct tcgactccgt ggaaatctcc ggcgtggaag   3120
atcggttcaa cgcctccctg ggcacatacc acgatctgct gaaaattatc aaggacaagg   3180
acttcctgga caatgaggaa aacgaggaca ttctggaaga tatcgtgctg accctgacac   3240
tgtttgagga cagagagatg atcgaggaac ggctgaaaac ctatgcccac ctgttcgacg   3300
acaaagtgat gaagcagctg aagcggcgga tataccggg ctggggcagg ctgagccgga   3360
agctgatcaa cggcatccgg gacaagcagt ccggcaagac aatcctggat ttcctgaagt   3420
ccgacggctt cgccaacaga aacttcatgc agctgatcca cgacgacagc ctgaccttta   3480
agaggacat  ccagaaagcc caggtgtccg gccagggcga tagcctgcac gagcacattg   3540
ccaatctggc cggcagcccc gccattaaga agggcatcct gcagacagtg aaggtggtgg   3600
acgagctcgt gaaagtgatg ggccggcaca gcccgagaa catcgtgatc gaaatggcca   3660
gagagaacca gaccacccag aagggacaga gaacagccg  cgagagaatg aagcggatcg   3720
aagagggcat caaagagctg ggcagccaga tcctgaaaga acaccccgtg gaaaacaccc   3780
agctgcagaa cgagaagctg tacctgtact acctgcagaa tgggcgggat atgtacgtgg   3840
accaggaact ggacatcaac cggctgtccg actacgatgt ggaccatatc gtgcctcaga   3900
gctttctgaa ggacgactcc atcgacaaca aggtgctgac cagaagcgac aagaaccggg   3960
gcaagagcga caacgtgccc tccgaagagg tcgtgaagaa gatgaagaac tactggcggc   4020
agctgctgaa cgccaagctg attacccaga gaaagttcga caatctgacc aaggccgaga   4080
gaggcggcct gagcgaactg gataaggccg gcttcatcaa gagacagctg gtggaaaccc   4140
ggcagatcac aaagcacgtg gcacagatcc tggactcccg gatgaacact aagtacgacg   4200
agaatgacaa gctgatccgg gaagtgaaag tgatcaccct gaagtccaag ctggtgtccg   4260
```

-continued

```
atttccggaa ggatttccag ttttacaaag tgcgcgagat caacaactac caccacgccc    4320
acgacgccta cctgaacgcc gtcgtgggaa ccgccctgat caaaaagtac cctaagctgg    4380
aaagcgagtt cgtgtacggc gactacaagg tgtacgacgt gcggaagatg atcgccaaga    4440
gcgagcagga atcggcaag gctaccgcca agtacttctt ctacagcaac atcatgaact     4500
ttttcaagac cgagattacc ctggccaacg gcgagatccg gaagcggcct ctgatcgaga    4560
caaacggcga aaccgggag atcgtgtggg ataagggccg ggattttgcc accgtgcgga     4620
aagtgctgag catgccccaa gtgaatatcg tgaaaaagac cgaggtgcag acaggcggct    4680
tcagcaaaga gtctatcctg cccaagagga acagcgataa gctgatcgcc agaaagaagg    4740
actgggaccc taagaagtac ggcggcttcg acagccccac cgtggcctat tctgtgctgg    4800
tggtggccaa agtggaaaag gcaagtcca agaaactgaa gagtgtgaaa gagctgctgg     4860
ggatcaccat catggaaaga agcagcttcg agaagaatcc catcgacttt ctggaagcca    4920
agggctacaa agaagtgaaa aaggacctga tcatcaagct gcctaagtac tccctgttcg    4980
agctggaaaa cggccggaag agaatgctgg cctctgccgg cgaactgcag aagggaaacg    5040
aactggcct gcctccaaa tatgtgaact tcctgtacct ggccagccac tatgagaagc      5100
tgaagggctc ccccgaggat aatgagcaga acagctgtt tgtggaacag cacaagcact    5160
acctggacga gatcatcgag cagatcagcg agttctccaa gagagtgatc ctggccgacg    5220
ctaatctgga caaagtgctg tccgcctaca caagcaccg gataagccc atcagagagc      5280
aggccgagaa tatcatccac ctgtttaccc tgaccaatct gggagcccct gccgccttca    5340
agtactttga caccaccatc gaccggaaga ggtacaccag caccaaagag gtgctggacg    5400
ccaccctgat ccaccagagc atcaccggcc tgtacgagac acggatcgac ctgtctcagc    5460
tgggaggcga caaaggccg gcggccacga aaaaggccgg ccaggcaaaa agaaaaagt      5520
aagaattcct agagctcgct gatcagcctc gactgtgcct tctagttgcc agccatctgt    5580
tgtttgcccc tccccgtgc cttccttgac cctggaaggt gccactccca ctgtcctttc     5640
ctaataaaat gaggaaattg catcgcattg tctgagtagg tgtcattcta ttctgggggg    5700
tggggtgggg caggacagca agggggagga ttgggaagag aatagcaggc atgctgggga    5760
gcggccgcag gaaccctag tgatggagtt ggccactccc tctctgcgcg ctcgctcgct    5820
cactgaggcc gggcgaccaa aggtcgcccg acgcccgggc tttgcccggg cggcctcagt    5880
gagcgagcga gcgcgcagct gcctgcaggg gcgcctgatg cggtattttc tccttacgca    5940
tctgtgcggt atttcacacc gcatacgtca aagcaaccat agtacgcgcc ctgtagcggc    6000
gcattaagcg cggcgggtgt ggtggttacg cgcagcgtga ccgctacact tgccagcgcc    6060
ctagcgcccg ctcctttcgc tttcttccct tcctttctcg ccacgttcgc cggctttccc    6120
cgtcaagctc taaatcgggg gctcccttta gggttccgat ttagtgcttt acggcacctc    6180
gaccccaaaa aacttgattt gggtgatggt tcacgtagtg gccatcgcc ctgatagacg      6240
gttttttcgcc cttgacgtt ggagtccacg ttctttaata gtggactctt gttccaaact     6300
ggaacaacac tcaaccctat ctcgggctat tctttgatt tataagggat tttgccgatt      6360
tcggcctatt ggttaaaaaa tgagctgatt taacaaaaat ttaacgcgaa ttttaacaaa    6420
atattaacgt ttacaatttt atggtgcact ctcagtacaa tctgctctga tgccgcatag    6480
ttaagccagc cccgacaccc gccaacaccc gctgacgcgc cctgacgggc ttgtctgctc    6540
ccggcatccg cttacagaca agctgtgacc gtctccggga gctgcatgtg tcagaggttt    6600
tcaccgtcat caccgaaacg cgcgagacga aagggcctcg tgatacgcct atttttatag    6660
```

```
gttaatgtca tgataataat ggtttcttag acgtcaggtg gcacttttcg gggaaatgtg    6720
cgcggaaccc ctatttgttt attttttctaa atacattcaa atatgtatcc gctcatgaga   6780
caataaccct gataaatgct tcaataatat tgaaaaagga agagtatgag tattcaacat    6840
ttccgtgtcg cccttattcc cttttttgcg gcattttgcc ttcctgtttt tgctcaccca    6900
gaaacgctgg tgaaagtaaa agatgctgaa gatcagttgg gtgcacgagt gggttacatc    6960
gaactggatc tcaacagcgg taagatcctt gagagttttc gccccgaaga acgttttcca    7020
atgatgagca cttttaaagt tctgctatgt ggcgcggtat tatcccgtat tgacgccggg    7080
caagagcaac tcggtcgccg catacactat tctcagaatg acttggttga gtactcacca    7140
gtcacagaaa agcatcttac ggatggcatg acagtaagag aattatgcag tgctgccata    7200
accatgagtg ataacactgc ggccaactta cttctgacaa cgatcggagg accgaaggag    7260
ctaaccgctt ttttgcacaa catgggggat catgtaactc gccttgatcg ttgggaaccg    7320
gagctgaatg aagccatacc aaacgacgag cgtgacacca cgatgcctgt agcaatggca    7380
acaacgttgc gcaaactatt aactggcgaa ctacttactc tagcttcccg gcaacaatta    7440
atagactgga tggaggcgga taaagttgca ggaccacttc tgcgctcggc ccttccggct    7500
ggctggttta ttgctgataa atctggagcc ggtgagcgtg gaagccgcgg tatcattgca    7560
gcactggggc cagatggtaa gccctcccgt atcgtagtta tctacacgac ggggagtcag    7620
gcaactatgg atgaacgaaa tagacagatc gctgagatag gtgcctcact gattaagcat    7680
tggtaactgt cagaccaagt ttactcatat atactttaga ttgatttaaa acttcatttt    7740
taatttaaaa ggatctaggt gaagatcctt tttgataatc tcatgaccaa aatcccttaa    7800
cgtgagtttt cgttccactg agcgtcagac cccgtagaaa agatcaaagg atcttcttga    7860 gatcctttt ttctgcgcgt aatctgctgc ttgcaaacaa aaaaaccacc gctaccagcg    7920
gtggtttgtt tgccggatca agagctacca actctttttc cgaaggtaac tggcttcagc    7980
agagcgcaga taccaaatac tgtccttcta gtgtagccgt agttaggcca ccacttcaag    8040
aactctgtag caccgcctac atacctcgct ctgctaatcc tgttaccagt ggctgctgcc    8100
agtggcgata agtcgtgtct taccgggttg gactcaagac gatagttacc ggataaggcg    8160
cagcggtcgg gctgaacggg gggttcgtgc acacagccca gcttggagcg aacgacctac    8220
accgaactga gatacctaca gcgtgagcta tgagaaagcg ccacgcttcc cgaagggaga    8280
aaggcggaca ggtatccggt aagcggcagg gtcggaacag gagagcgcac gagggagctt    8340
ccagggggaa acgcctggta tctttatagt cctgtcgggt ttcgccacct ctgacttgag    8400
cgtcgatttt tgtgatgctc gtcagggggg cggagcctat ggaaaaacgc cagcaacgcg    8460
gcctttttac ggttcctggc cttttgctgg ccttttgctc acatgt             8506
```

<210> SEQ ID NO 35
<211> LENGTH: 238
<212> TYPE: PRT
<213> ORGANISM: Aequorea victoria

<400> SEQUENCE: 35

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
            50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
            130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
            195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 36
<211> LENGTH: 34
<212> TYPE: PRT
<213> ORGANISM: Homo sapiens

<400> SEQUENCE: 36

Glu Thr Leu Pro Ser Gly Trp Glu Gln Arg Lys Asp Pro His Gly Arg
1               5                   10                  15

Thr Tyr Tyr Val Asp His Asn Thr Arg Thr Thr Thr Trp Glu Arg Pro
                20                  25                  30

Gln Pro

<210> SEQ ID NO 37
<211> LENGTH: 34
<212> TYPE: PRT
<213> ORGANISM: Homo sapiens

<400> SEQUENCE: 37

Gln Pro Leu Pro Pro Gly Trp Glu Arg Arg Val Asp Asp Arg Arg
1               5                   10                  15

Val Tyr Tyr Val Asp His Asn Thr Arg Thr Thr Thr Trp Gln Arg Pro
                20                  25                  30

Thr Met

<210> SEQ ID NO 38
<211> LENGTH: 39
<212> TYPE: PRT
<213> ORGANISM: Homo sapiens

<400> SEQUENCE: 38

Glu Asn Asp Pro Tyr Gly Pro Leu Pro Pro Gly Trp Glu Lys Arg Val
1               5                   10                  15

Asp Ser Thr Asp Arg Val Tyr Phe Val Asn His Asn Thr Lys Thr Thr
            20                  25                  30

Gln Trp Glu Asp Pro Arg Thr
        35

<210> SEQ ID NO 39
<211> LENGTH: 34
<212> TYPE: PRT
<213> ORGANISM: Homo sapiens

<400> SEQUENCE: 39

Glu Pro Leu Pro Glu Gly Trp Glu Ile Arg Tyr Thr Arg Gly Val
1               5                   10                  15

Arg Tyr Phe Val Asp His Asn Thr Arg Thr Thr Thr Phe Lys Asp Pro
            20                  25                  30

Arg Asn

<210> SEQ ID NO 40
<211> LENGTH: 34
<212> TYPE: PRT
<213> ORGANISM: Homo sapiens

<400> SEQUENCE: 40

Asp Ala Leu Pro Ala Gly Trp Glu Gln Arg Glu Leu Pro Asn Gly Arg
1               5                   10                  15

Val Tyr Tyr Val Asp His Asn Thr Lys Thr Thr Thr Trp Glu Arg Pro
            20                  25                  30

Leu Pro

<210> SEQ ID NO 41
<211> LENGTH: 33
<212> TYPE: PRT
<213> ORGANISM: Homo sapiens

<400> SEQUENCE: 41

Pro Leu Pro Pro Gly Trp Glu Lys Arg Thr Asp Pro Arg Gly Arg Phe
1               5                   10                  15

Tyr Tyr Val Asp His Asn Thr Arg Thr Thr Thr Trp Gln Arg Pro Thr
            20                  25                  30

Ala

<210> SEQ ID NO 42
<211> LENGTH: 37
<212> TYPE: PRT
<213> ORGANISM: Homo sapiens

<400> SEQUENCE: 42

His Asp Pro Leu Gly Pro Leu Pro Pro Gly Trp Glu Lys Arg Gln Asp
1               5                   10                  15

Asn Gly Arg Val Tyr Tyr Val Asn His Asn Thr Arg Thr Thr Gln Trp
            20                  25                  30

Glu Asp Pro Arg Thr
        35

<210> SEQ ID NO 43
<211> LENGTH: 34
<212> TYPE: PRT
<213> ORGANISM: Homo sapiens

<400> SEQUENCE: 43

Pro Ala Leu Pro Pro Gly Trp Glu Met Lys Tyr Thr Ser Glu Gly Val
1               5                   10                  15

Arg Tyr Phe Val Asp His Asn Thr Arg Thr Thr Thr Phe Lys Asp Pro
            20                  25                  30

Arg Pro

<210> SEQ ID NO 44
<211> LENGTH: 34
<212> TYPE: PRT
<213> ORGANISM: Homo sapiens

<400> SEQUENCE: 44

Ser Pro Leu Pro Pro Gly Trp Glu Glu Arg Gln Asp Ile Leu Gly Arg
1               5                   10                  15

Thr Tyr Tyr Val Asn His Glu Ser Arg Arg Thr Gln Trp Lys Arg Pro
            20                  25                  30

Thr Pro

<210> SEQ ID NO 45
<211> LENGTH: 34
<212> TYPE: PRT
<213> ORGANISM: Homo sapiens

<400> SEQUENCE: 45

Ser Gly Leu Pro Pro Gly Trp Glu Glu Lys Gln Asp Glu Arg Gly Arg
1               5                   10                  15

Ser Tyr Tyr Val Asp His Asn Ser Arg Thr Thr Thr Thr Lys Pro
            20                  25                  30

Thr Val

<210> SEQ ID NO 46
<211> LENGTH: 34
<212> TYPE: PRT
<213> ORGANISM: Homo sapiens

<400> SEQUENCE: 46

Gly Phe Leu Pro Lys Gly Trp Glu Val Arg His Ala Pro Asn Gly Arg
1               5                   10                  15

Pro Phe Phe Ile Asp His Asn Thr Lys Thr Thr Thr Trp Glu Asp Pro
            20                  25                  30

Arg Leu

<210> SEQ ID NO 47
<211> LENGTH: 34
<212> TYPE: PRT
<213> ORGANISM: Homo sapiens

<400> SEQUENCE: 47

Gly Pro Leu Pro Pro Gly Trp Glu Glu Arg Thr His Thr Asp Gly Arg
1               5                   10                  15

Ile Phe Tyr Ile Asn His Asn Ile Lys Arg Thr Gln Trp Glu Asp Pro
            20                  25                  30

Arg Leu

<210> SEQ ID NO 48
<211> LENGTH: 34
<212> TYPE: PRT
<213> ORGANISM: Homo sapiens

<400> SEQUENCE: 48

Pro Glu Leu Pro Glu Gly Tyr Glu Gln Arg Thr Thr Val Gln Gly Gln
1               5                   10                  15

Val Tyr Phe Leu His Thr Gln Thr Gly Val Ser Thr Trp His Asp Pro
            20                  25                  30

Arg Ile

<210> SEQ ID NO 49
<211> LENGTH: 34
<212> TYPE: PRT
<213> ORGANISM: Homo sapiens

<400> SEQUENCE: 49

Gly Pro Leu Pro Pro Gly Trp Glu Val Arg Ser Thr Val Ser Gly Arg
1               5                   10                  15

Ile Tyr Phe Val Asp His Asn Asn Arg Thr Thr Gln Phe Thr Asp Pro
            20                  25                  30

Arg Leu

<210> SEQ ID NO 50
<211> LENGTH: 34
<212> TYPE: PRT
<213> ORGANISM: Homo sapiens

<400> SEQUENCE: 50

Asn Asp Leu Pro Asp Gly Trp Glu Glu Arg Arg Thr Ala Ser Gly Arg
1               5                   10                  15

Ile Gln Tyr Leu Asn His Ile Thr Arg Thr Thr Gln Trp Glu Arg Pro
            20                  25                  30

Thr Arg

<210> SEQ ID NO 51
<211> LENGTH: 34
<212> TYPE: PRT
<213> ORGANISM: Homo sapiens

<400> SEQUENCE: 51

Pro Asp Leu Pro Glu Gly Tyr Glu Gln Arg Thr Thr Gln Gln Gly Gln
1               5                   10                  15

Val Tyr Phe Leu His Thr Gln Thr Gly Val Ser Thr Trp His Asp Pro
            20                  25                  30

Arg Val

<210> SEQ ID NO 52
<211> LENGTH: 34
<212> TYPE: PRT
<213> ORGANISM: Homo sapiens

<400> SEQUENCE: 52

Gly Pro Leu Pro Pro Gly Trp Glu Ile Arg Asn Thr Ala Thr Gly Arg
1               5                   10                  15

Val Tyr Phe Val Asp His Asn Asn Arg Thr Thr Gln Phe Thr Asp Pro
            20                  25                  30

Arg Leu

<210> SEQ ID NO 53
<211> LENGTH: 34
<212> TYPE: PRT
<213> ORGANISM: Homo sapiens

<400> SEQUENCE: 53

Ala Pro Leu Pro Pro Gly Trp Glu Gln Arg Val Asp Gln His Gly Arg
1               5                   10                  15

Val Tyr Tyr Val Asp His Val Glu Lys Arg Thr Thr Trp Asp Arg Pro
                20                  25                  30

Glu Pro

<210> SEQ ID NO 54
<211> LENGTH: 34
<212> TYPE: PRT
<213> ORGANISM: Homo sapiens

<400> SEQUENCE: 54

Glu Pro Leu Pro Pro Gly Trp Glu Arg Arg Val Asp Asn Met Gly Arg
1               5                   10                  15

Ile Tyr Tyr Val Asp His Phe Thr Arg Thr Thr Thr Trp Gln Arg Pro
                20                  25                  30

Thr Leu

<210> SEQ ID NO 55
<211> LENGTH: 34
<212> TYPE: PRT
<213> ORGANISM: Homo sapiens

<400> SEQUENCE: 55

Gly Pro Leu Pro Pro Gly Trp Glu Lys Arg Thr Asp Ser Asn Gly Arg
1               5                   10                  15

Val Tyr Phe Val Asn His Asn Thr Arg Ile Thr Gln Trp Glu Asp Pro
                20                  25                  30

Arg Ser

<210> SEQ ID NO 56
<211> LENGTH: 34
<212> TYPE: PRT
<213> ORGANISM: Homo sapiens

<400> SEQUENCE: 56

Lys Pro Leu Pro Glu Gly Trp Glu Met Arg Phe Thr Val Asp Gly Ile
1               5                   10                  15

Pro Tyr Phe Val Asp His Asn Arg Arg Thr Thr Thr Tyr Ile Asp Pro
                20                  25                  30

Arg Thr

<210> SEQ ID NO 57
<211> LENGTH: 33
<212> TYPE: PRT
<213> ORGANISM: Homo sapiens

<400> SEQUENCE: 57

Pro Leu Pro Pro Asn Trp Glu Ala Arg Ile Asp Ser His Gly Arg Val
1               5                   10                  15

Phe Tyr Val Asp His Val Asn Arg Thr Thr Thr Trp Gln Arg Pro Thr
                20                  25                  30

Ala

<210> SEQ ID NO 58
<211> LENGTH: 34
<212> TYPE: PRT

<213> ORGANISM: Homo sapiens

<400> SEQUENCE: 58

Leu Glu Leu Pro Arg Gly Trp Glu Ile Lys Thr Asp Gln Gln Gly Lys
1               5                   10                  15

Ser Phe Phe Val Asp His Asn Ser Arg Ala Thr Thr Phe Ile Asp Pro
            20                  25                  30

Arg Ile

<210> SEQ ID NO 59
<211> LENGTH: 34
<212> TYPE: PRT
<213> ORGANISM: Homo sapiens

<400> SEQUENCE: 59

Glu Ala Leu Pro Pro Asn Trp Glu Ala Arg Ile Asp Ser His Gly Arg
1               5                   10                  15

Ile Phe Tyr Val Asp His Val Asn Arg Thr Thr Thr Trp Gln Arg Pro
            20                  25                  30

Thr Ala

<210> SEQ ID NO 60
<211> LENGTH: 34
<212> TYPE: PRT
<213> ORGANISM: Homo sapiens

<400> SEQUENCE: 60

Leu Glu Leu Pro Arg Gly Trp Glu Met Lys His Asp His Gln Gly Lys
1               5                   10                  15

Ala Phe Phe Val Asp His Asn Ser Arg Thr Thr Thr Phe Ile Asp Pro
            20                  25                  30

Arg Leu

<210> SEQ ID NO 61
<211> LENGTH: 27
<212> TYPE: PRT
<213> ORGANISM: Homo sapiens

<400> SEQUENCE: 61

Gly Trp Glu Glu Lys Val Asp Asn Leu Gly Arg Thr Tyr Tyr Val Asn
1               5                   10                  15

His Asn Asn Arg Thr Thr Gln Trp His Arg Pro
            20                  25

<210> SEQ ID NO 62
<211> LENGTH: 29
<212> TYPE: PRT
<213> ORGANISM: Homo sapiens

<400> SEQUENCE: 62

Pro Ser Gly Trp Glu Glu Arg Lys Asp Ala Lys Gly Arg Thr Tyr Tyr
1               5                   10                  15

Val Asn His Asn Asn Arg Thr Thr Thr Trp Thr Arg Pro
            20                  25

<210> SEQ ID NO 63
<211> LENGTH: 31
<212> TYPE: PRT
<213> ORGANISM: Homo sapiens

<400> SEQUENCE: 63

Pro Pro Gly Trp Glu Met Arg Ile Ala Pro Asn Gly Arg Pro Phe Phe
1               5                   10                  15

Ile Asp His Asn Thr Lys Thr Thr Thr Trp Glu Asp Pro Arg Leu
            20                  25                  30

<210> SEQ ID NO 64
<211> LENGTH: 31
<212> TYPE: PRT
<213> ORGANISM: Homo sapiens

<400> SEQUENCE: 64

Pro Pro Gly Trp Glu Glu Arg Ile His Leu Asp Gly Arg Thr Phe Tyr
1               5                   10                  15

Ile Asp His Asn Ser Lys Ile Thr Gln Trp Glu Asp Pro Arg Leu
            20                  25                  30

<210> SEQ ID NO 65
<211> LENGTH: 1493
<212> TYPE: PRT
<213> ORGANISM: Artificial Sequence
<220> FEATURE:
<223> OTHER INFORMATION: Synthetic

<400> SEQUENCE: 65

Met Pro Leu Pro Pro Gly Trp Glu Gln Arg Val Asp Gln His Gly Arg
1               5                   10                  15

Val Tyr Tyr Val Asp His Val Glu Lys Arg Thr Thr Trp Asp Arg Pro
            20                  25                  30

Glu Pro Leu Pro Pro Gly Trp Glu Arg Arg Val Asp Asn Met Gly Arg
        35                  40                  45

Ile Tyr Tyr Val Asp His Phe Thr Arg Thr Thr Thr Trp Gln Arg Pro
    50                  55                  60

Thr Leu Thr Gly Ala Thr Met Asp Tyr Lys Asp His Asp Gly Asp Tyr
65                  70                  75                  80

Lys Asp His Asp Ile Asp Tyr Lys Asp Asp Asp Lys Met Ala Pro
                85                  90                  95

Lys Lys Lys Arg Lys Val Gly Ile His Gly Val Pro Ala Ala Asp Lys
            100                 105                 110

Lys Tyr Ser Ile Gly Leu Asp Ile Gly Thr Asn Ser Val Gly Trp Ala
        115                 120                 125

Val Ile Thr Asp Glu Tyr Lys Val Pro Ser Lys Lys Phe Lys Val Leu
    130                 135                 140

Gly Asn Thr Asp Arg His Ser Ile Lys Lys Asn Leu Ile Gly Ala Leu
145                 150                 155                 160

Leu Phe Asp Ser Gly Glu Thr Ala Glu Ala Thr Arg Leu Lys Arg Thr
                165                 170                 175

Ala Arg Arg Arg Tyr Thr Arg Arg Lys Asn Arg Ile Cys Tyr Leu Gln
            180                 185                 190

Glu Ile Phe Ser Asn Glu Met Ala Lys Val Asp Asp Ser Phe Phe His
        195                 200                 205

Arg Leu Glu Glu Ser Phe Leu Val Glu Asp Lys Lys His Glu Arg
    210                 215                 220

His Pro Ile Phe Gly Asn Ile Val Asp Glu Val Ala Tyr His Glu Lys
225                 230                 235                 240

Tyr Pro Thr Ile Tyr His Leu Arg Lys Lys Leu Val Asp Ser Thr Asp
                245                 250                 255

```
Lys Ala Asp Leu Arg Leu Ile Tyr Leu Ala Leu Ala His Met Ile Lys
                260                 265                 270

Phe Arg Gly His Phe Leu Ile Glu Gly Asp Leu Asn Pro Asp Asn Ser
            275                 280                 285

Asp Val Asp Lys Leu Phe Ile Gln Leu Val Gln Thr Tyr Asn Gln Leu
        290                 295                 300

Phe Glu Glu Asn Pro Ile Asn Ala Ser Gly Val Asp Ala Lys Ala Ile
305                 310                 315                 320

Leu Ser Ala Arg Leu Ser Lys Ser Arg Arg Leu Glu Asn Leu Ile Ala
                325                 330                 335

Gln Leu Pro Gly Glu Lys Lys Asn Gly Leu Phe Gly Asn Leu Ile Ala
            340                 345                 350

Leu Ser Leu Gly Leu Thr Pro Asn Phe Lys Ser Asn Phe Asp Leu Ala
        355                 360                 365

Glu Asp Ala Lys Leu Gln Leu Ser Lys Asp Thr Tyr Asp Asp Asp Leu
    370                 375                 380

Asp Asn Leu Leu Ala Gln Ile Gly Asp Gln Tyr Ala Asp Leu Phe Leu
385                 390                 395                 400

Ala Ala Lys Asn Leu Ser Asp Ala Ile Leu Leu Ser Asp Ile Leu Arg
                405                 410                 415

Val Asn Thr Glu Ile Thr Lys Ala Pro Leu Ser Ala Ser Met Ile Lys
            420                 425                 430

Arg Tyr Asp Glu His His Gln Asp Leu Thr Leu Leu Lys Ala Leu Val
        435                 440                 445

Arg Gln Gln Leu Pro Glu Lys Tyr Lys Glu Ile Phe Phe Asp Gln Ser
    450                 455                 460

Lys Asn Gly Tyr Ala Gly Tyr Ile Asp Gly Gly Ala Ser Gln Glu Glu
465                 470                 475                 480

Phe Tyr Lys Phe Ile Lys Pro Ile Leu Glu Lys Met Asp Gly Thr Glu
                485                 490                 495

Glu Leu Leu Val Lys Leu Asn Arg Glu Asp Leu Leu Arg Lys Gln Arg
            500                 505                 510

Thr Phe Asp Asn Gly Ser Ile Pro His Gln Ile His Leu Gly Glu Leu
        515                 520                 525

His Ala Ile Leu Arg Arg Gln Glu Asp Phe Tyr Pro Phe Leu Lys Asp
    530                 535                 540

Asn Arg Glu Lys Ile Glu Lys Ile Leu Thr Phe Arg Ile Pro Tyr Tyr
545                 550                 555                 560

Val Gly Pro Leu Ala Arg Gly Asn Ser Arg Phe Ala Trp Met Thr Arg
                565                 570                 575

Lys Ser Glu Glu Thr Ile Thr Pro Trp Asn Phe Glu Glu Val Val Asp
            580                 585                 590

Lys Gly Ala Ser Ala Gln Ser Phe Ile Glu Arg Met Thr Asn Phe Asp
        595                 600                 605

Lys Asn Leu Pro Asn Glu Lys Val Leu Pro Lys His Ser Leu Leu Tyr
    610                 615                 620

Glu Tyr Phe Thr Val Tyr Asn Glu Leu Thr Lys Val Lys Tyr Val Thr
625                 630                 635                 640

Glu Gly Met Arg Lys Pro Ala Phe Leu Ser Gly Glu Gln Lys Lys Ala
                645                 650                 655

Ile Val Asp Leu Leu Phe Lys Thr Asn Arg Lys Val Thr Val Lys Gln
            660                 665                 670

Leu Lys Glu Asp Tyr Phe Lys Lys Ile Glu Cys Phe Asp Ser Val Glu
```

```
                    675                 680                 685
Ile Ser Gly Val Glu Asp Arg Phe Asn Ala Ser Leu Gly Thr Tyr His
690                 695                 700

Asp Leu Leu Lys Ile Ile Lys Asp Lys Asp Phe Leu Asp Asn Glu Glu
705                 710                 715                 720

Asn Glu Asp Ile Leu Glu Asp Ile Val Leu Thr Leu Thr Leu Phe Glu
                725                 730                 735

Asp Arg Glu Met Ile Glu Glu Arg Leu Lys Thr Tyr Ala His Leu Phe
                740                 745                 750

Asp Asp Lys Val Met Lys Gln Leu Lys Arg Arg Tyr Thr Gly Trp
                755                 760                 765

Gly Arg Leu Ser Arg Lys Leu Ile Asn Gly Ile Arg Asp Lys Gln Ser
770                 775                 780

Gly Lys Thr Ile Leu Asp Phe Leu Lys Ser Asp Gly Phe Ala Asn Arg
785                 790                 795                 800

Asn Phe Met Gln Leu Ile His Asp Asp Ser Leu Thr Phe Lys Glu Asp
                805                 810                 815

Ile Gln Lys Ala Gln Val Ser Gly Gln Gly Asp Ser Leu His Glu His
                820                 825                 830

Ile Ala Asn Leu Ala Gly Ser Pro Ala Ile Lys Lys Gly Ile Leu Gln
                835                 840                 845

Thr Val Lys Val Val Asp Glu Leu Val Lys Val Met Gly Arg His Lys
850                 855                 860

Pro Glu Asn Ile Val Ile Glu Met Ala Arg Glu Asn Gln Thr Thr Gln
865                 870                 875                 880

Lys Gly Gln Lys Asn Ser Arg Glu Arg Met Lys Arg Ile Glu Glu Gly
                885                 890                 895

Ile Lys Glu Leu Gly Ser Gln Ile Leu Lys Glu His Pro Val Glu Asn
                900                 905                 910

Thr Gln Leu Gln Asn Glu Lys Leu Tyr Leu Tyr Tyr Leu Gln Asn Gly
                915                 920                 925

Arg Asp Met Tyr Val Asp Gln Glu Leu Asp Ile Asn Arg Leu Ser Asp
930                 935                 940

Tyr Asp Val Asp His Ile Val Pro Gln Ser Phe Leu Lys Asp Asp Ser
945                 950                 955                 960

Ile Asp Asn Lys Val Leu Thr Arg Ser Asp Lys Asn Arg Gly Lys Ser
                965                 970                 975

Asp Asn Val Pro Ser Glu Glu Val Val Lys Lys Met Lys Asn Tyr Trp
                980                 985                 990

Arg Gln Leu Leu Asn Ala Lys Leu Ile Thr Gln Arg Lys Phe Asp Asn
                995                 1000                1005

Leu Thr Lys Ala Glu Arg Gly Gly Leu Ser Glu Leu Asp Lys Ala
        1010                1015                1020

Gly Phe Ile Lys Arg Gln Leu Val Glu Thr Arg Gln Ile Thr Lys
        1025                1030                1035

His Val Ala Gln Ile Leu Asp Ser Arg Met Asn Thr Lys Tyr Asp
        1040                1045                1050

Glu Asn Asp Lys Leu Ile Arg Glu Val Lys Val Ile Thr Leu Lys
        1055                1060                1065

Ser Lys Leu Val Ser Asp Phe Arg Lys Asp Phe Gln Phe Tyr Lys
        1070                1075                1080

Val Arg Glu Ile Asn Asn Tyr His His Ala His Asp Ala Tyr Leu
        1085                1090                1095
```

```
Asn Ala Val Val Gly Thr Ala Leu Ile Lys Lys Tyr Pro Lys Leu
    1100            1105                1110

Glu Ser Glu Phe Val Tyr Gly Asp Tyr Lys Val Tyr Asp Val Arg
    1115            1120                1125

Lys Met Ile Ala Lys Ser Glu Gln Glu Ile Gly Lys Ala Thr Ala
    1130            1135                1140

Lys Tyr Phe Phe Tyr Ser Asn Ile Met Asn Phe Phe Lys Thr Glu
    1145            1150                1155

Ile Thr Leu Ala Asn Gly Glu Ile Arg Lys Arg Pro Leu Ile Glu
    1160            1165                1170

Thr Asn Gly Glu Thr Gly Glu Ile Val Trp Asp Lys Gly Arg Asp
    1175            1180                1185

Phe Ala Thr Val Arg Lys Val Leu Ser Met Pro Gln Val Asn Ile
    1190            1195                1200

Val Lys Lys Thr Glu Val Gln Thr Gly Gly Phe Ser Lys Glu Ser
    1205            1210                1215

Ile Leu Pro Lys Arg Asn Ser Asp Lys Leu Ile Ala Arg Lys Lys
    1220            1225                1230

Asp Trp Asp Pro Lys Lys Tyr Gly Gly Phe Asp Ser Pro Thr Val
    1235            1240                1245

Ala Tyr Ser Val Leu Val Val Ala Lys Val Glu Lys Gly Lys Ser
    1250            1255                1260

Lys Lys Leu Lys Ser Val Lys Glu Leu Leu Gly Ile Thr Ile Met
    1265            1270                1275

Glu Arg Ser Ser Phe Glu Lys Asn Pro Ile Asp Phe Leu Glu Ala
    1280            1285                1290

Lys Gly Tyr Lys Glu Val Lys Lys Asp Leu Ile Ile Lys Leu Pro
    1295            1300                1305

Lys Tyr Ser Leu Phe Glu Leu Glu Asn Gly Arg Lys Arg Met Leu
    1310            1315                1320

Ala Ser Ala Gly Glu Leu Gln Lys Gly Asn Glu Leu Ala Leu Pro
    1325            1330                1335

Ser Lys Tyr Val Asn Phe Leu Tyr Leu Ala Ser His Tyr Glu Lys
    1340            1345                1350

Leu Lys Gly Ser Pro Glu Asp Asn Glu Gln Lys Gln Leu Phe Val
    1355            1360                1365

Glu Gln His Lys His Tyr Leu Asp Glu Ile Ile Glu Gln Ile Ser
    1370            1375                1380

Glu Phe Ser Lys Arg Val Ile Leu Ala Asp Ala Asn Leu Asp Lys
    1385            1390                1395

Val Leu Ser Ala Tyr Asn Lys His Arg Asp Lys Pro Ile Arg Glu
    1400            1405                1410

Gln Ala Glu Asn Ile Ile His Leu Phe Thr Leu Thr Asn Leu Gly
    1415            1420                1425

Ala Pro Ala Ala Phe Lys Tyr Phe Asp Thr Thr Ile Asp Arg Lys
    1430            1435                1440

Arg Tyr Thr Ser Thr Lys Glu Val Leu Asp Ala Thr Leu Ile His
    1445            1450                1455

Gln Ser Ile Thr Gly Leu Tyr Glu Thr Arg Ile Asp Leu Ser Gln
    1460            1465                1470

Leu Gly Gly Asp Lys Arg Pro Ala Ala Thr Lys Lys Ala Gly Gln
    1475            1480                1485
```

Ala Lys Lys Lys Lys
    1490

<210> SEQ ID NO 66
<211> LENGTH: 1616
<212> TYPE: PRT
<213> ORGANISM: Artificial Sequence
<220> FEATURE:
<223> OTHER INFORMATION: Synthetic

<400> SEQUENCE: 66

Met Pro Leu Pro Pro Gly Trp Glu Gln Arg Val Asp Gln His Gly Arg
1               5                   10                  15

Val Tyr Tyr Val Asp His Val Glu Lys Arg Thr Thr Trp Asp Arg Pro
            20                  25                  30

Glu Pro Leu Pro Pro Gly Trp Glu Arg Arg Val Asp Asn Met Gly Arg
        35                  40                  45

Ile Tyr Tyr Val Asp His Phe Thr Arg Thr Thr Thr Trp Gln Arg Pro
    50                  55                  60

Thr Leu Glu Ser Val Arg Asn Tyr Glu Gln Trp Gln Leu Gln Arg Ser
65                  70                  75                  80

Gln Leu Gln Gly Ala Met Gln Gln Phe Asn Gln Arg Phe Ile Tyr Gly
                85                  90                  95

Asn Gln Asp Leu Phe Ala Thr Ser Gln Ser Lys Glu Phe Asp Pro Leu
            100                 105                 110

Gly Pro Leu Pro Pro Gly Trp Glu Lys Arg Thr Asp Ser Asn Gly Arg
        115                 120                 125

Val Tyr Phe Val Asn His Asn Thr Arg Ile Thr Gln Trp Glu Asp Pro
    130                 135                 140

Arg Ser Gln Gly Gln Leu Asn Glu Lys Pro Leu Pro Glu Gly Trp Glu
145                 150                 155                 160

Met Arg Phe Thr Val Asp Gly Ile Pro Tyr Phe Val Asp His Asn Arg
                165                 170                 175

Arg Thr Thr Thr Tyr Ile Asp Pro Arg Thr Gly Gly Thr Gly Ala
            180                 185                 190

Thr Met Asp Tyr Lys Asp His Asp Gly Asp Tyr Lys Asp His Asp Ile
        195                 200                 205

Asp Tyr Lys Asp Asp Asp Asp Lys Met Ala Pro Lys Lys Lys Arg Lys
    210                 215                 220

Val Gly Ile His Gly Val Pro Ala Ala Asp Lys Lys Tyr Ser Ile Gly
225                 230                 235                 240

Leu Asp Ile Gly Thr Asn Ser Val Gly Trp Ala Val Ile Thr Asp Glu
                245                 250                 255

Tyr Lys Val Pro Ser Lys Lys Phe Lys Val Leu Gly Asn Thr Asp Arg
            260                 265                 270

His Ser Ile Lys Lys Asn Leu Ile Gly Ala Leu Leu Phe Asp Ser Gly
        275                 280                 285

Glu Thr Ala Glu Ala Thr Arg Leu Lys Arg Thr Ala Arg Arg Arg Tyr
    290                 295                 300

Thr Arg Arg Lys Asn Arg Ile Cys Tyr Leu Gln Glu Ile Phe Ser Asn
305                 310                 315                 320

Glu Met Ala Lys Val Asp Asp Ser Phe Phe His Arg Leu Glu Glu Ser
                325                 330                 335

Phe Leu Val Glu Glu Asp Lys Lys His Glu Arg His Pro Ile Phe Gly
            340                 345                 350

```
Asn Ile Val Asp Glu Val Ala Tyr His Glu Lys Tyr Pro Thr Ile Tyr
            355                 360                 365

His Leu Arg Lys Lys Leu Val Asp Ser Thr Asp Lys Ala Asp Leu Arg
    370                 375                 380

Leu Ile Tyr Leu Ala Leu Ala His Met Ile Lys Phe Arg Gly His Phe
385                 390                 395                 400

Leu Ile Glu Gly Asp Leu Asn Pro Asp Asn Ser Asp Val Asp Lys Leu
                405                 410                 415

Phe Ile Gln Leu Val Gln Thr Tyr Asn Gln Leu Phe Glu Glu Asn Pro
            420                 425                 430

Ile Asn Ala Ser Gly Val Asp Ala Lys Ala Ile Leu Ser Ala Arg Leu
        435                 440                 445

Ser Lys Ser Arg Arg Leu Glu Asn Leu Ile Ala Gln Leu Pro Gly Glu
    450                 455                 460

Lys Lys Asn Gly Leu Phe Gly Asn Leu Ile Ala Leu Ser Leu Gly Leu
465                 470                 475                 480

Thr Pro Asn Phe Lys Ser Asn Phe Asp Leu Ala Glu Asp Ala Lys Leu
                485                 490                 495

Gln Leu Ser Lys Asp Thr Tyr Asp Asp Asp Leu Asp Asn Leu Leu Ala
            500                 505                 510

Gln Ile Gly Asp Gln Tyr Ala Asp Leu Phe Leu Ala Ala Lys Asn Leu
        515                 520                 525

Ser Asp Ala Ile Leu Leu Ser Asp Ile Leu Arg Val Asn Thr Glu Ile
    530                 535                 540

Thr Lys Ala Pro Leu Ser Ala Ser Met Ile Lys Arg Tyr Asp Glu His
545                 550                 555                 560

His Gln Asp Leu Thr Leu Leu Lys Ala Leu Val Arg Gln Gln Leu Pro
                565                 570                 575

Glu Lys Tyr Lys Glu Ile Phe Phe Asp Gln Ser Lys Asn Gly Tyr Ala
            580                 585                 590

Gly Tyr Ile Asp Gly Gly Ala Ser Gln Glu Glu Phe Tyr Lys Phe Ile
        595                 600                 605

Lys Pro Ile Leu Glu Lys Met Asp Gly Thr Glu Glu Leu Leu Val Lys
    610                 615                 620

Leu Asn Arg Glu Asp Leu Leu Arg Lys Gln Arg Thr Phe Asp Asn Gly
625                 630                 635                 640

Ser Ile Pro His Gln Ile His Leu Gly Glu Leu His Ala Ile Leu Arg
                645                 650                 655

Arg Gln Glu Asp Phe Tyr Pro Phe Leu Lys Asp Asn Arg Glu Lys Ile
            660                 665                 670

Glu Lys Ile Leu Thr Phe Arg Ile Pro Tyr Tyr Val Gly Pro Leu Ala
        675                 680                 685

Arg Gly Asn Ser Arg Phe Ala Trp Met Thr Arg Lys Ser Glu Glu Thr
    690                 695                 700

Ile Thr Pro Trp Asn Phe Glu Glu Val Val Asp Lys Gly Ala Ser Ala
705                 710                 715                 720

Gln Ser Phe Ile Glu Arg Met Thr Asn Phe Asp Lys Asn Leu Pro Asn
                725                 730                 735

Glu Lys Val Leu Pro Lys His Ser Leu Leu Tyr Glu Tyr Phe Thr Val
            740                 745                 750

Tyr Asn Glu Leu Thr Lys Val Lys Tyr Val Thr Glu Gly Met Arg Lys
        755                 760                 765

Pro Ala Phe Leu Ser Gly Glu Gln Lys Lys Ala Ile Val Asp Leu Leu
```

```
              770                 775                 780
Phe Lys Thr Asn Arg Lys Val Thr Val Lys Gln Leu Lys Glu Asp Tyr
785                 790                 795                 800

Phe Lys Lys Ile Glu Cys Phe Asp Ser Val Glu Ile Ser Gly Val Glu
                805                 810                 815

Asp Arg Phe Asn Ala Ser Leu Gly Thr Tyr His Asp Leu Leu Lys Ile
                820                 825                 830

Ile Lys Asp Lys Asp Phe Leu Asp Asn Glu Glu Asn Glu Asp Ile Leu
                835                 840                 845

Glu Asp Ile Val Leu Thr Leu Thr Leu Phe Glu Asp Arg Glu Met Ile
850                 855                 860

Glu Glu Arg Leu Lys Thr Tyr Ala His Leu Phe Asp Asp Lys Val Met
865                 870                 875                 880

Lys Gln Leu Lys Arg Arg Arg Tyr Thr Gly Trp Gly Arg Leu Ser Arg
                885                 890                 895

Lys Leu Ile Asn Gly Ile Arg Asp Lys Gln Ser Gly Lys Thr Ile Leu
                900                 905                 910

Asp Phe Leu Lys Ser Asp Gly Phe Ala Asn Arg Asn Phe Met Gln Leu
                915                 920                 925

Ile His Asp Asp Ser Leu Thr Phe Lys Glu Asp Ile Gln Lys Ala Gln
                930                 935                 940

Val Ser Gly Gln Gly Asp Ser Leu His Glu His Ile Ala Asn Leu Ala
945                 950                 955                 960

Gly Ser Pro Ala Ile Lys Lys Gly Ile Leu Gln Thr Val Lys Val Val
                965                 970                 975

Asp Glu Leu Val Lys Val Met Gly Arg His Lys Pro Glu Asn Ile Val
                980                 985                 990

Ile Glu Met Ala Arg Glu Asn Gln Thr Thr Gln Lys Gly Gln Lys Asn
                995                 1000                1005

Ser Arg Glu Arg Met Lys Arg Ile Glu Glu Gly Ile Lys Glu Leu
   1010                1015                1020

Gly Ser Gln Ile Leu Lys Glu His Pro Val Glu Asn Thr Gln Leu
   1025                1030                1035

Gln Asn Glu Lys Leu Tyr Leu Tyr Tyr Leu Gln Asn Gly Arg Asp
   1040                1045                1050

Met Tyr Val Asp Gln Glu Leu Asp Ile Asn Arg Leu Ser Asp Tyr
   1055                1060                1065

Asp Val Asp His Ile Val Pro Gln Ser Phe Leu Lys Asp Asp Ser
   1070                1075                1080

Ile Asp Asn Lys Val Leu Thr Arg Ser Asp Lys Asn Arg Gly Lys
   1085                1090                1095

Ser Asp Asn Val Pro Ser Glu Glu Val Val Lys Lys Met Lys Asn
   1100                1105                1110

Tyr Trp Arg Gln Leu Leu Asn Ala Lys Leu Ile Thr Gln Arg Lys
   1115                1120                1125

Phe Asp Asn Leu Thr Lys Ala Glu Arg Gly Gly Leu Ser Glu Leu
   1130                1135                1140

Asp Lys Ala Gly Phe Ile Lys Arg Gln Leu Val Glu Thr Arg Gln
   1145                1150                1155

Ile Thr Lys His Val Ala Gln Ile Leu Asp Ser Arg Met Asn Thr
   1160                1165                1170

Lys Tyr Asp Glu Asn Asp Lys Leu Ile Arg Glu Val Lys Val Ile
   1175                1180                1185
```

```
Thr Leu Lys Ser Lys Leu Val Ser Asp Phe Arg Lys Asp Phe Gln
    1190            1195            1200

Phe Tyr Lys Val Arg Glu Ile Asn Asn Tyr His His Ala His Asp
    1205            1210            1215

Ala Tyr Leu Asn Ala Val Val Gly Thr Ala Leu Ile Lys Lys Tyr
    1220            1225            1230

Pro Lys Leu Glu Ser Glu Phe Val Tyr Gly Asp Tyr Lys Val Tyr
    1235            1240            1245

Asp Val Arg Lys Met Ile Ala Lys Ser Glu Gln Glu Ile Gly Lys
    1250            1255            1260

Ala Thr Ala Lys Tyr Phe Phe Tyr Ser Asn Ile Met Asn Phe Phe
    1265            1270            1275

Lys Thr Glu Ile Thr Leu Ala Asn Gly Glu Ile Arg Lys Arg Pro
    1280            1285            1290

Leu Ile Glu Thr Asn Gly Glu Thr Gly Glu Ile Val Trp Asp Lys
    1295            1300            1305

Gly Arg Asp Phe Ala Thr Val Arg Lys Val Leu Ser Met Pro Gln
    1310            1315            1320

Val Asn Ile Val Lys Lys Thr Glu Val Gln Thr Gly Gly Phe Ser
    1325            1330            1335

Lys Glu Ser Ile Leu Pro Lys Arg Asn Ser Asp Lys Leu Ile Ala
    1340            1345            1350

Arg Lys Lys Asp Trp Asp Pro Lys Lys Tyr Gly Gly Phe Asp Ser
    1355            1360            1365

Pro Thr Val Ala Tyr Ser Val Leu Val Val Ala Lys Val Glu Lys
    1370            1375            1380

Gly Lys Ser Lys Lys Leu Lys Ser Val Lys Glu Leu Leu Gly Ile
    1385            1390            1395

Thr Ile Met Glu Arg Ser Ser Phe Glu Lys Asn Pro Ile Asp Phe
    1400            1405            1410

Leu Glu Ala Lys Gly Tyr Lys Glu Val Lys Lys Asp Leu Ile Ile
    1415            1420            1425

Lys Leu Pro Lys Tyr Ser Leu Phe Glu Leu Glu Asn Gly Arg Lys
    1430            1435            1440

Arg Met Leu Ala Ser Ala Gly Glu Leu Gln Lys Gly Asn Glu Leu
    1445            1450            1455

Ala Leu Pro Ser Lys Tyr Val Asn Phe Leu Tyr Leu Ala Ser His
    1460            1465            1470

Tyr Glu Lys Leu Lys Gly Ser Pro Glu Asp Asn Glu Gln Lys Gln
    1475            1480            1485

Leu Phe Val Glu Gln His Lys His Tyr Leu Asp Glu Ile Ile Glu
    1490            1495            1500

Gln Ile Ser Glu Phe Ser Lys Arg Val Ile Leu Ala Asp Ala Asn
    1505            1510            1515

Leu Asp Lys Val Leu Ser Ala Tyr Asn Lys His Arg Asp Lys Pro
    1520            1525            1530

Ile Arg Glu Gln Ala Glu Asn Ile Ile His Leu Phe Thr Leu Thr
    1535            1540            1545

Asn Leu Gly Ala Pro Ala Ala Phe Lys Tyr Phe Asp Thr Thr Ile
    1550            1555            1560

Asp Arg Lys Arg Tyr Thr Ser Thr Lys Glu Val Leu Asp Ala Thr
    1565            1570            1575
```

Leu Ile His Gln Ser Ile Thr Gly Leu Tyr Glu Thr Arg Ile Asp
    1580                1585                1590

Leu Ser Gln Leu Gly Gly Asp Lys Arg Pro Ala Ala Thr Lys Lys
    1595                1600                1605

Ala Gly Gln Ala Lys Lys Lys Lys
    1610                1615

<210> SEQ ID NO 67
<211> LENGTH: 4479
<212> TYPE: DNA
<213> ORGANISM: Artificial Sequence
<220> FEATURE:
<223> OTHER INFORMATION: Synthetic

<400> SEQUENCE: 67

| | | | | | |
|---|---|---|---|---|---|
| atgcccttgc | cacctggttg | ggagcagaga | gtggaccagc | acgggcgagt | ttactatgta | 60 |
| gatcatgttg | agaaaagaac | aacatgggat | agaccagaac | ctctacctcc | tggctgggaa | 120 |
| cggcgggttg | acaacatggg | acgtatttat | tatgttgacc | atttcacaag | aacaacaacg | 180 |
| tggcagaggc | caacactgac | cggtgccacc | atggactata | aggaccacga | cggagactac | 240 |
| aaggatcatg | atattgatta | caaagacgat | gacgataaga | tggccccaaa | gaagaagcgg | 300 |
| aaggtcggta | tccacggagt | cccagcagcc | gacaagaagt | acagcatcgg | cctggacatc | 360 |
| ggcaccaact | ctgtgggctg | gccgtgatc | accgacgagt | acaaggtgcc | agcaagaaa | 420 |
| ttcaaggtgc | tgggcaacac | cgaccggcac | agcatcaaga | agaacctgat | cggagccctg | 480 |
| ctgttcgaca | gcggcgaaac | agccgaggcc | acccggctga | agagaaccgc | cagaagaaga | 540 |
| tacaccagac | ggaagaaccg | gatctgctat | ctgcaagaga | tcttcagcaa | cgagatggcc | 600 |
| aaggtggacg | acagcttctt | ccacagactg | gaagagtcct | tcctggtgga | agaggataag | 660 |
| aagcacgagc | ggcaccccat | cttcggcaac | atcgtggacg | aggtggccta | ccacgagaag | 720 |
| tacccccacc | tctaccacct | gagaaagaaa | ctggtggaca | gcaccgacaa | ggccgacctg | 780 |
| cggctgatct | atctggccct | ggcccacatg | atcaagttcc | ggggccactt | cctgatcgag | 840 |
| ggcgacctga | accccgacaa | cagcgacgtg | gacaagctgt | tcatccagct | ggtgcagacc | 900 |
| tacaaccagc | tgttcgagga | aaaccccatc | aacgccagcg | gcgtggacgc | caaggccatc | 960 |
| ctgtctgcca | gactgagcaa | gagcagacgg | ctggaaaatc | tgatcgccca | gctgcccggc | 1020 |
| gagaagaaga | atggcctgtt | cggaaacctg | attgccctga | gcctgggcct | gacccccaac | 1080 |
| ttcaagagca | acttcgacct | ggccgaggat | gccaaactgc | agctgagcaa | ggacacctac | 1140 |
| gacgacgacc | tggacaacct | gctggcccag | atcggcgacc | agtacgccga | cctgtttctg | 1200 |
| gccgccaaga | acctgtccga | cgccatcctg | ctgagcgaca | tcctgagagt | gaacaccgag | 1260 |
| atcaccaagg | cccccctgag | cgcctctatg | atcaagagat | acgacgagca | ccaccaggac | 1320 |
| ctgaccctgc | tgaaagctct | cgtgcggcag | cagctgcctg | agaagtacaa | agagattttc | 1380 |
| ttcgaccaga | gcaagaacgg | ctacgccggc | tacattgacg | gcggagccag | ccaggaagag | 1440 |
| ttctacaagt | tcatcaagcc | catcctggaa | aagatggacg | gcaccgagga | actgctcgtg | 1500 |
| aagctgaaca | gagaggacct | gctgcggaag | cagcggacct | tcgacaacgg | cagcatcccc | 1560 |
| caccagatcc | acctgggaga | gctgcacgcc | attctgcggc | ggcaggaaga | tttttaccca | 1620 |
| ttcctgaagg | acaaccggga | aaagatcgag | aagatcctga | ccttccgcat | ccctactac | 1680 |
| gtgggccctc | tggccagggg | aaacagcaga | ttcgcctgga | tgaccagaaa | gagcgaggaa | 1740 |
| accatcaccc | cctggaactt | cgaggaagtg | gtggacaagg | gcgcttccgc | ccagagcttc | 1800 |

```
atcgagcgga tgaccaactt cgataagaac ctgcccaacg agaaggtgct gcccaagcac    1860
agcctgctgt acgagtactt caccgtgtat aacgagctga ccaaagtgaa atacgtgacc    1920
gagggaatga gaaagcccgc cttcctgagc ggcgagcaga aaaaggccat cgtggacctg    1980
ctgttcaaga ccaaccggaa agtgaccgtg aagcagctga agaggactac cttcaagaaa    2040
atcgagtgct tcgactccgt ggaaatctcc ggcgtggaag atcggttcaa cgcctccctg    2100
ggcacatacc acgatctgct gaaaattatc aaggacaagg acttcctgga caatgaggaa    2160
aacgaggaca ttctggaaga tatcgtgctg accctgacac tgtttgagga cagagagatg    2220
atcgaggaac ggctgaaaac ctatgcccac ctgttcgacg acaaagtgat gaagcagctg    2280
aagcggcgga gatacaccgg ctggggcagg ctgagccgga agctgatcaa cggcatccgg    2340
gacaagcagt ccggcaagac aatcctggat ttcctgaagt ccgacggctt cgccaacaga    2400
aacttcatgc agctgatcca cgacgacagc ctgaccttta aagaggacat ccagaaagcc    2460
caggtgtccg gccagggcga tagcctgcac gagcacattg ccaatctggc cggcagcccc    2520
gccattaaga agggcatcct gcagacagtg aaggtggtgg acgagctcgt gaaagtgatg    2580
ggccggcaca agcccgagaa catcgtgatc gaaatggcca gagagaacca gaccacccag    2640
aagggacaga gaacagccg cgagagatg aagcggatcg aagagggcat caaagagctg    2700
ggcagccaga tcctgaaaga acaccccgtg gaaaacaccc agctgcagaa cgagaagctg    2760
tacctgtact acctgcagaa tgggcgggat atgtacgtgg accaggaact ggacatcaac    2820
cggctgtccg actacgatgt ggaccatatc gtgcctcaga gctttctgaa ggacgactcc    2880
atcgacaaca aggtgctgac cagaagcgac aagaaccggg gcaagagcga caacgtgccc    2940
tccgaagagg tcgtgaagaa gatgaagaac tactggcggc agctgctgaa cgccaagctg    3000
attcccaga gaaagttcga caatctgacc aaggccgaga gagcggcct gagcgaactg    3060
gataaggccg gcttcatcaa gagacagctg gtggaaaccc ggcagatcac aaagcacgtg    3120
gcacagatcc tggactcccg gatgaacact aagtacgacg agaatgacaa gctgatccgg    3180
gaagtgaaag tgatcaccct gaagtccaag ctggtgtccg atttccggaa ggatttccag    3240
ttttacaaag tgcgcgagat caacaactac caccacgccc acgacgccta cctgaacgcc    3300
gtcgtgggaa ccgccctgat caaaaagtac cctaagctgg aaagcgagtt cgtgtacggc    3360
gactacaagg tgtacgacgt gcggaagatg atcgccaaga gcgagcagga atcggcaag    3420
gctaccgcca agtacttctt ctacagcaac atcatgaact ttttcaagac cgagattacc    3480
ctggccaacg gcgagatccg gaagcggcct ctgatcgaga caacggcga accggggag    3540
atcgtgtggg ataagggccg ggattttgcc accgtgcgga agtgctgag catgccccaa    3600
gtgaatatcg tgaaaaagac cgaggtgcag acaggcggct tcagcaaaga gtctatcctg    3660
cccaagagga cagcgataa gctgatcgcc agaaagaagg actgggaccc taagaagtac    3720
ggcggcttcg acagccccac cgtggcctat tctgtgctgg tggtggccaa agtggaaaag    3780
ggcaagtcca gaaactgaa gagtgtgaaa gagctgctgg ggatcaccat catggaaaga    3840
agcagcttcg agaagaatcc catcgacttt ctggaagcca gggctacaa agaagtgaaa    3900
aaggacctga tcatcaagct gcctaagtac tcccctgttcg agctgaaaaa cggccggaag    3960
agaatgctgg cctctgccgg cgaactgcag aagggaaacg aactggccct gcctccaaa    4020
tatgtgaact tcctgtacct ggccagccac tatgagaagc tgaagggctc ccccgaggat    4080
aatgagcaga acagctgtt tgtggaacag cacaagcact acctggacga gatcatcgag    4140
cagatcagcg agttctccaa gagagtgatc ctggccgacg ctaatctgga caaagtgctg    4200
```

```
tccgcctaca acaagcaccg ggataagccc atcagagagc aggccgagaa tatcatccac  4260
ctgtttaccc tgaccaatct gggagcccct gccgccttca agtactttga caccaccatc  4320
gaccggaaga ggtacaccag caccaaagag gtgctggacg ccaccctgat ccaccagagc  4380
atcaccggcc tgtacgagac acggatcgac ctgtctcagc tgggaggcga caaaaggccg  4440
gcggccacga aaaaggccgg ccaggcaaaa aagaaaaag                         4479
```

<210> SEQ ID NO 68
<211> LENGTH: 4848
<212> TYPE: DNA
<213> ORGANISM: Artificial Sequence
<220> FEATURE:
<223> OTHER INFORMATION: Synthetic

<400> SEQUENCE: 68

```
atgcccttgc cacctggttg ggagcagaga gtggaccagc acgggcgagt ttactatgta    60
gatcatgttg agaaaagaac aacatgggat agaccagaac ctctacctcc tggctgggaa   120
cggcgggttg acaacatggg acgtatttat tatgttgacc atttcacaag aacaacaacg   180
tggcagaggc caacactgga atccgtccgg aactatgaac aatggcagct acagcgtagt   240
cagcttcaag gagcaatgca gcagtttaac cagagattca tttatgggaa tcaagattta   300
tttgctacat cacaaagtaa agaatttgat cctcttggtc cattgccacc tggatgggag   360
aagagaacag acagcaatgg cagagtatat ttcgtcaacc acaacacacg aattacacaa   420 tggaagacc ccagaagtca aggtcaatta aatgaaaagc ccttacctga aggttgggaa   480
atgagattca cagtggatgg aattccatat tttgtggacc acaatagaag aactaccacc   540
tatatagatc cccgcacagg cggaggaacc ggtgccacca tggactataa ggaccacgac   600
ggagactaca aggatcatga tattgattac aaagacgatg acgataagat ggccccaaag   660
aagaagcgga aggtcggtat ccacggagtc ccagcagccg acaagaagta cagcatcggc   720
ctggacatcg gcaccaactc tgtgggctgg gccgtgatca ccgacgagta caaggtgccc   780
agcaagaaat tcaaggtgct gggcaacacc gaccggcaca gcatcaagaa gaacctgatc   840
ggagccctgc tgttcgacag cggcgaaaca gccgaggcca cccggctgaa gagaaccgcc   900
agaagaagat acaccagacg gaagaaccgg atctgctatc tgcaagagat cttcagcaac   960
gagatggcca aggtggacga cagcttcttc cacagactgg aagagtcctt cctggtggaa  1020
gaggataaga agcacgagcg gcaccccatc ttcggcaaca tcgtggacga ggtggcctac  1080
cacgagaagt accccaccat ctaccacctg agaaagaaac tggtggacag caccgacaag  1140
gccgacctgc ggctgatcta tctggccctg gcccacatga tcaagttccg gggccacttc  1200
ctgatcgagg gcgacctgaa ccccgacaac agcgacgtgg acaagctgtt catccagctg  1260
gtgcagacct acaaccagct gttcgaggaa aaccccatca acgccagcgg cgtggacgcc  1320
aaggccatcc tgtctgccag actgagcaag agcagacgtg tggaaaatct gatcgcccag  1380
ctgcccggcg agaagaagaa tggcctgttc ggaaacctga ttgccctgag cctgggcctg  1440 accccccaact tcaagagcaa cttcgacctg gccgaggatg ccaaactgca gctgagcaag  1500
gacacctacg acgacgacct ggacaacctg ctggcccaga tcggcgacca gtacgccgac  1560
ctgtttctgg ccgccaagaa cctgtccgac gccatcctgc tgagcgacat cctgagagtg  1620
aacaccgaga tcaccaaggc ccccctgagc gcctctatga tcaagagata cgacgagcac  1680
caccaggacc tgaccctgct gaaagctctc gtgcggcagc agctgcctga aagtacaaa  1740
```

```
gagattttct tcgaccagag caagaacggc tacgccggct acattgacgg cggagccagc   1800
caggaagagt tctacaagtt catcaagccc atcctggaaa agatggacgg caccgaggaa   1860
ctgctcgtga agctgaacag agaggacctg ctgcggaagc agcggacctt cgacaacggc   1920
agcatccccc accagatcca cctgggagag ctgcacgcca ttctgcggcg gcaggaagat   1980
ttttacccat tcctgaagga caaccgggaa aagatcgaga agatcctgac cttccgcatc   2040
ccctactacg tgggccctct ggccagggga aacagcagat cgcctggat gaccagaaag   2100 agcgaggaaa ccatcacccc ctggaacttc gaggaagtgg tggacaaggg cgcttccgcc   2160
cagagcttca tcgagcggat gaccaacttc gataagaacc tgcccaacga aaaggtgctg   2220
cccaagcaca gcctgctgta cgagtacttc accgtgtata cgagctgac caaagtgaaa   2280 tacgtgaccg agggaatgag aaagcccgcc ttcctgagcg gcgagcagaa aaaggccatc   2340
gtggacctgc tgttcaagac caaccggaaa gtgaccgtga agcagctgaa agaggactac   2400
ttcaagaaaa tcgagtgctt cgactccgtg gaaatctccg gcgtggaaga tcggttcaac   2460
gcctccctgg gcacatacca cgatctgctg aaaattatca aggacaagga cttcctggac   2520
aatgaggaaa acgaggacat tctggaagat atcgtgctga ccctgacact gtttgaggac   2580
agagagatga tcgaggaacg gctgaaaacc tatgcccacc tgttcgacga caaagtgatg   2640
aagcagctga agcggcggag atacaccggc tggggcaggc tgagccggaa gctgatcaac   2700
ggcatccggg acaagcagtc cggcaagaca atcctggatt tcctgaagtc cgacggcttc   2760
gccaacagaa acttcatgca gctgatccac gacgacagcc tgaccttta agaggacatc   2820 cagaaagccc aggtgtccgg ccagggcgat agcctgcacg agcacattgc caatctggcc   2880
ggcagccccg ccattaagaa gggcatcctg cagacagtga aggtggtgga cgagctcgtg   2940
aaagtgatgg gccggcacaa gcccgagaac atcgtgatcg aaatggccag agagaaccag   3000
accacccaga agggacagaa gaacagccgc gagagaatga gcggatcga gagggcatc   3060 aaagagctgg gcagccagat cctgaaagaa caccccgtgg aaaacaccca gctgcagaac   3120
gagaagctgt acctgtacta cctgcagaat gggcgggata tgtacgtgga ccaggaactg   3180
gacatcaacc ggctgtccga ctacgatgtg gaccatatcg tgcctcagag ctttctgaag   3240
gacgactcca tcgacaacaa ggtgctgacc agaagcgaca gaaccgggg caagagcgac   3300 aacgtgccct ccgaagaggt cgtgaagaag atgaagaact actggcggca gctgctgaac   3360
gccaagctga ttacccagag aaagttcgac aatctgacca aggccgagag aggcggcctg   3420
agcgaactgg ataaggccgg cttcatcaag agacagctgg tggaaacccg gcagatcaca   3480
aagcacgtgg cacagatcct ggactcccgg atgaacacta gtacgacga gaatgacaag   3540 ctgatccggg aagtgaaagt gatcacccta aagtccaagc tggtgtccga tttccggaag   3600
gatttccagt tttacaaagt gcgcgagatc aacaactacc accacgccca cgacgcctac   3660
ctgaacgccg tcgtgggaac cgccctgatc aaaaagtacc ctaagctgga aagcgagttc   3720
gtgtacggcg actacaaggt gtacgacgtg cggaagatga tcgccaagag cgagcaggaa   3780
atcggcaagg ctaccgccaa gtacttcttc tacagcaaca tcatgaactt tttcaagacc   3840
gagattaccc tggccaacgg cgagatccgg aagcggcctc tgatcgagac aaacggcgaa   3900
accggggaga tcgtgtggga taagggccgg gattttgcca ccgtgcggaa agtgctgagc   3960
atgccccaag tgaatatcgt gaaaaagacc gaggtgcaga caggcggctt cagcaaagag   4020
tctatcctgc ccaagaggaa cagcgataag ctgatcgcca aagaagga ctgggaccct   4080 aagaagtacg gcggcttcga cagccccacc gtggcctatt ctgtgctggt ggtggccaaa   4140
```

```
gtggaaaagg gcaagtccaa gaaactgaag agtgtgaaag agctgctggg gatcaccatc    4200
atggaaagaa gcagcttcga gaagaatccc atcgactttc tggaagccaa gggctacaaa    4260
gaagtgaaaa aggacctgat catcaagctg cctaagtact ccctgttcga gctggaaaac    4320
ggccggaaga gaatgctggc ctctgccggc gaactgcaga gggaaacga actggccctg    4380 ccctccaaat atgtgaactt cctgtacctg gccagccact atgagaagct gaagggctcc    4440
cccgaggata tgagcagaa acagctgttt gtggaacagc acaagcacta cctggacgag    4500
atcatcgagc agatcagcga gttctccaag agagtgatcc tggccgacgc taatctggac    4560
aaagtgctgt ccgcctacaa caagcaccgg gataagccca tcagagagca ggccgagaat    4620
atcatccacc tgtttaccct gaccaatctg ggagccctg ccgccttcaa gtactttgac    4680
accaccatcg accggaagag gtacaccagc accaaagagg tgctggacgc caccctgatc    4740
caccagagca tcaccggcct gtacgagaca cggatcgacc tgtctcagct gggaggcgac    4800
aaaaggccgg cggccacgaa aaaggccggc caggcaaaaa agaaaaag                 4848
```

<210> SEQ ID NO 69
<211> LENGTH: 717
<212> TYPE: DNA
<213> ORGANISM: Artificial Sequence
<220> FEATURE:
<223> OTHER INFORMATION: Synthetic

<400> SEQUENCE: 69

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaag       717
```

<210> SEQ ID NO 70
<211> LENGTH: 114
<212> TYPE: DNA
<213> ORGANISM: Artificial Sequence
<220> FEATURE:
<223> OTHER INFORMATION: Synthetic Polynucleotide

<400> SEQUENCE: 70

```
aaaggacgaa acaccgggtc ttcgagaaga cctgttttag agctagaaat agcaagttaa     60
aataaggcta gtccgttatc aacttgaaaa agtggcaccg agtcggtgct tttt          114
```

<210> SEQ ID NO 71
<211> LENGTH: 114
<212> TYPE: DNA
<213> ORGANISM: Artificial Sequence
<220> FEATURE:

<223> OTHER INFORMATION: Synthetic Polynucleotide

<400> SEQUENCE: 71
aaaaagcacc gactcggtgc cacttttttca agttaaaaac ggactagcct tattttaact    60
tgctatttct agctctaaaa caggtcttct cgaagacccg gtgtttcgtc cttt          114

<210> SEQ ID NO 72

<400> SEQUENCE: 72

000

<210> SEQ ID NO 73

<400> SEQUENCE: 73

000

<210> SEQ ID NO 74
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 74

Pro Ser Ala Pro
1

<210> SEQ ID NO 75
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 75

Pro Pro Xaa Tyr
1

<210> SEQ ID NO 76
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 76

Leu Pro Xaa Thr Gly
1               5

<210> SEQ ID NO 77
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 77

```
Ala Gly Val Phe
1

<210> SEQ ID NO 78
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 78

Gly Phe Leu Gly
1

<210> SEQ ID NO 79
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 79

Ala Leu Ala Leu
1

<210> SEQ ID NO 80
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 80

Ala Leu Ala Leu Ala
1               5
```